US008859756B2

(12) United States Patent
Ross et al.

(10) Patent No.: US 8,859,756 B2
(45) Date of Patent: Oct. 14, 2014

(54) STEREOSELECTIVE SYNTHESIS OF PHOSPHORUS CONTAINING ACTIVES

(75) Inventors: Bruce S. Ross, Plainsboro, NJ (US); Michael Joseph Sofia, Doylestown, PA (US); Ganapati Reddy Pamulapati, Plainsboro, NJ (US); Suguna Rachakonda, Twinsburg, OH (US); Hai-Ren Zhang, Ellicott City, MD (US)

(73) Assignee: Gilead Pharmasset LLC, Foster City, CA (US)

( * ) Notice: Subject to any disclaimer, the term of this patent is extended or adjusted under 35 U.S.C. 154(b) by 193 days.

(21) Appl. No.: 13/076,842

(22) Filed: Mar. 31, 2011

(65) Prior Publication Data

US 2011/0245484 A1 Oct. 6, 2011

Related U.S. Application Data

(60) Provisional application No. 61/319,513, filed on Mar. 31, 2010, provisional application No. 61/319,548, filed on Mar. 31, 2010.

(51) Int. Cl.
| | | |
|---|---|---|
| C07H 19/04 | (2006.01) | |
| C07F 9/6558 | (2006.01) | |
| C07F 9/655 | (2006.01) | |
| C07H 19/24 | (2006.01) | |
| C07F 9/6561 | (2006.01) | |
| C07H 19/10 | (2006.01) | |
| C07F 9/24 | (2006.01) | |
| C07H 19/044 | (2006.01) | |
| C07H 19/207 | (2006.01) | |
| C07H 19/052 | (2006.01) | |
| C07F 7/18 | (2006.01) | |
| C07H 19/06 | (2006.01) | |

(52) U.S. Cl.
CPC ............ *C07H 19/10* (2013.01); *C07F 9/65586* (2013.01); *C07H 19/04* (2013.01); *C07F 9/65517* (2013.01); *C07H 19/24* (2013.01); *C07F 9/65616* (2013.01); *C07F 9/242* (2013.01); *C07H 19/044* (2013.01); *C07H 19/207* (2013.01); *C07H 19/052* (2013.01); *C07F 9/2458* (2013.01); *C07F 7/1856* (2013.01); *C07H 19/06* (2013.01)
USPC ...................................... 536/26.1; 536/26.47

(58) Field of Classification Search
None
See application file for complete search history.

(56) References Cited

U.S. PATENT DOCUMENTS

| | | |
|---|---|---|
| 2,512,572 A | 6/1950 | Smith, Jr. et al. |
| 2,563,707 A | 8/1951 | Cosulich |
| 3,053,865 A | 9/1962 | Taub et al. |
| 3,097,137 A | 7/1963 | Beer et al. |
| 3,104,246 A | 9/1963 | Amiard et al. |
| 3,116,282 A | 12/1963 | Hunter |
| 3,480,613 A | 11/1969 | Walton |
| 3,524,844 A | 8/1970 | Keller-Juslen et al. |
| 3,590,028 A | 6/1971 | Arcamone et al. |
| 3,798,209 A | 3/1974 | Witkowski et al. |
| 3,852,267 A | 12/1974 | Meyer, Jr. et al. |
| 3,888,843 A | 6/1975 | Mizuno et al. |
| 3,923,785 A | 12/1975 | Ryder et al. |
| 3,929,992 A | 12/1975 | Sehgal et al. |
| 3,991,045 A | 11/1976 | Ishida et al. |
| 3,994,974 A | 11/1976 | Murakami et al. |
| 4,046,878 A | 9/1977 | Patelli et al. |
| 4,058,519 A | 11/1977 | Arcamone et al. |
| 4,107,423 A | 8/1978 | Arcamone et al. |
| RE29,835 E | 11/1978 | Witkowski et al. |
| 4,197,249 A | 4/1980 | Murdock et al. |
| 4,199,574 A | 4/1980 | Schaeffer |
| 4,203,898 A | 5/1980 | Cullinan et al. |
| 4,210,745 A | 7/1980 | Montgomery |
| 4,303,785 A | 12/1981 | Umezawa et al. |
| 4,307,100 A | 12/1981 | Langlois et al. |
| 4,323,573 A | 4/1982 | Schaeffer |
| 4,355,032 A | 10/1982 | Verheyden et al. |
| 4,418,068 A | 11/1983 | Jones |
| 4,572,912 A | 2/1986 | Yoshioka et al. |
| 4,604,463 A | 8/1986 | Miyasaka et al. |
| 4,673,668 A | 6/1987 | Ishizumi et al. |
| 4,724,232 A | 2/1988 | Rideout et al. |
| 4,753,935 A | 6/1988 | Nelson et al. |
| 4,760,137 A | 7/1988 | Robins et al. |
| 4,797,285 A | 1/1989 | Barenholz et al. |
| 4,808,614 A | 2/1989 | Hertel |
| 4,808,716 A | 2/1989 | Hol et al. |
| 4,814,470 A | 3/1989 | Colin et al. |
| 4,814,477 A | 3/1989 | Wijnberg et al. |

(Continued)

FOREIGN PATENT DOCUMENTS

| | | |
|---|---|---|
| BE | 799805 A1 | 11/1973 |
| BE | 842930 A1 | 10/1976 |

(Continued)

OTHER PUBLICATIONS

Gillespie et al. Phosphorus, Sulfur, and Silicon, 1997, vol. 122, pp. 205-208.*
Hostetler, K.Y. et al., "Synthesis and Antiretroviral Activity of Phospholipid Analogs of Azidothymidine and Other Antiviral Nucleosides," The Journal of Biological Chemistry, vol. 265, No. 11, pp. 6112-6115 (1990).
Hunston, R.N. et al., "Synthesis and Biological Properties of Some Cyclic Phosphotriesters Derived from 2'-Deoxy-5-Fluorouridine," vol. 27, No. 4, pp. 440-444 (1984).

(Continued)

*Primary Examiner* — Layla Bland
(74) *Attorney, Agent, or Firm* — Sheppard, Mullin, Richter & Hampton LLP

(57) ABSTRACT

Disclosed herein are phosphorus-containing actives, their use as actives for treating diseases, and a stereoselective process for preparing the same. Also disclosed herein are useful synthetic intermediates and processes for preparing the same.

16 Claims, 1 Drawing Sheet

(56) References Cited

U.S. PATENT DOCUMENTS

| | | |
|---|---|---|
| 4,861,870 A | 8/1989 | Oppico et al. |
| 4,880,784 A | 11/1989 | Robins et al. |
| 4,918,179 A | 4/1990 | Watanabe et al. |
| 4,923,986 A | 5/1990 | Murakata et al. |
| 4,957,924 A | 9/1990 | Beauchamp |
| 5,004,758 A | 4/1991 | Boehm et al. |
| 5,013,556 A | 5/1991 | Woodle et al. |
| 5,026,687 A | 6/1991 | Yarchoan et al. |
| 5,034,394 A | 7/1991 | Daluge |
| 5,041,246 A | 8/1991 | Garrison |
| 5,041,426 A | 8/1991 | Robins et al. |
| 5,075,445 A | 12/1991 | Jarvest et al. |
| 5,077,056 A | 12/1991 | Bally et al. |
| 5,077,057 A | 12/1991 | Szoka, Jr. |
| 5,091,188 A | 2/1992 | Haynes |
| 5,104,888 A | 4/1992 | Yoshioka et al. |
| 5,118,820 A | 6/1992 | Hertel |
| 5,130,421 A | 7/1992 | Starrett, Jr. et al. |
| 5,137,918 A | 8/1992 | Weiershausen et al. |
| 5,145,684 A | 9/1992 | Liversidge et al. |
| 5,149,794 A | 9/1992 | Yatvin et al. |
| 5,154,930 A | 10/1992 | Popescu et al. |
| 5,157,027 A | 10/1992 | Biller et al. |
| 5,192,549 A | 3/1993 | Barenolz et al. |
| 5,194,654 A | 3/1993 | Hostetler et al. |
| 5,196,438 A | 3/1993 | Martin et al. |
| 5,206,244 A | 4/1993 | Zahler et al. |
| 5,213,804 A | 5/1993 | Martin et al. |
| 5,223,263 A | 6/1993 | Hostetler et al. |
| 5,225,212 A | 7/1993 | Martin et al. |
| 5,246,937 A | 9/1993 | Harnden et al. |
| 5,256,641 A | 10/1993 | Yatvin et al. |
| 5,256,798 A | 10/1993 | Chou et al. |
| 5,277,914 A | 1/1994 | Szoka, Jr. |
| 5,316,771 A | 5/1994 | Barenholz et al. |
| 5,369,108 A | 11/1994 | Breslow et al. |
| 5,372,808 A | 12/1994 | Blatt et al. |
| 5,376,380 A | 12/1994 | Kikuchi et al. |
| 5,405,598 A | 4/1995 | Schinazi et al. |
| 5,411,947 A | 5/1995 | Hostetler et al. |
| 5,420,266 A | 5/1995 | Britton et al. |
| 5,426,183 A | 6/1995 | Kjell |
| 5,453,499 A | 9/1995 | Chou et al. |
| 5,462,724 A | 10/1995 | Schinazi et al. |
| 5,463,092 A | 10/1995 | Hostetler et al. |
| 5,484,926 A | 1/1996 | Dressman et al. |
| 5,494,911 A | 2/1996 | Bartlett et al. |
| 5,496,546 A | 3/1996 | Wang et al. |
| 5,538,865 A | 7/1996 | Reyes et al. |
| 5,538,975 A | 7/1996 | Dionne |
| 5,543,389 A | 8/1996 | Yatvin et al. |
| 5,543,390 A | 8/1996 | Yatvin et al. |
| 5,543,391 A | 8/1996 | Yatvin et al. |
| 5,549,910 A | 8/1996 | Szoka, Jr. |
| 5,554,728 A | 9/1996 | Basava et al. |
| 5,567,434 A | 10/1996 | Szoka, Jr. |
| 5,610,054 A | 3/1997 | Draper |
| 5,620,985 A | 4/1997 | Jacquesy et al. |
| 5,633,358 A | 5/1997 | Gruetzke et al. |
| 5,633,388 A | 5/1997 | Diana et al. |
| 5,635,517 A | 6/1997 | Muller et al. |
| 5,676,942 A | 10/1997 | Testa et al. |
| 5,695,784 A | 12/1997 | Pollinger et al. |
| 5,703,058 A | 12/1997 | Schinazi et al. |
| 5,711,944 A | 1/1998 | Gilbert et al. |
| 5,719,147 A | 2/1998 | Dorn et al. |
| 5,725,859 A | 3/1998 | Omer |
| 5,736,155 A | 4/1998 | Bally et al. |
| 5,738,845 A | 4/1998 | Imakawa |
| 5,738,846 A | 4/1998 | Greenwald et al. |
| 5,747,646 A | 5/1998 | Hakimi et al. |
| 5,767,097 A | 6/1998 | Tam |
| 5,792,834 A | 8/1998 | Hakimi et al. |
| 5,827,533 A | 10/1998 | Needham |
| 5,830,455 A | 11/1998 | Valtuena et al. |
| 5,830,905 A | 11/1998 | Diana et al. |
| 5,834,594 A | 11/1998 | Hakimi et al. |
| 5,837,257 A | 11/1998 | Tsai et al. |
| 5,846,964 A | 12/1998 | Ozeki |
| 5,849,696 A | 12/1998 | Chretien et al. |
| 5,852,195 A | 12/1998 | Romines et al. |
| 5,869,253 A | 2/1999 | Draper |
| 5,882,679 A | 3/1999 | Needham |
| 5,891,468 A | 4/1999 | Martin et al. |
| 5,891,874 A | 4/1999 | Colacino et al. |
| 5,905,070 A | 5/1999 | Schinazi et al. |
| 5,908,621 A | 6/1999 | Glue et al. |
| 5,922,757 A | 7/1999 | Chojkier |
| 5,925,643 A | 7/1999 | Chu |
| 5,928,636 A | 7/1999 | Alber et al. |
| 5,942,223 A | 8/1999 | Bazer et al. |
| 5,980,884 A | 11/1999 | Blatt et al. |
| 5,990,276 A | 11/1999 | Zhang et al. |
| 6,004,933 A | 12/1999 | Spruce et al. |
| 6,034,134 A | 3/2000 | Gold et al. |
| 6,043,077 A | 3/2000 | Barber et al. |
| 6,056,961 A | 5/2000 | Lavie et al. |
| 6,060,080 A | 5/2000 | Kikuchi et al. |
| 6,090,932 A | 7/2000 | McGee et al. |
| 6,130,326 A | 10/2000 | Ramasamy et al. |
| 6,132,763 A | 10/2000 | Fisher |
| 6,143,321 A | 11/2000 | Needham et al. |
| 6,156,501 A | 12/2000 | McGall et al. |
| 6,174,905 B1 | 1/2001 | Suzuki et al. |
| 6,180,134 B1 | 1/2001 | Zalipsky et al. |
| 6,200,598 B1 | 3/2001 | Needham |
| 6,214,375 B1 | 4/2001 | Modi |
| 6,224,903 B1 | 5/2001 | Martin et al. |
| 6,232,300 B1 | 5/2001 | Schinazi et al. |
| 6,239,159 B1 | 5/2001 | Brown et al. |
| 6,267,985 B1 | 7/2001 | Chen et al. |
| 6,294,192 B1 | 9/2001 | Patel et al. |
| 6,296,870 B1 | 10/2001 | Needham et al. |
| 6,320,078 B1 | 11/2001 | Suzuki et al. |
| 6,348,587 B1 | 2/2002 | Schinazi et al. |
| 6,372,883 B1 | 4/2002 | Attwood et al. |
| 6,383,471 B1 | 5/2002 | Chen et al. |
| 6,391,859 B1 | 5/2002 | Schinazi et al. |
| 6,395,300 B1 | 5/2002 | Straub et al. |
| 6,410,531 B1 | 6/2002 | Llinas-Brunet et al. |
| 6,420,380 B2 | 7/2002 | Llinas-Brunet et al. |
| 6,455,513 B1 | 9/2002 | McGuigan et al. |
| 6,455,690 B1 | 9/2002 | Tam et al. |
| 6,475,985 B1 | 11/2002 | Wagner et al. |
| 6,479,463 B1 | 11/2002 | Wang et al. |
| 6,495,677 B1 | 12/2002 | Ramasamy et al. |
| 6,509,320 B1 | 1/2003 | Wang et al. |
| 6,534,523 B1 | 3/2003 | Llinas-Brunet et al. |
| 6,552,183 B1 | 4/2003 | Ramasamy et al. |
| 6,552,197 B2 | 4/2003 | Kamihara et al. |
| 6,555,677 B2 | 4/2003 | Petrillo et al. |
| 6,569,463 B2 | 5/2003 | Patel et al. |
| 6,573,248 B2 | 6/2003 | Ramasamy et al. |
| 6,620,325 B2 | 9/2003 | Fuenfschilling et al. |
| 6,635,278 B1 | 10/2003 | Dahl et al. |
| 6,642,206 B2 | 11/2003 | Ramasamy et al. |
| 6,645,528 B1 | 11/2003 | Straub et al. |
| 6,653,455 B1 | 11/2003 | Johdo et al. |
| 6,660,721 B2 | 12/2003 | Devos et al. |
| 6,677,314 B2 | 1/2004 | Klecker et al. |
| 6,677,315 B2 | 1/2004 | Klecker et al. |
| 6,680,068 B2 | 1/2004 | Campbell et al. |
| 6,680,303 B2 | 1/2004 | Schinazi et al. |
| 6,682,715 B2 | 1/2004 | Klecker et al. |
| 6,683,045 B2 | 1/2004 | Klecker et al. |
| 6,703,374 B1 | 3/2004 | Klecker et al. |
| 6,726,925 B1 | 4/2004 | Needham |
| 6,753,309 B2 | 6/2004 | Klecker et al. |
| 6,777,395 B2 | 8/2004 | Bhat et al. |
| 6,784,166 B2 | 8/2004 | Devos et al. |
| 6,787,305 B1 | 9/2004 | Li et al. |
| 6,787,526 B1 | 9/2004 | Bryant et al. |
| 6,812,219 B2 | 11/2004 | LaColla et al. |
| 6,815,542 B2 | 11/2004 | Hong et al. |

(56) References Cited

U.S. PATENT DOCUMENTS

| | | |
|---|---|---|
| 6,846,810 B2 | 1/2005 | Martin et al. |
| 6,897,201 B2 | 5/2005 | Boyer et al. |
| 6,908,924 B2 | 6/2005 | Watanabe et al. |
| 6,911,424 B2 | 6/2005 | Schinazi et al. |
| 6,914,054 B2 | 7/2005 | Sommadossi et al. |
| 6,923,988 B2 | 8/2005 | Patel et al. |
| 6,932,983 B1 | 8/2005 | Straub et al. |
| 6,962,991 B2 | 11/2005 | Dempcy et al. |
| 6,977,257 B2 | 12/2005 | Parab et al. |
| 7,018,985 B1 | 3/2006 | Boyer et al. |
| 7,018,989 B2 | 3/2006 | McGuigan et al. |
| 7,060,294 B2 | 6/2006 | Batra et al. |
| 7,060,689 B2 | 6/2006 | Goins et al. |
| 7,070,801 B2 | 7/2006 | Yamazaki et al. |
| 7,081,449 B2 | 7/2006 | Pietrzkowski et al. |
| 7,105,493 B2 | 9/2006 | Sommadossi et al. |
| 7,105,499 B2 | 9/2006 | Carroll et al. |
| 7,125,855 B2 | 10/2006 | Bhat et al. |
| 7,148,206 B2 | 12/2006 | Sommadossi et al. |
| 7,163,929 B2 | 1/2007 | Sommadossi et al. |
| 7,202,224 B2 | 4/2007 | Eldrup et al. |
| 7,217,523 B2 | 5/2007 | Wagner |
| 7,265,152 B2 | 9/2007 | Saha et al. |
| 7,268,119 B2 | 9/2007 | Cook et al. |
| 7,307,065 B2 | 12/2007 | Schinazi et al. |
| 7,323,453 B2 | 1/2008 | Olsen et al. |
| 7,365,057 B2 | 4/2008 | LaColla et al. |
| 7,378,402 B2 | 5/2008 | Martin et al. |
| 7,390,791 B2 | 6/2008 | Becker et al. |
| 7,429,572 B2 | 9/2008 | Clark |
| 7,462,608 B2 | 12/2008 | Chen et al. |
| 7,601,820 B2 | 10/2009 | Wang et al. |
| 7,608,597 B2 | 10/2009 | Sommadossi et al. |
| 7,608,600 B2 | 10/2009 | Storer et al. |
| 7,635,689 B2 | 12/2009 | LaColla et al. |
| 7,879,815 B2 | 2/2011 | MacCoss et al. |
| 7,964,560 B2 | 6/2011 | Wang et al. |
| 7,964,580 B2 | 6/2011 | Sofia et al. |
| 8,173,621 B2 | 5/2012 | Du et al. |
| 8,334,270 B2 | 12/2012 | Sofia et al. |
| 2001/0034440 A1 | 10/2001 | Shepard et al. |
| 2002/0058635 A1 | 5/2002 | Averett |
| 2002/0142050 A1 | 10/2002 | Straub et al. |
| 2002/0198173 A1 | 12/2002 | Schinazi et al. |
| 2003/0050229 A1 | 3/2003 | Sommadossi et al. |
| 2003/0060400 A1 | 3/2003 | LaColla et al. |
| 2003/0120071 A1 | 6/2003 | McGuigan et al. |
| 2003/0144502 A1 | 7/2003 | Pietrzkowski et al. |
| 2003/0153744 A1 | 8/2003 | Mekouar et al. |
| 2003/0187018 A1 | 10/2003 | Llinas-Brunet et al. |
| 2004/0006007 A1 | 1/2004 | Gosselin et al. |
| 2004/0014108 A1 | 1/2004 | Eldrup et al. |
| 2004/0023240 A1 | 2/2004 | Marliere et al. |
| 2004/0023901 A1 | 2/2004 | Cook et al. |
| 2004/0059104 A1 | 3/2004 | Cook et al. |
| 2004/0063622 A1 | 4/2004 | Sommadossi et al. |
| 2004/0067901 A1 | 4/2004 | Bhat et al. |
| 2004/0072788 A1 | 4/2004 | Bhat et al. |
| 2004/0097461 A1 | 5/2004 | Sommadossi et al. |
| 2004/0097462 A1 | 5/2004 | Sommadossi et al. |
| 2004/0101535 A1 | 5/2004 | Sommadossi et al. |
| 2004/0102414 A1 | 5/2004 | Sommadossi et al. |
| 2004/0110717 A1 | 6/2004 | Carroll et al. |
| 2004/0167140 A1 | 8/2004 | Schinazi et al. |
| 2004/0191824 A1 | 9/2004 | Dempcy et al. |
| 2004/0214844 A1 | 10/2004 | Otto et al. |
| 2004/0224917 A1 | 11/2004 | Dahl et al. |
| 2004/0229839 A1 | 11/2004 | Babu et al. |
| 2004/0229840 A1 | 11/2004 | Bhat et al. |
| 2004/0248892 A1 | 12/2004 | Wang |
| 2004/0254141 A1 | 12/2004 | Schinazi et al. |
| 2004/0259934 A1 | 12/2004 | Olsen et al. |
| 2004/0265969 A1 | 12/2004 | Li et al. |
| 2004/0266996 A1 | 12/2004 | Rabi |
| 2005/0009737 A1 | 1/2005 | Clark |
| 2005/0020825 A1 | 1/2005 | Storer et al. |
| 2005/0026853 A1 | 2/2005 | Mekouar et al. |
| 2005/0031588 A1 | 2/2005 | Sommadossi et al. |
| 2005/0048116 A1 | 3/2005 | Straub et al. |
| 2005/0058710 A1 | 3/2005 | Straub et al. |
| 2005/0075309 A1 | 4/2005 | Storer et al. |
| 2005/0080034 A1 | 4/2005 | Standring et al. |
| 2005/0090660 A1 | 4/2005 | Watanabe et al. |
| 2005/0124532 A1 | 6/2005 | Sommadossi et al. |
| 2005/0130931 A1 | 6/2005 | Boyer et al. |
| 2005/0137161 A1 | 6/2005 | Sommadossi et al. |
| 2005/0142532 A1 | 6/2005 | Poo et al. |
| 2005/0148534 A1 | 7/2005 | Castellino et al. |
| 2005/0154056 A1 | 7/2005 | Yang et al. |
| 2005/0164960 A1 | 7/2005 | Olsen et al. |
| 2005/0190931 A1 | 9/2005 | Hsieh |
| 2005/0215513 A1 | 9/2005 | Boojamra et al. |
| 2005/0227947 A1 | 10/2005 | Chen et al. |
| 2005/0261237 A1 | 11/2005 | Boojamra et al. |
| 2005/0267018 A1 | 12/2005 | Blatt et al. |
| 2006/0003951 A1 | 1/2006 | Mekouar et al. |
| 2006/0014943 A1 | 1/2006 | Dempcy et al. |
| 2006/0034937 A1 | 2/2006 | Patel |
| 2006/0035866 A1 | 2/2006 | Cannizzaro et al. |
| 2006/0040890 A1 | 2/2006 | Martin et al. |
| 2006/0040927 A1 | 2/2006 | Blake et al. |
| 2006/0040944 A1 | 2/2006 | Gosselin et al. |
| 2006/0057196 A1 | 3/2006 | Hussain et al. |
| 2006/0079478 A1 | 4/2006 | Boojamra et al. |
| 2006/0110727 A9 | 5/2006 | McGall et al. |
| 2006/0122146 A1 | 6/2006 | Chun et al. |
| 2006/0122154 A1 | 6/2006 | Olsen et al. |
| 2006/0142238 A1 | 6/2006 | McGuigan |
| 2006/0144502 A1 | 7/2006 | Weder |
| 2006/0165655 A1 | 7/2006 | Babu et al. |
| 2006/0166964 A1 | 7/2006 | Hudyma et al. |
| 2006/0188570 A1 | 8/2006 | Batra et al. |
| 2006/0194749 A1 | 8/2006 | Keicher et al. |
| 2006/0199783 A1 | 9/2006 | Wang et al. |
| 2006/0241064 A1 | 10/2006 | Roberts et al. |
| 2006/0276511 A1 | 12/2006 | Serrano-Wu et al. |
| 2006/0293306 A1 | 12/2006 | Beaulieu et al. |
| 2007/0015905 A1 | 1/2007 | LaColla et al. |
| 2007/0026073 A1 | 2/2007 | Doney |
| 2007/0037735 A1 | 2/2007 | Gosselin et al. |
| 2007/0037773 A1 | 2/2007 | Sommadossi et al. |
| 2007/0042939 A1 | 2/2007 | LaColla et al. |
| 2007/0042988 A1 | 2/2007 | Klumpp et al. |
| 2007/0042990 A1 | 2/2007 | Gosselin et al. |
| 2007/0049754 A1 | 3/2007 | Boojamra et al. |
| 2007/0059360 A1 | 3/2007 | Jaiswal et al. |
| 2007/0060498 A1 | 3/2007 | Gosselin et al. |
| 2007/0060541 A1 | 3/2007 | Gosselin et al. |
| 2007/0077295 A1 | 4/2007 | Dahl et al. |
| 2007/0087960 A1 | 4/2007 | Storer et al. |
| 2007/0099902 A1 | 5/2007 | Dahl et al. |
| 2007/0197463 A1 | 8/2007 | Chun et al. |
| 2007/0225249 A1 | 9/2007 | Shi |
| 2007/0265222 A1 | 11/2007 | MacCoss et al. |
| 2007/0275912 A1 | 11/2007 | Bhat et al. |
| 2007/0275947 A1 | 11/2007 | Bergstrom |
| 2008/0014228 A1 | 1/2008 | Darmuzey et al. |
| 2008/0070861 A1 | 3/2008 | Clark |
| 2008/0139802 A1 | 6/2008 | Axt et al. |
| 2008/0253995 A1 | 10/2008 | Clark |
| 2008/0261913 A1 | 10/2008 | Sommadossi et al. |
| 2008/0286230 A1 | 11/2008 | Sommadossi et al. |
| 2008/0300200 A1 | 12/2008 | Babu et al. |
| 2009/0004135 A1 | 1/2009 | Clark |
| 2009/0036666 A1 | 2/2009 | Clark |
| 2009/0137521 A1 | 5/2009 | Hamilton et al. |
| 2009/0169504 A1 | 7/2009 | Sommadossi et al. |
| 2009/0176732 A1 | 7/2009 | Beigelman et al. |
| 2009/0233879 A1 | 9/2009 | Reddy et al. |
| 2009/0280084 A1 | 11/2009 | Schinazi et al. |
| 2009/0306007 A1 | 12/2009 | Wagner |
| 2009/0317361 A1 | 12/2009 | Cho et al. |
| 2010/0016251 A1 | 1/2010 | Sofia et al. |
| 2010/0016252 A1 | 1/2010 | Keana et al. |

(56) References Cited

U.S. PATENT DOCUMENTS

| | | |
|---|---|---|
| 2010/0021425 A1 | 1/2010 | Butler et al. |
| 2010/0022468 A1 | 1/2010 | Meppen et al. |
| 2010/0029008 A1 | 2/2010 | Stutz et al. |
| 2010/0035835 A1 | 2/2010 | Narjes et al. |
| 2010/0048917 A1 | 2/2010 | Wang et al. |
| 2010/0056770 A1 | 3/2010 | Axt et al. |
| 2010/0081628 A1 | 4/2010 | Du et al. |
| 2010/0137576 A1 | 6/2010 | Stec et al. |
| 2010/0152128 A1 | 6/2010 | Attenni et al. |
| 2010/0173863 A1 | 7/2010 | Schinazi et al. |
| 2010/0227801 A1 | 9/2010 | Hopkins |
| 2010/0234316 A1 | 9/2010 | MacCoss et al. |
| 2010/0234584 A1 | 9/2010 | Chang |
| 2010/0256098 A1 | 10/2010 | Appella et al. |
| 2010/0279973 A1 | 11/2010 | Chun et al. |
| 2010/0286083 A1 | 11/2010 | Bao et al. |
| 2010/0298257 A1 | 11/2010 | Ross et al. |
| 2010/0316594 A1 | 12/2010 | Sommadossi et al. |
| 2011/0015146 A1 | 1/2011 | Sofia et al. |
| 2011/0038833 A1 | 2/2011 | Clark |
| 2011/0070194 A1 | 3/2011 | Cho et al. |
| 2011/0124592 A1 | 5/2011 | McGuigan et al. |
| 2011/0245484 A1 | 10/2011 | Ross et al. |
| 2011/0251152 A1 | 10/2011 | Ross et al. |
| 2011/0257121 A1 | 10/2011 | Chang et al. |
| 2011/0257122 A1 | 10/2011 | Sofia et al. |
| 2011/0286962 A1 | 11/2011 | Sommadossi et al. |
| 2011/0293563 A1 | 12/2011 | Butler et al. |
| 2012/0107278 A1 | 5/2012 | Berrey et al. |
| 2012/0254824 A1 | 10/2012 | Bansod |
| 2013/0137654 A1 | 5/2013 | Ross et al. |
| 2013/0165401 A1 | 6/2013 | Ross et al. |
| 2013/0165644 A1 | 6/2013 | Ross et al. |

FOREIGN PATENT DOCUMENTS

| | | |
|---|---|---|
| BE | 898506 A1 | 4/1984 |
| CA | 956939 A1 | 10/1974 |
| CA | 995608 | 8/1976 |
| CN | 101108870 A | 1/2008 |
| DE | 2426304 A1 | 1/1975 |
| DE | 2510866 A1 | 10/1975 |
| DE | 2517596 A1 | 10/1975 |
| DE | 2539963 A1 | 3/1976 |
| DE | 2835661 A1 | 3/1979 |
| DE | 19914474 A1 | 10/1999 |
| EP | 0014853 A1 | 9/1980 |
| EP | 0062503 A1 | 10/1982 |
| EP | 0107486 A1 | 5/1984 |
| EP | 0173059 A2 | 3/1986 |
| EP | 0180276 A1 | 5/1986 |
| EP | 0184162 A2 | 6/1986 |
| EP | 0206459 A2 | 12/1986 |
| EP | 0206497 A2 | 12/1986 |
| EP | 0219829 A2 | 4/1987 |
| EP | 0242851 A1 | 10/1987 |
| EP | 0253738 A1 | 1/1988 |
| EP | 0321122 A2 | 6/1989 |
| EP | 0349242 A2 | 1/1990 |
| EP | 0350287 A2 | 1/1990 |
| EP | 0432695 A2 | 6/1991 |
| EP | 0495432 A1 | 7/1992 |
| EP | 0503537 A1 | 9/1992 |
| EP | 0524579 A1 | 1/1993 |
| EP | 0737686 A1 | 4/1995 |
| EP | 1828217 A2 | 9/2007 |
| EP | 1881001 A1 | 1/2008 |
| EP | 2097430 A1 | 9/2009 |
| EP | 2124555 A2 | 12/2009 |
| EP | 2207786 B1 | 3/2012 |
| FR | 2707988 A1 | 1/1995 |
| GB | 768821 A | 2/1957 |
| GB | 985598 A | 3/1965 |
| GB | 1209654 A | 10/1970 |
| GB | 1449708 | 9/1976 |
| GB | 1449708 A | 9/1976 |
| GB | 2004293 A | 3/1979 |
| GB | 2133005 A | 7/1984 |
| GB | 2136425 A | 9/1984 |
| JP | 47016483 U | 10/1972 |
| JP | 58219196 A | 12/1983 |
| JP | 60-19790 A | 1/1985 |
| JP | 5-238939 A | 9/1993 |
| SU | 508076 A1 | 10/1976 |
| WO | 88/07045 A1 | 9/1988 |
| WO | 89/02733 A1 | 4/1989 |
| WO | 90/00555 A1 | 1/1990 |
| WO | 91/16920 A1 | 11/1991 |
| WO | 91/17159 A1 | 11/1991 |
| WO | 91/17748 A1 | 11/1991 |
| WO | 91/18914 A1 | 12/1991 |
| WO | 91/19721 A1 | 12/1991 |
| WO | 92/10497 A1 | 6/1992 |
| WO | 92/14743 A2 | 9/1992 |
| WO | 93/00910 A1 | 1/1993 |
| WO | 94/09010 A1 | 4/1994 |
| WO | 94/26273 A1 | 11/1994 |
| WO | 95/09843 A1 | 4/1995 |
| WO | 95/13090 A1 | 5/1995 |
| WO | 95/16679 A1 | 6/1995 |
| WO | 95/24185 A1 | 9/1995 |
| WO | 95/30670 A2 | 11/1995 |
| WO | 95/31977 | 11/1995 |
| WO | 95/15132 A1 | 5/1996 |
| WO | 96/32403 A2 | 10/1996 |
| WO | 97/12033 A1 | 4/1997 |
| WO | 97/36554 A1 | 10/1997 |
| WO | 97/42949 A1 | 11/1997 |
| WO | 98/09964 A1 | 3/1998 |
| WO | 98/13344 A1 | 4/1998 |
| WO | 98/16184 A2 | 4/1998 |
| WO | 98/17679 A1 | 4/1998 |
| WO | 98/22496 A2 | 5/1998 |
| WO | 98/54185 A1 | 12/1998 |
| WO | 99/07734 A2 | 2/1999 |
| WO | 99/15194 A1 | 4/1999 |
| WO | 99/32139 A1 | 7/1999 |
| WO | 99/32140 A1 | 7/1999 |
| WO | 99/43691 A1 | 9/1999 |
| WO | 99/59621 A1 | 11/1999 |
| WO | 99/64016 A1 | 11/1999 |
| WO | 00/06529 A1 | 2/2000 |
| WO | 00/09531 A2 | 2/2000 |
| WO | 00/24355 A1 | 5/2000 |
| WO | 00/32153 A1 | 6/2000 |
| WO | 01/09121 A2 | 2/2001 |
| WO | 01/32153 A2 | 5/2001 |
| WO | 01/60315 A2 | 8/2001 |
| WO | 01/79246 A2 | 10/2001 |
| WO | 01/81359 A1 | 11/2001 |
| WO | 01/90121 A2 | 11/2001 |
| WO | 01/91737 A2 | 12/2001 |
| WO | 01/92282 A2 | 12/2001 |
| WO | 01/96353 A2 | 12/2001 |
| WO | 02/08187 A1 | 1/2002 |
| WO | 02/08198 A2 | 1/2002 |
| WO | 02/08251 A2 | 1/2002 |
| WO | 02/08256 A2 | 1/2002 |
| WO | 02/18404 A2 | 3/2002 |
| WO | 02/32414 A2 | 4/2002 |
| WO | 02/32920 A2 | 4/2002 |
| WO | 02/42172 A1 | 5/2002 |
| WO | 02/48116 A2 | 6/2002 |
| WO | 02/48157 A2 | 6/2002 |
| WO | 02/48165 A2 | 6/2002 |
| WO | 02/48172 A2 | 6/2002 |
| WO | 02/49165 A1 | 6/2002 |
| WO | 02/057287 A2 | 7/2002 |
| WO | 02/057425 A2 | 7/2002 |
| WO | 02/060926 A2 | 8/2002 |
| WO | 02/100415 A2 | 12/2002 |
| WO | 03/000713 A1 | 1/2003 |
| WO | 03/006490 A1 | 1/2003 |

(56) References Cited

FOREIGN PATENT DOCUMENTS

| | | |
|---|---|---|
| WO | 03/010141 A2 | 2/2003 |
| WO | 03/011877 A2 | 2/2003 |
| WO | 03/024461 A1 | 3/2003 |
| WO | 03/026589 A2 | 4/2003 |
| WO | 03/037895 A1 | 5/2003 |
| WO | 03/051899 A1 | 6/2003 |
| WO | 03/053989 A1 | 7/2003 |
| WO | 03/061576 A2 | 7/2003 |
| WO | 03/062256 A1 | 7/2003 |
| WO | 03/064456 A1 | 8/2003 |
| WO | 03/066885 A2 | 8/2003 |
| WO | 03/068244 A1 | 8/2003 |
| WO | 03/101993 A1 | 12/2003 |
| WO | 03/104250 A1 | 12/2003 |
| WO | 03/105770 A2 | 12/2003 |
| WO | 03/106477 A1 | 12/2003 |
| WO | 2004/000858 A2 | 12/2003 |
| WO | 2004/002422 A2 | 1/2004 |
| WO | 2004/002940 A1 | 1/2004 |
| WO | 2004/002944 A1 | 1/2004 |
| WO | 2004/002977 A1 | 1/2004 |
| WO | 2004/002999 A2 | 1/2004 |
| WO | 2004/003000 A2 | 1/2004 |
| WO | 2004/003138 A2 | 1/2004 |
| WO | 2004/007512 A2 | 1/2004 |
| WO | 2004/009020 A2 | 1/2004 |
| WO | 2004/009610 A2 | 1/2004 |
| WO | 2004/011478 A2 | 2/2004 |
| WO | 2004/014313 A2 | 2/2004 |
| WO | 2004/014852 A2 | 2/2004 |
| WO | 2004/035571 A1 | 4/2004 |
| WO | 2004/041201 A2 | 5/2004 |
| WO | 2004/046331 A2 | 6/2004 |
| WO | 2004/058792 A1 | 7/2004 |
| WO | 2004/065367 A1 | 8/2004 |
| WO | 2004/069856 A1 | 8/2004 |
| WO | 2004/080466 A1 | 9/2004 |
| WO | 2004/094452 A2 | 11/2004 |
| WO | 2004/096210 A1 | 11/2004 |
| WO | 2004/096234 A2 | 11/2004 |
| WO | 2004/096235 A2 | 11/2004 |
| WO | 2004/096286 A2 | 11/2004 |
| WO | 2004/106356 A1 | 12/2004 |
| WO | 2005/000864 A1 | 1/2005 |
| WO | 2005/002626 A2 | 1/2005 |
| WO | 2005/003147 A2 | 1/2005 |
| WO | 2005/007810 A2 | 1/2005 |
| WO | 2005/008877 A1 | 1/2005 |
| WO | 2005/009418 A2 | 2/2005 |
| WO | 2005/012327 A2 | 2/2005 |
| WO | 2005/020884 A2 | 3/2005 |
| WO | 2005/021568 A2 | 3/2005 |
| WO | 2005/028502 A1 | 3/2005 |
| WO | 2005/037214 A2 | 4/2005 |
| WO | 2005/067900 A2 | 7/2005 |
| WO | 2005/072361 A2 | 8/2005 |
| WO | 2005/082144 A2 | 9/2005 |
| WO | 2005/087788 A2 | 9/2005 |
| WO | 2005/095403 A2 | 10/2005 |
| WO | 2005/103045 A1 | 11/2005 |
| WO | 2005/123087 A2 | 12/2005 |
| WO | 2006/000922 A2 | 1/2006 |
| WO | 2006/012078 A2 | 2/2006 |
| WO | 2006/012440 A2 | 2/2006 |
| WO | 2006/020082 A1 | 2/2006 |
| WO | 2006/029081 A2 | 3/2006 |
| WO | 2006/031725 A2 | 3/2006 |
| WO | 2006/035061 A1 | 4/2006 |
| WO | 2006/037028 A2 | 4/2006 |
| WO | 2006/050161 A2 | 5/2006 |
| WO | 2006/061576 A2 | 6/2006 |
| WO | 2006/063149 A1 | 6/2006 |
| WO | 2006/063717 A2 | 6/2006 |
| WO | 2006/065335 A2 | 6/2006 |
| WO | 2006/065590 A2 | 6/2006 |
| WO | 2006/093801 A1 | 9/2006 |
| WO | 2006/100310 A1 | 9/2006 |
| WO | 2006/100439 A1 | 9/2006 |
| WO | 2006/116557 A1 | 11/2006 |
| WO | 2006/120251 A1 | 11/2006 |
| WO | 2006/120252 A2 | 11/2006 |
| WO | 2006/121820 | 11/2006 |
| WO | 2006/121820 A1 | 11/2006 |
| WO | 2007/002191 A2 | 1/2007 |
| WO | 2007/002602 A2 | 1/2007 |
| WO | 2007/014920 A1 | 2/2007 |
| WO | 2007/014921 A1 | 2/2007 |
| WO | 2007/014922 A1 | 2/2007 |
| WO | 2007/014925 A1 | 2/2007 |
| WO | 2007/014926 A1 | 2/2007 |
| WO | 2007/015824 A2 | 2/2007 |
| WO | 2007/020193 A2 | 2/2007 |
| WO | 2007/027248 A2 | 3/2007 |
| WO | 2007/038507 A2 | 4/2007 |
| WO | 2007/039142 A1 | 4/2007 |
| WO | 2007/039145 A1 | 4/2007 |
| WO | 2007/065829 A1 | 6/2007 |
| WO | 2007/069923 A1 | 6/2007 |
| WO | 2007/070556 A2 | 6/2007 |
| WO | 2007/076034 A2 | 7/2007 |
| WO | 2007/088148 A1 | 8/2007 |
| WO | 2007/092000 A1 | 8/2007 |
| WO | 2007/093901 A1 | 8/2007 |
| WO | 2007/095269 A2 | 8/2007 |
| WO | 2008/010921 A2 | 1/2008 |
| WO | 2008/024843 A2 | 2/2008 |
| WO | 2008/045419 A1 | 4/2008 |
| WO | 2008/048128 A1 | 4/2008 |
| WO | 2008/062206 A2 | 5/2008 |
| WO | 2008/079206 A1 | 7/2008 |
| WO | 2008/082601 A2 | 7/2008 |
| WO | 2008/085508 A2 | 7/2008 |
| WO | 2008/121634 A2 | 10/2008 |
| WO | 2008/142055 A2 | 11/2008 |
| WO | 2009/009951 A1 | 1/2009 |
| WO | 2009/029844 A1 | 3/2009 |
| WO | 2009/052287 A1 | 4/2009 |
| WO | 2009/067409 A1 | 5/2009 |
| WO | 00/37110 A2 | 6/2009 |
| WO | 2009/115893 A2 | 9/2009 |
| WO | 2009/120878 A2 | 10/2009 |
| WO | 2009/129120 A2 | 10/2009 |
| WO | 2009/132123 A1 | 10/2009 |
| WO | 2009/152095 A2 | 12/2009 |
| WO | 2010/042834 A1 | 4/2010 |
| WO | 2010/075517 A2 | 7/2010 |
| WO | 2010/075549 A2 | 7/2010 |
| WO | 2010/075554 A2 | 7/2010 |
| WO | 2010/080878 A1 | 7/2010 |
| WO | 2010/081082 A2 | 7/2010 |
| WO | 2010/133569 A1 | 11/2010 |
| WO | 2010/135569 A1 | 11/2010 |
| WO | 2011/035231 A1 | 3/2011 |
| WO | 2011/123668 A2 | 10/2011 |
| ZA | 66/7585 | 12/1965 |
| ZA | 68/2378 | 4/1967 |

OTHER PUBLICATIONS

Haleblian, J.K., "Characterization of Habits and Crystalline Modification of Solids and Their Pharmaceutical Applications," Journal of Pharmaceutical Sciences, vol. 64, No. 8, pp. 1269-1288 (1975).

Kryuchkov, A.A., et al., "Influence of Solvent on the Strength of Cyclic Oxygen-Containing Phosphorus Acids," Bulletin of the Academy of Sciences of the USSR, vol. 36, No. 6, Part 1, pp. 1145-1148 (1987).

Kotra, L.P. et al., "Structure-Activity Relationships of 2'-Deoxy-2'-2'-difluoro-L-erythro-pentofuranosyl Nucleosides," Journal of Medicinal Chemistry, vol. 40, No. 22, pp. 3635-3644 (1997).

Li, N. S. et al., "Synthesis of the Phosphoramidite Derivative of 2'-Deoxy-2'-C-B-methylcytidine," Journal of Organic Chemistry, vol. 68, No. 17, pp. 6799-6802 (2003).

Freed, J.J. et al., "Evidence for Acyloxymethyl Esters of Pyrimidine 5'-Deoxyribonucleotides as Extracellular Sources of Active

(56) References Cited

OTHER PUBLICATIONS

5'-Deoxyribonucleotides in Cultured Cells," Biochemical Pharmacology, vol. 38, No. 19, pp. 3193-3198 (1989).
Kucera, L.S. et al., "Novel Membrane-Interactive Ether Lipid Analogs that Inhibit Infectious HIV-1 Production and Induce Defective Virus Formation," AIDS Research and Human Retroviruses, vol. 6, No. 4, pp. 491-501 (1990).
Khamnei, S. et al., "Neighboring Group Catalysis in the Design of Nucleotide Prodrugs," Journal of Medicinal Chemistry, vol. 39, No. 20, pp. 4109-4115 (1996).
Hostetler, K.Y. et al., "Greatly Enhanced Inhibition of Human Immunodeficiency Virus Type 1 Replication in CEM and HT4-6C Cells by 3'-Deoxythymidine Diphosphate Dimyristoylglycerol, a Lipid Prodrug of 3'-Deoxythymidine," Antimicrobial Agents and Chemotherapy, vol. 36, No. 9, pp. 2025-2029 (1992).
Jones, R.J. et al., "Minireview: Nucleotide Prodrugs," Antiviral Research, vol. 27, pp. 1-17 (1995).
Hertel, L.W. et al., "Synthesis of 2-Deoxy-2,2-difluoro-D-ribose and 2-Deoxy-2,2-difluoro-D-ribofuranosyl Nucleosides," Journal of Organic Chemistry, vol. 53, No. 11, pp. 2406-2409 (1988).
Neidlein, R. et al., "Mild Preparation of 1-Benzyloxyiminoalkylphosphonic Dichlorides: Application to the Synthesis of Cyclic Phosphonic Diesters and Cyclic Monoester Amides," Heterocycles, vol. 35, No. 2, pp. 1185-1203 (1993).
Starrett, Jr., J.E. et al., "Synthesis, Oral Bioavailability Determination, and in Vitro Evaluation of Prodrugs of the Antiviral Agent 9-[2-(Phosphonomethoxy)ethyl]adenine (PMEA)," Journal of Medicinal Chemistry, vol. 37, No. 12, pp. 1857-1864 (1994).
Meier, C. et al., "Cyclic Saligenyl Phosphotriesters of 2',3'-Dideoxy-2',3'-didehydrothymidine (d4T)—A New Pro-Nucleotide Approach," Bioorganic & Medicinal Chemistry Letters, vol. 7, No. 2, pp. 99-104 (1997).
Piantadosi, C. et al., "Synthesis and Evaluation of Novel Ether Lipid Nucleoside Conjugates for Anti-HIV-1 Activity," Journal of Medicinal Chemistry, vol. 34, No. 4, pp. 1408-1414 (1991).
Shih, Y.E. et al., "Preparation and Structures of 2-Dimethylamino-4-phenyl-1,3,2-dioxaphosphorinane-2-oxides," Bull. Inst. Chem. Academia Sinica, No. 41, pp. 9-16 (1994).
Mitchell, A.G. et al., "Bioreversible Protection for the Phospho Group: Bioactivation of the Di(4-acyloxybenzyl) and Mono(4-acyloxybenzyl) Phosphoesters of Methylphosphonate and Phosphonoacetate," Journal of the Chemical Society, Perkin Transactions, pp. 2345-2353 (1992).
Otto, M.J., "Evaluation of nucleoside analogs in the hepatitis C virus replicon system," Framing the Knowledge of Therapeutics for Viral Hepatitis, Schmazi and Schiff, eds., pp. 247-261 (2006).
Nifantyev, E.E. et al., "Synthesis and Structure of Some Stable Phospholane-Phospholanes," Phosphorus, Sulfur, and Silicon, vol. 113, pp. 1-13 (1996).
Olsen, D.B. et al., "2'-Modified Nucleoside Analogs as Inhibitors of Hepatitis C RNA Replication," Program and Abstracts of Sixteenth Intl Conf. on Antiviral Research, Abstract No. 121, vol. 57, No. 3, p. A76 (2003).
Stuyver, L.J. et al., "Ribonucleoside Analogue That Blocks Replication of Bovine Viral Diarrhea and Hepatitis C Viruses in Culture," Antimicrobial Agents and Chemotherapy, vol. 47, No. 1, pp. 244-254 (2003).
Barnett, C.J. et al., "Structure-Activity Relationships of Dimeric Catharanthus Alkaloids. 1. Deacetylvinblastine Amide (Vindesine) Sulfate," Journal of Medicinal Chemistry, vol. 21, No. 1, pp. 88-96 (1978).
Andrews, R.C. et al., "Asymmetric Total Synthesis of (−)-Podophyllotoxin," J. Am. Chem. Soc., vol. 110, No. 23, pp. 7854-7858 (1988).
Arcamone, F. et al., "Adriamycin, 14-Hydroxydaunomycin, a New Antitumor Antobiotic from *S. peucetius* var. caesius," Biotechnology and Bioengineering, vol. XI, pp. 1101-1110 (1969).
Arcamone, F. et al., "Synthesis and Antitumor Properties of New Glycosides of Daunomycinone and Adriamycinone," Journal of Medicinal Chemistry, vol. 18, No. 7, pp. 703-707 (1975).
Arcamone, F. et al., "Synthesis and antitumor activity of new daunorubicin and adriamycin analogues," Experientia, vol. 34, No. 10, pp. 1255-1257 (1978).
Arnold, A.M. et al., "Etoposide: A New Anti-Cancer Agent," The Lancet, vol. 2, pp. 912-915 (1981).
Ashton, W.T. et al., "Activation by Thymidine Kinase and Potent Antiherpetic Activity of 2'-Nor-2'-Deoxyguanosine (2'NDG)," Biochemical and Biophysical Research Communications, vol. 108, No. 4, pp. 1716-1721 (1982).
Bauta, W.E. et al., "A New Process for Antineoplastic Agent Clofarabine," Organic Process Research & Development, vol. 8, No. 6, pp. 889-896 (2004).
Baker, D.C. et al., "Studies Related to the Total Synthesis of Pentostatin. Approaches to the Synthesis of (8R)-3,6,7,8-Tetrahydroimidazo-[4,5-d][1,3]diazepin-8-ol and N-3 Alkyl Congeners (1a)," J. Heterocyclic Chem., vol. 20, pp. 629-633 (1983).
Balzarini, J. et al., "Mechanism of anti-HIV action of masked alaninyl d4T-MP derivatives," Proc. Natl. Acad. Sci., vol. 93, pp. 7295-7299 (Jul. 1996).
Brands, K.M.J. et al., "Efficient Synthesis of NK1 Receptor Antagonist Aprepitant Using a Crystallization-Induced Diastereoselective Transformation," J. Am. Chem. Soc., vol. 125, pp. 2129-2135 (2003).
Bush, E.J. et al., "Asymmetric Total Synthesis of (−)-Podophyllotoxin," J. Chem. Soc., Chem. Commun., pp. 1200-1201 (1993).
Brox, L.W. et al., "Studies on the Growth Inhibition and Metabolism of 2'-Deoxy-2'-fluorocytidine in Cultured Human Lymphoblasts," Cancer Research, vol. 34, pp. 1838-1842 (1974).
Yoshioka, T. et al., "Studies on Hindered Phenols and Analogues. 1. Hypolipidemic and Hypoglycemic Agents with Ability to Inhibit Lipid Peroxidation," J. Med. Chem., vol. 32, No. 2, pp. 421-428 (1989).
Zee-Cheng, R.K.Y. et al., "Antineoplastic Agents. Structure-Activity Relationship Study of Bis(substituted aminoalkylamino)anthraquinones," J. Med. Chem., vol. 21, No. 3, pp. 291-294 (1978).
Sorbera, L.A. et al., "SDZ-RAD," Drugs of the Future, vol. 24, No. 1, pp. 22-29 (1999).
Oxford, A.E. et al., "CXCIX. Studies in the Biochemistry of Micro-Organisms," BioChem. J., vol. 27, pp. 1473-1478 (1933).
Clutterbuck, P.W. et al., "LXXXVI. Studies in the Biochemistry of Micro-Organisms," Biochem. J., vol. 27, pp. 654-667 (1933).
Clutterbuck, P.W. et al., "CLXXI. Studies in the Biochemistry of Micro-Organisms," Biochem. J., vol. 26, pp. 1441-1458 (1932).
McGuigan, C. et al., "Phosphoramidate ProTides of 2'-C-Methylguanosine as Highly Potent Inhibitors of Hepatitis C Virus. Study of Their in Vitro and in Vivo Properties," J. Med. Chem., vol. 53, No. 13, pp. 4949-4957 (2010).
Mizuno, K. et al., "Studies on Bredinin. I Isolation, Characterization and Biological Properties," The Journal of Antibiotics, vol. 27, No. 10, pp. 775-782 (1974).
Fahy, J. et al., "Vinca Alkaloids in Superacidic Media: A Method for Creating a New Family of Antitumor Derivatives," J. Am. Chem. Soc., vol. 119, No. 36, pp. 8576-8577 (1997).
Matsumoto, H. et al., "A Convenient Synthesis of 9-(2-Hydroxyethoxymethyl)guanine (Acyclovir) and Related Compounds," Chem. Pharm. Bull., vol. 36, No. 3, pp. 1153-1157 (1988).
Gauze, G.F. et al., "Production of Antitumor Antibiotic Carminomycin by *Actinomadura carminata* Sp. Nov.," pp. 675-678 (1973).
Moncrief, J.W. et al., "Structures of Leurocristine (Vincristine) and Vincaleukoblastine. X-Ray Analysis of Leurocristine Methiodide," J. Am. Chem. Soc., vol. 87, No. 21, pp. 4963-4964 (1965).
Cahard, D. et al., "Aryloxy Phosphoramidate Triesters as Pro-Tides," Mini-Reviews in Medicinal Chemistry, vol. 4, No. 4, pp. 371-381 (2004).
Knaggs, M.H. et al., "A QSAR Study Investigating the Effect of L-Alanine Ester Variation on the Anti-HIV Activity of Some Phosphoramidate Derivatives of d4T," Bioorganic & Medicinal Chemistry Letters, vol. 10, No. 18, pp. 2075-2078 (2000).
Zon, G., Ph.D., "Cyclophosphamide Analogues," Progress in Medicinal Chemistry, vol. 19, pp. 205-246 (1982).
International Preliminary Report on Patentability issued in PCT/US2009/069420, mailed May 18, 2012 (2 pages).

(56) References Cited

OTHER PUBLICATIONS

Cahard, D., et al., "Aryloxy Phosphoramidate Triesters as Pro-Tides," Mini-reviews in Medicinal Chemistry, vol. 4, No. 4, pp. 371-381 (2004).
Murakami, E., et al., "The Mechanism of Action of B-D-2'-Deoxy-2'-Fluoro-2'-C-Methylcytidine Involves a Second Metabolic Pathway Leading to B-D-2'-Deoxy-2'-Fluoro-2'-C-Methyluridine 5'-Triphosphate, a Potent Inhibitor of the Hepatitis C Virus RNA-Dependant RNA Polymerase," Antimicrobial Agents and Chemotherapy, vol. 52, No. 2, pp. 458-464 (2008).
Hecker et al., "Prodrugs of Phosphates and Phosphonates," J. Med. Chem., vol. 51, pp. 2328-234 (2008).
Chou et al., "Evidence that Human Histidine Triad Nucleotide Binding Protein 3 (Hint3) is a Distinct Branch of the Histidine Triad (HIT) Superfamily," J. Mol. Biol., vol. 373, pp. 978-989 (2007).
Chou et al., "Phosphoramidate Pronucleotides: A Comparison of the Phosphoramidase Substrate Specificity of Human and *Escherichia coli* Histidine Triad Nucleotide Binding Proteins," Mol. Pharm., vol. 4, pp. 208-217 (2007).
Chou et al., "31P NMR and Genetic Analysis Establish hinT as the Only *Escherchia coli* Purine Nucleoside Phosphoramidase and as Essential for Growth under High Salt Conditions," J. Biol. Chem., vol. 280, pp. 15356-15361 (2005).
Aquaro et al., "Activities of Masked 2'3'-Dideoxynucleoside Monophosphate Derivatives against Human Immunodeficiency Virus in Resting Macrophages," Antimicrobial Agents and Chemotherapy, vol. 1, pp. 173-177 (2000).
Chapman et al., "Practical Synthesis, Separation, and Stereochemical Assignment of the PMPA Pro-Drug GS-7340," Nucleotides, Nucleosides and Nucleic Acids, vol. 20(4-7), pp. 621-628 (2001).
Chapman et al., "Purification of PMPA Amidate Prodrugs by SMB Chromatography of the Diastereomerically Pure GS-7340," Nucleotides, Nucleosides and Nucleic Acids, vol. 20(4-7), pp. 1085-1090 (2001).
Clark et al., "Design, Synthesis, and Antiviral Activity of 2'-Deoxy-2'-fluoro-2'-C-methylcytidine, a Potent Inhibitor of Hepatitis C Virus Replication," J. Med. Chem., vol. 48, No. 17, pp. 5504-5508 (2005).
Eisenberg et al., "Metabolism of GS-7340, A Novel Phenyl Monophosphoramidate Intracellular Prodrug of PMPA, In Blood," Nucleosides, Nucleotides & Nucleic Acids, vol. 20(4-7), pp. 1091-1098 (2001).
Howes et al., "The Regiospecific One-Pot Phosphorylation of Either the 5' or 2'-Hydroxyl in 3'-Deoxycytidines Without Protection: Critical Role of the Base," Nucleosides, Nucleotides and Nucleic Acids, vol. 22. No. 5, pp. 687-689 (2003).
Lee et al., "Selective Intracellular Activation of a Novel Prodrug of the Human Immunodeficiency Virus Reverse Transcriptase Inhibitor Tenofovir Leads to Preferential Distribution and Accumulation in Lymphatic Tissue," Antimicrobial Agents and Chemotherapy, vol. 49, No. 5, pp. 1898-1906 (2005).
Ma et al., "Characterization of the Metabolic Activation of Hepatitis C Virus Nucleoside Inhibitor beta-D-2'-Deoxy-2'- fluoro-2'-C-methylcytidine (PSI-6130) and Identification of a Novel Active 5'-Triphosphate Species," J. Biol. Chem., vol. 282, No. 41, pp. 29812-29820 (2007).
McGuigan et al., "Synthesis, anti-human immunodeficiency virus activity and esterase lability of some novel carboxylic ester-modified phosphoramidate derivatives of stavudine (d4T)," Antiviral Chemistry and Chemotherapy, vol. 9, pp. 473-479 (1998).
Murakami et al., "Mechanism of Activation of beta-D-2'-Deoxy-2'-Fluoro-2'-C-Methylcytidine and Inhibition of Hepatitis C Virus NS5B RNA Polymerase," Antiviral Chemistry & Chemotherapy, vol. 51, No. 2, pp. 503-509 (2007).
Murakami et al., "The Mechanism of Action of beta-D-2'-Deoxy-2'-Fluoro-2'-C-Methylcytidine Involves a Second Metabolic Pathway Leading to beta-D-2'-Deoxy-2'-Fluoro-2'-C-Methyluridine 5'-Triphosphate, a Potent Inhibitor of the Hepatitis C Virus RNA-Dependent RNA Polymerase," Antimicrobial Agents and Chemotherapy, vol. 52, No. 2, pp. 458-464 (2008).

Perrone et al., "Application of the Phosphoramidate ProTide Approach to 4'-Azidouridine Confers Sub-micromolar Potency versus Hepatitis C Virus on an Inactive Nucleoside," J. Med. Chem., vol. 50, No. 8., pp. 1840-1849 (2007).
Ray et al., "Intracellular Metabolism of the Nucleotide Prodrug GS-9131, a Potent Anti-Human Immunodeficiency Virus Agent," Antimicrobial Agents and Chemotherapy, vol. 52, No. 2, pp. 648-654 (2008).
Stuyver et al., "Inhibition of the Subgenomic Hepatitis C Virus Replicon in Huh-7 Cells by 2'-Deoxy-2'-Fluorocytidine," Antiviral Chemistry & Chemotherapy, vol. 48, No. 2, pp. 651-654 (2004).
International Preliminary Report on Patentability issued in PCT/US2011/030762, mailed Oct. 2, 2012 (12 pages).
International Search Report and Written Opinion of the International Searching Authority issued in PCT/US2011/030762, mailed Mar. 2, 2012 (20 pages).
Stella, V.J., "Prodrugs as Therapeutics," Expert Opin. Ther. Patents, vol. 14, No. 3, pp. 277-280 (2004).
Wittine, K. et al., "The novel phosphoramidate derivatives of NSAID 3-hydroxypropylamides: Synthesis, cytostatic and antiviral activity evaluations," European J. Med. Chem., vol. 44, pp. 143-151 (2009).
Zhu, T. et al., "Design and synthesis of HCV agents with sequential triple inhibitory potentials," Bioorg. Med. Chem. Lett., vol. 20, pp. 5212-5216 (2010).
McGuigan, C. et al., "Design, synthesis and evaluation of a novel double pro-drug: INX-08189. A new clinical candidate for hepatitis C virus," Bioorg. Med. Chem. Lett., vol. 20, pp. 4850-4854 (2010).
Lehsten, D.M. et al., "An Improved Procedure for the Synthesis of Nucleoside Phosphoramidates," Org. Proc. Res. & Dev., vol. 6, pp. 819-822 (2002).
Asif, G. et al., "Pharmacokinetics of the Antiviral Agent B-D-2'-Deoxy-2'-Fluoro-2'-C-Methylcytidine in Rhesus Monkeys," Antimicrobial Agents and Chemotherapy, vol. 51, No. 8, pp. 2877-2882 (2007).
Battaglia, A.M. et al., "Combination Therapy with Interferon and Ribavirin in the Treatment of Chronic Hepatitis C Infection," The Annals of Pharmacotherapy, vol. 34, pp. 487-494 (2000).
Berenguer, M. et al., "Hepatitis C Virus in the Transplant Setting," Antiviral Therapy 3 (Supplement 3), pp. 126-136 (1997).
Chawla, G. et al., "Challenges in Polymorphism of Pharmaceuticals," CRIPS, vol. 5, No. 1, pp. 9-12 (2004).
Bhat, B. et al., "Synthesis and Pharmacokinetic Properties of Nucleoside Analogues as Possible Inhibitors of HCV RNA Replication," Antiviral Research, Abstract No. 120, vol. 57, No. 3, p. A75 (2003).
Chu, M. et al., "Structure of Sch 68631: A New Hepatitis C Virus Proteinase Inhibitor from *Streptomyces* sp.," Tetrahedron Letters, vol. 37, No. 40, pp. 7229-7232 (1996).
De Lombaert, S. et al., "N-Phosphonomethyl Dipeptides and Their Phosphonate Prodrugs, a New Generation of Neutral Endopeptidase (NEP, EC 3.4.24.11) Inhibitors," Journal of Medicinal Chemistry, vol. 37, No. 4, pp. 498-511 (1994).
Farquhar, D. et al., "Synthesis and Biological Evaluation of 9-[5'-(2-Oxo-1,3,2-oxazaphosphorinan-2-yl)-B-D-arabinosyl] adenine and 9[5'-(2-Oxo-1,3,2-dioxaphosphorinan-2-yl)-B-D-arabinosyl]adenine: Potential Neutral Precursors of 9-[B-D-Arabinofuranosyl]adenine 5'-Monophosphate," Journal of Medicinal Chemistry, vol. 28, No. 9, pp. 1358-1361 (1985).
Eldrup, A.B. et al., "Structure Activity Relationship of 2' Modified Nucleosides for Inhibition of Hepatitis C Virus," Antiviral Research, Abstract No. 119, vol. 57, No. 3, p. A75 (2003).
Edmundson, R.S. et al., "Cyclic Organophosphorus Compounds. Part 23. Configurational Assignments in the 4-Phenyl-1,3,2lambda-dioxaphosphorinane Series. X-Ray Molecular Structure of cis-2-Benzylamino-4-phenyl-1,3,2-dioxaphosphorinane 2-Oxide," Journal of Chemical Research (S), pp. 122-123 (1989).
Farquhar, D. et al., "Synthesis and Biological Evaluation of Neutral Derivatives of 5-Fluoro-2'-deoxyuridine 5'-Phosphate," Journal of Medicinal Chemistry, vol. 26, No. 8, pp. 1153-1158 (1983).
Chu, M. et al., "Isolation and Structure of SCH 351633: A Novel Hepatitis C Virus (HCV) NS3 Protease Inhibitor from the Fungus Penicillium Griseofulvum," Bioorganic & Medicinal Chemistry letters, vol. 9, pp. 1949-1952 (1999).

(56) References Cited

OTHER PUBLICATIONS

Eldrup, A.B. et al., "Structure-Activity Relationship of Purine Ribonucleosides for Inhibition of Hepatitis C Virus RNA-Dependent RNA Polymerase," Journal of Medicinal Chemistry, vol. 47, No. 9, pp. 2283-2295 (2004).
Davis, G.L., "Current Therapy for Chronic Hepatitis C," Gastroenterology, vol. 118, No. 2, pp. S104-S114 (2000).
Kahl, R., "The Liver," Toxicology, Marquardt et al. eds., Chapter 13, pp. 273-296 (1999).
Kryuchkov, A.A. et al., "Influence of Solvent on the Strength of Cyclic Oxygen-Containing Phosphorus Acids," Bull. of the Academy of Sciences of the USSR, Division of Chemical Science, vol. 36, No. 6, pp. 1145-1148 (1987).
Kingsbury, W.D. et al., "Synthesis of Water-Soluble (Aminoalkyl)Camptothecin Analogues: Inhibition of Topoisomerase I and Antitumor Activity," J. Med. Chem., vol. 34, No. 1, pp. 98-107 (1991).
Kino, T. et al., "FK-506, A Novel Immunosuppressant Isolated From a Streptomyces," The Journal of Antibiotics, vol. XL, No. 9, pp. 1249-1255 (1987).
Krapcho, A.P. et al., "6,9-Bis[(aminoalkyl)amino]Benzo[g]isoquinoline-5,10-diones. A Novel Class of Chromophore-Modified Antitumor Anthracene-9,10-diones: Synthesis and Antitumor Evaluations," J. Med. Chem., vol. 37, No. 6, pp. 828-837 (1994).
Kazimierczuk, Z. et al., "Synthesis of 2'-Deoxytubercidin, 2'-Deoxyadenosine, and Related 2'-Deoxynucleosides via a Novel Direct Stereospecific Sodium Salt Glycosylation Procedure," J. Am. Chem. Soc., vol. 106, No. 21, pp. 6379-6382 (1984).
Kaneko, T. et al., "Total Synthesis of (+) Podophyllotoxin," Tetrahedron Letters, vol. 28, No. 5, pp. 517-520 (1987).
Marumoto, R. et al., "One-Step Halogenation at the 2'-Position of Uridine, and Related Reactions of Cytidine and N4-Acetylcytidine," Chem. Pharm. Bull., vol. 22, No. 1, pp. 128-134 (1974).
Mehellou, Y. et al., "Aryloxy Phosphoramidate Triesters: a Technology for Delivering Monophosphorylated Nucleosides and Sugars into Cells," ChemMedChem, vol. 4, pp. 1779-1791 (2009).
Montgomery, J.A. et al., "An Improved Procedure for the Preparation of 9-B-D-Arabinofuranosyl 1-2-fluoroadenine," J. Heterocyclic Chem., vol. 16, pp. 157-160 (1979).
Montgomery, J.A. et al., "Nucleosides of 2-Fluoroadenine," J. Med. Chem., vol. 12, pp. 498-504 (1969).
Montgomery, J.A. et al., "Synthesis and Biologic Activity of 2'-Flouro-2-halo Derivatives of 9-B-D-Arabinofuranosyladenine," J. Med. Chem., vol. 35, No. 2, pp. 397-401 (1992).
Mangatal, L. et al., "Application of the Vicinal Oxyamination Reaction with Asymmetric Induction to the Hemisynthesis of Taxol and Analogues," Tetrahedron, vol. 45, No. 13, pp. 4177-4190 (1989).
Lin, T. et al., "Synthesis and Antiviral Activity of Various 3'-Azido,3'-Amino,2',3'-Unsaturated, and 2',3'-Dideoxy Analogues of Pyrimidine Deoxyribonucleosides against Retroviruses," J. Med. Chem., vol. 30, No. 2, pp. 440-444 (1987).
Murdock, K.C. et al., "Antitumor Agents. 1. 1,4-Bis[(aminoalkyl)amino]-9,10-anthracenediones," Journal of Medicinal Chemistry, vol. 22, No. 9, pp. 1024-1030 (1979).
McGuigan, C. et al., "Aryl Phosphoramidate Derivatives of d4T Have Improved Anti-HIV Efficacy in Tissue Culture and May Act by the Generation of a Novel Intracellular Metabolite," J. Med. Chem., vol. 39, No. 8, pp. 1748-1753 (1996).
Martin, J.C. et al., "9-[(1,3-Dihydroxy-2-propoxy)methyl]guanine: A New Potent and Selective Antiherpes Agent," J. Med. Chem., vol. 26, No. 5, pp. 759-761 (1983).
March, J., "Aliphatic Nucleophilic Substitution," Advanced Organic Chemistry, Chapter 10, pp. 348-357, 4th ed. John Wiley & Sons (1992).
Neuss, N. et al., "Vinca Alkaloids. XXI. The Structures of the Oncolytic Alkaloids Vinblastine (VLB) and Vincristine (VCR)," J. Am. Chem. Soc., vol. 86, pp. 1440-1442 (1964).

Noble, R.L. et al., "Role of Chance Observations in Chemotherapy: Vinca Rosea," Annals New York Academy of Sciences, vol. 76, pp. 882-894 (1958).
Nicolaou, K.C. et al., "Total synthesis of taxol," Nature, vol. 367, pp. 630-634 (1994).
Ogilvie, K.K. et al., "Biologically active acyclonucleoside analogues. II. The synthesis of 9-[[2-hydroxy-1-(hydroxymethyl)ethoxy]methyl]guanine (BIOLF-62)," Can. J. Chem., vol. 60, pp. 3005-3010 (1982).
Oliveto, E.P. et al., "16-Alkylated Corticoids. III. 16B-Methyl-9a-Fluoroprednisolone 21-Acetate," J. Am. Chem. Soc., vol. 80, pp. 6687-6688 (1958).
Pandit, U.K. et al., "A New Class of Nucleoside Analogues. Synthesis of N1-Pyrimidynyl-and N9-Puriny1-4'-Hydroxy-3-(Hydroxymethyl) Butanes," Synthetic Communications, vol. 2, No. 6, pp. 345-351 (1972).
Penco, S., "Antitumour Anthracyclines: New Developments," Process Biochemistry, pp. 12-17 (1980).
Parkes, K.E.B., "Studies toward the Large-Scale Synthesis of the HIV Proteinase Inhibitor Ro 31-8959," J. Org. Chem., vol. 59, No. 13, pp. 3656-3664 (1994).
Rosenberg, I. et al., "Phosphonylmethoxyalkyl and Phosphonylalkyl Derivatives of Adenine," Collection Czechoslovak Chem. Commun., vol. 53, pp. 2753-2777 (1988).
Remiszewski, S.W. et al., "N-Hydroxy-3-phenyl-2-propenamides as Novel Inhibitors of Human Histone Deacetylase with in Vivo Antitumor Activity: Discovery of (2E)-N-Hydroxy-344-[[(2-hydroxyethyl)[2-(1H-indol-3-yl)ethyl]amino] methyl]-phenyl]-2-propenannide (NVP-LAQ824)," J. Med. Chem., vol. 46, No. 21, pp. 4609-4624 (2003).
Shannahoff, D.H. et al., "2,2'-Anhydropyrimidine Nucleosides. Novel Syntheses and Reactions," J. Org. Chem., vol. 38, No. 3, pp. 593-598 (1973).
Seeger, D.R. et al., "Analogs of Pteroylglutamic Acid. III. 4-Amino Derivatives," J. Am. Chem. Soc., vol. 71, pp. 1753-1758 (1949).
Schultze, L.M. et al., "Practical Synthesis of the anti-HIV Drug, PMPA," Tetrahedron Letters, vol. 39, pp. 1853-1856 (1998).
Sawada, S. et al., "Synthesis and Antitumor Activity of 20(S)-Camptothecin Derivatives: Carbamate-Linked, Water-Soluble Derivatives of 7-Ethyl-10-hydroxycamptothecin," Chem. Pharm. Bull., vol. 39, No. 6, pp. 1446-1454 (1991).
Smith, D.B. et al., "The Design, Synthesis, and Antiviral Activity of 4'-Azidocytidine Analogues against Hepatitis C Virus Replication: The Discovery of 4'-Azidoarabinocytidine," J. Med. Chem., vol. 52, No. 1, pp. 219-223 (2009).
Showalter, H.D.H. et al., "Adenosine Deaminase Inhibitors. Synthesis and Biological Evaluation of (±)-3,6,7,8-Tetrahydro-3-[(92-hydroxyethoxy)methyl]imidazo[4,5-d][1,3]diazepin-8-ol and Some Selected C-5 Homologues of Pentostatin," J. Med. Chem., vol. 26, No. 10, pp. 1478-1482 (1983).
Smith, D.B. et al., "The Design, Synthesis, and Antiviral Activity of Monofluoro and Difluoro Analogues of 4'-Azidocytidine Against Hepatitis C Virus Replication: The Discovery of 4'-Azido-2'-deoxy-2'-fluorocytidine and 4'-Azido-2'-dideoxy-2',2'-difluorocytidine," J. Med. Chem., vol. 52, No. 9, pp. 2971-2978 (2009).
Seeger, D.R. et al., "Antagonist for Pteroylglutamic Acid," J. Am. Chem. Soc., p. 2567 (1947).
Sawada, S. et al., "Synthesis and Antitumor Activity of 20(S)-Camptothecin Derivatives: A-Ring Modifiied and 7,10-Disubstituted Camptothecins," Chem. Pharm. Bull., vol. 39, No. 12, pp. 3183-3188 (1991).
Smith, D.B. et al., "Design, synthesis, and antiviral properties of 4'-substituted ribonucleosides as inhibitors of hepatitis C virus replication: The discovery of R1479," Bioorganic & Medicinal Chemistry Letters, vol. 17, pp. 2570-2576 (2007).
Taub, D. et al., "16B-Methyl Cortical Steroids," J. Am. Chem. Soc., vol. 82, pp. 4012-4026 (1960).
Taub, D. et al., "16B-Methyl Cortical Steroids," J. Am. Chem. Soc., p. 4435 (1958).
Turner, S.R. et al., "Tipranavir (PNU-140690): A Potent, Orally Bioavailable Nonpeptidic HIV Protease Inhibitor of the 5,6-Dihydro-4-hydroxy-2-pyrone Sulfonamide Class," J. Med. Chem., vol. 41, No. 18, pp. 3467-3476 (1998).

(56) References Cited

OTHER PUBLICATIONS

Umezawa, H. et al., "Tetrahydropyranyl Derivatives of Daunomycin and Adriamycin," The Journal of Antibiotics, vol. XXXII, No. 10, pp. 1082-1084 (1979).

Valette, G. et al., "Decomposition Pathways and in Vitro HIV Inhibitory Effects of IsoddA Pronucleotides: Toward a Rational Approach for Intracellular Delivery of Nucleoside 5'-Monophosphates," J. Med. Chem., vol. 39, No. 10, pp. 1981-1990 (1996).

Venner, H., "Synthese der len naturlichen entsprechenden 2-Desoxy-Nucleoside des Adenins, Guanins and Hypoxanthins," Ber., pp. 140-149 (1960).

Walton, E. et al., "Branched-Chain Sugar Nucleosides. A New Type of Biologically Active Nucleoside," J. Am. Chem. Soc., vol. 88, No. 19, pp. 4524-4525 (1966).

Wani, M.G. et al., "Plant Antitumor Agents. 23. Synthesis and Antileukemic Activity of Camptothecin Analogues," J. Med. Chem., vol. 29, No. 11, pp. 2358-2363 (1986).

Wani, M.G. et al., "Plant Antitumor Agents. VI. The Isolation and Structure of Taxol, a Novel Antileukemic and Antitumor Agent from Taxus brevifolia," J. Am. Chem. Soc., vol. 93, No. 9, pp. 2325-2327 (1971).

Webb II, R.R. et al., "Synthesis of 2',3'-Dideoxyinosine," Nucleosides & Nucleotides, vol. 7, No. 2, pp. 147-153 (1988).

Woo, P.W.K. et al., "A Novel Adenosine and Ara-A Deaminase Inhibitor, (R)-3-(2-Deoxy-B-D-erythro-pento-furanosyl)-3,6,7,8-tetrahydroimidazo[4,5-d] [1,3] diazepin-8-ol," J. Heterocyclic Chem., vol. 11, pp. 641-643 (1974).

International Search Report and Written Opinion of the International Searching Authority issued in PCT/US2009/069420, mailed May 8, 2012 (16 pages).

Wolff, M.E., "Some Considerations for Prodrug Design," Burger's Medicinal Chemistry and Drug Discovery, vol. 1, pp. 975-977 (5th ed. 1995).

Stuyver, L.J. et al., "Dynamics of Subgenomic Hepatitis C Virus Replicon RNA Levels in Huh-7 Cells after Exposure to Nucleoside Antimetabolites," Journal of Virology, vol. 77, No. 19, pp. 10689-10694 (2003).

Byrn, S.R. et al., "Hydrates and Solvates," Solid-State Chemistry of Drugs, Chapter 11, pp. 233-247 (2nd ed. 1999).

Rouhi, A.M. et al., "The Right Stuff," Chemical & Engineering News, vol. 81, No. 8, pp. 32-35 (2003).

Byrn, S. et al., "Pharmaceutical Solids: A Strategic Approach to Regulatory Considerations," Pharmaceutical Research, vol. 12, No. 7, pp. 945-954 (1995).

Morissette, Sr et al., "High-throughput crystallization: polymorphs, salts, co-crystals and solvates of pharmaceutical solids," Advanced Drug Delivery Reviews, vol. 56, pp. 275-300 (2004).

McGuigan, C. et al., "Anti-cancer ProTides: tuning the activity of BVDU phosphoramidates related to thymectacin," Bioorganic & Medicinal Chemistry, vol. 13, pp. 3219-3227 (2005).

Ben-Hattar, J. et al., "Facile Synthesis of Base-Labile 2'-Deoxyribonucleosides: An Improved Synthesis of 2'-Deoxy-5-Aza-Cytidine," Nucleosides & Nucleotides, vol. 6, Nos. 1 & 2, pp. 393-394 (1987).

Brazhnikova, M.G. et al., "Physical and Chemical Characteristics and Structure of Carminomycin, A New Antitumor Antibiotic," The Journal of Antibiotics, vol. XXVII, No. 4, pp. 254-259 (1974).

Berman, J.D. et al., "Activity of Purine Analogs Against Leishmania Donovani in Vivo," Antimicrobial Agents and Chemotherapy, vol. 31, No. 1, pp. 111-113 (1987).

Beach, J. W. et al., "Synthesis of Enantiomerically Pure (2'R, 5'S)-(-)-1-[2-(Hydroxymethyl)oxathiolan-5-yl]cytosine as a Potent Antiviral Agent against Hepatitis B Virus (HBV) and Human Immunodeficiency Virus (HIV)," J. Org. Chem, vol. 57, pp. 2217-2219 (1992).

Crimmins, M.T. et al., "An Efficient Asymmetric Approach to Carbocyclic Nucleosides: Asymmetric Synthesis of 1592U89, a Potent Inhibitor of HIV Reverse Transcriptase," J. Org. Chem., vol. 61, No. 13, pp. 4192-4193 (1996).

Chou, T.S. et al., "Stereospecific Synthesis of 2-Deoxy-2,2-difluororibonolactone and Its Use in the Preparation of 2'-Deoxy-2',2'-difluoro-B-D-ribofuranosyl Pyrimidine Nucleosides: The Key Role of Selective Crystallization," Synthesis, pp. 565-570 (Jun. 1992).

Cosulich, D.B. et al., "Analogs of Pteroylglutamic Acid. I.," J. Am. Chem. Soc., vol. 70, pp. 1922-1926 (1948).

Clark, J.L. et al., "Design, Synthesis, and Antiviral Activity of 2'-Deoxy-2'-fluoro-2'-C-methylcytidine, a Potent Inhibitor of Hepatitis C Virus Replication," J. Med. Chem., vol. 48, No. 17, pp. 5504-5508 (2005).

Chan, E. et al., "Total Synthesis of (8R)-3-(2-Deoxy-B-D-erythro-pentofuranosyl)-3,6,7,8-tetrahydroimidazo[4,5-d][1,3] diazepin-8-ol (Pentostatin), the Potent Inhibitor of Adenosine Deaminase," J. Org. Chem., vol. 47, No. 18, pp. 3457-3464 (1982).

Chu, C.K. et al., "An Efficient Total Synthesis of 3'-Azido-3'-Deoxythymidine (AZT) and 3'-Azido-2', 3'-Dideoxyuridine (AZDDU, CS-87) From D-Mannitol," Tetrahedron Letters, vol. 29, No. 42, pp. 5349-5352 (1988).

Christensen, L.F. et al., "Synthesis and Biological Activity of Selected 2,6-Disubstituted-(2-Deoxy-alpha-and -beta-D-erythro-pentofuranosyl)purines," J. Med. Chem., vol. 15, No. 7, pp. 735-739 (1972).

Di Marco, A. et al., "Daunomycin, a New Antibiotic of the Rhodomycin Group," Nature, vol. 201, pp. 706-707 (Feb. 15, 1964).

Erion, M.D., "Prodrugs for Liver-targeted Drug Delivery," Biotechnology: Pharmaceutical Aspects, vol. V, pp. 541-572 (2007).

Eldrup, A.B. et al., "Structure-Activity Relationship of Heterobase-Modified 2'-C-Methyl Ribonucleosides as Inhibitors of Hepatitis C Virus RNA Replication," J. Med. Chem., vol. 47, No. 21, pp. 5284-5297 (2004).

Evans, C.A. et al., "Divergent Asymmetric Syntheses of Dioxolane Nuccleoside Analogues," Tetrahedron: Asymmetry, vol. 4, No. 11, pp. 2319-2322 (1993).

Fors, K.S. et al., "A Convergent, Scalable Synthesis of HIV Protease Inhibitor PNU-140690," J. Org. Chem., vol. 63, No. 21, pp. 7348-7356 (1998).

Fretz, H. et al., "Rapamycin and FK506 Binding Proteins (Immunophilins)," J. Am. Chem. Soc., vol. 113, pp. 1409-1411 (1991).

Fukukawa, K. et al., "Synthesis of Bredinin From 5-Aminoimidazole-4-Carboamide-Ribofuranoside (AICA-riboside)," Chem. Pharm. Bull., vol. 32, No. 4, pp. 1644-1646 (1984).

Guillory, J.K., "Generation of Polymorphs, Hydrates, Solvates, and Amorphous Solids," Polymorphism in Pharmaceutical Solids, pp. 183-226 (1999).

Goris, N. et al., "2'-C-Methylcytidine as potent and selective inhibitor of the replication of foot-and-mouth disease virus," Antiviral Research, vol. 73, pp. 161-168 (2007).

Gorman, M. et al., "Vinca Alkaloids. IV. Structural Features of Leurosine and Vincaleukoblastine, Representatives of a New Type of Indole-Indoline Alkaloids," J. Am. Chem. Soc., vol. 81, pp. 4745-4746 (1959).

Glinski, R.P. et al., "Nucleotide Synthesis. IV. Phosphorylated 3'-Amino-3'-deoxythymidine and 5'-Amino-5'- deoxythymidine and Derivatives," J. Org. Chem., vol. 38, No. 25, pp. 4299-4305 (1973).

Gorman, M. - M et al "Vinca Alkaloids III. Characterization of Leurosine and Vincaleukoblastine, New Alkaloids From Vinca Rosea Linn," J. Am. Chem. Soc., vol. 81, pp. 4754-4755 (1959).

Gensler, W.J. et al., "Synthesis of Podophyllotoxin," J. Am. Chem. Soc., vol. 84, pp. 1748-1749 (1962).

Holy, A. et al., "Synthesis of 9-(2-Phosphonylmethoxyethyl)Adenine and Related Compounds," Collection Czechoslovak Chem. Comm., vol. 52, pp. 2801-2809 (1987).

Hale, J.J. et al., "Structural Optimization Affording 2-(R)-(1-(R)-3,5-Bis(trifluoromethyl)phenylethoxy)-3-(S)-(4-fluoro) phenyl-4-(3-oxo-1,2,4-triazol-5-yl)methylmorpholine, a Potent, Orally Active, Long-Acting Morpholine Acetal Human NK-1 Receptor Antagonist," J. Med. Chem., vol. 41, No. 23, pp. 4607-4614 (1998).

Hannah, J. et al., "Carba-acyclonucleoside Antiherpetic Agents," J. Heterocyclic Chem., vol. 26, pp. 1261-1271 (1989).

(56) References Cited

OTHER PUBLICATIONS

Holton, R.A. et al., "First Total Synthesis of Taxol. 2. Completion of the C and D Rings," J. Am. Chem. Soc., vol. 116, pp. 1599-1600 (1994).
Horwitz, J.P. et al., "Nucleosides. V. The Monomesylates of 1-(2'-Deoxy-B-D-Iyxofuranosyl)thymine," J. Org. Chem., vol. 29, pp. 2076-2078 (1964).
Holton, R.A. et al., "First Total Synthesis of Taxol. 1. Functionalization of the B Ring," J. Am. Chem. Soc., vol. 116, pp. 1597-1598 (1994).
Harnden, M.R. et al., "Synthesis and Antiviral Activity of 9[4-Hydroxy-3-(hydroxymethyl)but-1-yl]purines," J. Med. Chem., vol. 30, No. 9, pp. 1636-1642 (1987).
Horwitz, J.P. et al.' "Nucleosides. IX. The Formation of 2',3'-Unsaturated Pyrimidine Nucleosides via a Novel B-Elimination," J. Org. Chem., vol. 31, pp. 205-211 (1966).
Horwitz, J.P. et al., "Nucleosides. XI. 2',3'-Dideoxycytidine," J. Org. Chem., vol. 32, pp. 817-818 (1967).
Hayashi, M. et al., "Studies on Bredinin. III. Chemical Synthesis of Bredinin (A Novel Imidazole Nucleoside)," Chem. Pharm. Bull., vol. 23, No. 1, pp. 245-246 (1975).
Humber, D.C. et al., "Expeditious Preparation of (−)-2'-Deoxy-3'-Thiacytidine (3TC)," Tetrahedron Letters, vol. 33, No. 32, pp. 4625-4628 (1992).
Holy, A. et al., "Synthesis of Enantiomeric N-(2-Phosphonomethoxypropyl) Derivatives of Purine and Pyrimidine Bases. II. The Synthon Approach," Collect. Czech. Chem. Commun., vol. 60, pp. 1390-1409 (1995).
Hostetler, K.Y. et al., "Synthesis and Antiretroviral Activity of Phospholipid Analogs of Azidothymidine and Other Antiviral Nucleosides," The Journal of Biological Chemistry, vol. 265, No. 11, pp. 6112-6117 (1990).
Jones, T.K. et al., "Total Synthesis of the Immunosuppressant (−)-FK-506," J. Am. Chem. Soc., vol. 111, No. 3, pp. 1157-1159 (1989).
Jones, C.D. et al., "Antiestrogens. 2. Structure-Activity Studies in a Series of 3-Aroyl-2-arylbenzo[b]thiophene Derivatives Leading to [6-Hydroxy-2-(4-hydroxypheny)benzo[b]thien-3-y][4-[2-(1-piperidiny)ethoxy]-phenyl]methanone Hydrochloride (LY156758), a Remarkably Effective Estrogen Antagonist with Only Minimal Intrinsic Estrogencity," J. Med. Chem., vol. 27, No. 8, pp. 1057-1066 (1984).
Jenkins, S.R. et al., "Branched-Chain Sugar Nucleosides. IV. 2'-C-Methyladenosine," J. Org. Chem., vol. 33, No. 6, pp. 2490-2494 (1968).
Jeong, L.S. et al., "Asymmetric Synthesis and Biological Evaluation of B-L-(2R,5R)-and alpha-L-(2R,5R)-1,3-Oxathiolane-Pyrimidine and -Purine Nucleosides as Potential Anti-HIV Agents," J. Med. Chem., vol. 36, No. 2, pp. 181-195 (1993).
Ikehara, M. et al., "Studies of Nucleosides and Nucleotides. XXIV. Purine Cyclonucleosides. I. 8,2'-Cyclonucleoside Derived from 2-Chloro-8-mercapto-9-B-D-xylofuranosyladenine," J. Am. Chem. Soc., vol. 87, No. 3, pp. 606-610 (1965).
Ikehara, M. et al., "A New Type of 'Cyclonucleoside' Derived from 2-Chloro-8-mercapto-9-B-D-xylofuranosyladenine," J. Am. Chem. Soc., vol. 85, pp. 2344-2345 (1963).
J.K. Guillory Polymorphism in Pharmaceutical Solids (1999); pp. 183-226; H.G. Brittain (Ed.); Marcel Dekker, Inc. (New York).
U.S. Appl. No. 13/925,078, filed Jun. 24, 2013—Pending claims as of Oct. 4, 2013.
U.S. Appl. No. 13/936,448, filed Jul. 8, 2013—Allowed claims as of Oct. 4, 2013.
European Communication issued in corresponding application No. 11714466.7 dated Jan. 9, 2013 (3 pages).
New Zealand Office Action issued in corresponding application No. 603239 dated May 21, 2013 (2 pages).
Adelfinskaya, O., et al., "Polymerase-catalyzed synthesis of DNA from phosphoramidate conjugates of deoxynucleotides and amino acids," Nucleic Acids Research, vol. 35, No. 15, pp. 5060-5072 (2007).
Siddiqui, A.Q., et al., "Design and synthesis of lipophilic phosphoramidate d4T-MP prodrugs expressing high potency against HIV in cell culture: structural determinants for in vitro activity and QSAR," J. Med. Chem., vol. 42, pp. 4122-4128 (1999).
Pliml, et al., "Synthesis of a 2-deoxy-D-ribofuranosyl-5-azacytosine," Collect. Czech. Chem. Commun., vol. 29, p. 2576 (1964).
Piskala, et al., "Synthesis of 5-Azapyrimidine Deoxyribonucleosides via Acylglycosyl Isocyanates," Nucleic Acid Chemistry Part 1 (Wiley, New York 1978).
Chan, et al., "Total Synthesis of (8R)-3-(-2-Deoxy-beta-D-erythro-pentofuranosyl)-3,6,7,8-tetrahydroimidazo[4,5-d][1,3] diazepin-8-ol (Pentostatin), the Potent Inhibitor of Adenosine Deaminase," J. Org. Chem., vol. 42, pp. 3457-3464 (1982).
Prashad, et al., "An Efficient and Large-Scale Enantioselective Synthesis of PNP405: A Purine Nucleoside Phosphorylate Inhibitor," J. Org. Chem., vol. 67, pp. 6612-6617 (2002).
Birch, et al., "A total synthesis of mycophenolic acid," Aust. J. Chem., vol. 22, pp. 2635-2644 (1969).
Ishizumi, et al., "Stereospecific Total Synthesis of 9-Aminoanthracyclines: (+)-9-Amino-9-deoxydaunomycin and related compounds," J. Org. Chem., vol. 52, p. 4477-4484 (1987).
Acton, et al., "Total synthesis of the antitumor antibiotic daunorubicin. Coupling of the sugar and aglycone," J. Med. Chem., vol. 17, p. 659-660 (1974).
Stowell, et al., "The synthesis of N-Hydroxy-N'-phenyloctanediamide and its inhibitory effect on proliferation of AXC rat prostate cancer cells," J. Med. Chem., vol. 38, pp. 1411-1413 (1995).
Piper, et al., "A convenient synthesis of aminopterin and homologs via 6-(Bromomethyl)-2,4-diaminopteridine hydrobromide (1)," J. Heterocycl. Chem., vol. 11, pp. 279-280 (1974).
Stuyver, et al., "Inhibition of hepatitis C replicon RNA synthesis by B-D-T-deoxy-2'-fluoro-2'-C-methylcytidine: a specific inhibitor of hepatitis C virus replication," Antiviral Chem. Chemother, vol. 17, pp. 79-87 (2006).
Sofia et al., "Discovery of a beta-D-2'-Deoxy-2'-alpha-fluoro-2'-beta-C-methyluridine nucleotide prodrug (PSI-7977) for the treatment of hepatitis C virus," J. Med. Chem., vol. 53, pp. 7202-7218 (2010).
Furman, Phillip A., et al., "PSI-7851: A Novel Liver-Targeting Nucleotide Prodrug for the Treatment of Hepatitis C," Hepatology (2008) 48(4 Suppl):1161A (Abstract #1901).
Furman, Phillip A., et al., "PSI-7851: A Novel Liver-Targeting Nucleotide Prodrug for the Treatment of Hepatitis C," Presented at the 59th Annual Meeting of the American Association for the Study of Liver Diseases, San Francisco, CA, Oct. 31-Nov. 4, 2008.
Furman, P.A., et al., "b-D-2'-Deoxy-2'-fluoro-2'-C-methyluridine Phosphoramidates are Potent and Selective Inhibitors of HCV RNA Replication," Presented at the 15th International Symposium on Hepatitis C Virus & Related Viruses, San Antonio, TX, Oct. 5-9, 2008.
Sofia, Michael J., et al., "Beta-D-2'-Deoxy-2'-fluoro-2'-C-methyluridine (PSI-6206) phosphoramidates: Potent liver targeting nucleoside inhibitors of HCV RNA replication," 236th ACS National Meeting, Philadelphia, PA, Aug. 20, 2008 (Abstract MEDI 330).
International Search Report for PCT/US2009/046619 mailed Sep. 23, 2010 (4 pages).
International Preliminary Report on Patentability for PCT/US2011/030725 mailed Oct. 2, 2012 (17 pages).
Abraham et al., "Synthesis and Biological Activity of Aromatic Amino Acid Phosphoramidates of 5-fluoro-2'deoxyuridine and 1-beta-Arabinofuranosylcytosine: Evidence of Phosphoramidase Activity," J. Med. Chem., vol. 39, No. 23, pp. 4569-4575, (1996).
Pogam et al., "No Evidence of R7128 Drug Resistance After Up to 4 Weeks Treatment of GT1, 2 and 3 Hepatitis C Virus Infected Individuals", 44th Annual Meeting of European Association for the Study of the Liver (EASL), Copenhagen, Denmark (Apr. 22-26, 2009).
Sofia et al., "beta-D-2'-Deoxy-2'-C-methyluridine Phosphoramidates: Potent and Selective Inhibitors of HCV RNA Replication", Poster #P-259, 14th International Symposium on Hepatitis C Virus and Related Viruses, Glasgow, Scotland, UK (Sep. 9 to 13, 2007).

(56) References Cited

OTHER PUBLICATIONS

Sofia, M.J., "beta-D-2'-Deoxy-2'-fluoro-2'-C-methyluridine Phosphoramidates: Potent and Selective Inhibitors of HCV RNA Replication", 2nd International Workshop on HCV—Resistance and New Compounds (Oct. 31, 2007).

Sofia et al., "beta-D-2'-Deoxy-2'-fluoro-2'-C-methyluridine Phosphoramidates: Potent and Selective Inhibitors of HCV RNA Replication", 2nd International Workshop on HCV, Poster #7 (Oct. 31, 2007).

Sofia, M.J., "R7128, A Potent and Selective Nucleoside Inhibitor of HCV NS5B Polymerase: An Overview of Clinical Efficacy and Progress Toward Second Generation Inhibitors", HCV Drug Discovery 2008, Chicago, IL (Apr. 28, 2008).

Abraham et al., "Synthesis, Biological Activity and Decomposition Studies of Amino Acid Phosphomonoester Amidates of Acyclovir," Nucleosides, Nucleotides and Nucleic Acids, vol. 16, No. 10, pp. 2079-2092 (1997).

Chang et al., "Amino Acid Phosphoramidate Monoesters of 3'-Azido-3'-deoxythymidine: Relationship between Antiviral Potency and Intracellular Metabolism," J. Med. Chem., vol. 44, No. 2, pp. 223-231 (2001).

Chen et al., "In Vivo Pharmacokinetics and Metabolism of Anti-Human Immunodeficiency Virus Agent D4t-5'-[P-Bromophenyl Methoxyalaninyl Phosphate] (Sampidine) in Mice," Drug Metabolism and Disposition, vol. 29, No. 7, pp. 1035-1041 (2001).

Chen et al., "Metabolism of Stavudine-5.4P-Bromophenyl Methoxyalaninyl Phosphate], Stampidine, in Mice, Dogs, and Cats," Drug Metabolism and Disposition, vol. 30, No. 12, pp. 1523-1531 (2002).

Cihlar et al. "Design and Profiling of GS-9148, a Novel Nucleotide Analog Active against Nucleoside-Resistant Variants of Human Immunodeficiency Virus Type 1, and Its Orally Bioavailable Phosphonoamidate Prodrug, GS-9131," Antimicrobial Agents and Chemotherapy, vol. 52, No. 2, pp. 655-665 (2008).

Congiatu et al. "Molecular Modeling Studies on the Binding of Some Protides to the Putative Human Phosphoramidase Hint1," Nucleosides, Nucleotides and Nucleic Acids, vol. 26, pp. 1121-1124 (2007).

Congiatu et al., "Naphthyl Phosphoramidate Derivatives of BVdU as Potential Anticancer Agents: Design, Synthesis and Biological Evaluation," Nucleosides, Nucleotides, and Nucleic Acids, vol. 24, No. 5-7, pp. 485-489 (2005).

Curley et al., "Synthesis and anti-HIV evaluation of some phosphoramidate derivatives of AZT: studies on the effect of chain elongation on biological activity," Antiviral Research, vol. 14, pp. 345-356 (1990).

D'Cruz et al., "Stampidine: a selective oculo-genital microbicide," Journal of Antimicrobial Chemotherapy, vol. 56, pp. 10-19 (2005).

Drontle et al., "Designing a Pronucleotide Stratagem: Lessons from Amino Acid Phosphoramidates of Anticancer and Antiviral Pyrimidines," MiniReviews in Medicinal Chemistry, vol. 4, No. 4, pp. 409-419 (2004).

Egron et al., "S-Acyl-2-thioethyl Phosphoramidate Diester Derivatives as Mononucleotide Prodrugs" J. Med. Chem., vol. 46, No. 21, pp. 4564-4571 (2003).

Iyer et al., "Synthesis, in Vitro Anti-Breast Cancer Activity, and Intracellular Decomposition of Amino Acid Methyl Ester and Alkyl Amide Phosphoramidate Monoesters of 3'-Azido-3'-deoxythymidine (AZT)," J. Med. Chem., vol. 43, No. 11, pp. 2266-2274 (2000).

Kim et al., "Monitoring the Intracellular Metabolism of Nucleoside Phosphoramidate Pronucleotides by 31P NMR," Nucleosides, Nucleotides and Nucleic Acid, vol. 23, No. 1 & 2, pp. 483-493 (2004).

McGuigan et al., "Aryl phosphate derivatives of AZT retain activity against HIV1 in cell lines which are resistant to the action of AZT," Antiviral Research, vol. 17, pp. 311-321 (1992).

McGuigan et al., "Application of Phosphoramidate ProTide Technology Significantly Improves Antiviral Potency of Carbocyclic Adenosine Derivatives," J. Med. Chem., vol. 49, No. 24, pp. 7215-7226 (2006).

McGuigan et al., "Application of Phosphoramidate Pronucleotides Technology to Abacavir Leads to a Significant Enhancement of Antiviral Potency," J. Med. Chem., vol. 48, No. 10, pp. 3504-3515 (2005).

McGuigan et al., "Synthesis and anti-HIV activity of some novel chain-extended phosphoramidate derivatives of d4T (stavudine): esterase hydrolysis as a rapid predictive test for antiviral potency," Antiviral Chemistry and Chemotherapy, vol. 9, pp. 109-115 (1998).

McGuigan et al., "Synthesis and evaluation of some novel phosphoramidate derivatives of 3'-azido-3'-deoxythymidine (AZT) as anti-HIV compounds," Antiviral Chemistry and Chemotherapy, vol. 1, No. 2, pp. 107-113 (1990).

McIntee et al., "Probing the Mechanism of Action and Decomposition of Amino Acid Phosphomonoester Amidates of Antiviral Nucleoside Prodrugs," J. Med. Chem., vol. 40, No. 21, pp. 3323-3331 (1997).

Perrone et al., "First Example of Phosphoramidate Approach Applied to a 4'-Substituted Purine Nucleoside (4'Azidoadenosine): Conversion of an Inactive Nucleoside to a Submicromolar Compound versus Hepatitis C Virus," J. Med. Chem., vol. 50, No. 22, pp. 5463-5470 (2007).

Saboulard et al., "Characterization of the Activation Pathway of Phosphoramidate Triester Prodrugs of Stavudine and Zidovudine," Mol. Pharmacol., vol. 56, pp. 693-704 (1999).

Schultz, C., "Prodrugs of Biologically Active Phosphate Esters," Bioorg. and Med. Chem., vol. 11, pp. 885-898 (2003).

Siccardi et al., "Stereoselective and Concentration-Dependent Polarized Epithelial Permeability of a Series of Phosphoramidate Triester Prodrugs of d4T: An in Vitro Study in Caco-2 and Madin-Darby Canine Kidney Cell Monolayers," J. Pharmacol. and Exp. Ther., vol. 307, No. 3, pp. 1112-1119 (2003).

Siccardi et al., "Stereospecific chemical and enzymatic stability of phosphoramidate triester prodrugs of d4T in vitro," European Journal of Pharmaceutical Sciences, vol. 22, pp. 25-31 (2004).

Siddiqui et al., "Enhancing the Aqueous Solubility of d4T-based Phosphoramidate Prodrugs," Bioorg. and Med. Chem. Lett., vol. 10, pp. 381-384 (2000).

Song et al., "Pharmacokinetics of Amino Acid Phosphoramidate Monoesters of Zidovudine in Rats," Antimicrobial Agents and Chemotherapy, vol. 46, No. 5, pp. 1357-1363 (2002).

Uckun et al., "In Vivo Pharmacokinetics and Toxicity Profile of the Anti-HIV Agent Stampidine in Dogs and Feline Immunodeficiency Virus-infected Cats," Arzneim.-Forsch./Drug Res., vol. 56, No. 2a, pp. 176-192 (2006).

Venkatachalam et al., "Synthesis and metabolism of naphthyl substituted phosphoramidate derivatives of stavudine," Bioorg. and Med. Chem., vol. 14, pp. 5161-5177 (2006).

Venkatachalam et al., "Rational Drug Design of Multifunctional Phosphoramidate Substituted Nucleoside Analogs," Current Pharmaceutical Design, vol. 10, No. 15, pp. 1713-1726 (2004).

Wagner et al., "Antiviral Nucleoside Drug Delivery via Amino Acid Phosphoramidates," Nucleosides, Nucleotides and Nucleic Acids, vol. 18, No. 4 & 5, pp. 913-919 (1999).

Wu et al., "Synthesis and Biological Activity of a Gemcitabine Phosphoramidate Prodrug," J. Med. Chem., vol. 50, No. 15, pp. 3743-3746 (2007).

Gunic et al., "6-Hydrazinopurine 2'-methyl ribonucleosides and their 5'-monophosphate prodrugs as potent hepatitis C virus inhibitors," Bioorg. & Med. Chem. Lett., vol. 17, pp. 2456-2458 (2007).

International Search Report issued in International PCT application No. PCT/US2008/058183 mailed Mar. 31, 2010 (10 pages).

International Preliminary Examination Report along with Written Opinion of the International Searching Authority issued in International PCT application No. PCT/US2008/058183 issued Apr. 7, 2010 (17 pages).

Baschang et al., "Neue Derivate von Thymidin-3',5'-cyclophosphat," Angew. Chem., vol. 85, No. 1, pp. 44-45 (1973).

Broeders et al., "A 400- and 600-Mhz 'H NMR Confromational Study on Nucleoside Cyclic 3', 5' PV-TBP Systems. Conformational Transmission Induces Diequatorial Orientation of the 3',

(56) References Cited

OTHER PUBLICATIONS

5'-Dioxaphosphorinane Ring in a Nonchair Confirmation," J. Am. Chem. Soc., vol. 112, No. 21, pp. 7475-7482 (1990).

Engels et al., "Cyclophosphate, III. Synthese and Eignschaften von Uridin-3',5'-cyclophosphat-estern," Chemische Berichte, vol. 110, No. 6, pp. 2019-2027 (1977).

Lopez Aparicio et al., "Synthesis of Saccharinic Acid Derivatives," Carbohydrate Research, vol. 129, pp. 99-109 (1984).

Nelson et al., "The Question of Chair-twist Equilibria for the Phosphate Rings of Nucleoside Cyclic 3',5' Monophosphates. 1H NMR and X-ray Crystallographic Study of Diastereomers of Thymidine Phenyl Cyclic 3',5'-Monophosphate," J. Am. Chem. Soc., vol. 109, No. 13, pp. 4058-4064 (1987).

Gromova et al., "Optical Rotatory Dispersion and Circular Dichroism of Mono- and Oligonucleotide-Amino Acids (Amidates)," Biochim. Biophys. Acta., vol. 240, No. 1, pp. 1-11 (1971).

Harris et al., "Synthesis and antiviral evaluation of phosphoramidate derivatives of (E)-5-(2-bromovinyl)-2'-deoxyuridine," Antiviral Chemistry & Chemotherapy, vol. 12, No. 5, pp. 293-300 (2001).

Juodka et al., "Oligonucleotides and Nucleotide-Peptides. XXXIV. Synthesis and Some Properties of Complex Nucleotidyl (Oligonucleotidyl)-(P-N)-Amino Acids (Peptides) and Their Ethyl Esters," J. Carbohydrates Nucleosides Nucleotides, vol. 6, No. 4, pp. 333-357 (1979).

Juodka et al., "Oligonucleotides and Nucleotide-Peptides. XXXIV. Some Properties of Nucleotidyl-(5'-N)-Amino Acid Esters Differing in Amino Acid and Nucleotide Components," J. Carbohydrates Nucleosides Nucleotides, vol. 8, No. 1, pp. 19-39 (1981).

Juodka et al., "Oligonucleotides and Nucleotide-Peptides. XXXVII. On the Mechanism of Hydrolysis of Uridyly1-(5'-N)-Amino Acids. Intramolecular Catalysis by the alpha-Carboxyl Group of Amino Acids," J. Carbohydrates Nucleosides Nucleotides, vol. 8, No. 6, pp. 519-535 (1981).

Lackey et al., "Enzyme-catalyzed therapeutic agent (ECTA) design: activation of the antitumor ECTA compound NB1011 by thymidylate synthase," Biochemical Pharmacology, vol. 61, No. 2, pp. 179-189 (2001).

McIntee et al., "Amino Acid Phosphoramidate Nucleosides: Potential ADEPT/GDEPT Substrates," Bioorganic & Medicinal Chemistry Letters, vol. 11, No. 21, pp. 2803-2805 (2001).

Remy et al., "Studies on Flourinated Pyrimidines. XIV. The Synthesis of Derivatives of 5-Fluoro-2'-deoxyuridine 5'-Phosphate and Related Compounds," J. Org. Chem., vol. 27, No. 7, pp. 2491-2500 (1962).

Smirnov et al., "A Fluorescent Study of Tryptophan Derivatives of Oligonucleotides and Their Helical Complexes with Polyuridylic," FEBS Letters, vol. 51. No. 1, pp. 211-214 (1975).

Yuodka et al., "Oligonucleotides and Polynucleotides. XXVI. Synthesis of Esters of Nucleotidyl- and Oligonucleotidyl-(5'-N)-(Amino Acid)S and -Peptides," Soviet Journal of Bioorganic Chemistry, vol. 2, No. 11 pp. 1089-1094(1976) Translated from Russian.

U.S. Appl. No. 60/392,350, filed on Jun. 28, 2002.

U.S. Appl. No. 60/392,351, filed on Jun. 28, 2002.

Eldrup et al., "Oral Session V: Hepatitis C Virus, Flaviviruses," Program and Abstracts, The Sixteenth International Conference on Antiviral Research, p. A75, Abstract 119 (Apr. 27 to May 1, 2003).

International Search Report issued in International Application No. PCT/US2005/025916 mailed Jun. 15, 2006 (2 pages).

Pierra et al., "Synthesis and Pharmacokinetics of Valopicitabine (NM283), an Efficient Prodrug of the Potent Anti-HCV Agent 2'-C-Methylcytidine," J. Med. Chem., vol. 49, No. 22, pp. 6614-6620 (2006).

Stuyver et al., "Inhibition of hepatitis C replicon RNA synthesis by B-D-2'-deoxy-2'-fluoro-2'-C-methlcytidine: a specific inhibitor of hepatitis C virus replication," Antiviral Chemistry & Chemotherapy, vol. 17, No. 2, pp. 79-87 (2006).

Goekjian et al., "Synthesis of Fluorinated Marcocyclic Bis(indolyl)maleimides as Potential 19F NMR Probes for Protein Kinase C," J. Org. Chem. vol., 64., No. 12, pp. 4238-4246 (1999).

Hernandez et al., "Synthesis of Highly Functionalized Chiral Nitriles by Radical Fragmentation of beta-Hydroxy Azides. Convenient Transformation of Aldononitriles into 1,4- and 1,5-Iminoalditols," J. Org. Chem., vol. 69. No. 24, pp. 8437-8444 (2004).

Novak, J. J. K., "Chiroptical Properties of 2-Methyl-1,4-Lactones: Revised Absolute Configuration of 2-Deoxy-2-C-Methyl-erythro-D-Pentono-1,4-Lactones," Collection Czechoslov. Chem. Commun., vol. 39, pp. 869-882 (1974).

Novak, J. J. K., "Nucleic Acid Components and Their Analogues CXLIII. Nucleosides Derived from 2-Deoxy-2(R)-C-Methyl-erythro-D-Pentose," Collection Czechoslov. Chem. Commun., vol. 36, pp. 3670-3677 (1971).

Oishi et al., "Asymmetric Dihydroxylation of Chiral Olefins. High Control of Diastereofacial Selection," Tet. Lett., vol. 34, No. 22, pp. 3573-3576 (1993).

Xiao-Ling et al., "Study on the Chirality of Sulfur in Ethyl (2S, 3R,4R)-4,5-0-Isopropylidene-2,3-sulfiny1-2,3,4,5-tetrahydroxy-pentanoate", Acta Chimica Sinica, vol. 55, pp. 600-604 (1997).

Xiao-Ling et al., "The Synthesis of (2S,3R)-Sphingosine from D-Mannitol", Acta Chimica Sinica, vol. 54, pp. 826-832 (1996).

International Search Report issued in International Application No. PCT/US2004/012472 mailed Dec. 30, 2004 (4 pages).

International Search Report issued in International Application No. PCT/EP2006/069060 mailed Jan. 30, 2007 (4 pages).

International Search Report issued in International Application No. PCT/US2005/032406 mailed May 8, 2008 (3 pages).

Bartenschlager et al., "Nonstructural Protein 3 of the Hepatitis C Virus Encodes a Serine-Type Proteinase Required for Cleavage at the NS3/4 and NS4/5 Junctions," J. Virol., vol. 67, No. 7, pp. 3835-3844 (1993).

Bartenschlager et al., "Kinetic and Structural Analyses of Hepatitis C Virus Polyprotein Processing," J. Virol., vol. 68, No. 8, pp. 5045-5055 (1994).

Bazan et al., "Detection of a Trypsin-like Serine Protease Domain in Flaviviruses and Pestiviruses," Virology, vol. 171, pp. 637-639 (1989).

Beaulieu et al., "Inhibitors of the HCV NS5B polymerase: New hope for the treatment of hepatitis C infections," Current Opinion in Investigational Drugs, vol. 5, No. 8, pp. 838-850 (2004).

Behrens et al., "Identification and properties of the RNA-dependent RNA polymerase of hepatitis C virus," The EMBO Journal, vol. 15, No. 1, pp. 12-22 (1996).

Calisher et al., "Antigenic Relationships between Flaviviruses as Determined by Cross-neutralization Tests with Polyclonal Antisera," J. Gen. Virol., vol. 70, pp. 37-43 (1989).

Carroll et al., "Nucleoside Analog Inhibitors of Hepatitis C Virus Replication," Infectious Disorders—Drug Targets, vol. 6, No. 1, pp. 17-29 (2006).

Eckart et al., "The Hepatitis C Virus Encodes a Serine Protease Involved in Processing of the Putative Nonstructural Proteins from the Viral Polyprotein Precursor," Biochemical and Biophysical Research Communications, vol. 192, No. 2, pp. 399-406 (1993).

Failla et al., "Both NS3 and NS4A are Required for Proteolytic Processing of Hepatitis C Virus Nonstructural Proteins," J. Virol., vol. 68, No. 6, pp. 3753-3760 (1994).

Rice, C. M., "Flaviviridae: the Viruses and Their Replication," Fields Virology, 3rd Edition, vol. 1, pp. 931-959 (1996).

Gorbalenya et al., "A conserved NTP-motif in putative helicases," Nature, vol. 333, p. 22 (1988).

Gorbalenya et al., "N-terminal domains of putative helicases of flavi- and pestiviruses may be serine proteases," Nucleic Acids Research, vol. 17, No. 10, pp. 3889-3897 (1989).

Grakoui et al., "Characterization of the Hepatitis C Virus-Encoded Serine Proteinase: Determination of Proteinase-Dependent Polyprotein Clevage Sites," J. Virol., vol. 67, No. 5, pp. 2832-2843 (1993).

Grakoui et al., "A second hepatitis C virus-encoded proteinase," Proc. Natl. Acad. Sci., vol. 90, pp. 10583-10587 (1993).

Griffith et al., "HCV Anti-viral Agents," Annual Reports in Medicinal Chemistry, vol. 39, pp. 223-237 (2004).

Halstead, S. B., "Selective Primary Health Care: Strategies for Control of Disease in the Developing World. XI. Dengue," Review of Infectious Diseases, vol. 6, No. 2, pp. 251-263 (1984).

(56) References Cited

OTHER PUBLICATIONS

Halstead, S. B., "Pathogenesis of Dengue: Challenges to Molecular Biology," Science, vol. 239, pp. 476-481 (1988).
Hijikata et al., "Two Distinct Proteinase Activities required for the Processing of a Putative Nonstructural Precursor Protein of Hepatitis C Virus," J. Virol., vol. 67, No. 8, pp. 4665-4675 (1993).
Jin et al- "Expression, Isolation, and characterization of the Hepatitis C Virus ATPase/RNA Helicase," Archives of Biochemistry and Biophysics, vol. 323, No. 1, pp. 47-53 (1995).
Kim et al., "C-Terminal Domain of the Hepatitis C Virus NS3 Protein Contains an RNA Helicase Activity," Biochemical and Biophysical Research Communications, vol. 215, No. 1, pp. 160-166 (1995).
Koonin et al., "Evolution and Taxonomy of Positive-Strand RNA Viruses: Implications of Comparatives Analysis of Amino Acid Sequences," Critical Reviews in Biochemistry and Molecular Biology, vol. 28, No. 5, pp. 375-430 (1993).
Lohmann et al., "Biochemical Properties of Hepatitis C Virus NS5B RNA-Dependent RNA Polymerase and Identification of Amino Acid Sequence Motifs Essential for Enzymatic Activity," J. Virol., vol. 71, No. 11, pp. 8416-8428 (1997).
Meyers et al., "Molecular Characterization of Pestiviruses," Advance in Virus Research, vol. 47, pp. 53-119 (1996).
Moennig et al., "The Pestiviruses," Advances in Virus Research, vol. 41, pp. 53-99 (1992).
Monath, T. P., M.D., "Japanese Encephalitis—A Plague of the Orient," N. Engl. J. Med., vol. 319, No. 10, pp. 641-643 (Sep. 8, 1988).
Ni et al., "Progress and development of small molecule HCV antivirals," Current Opinion in Drug Discovery & Development, vol. 7, No. 4, pp. 446-459 (2004).
Tan et al., "Hepatitis C Therapeutics: current Status and Emerging Strategies," Nature Reviews, vol. 1, pp. 867-881 (2002).
Tomei et al., "NS3 Is a Serine Protease Required for Processing of Hepatitis C Virus Polyprotein," J. Virol., vol. 67, No. 7, pp. 4017-4026 (1993).
Walker et al., "Promising candidates for the treatment of chronic hepatitis C," Expert Opin. Investig. Drugs, vol. 12, No. 8, pp. 1269-1280 (2003).
Warrener et al., "Pestivirus NS3 (p80) Protein Possesses RNA Helicase Activity," J. Virol., vol. 69, No. 3, pp. 1720-1726 (1995).
Wiskerchen et al., Pestivirus Gene Expression: Protein p80 of Bovine Viral Diarrhea Virus Is a Proteinase Involved in Polyprotein Processing, Virology, vol. 184, pp. 341-350 (1991).
Wu et al., "Targeting NS5B RNA-Dependent RNA Polymerase for Anti-HCV Chemotherapy," Current Drug Targets—Infectious Disorders, vol. 3, No. 3, pp. 207-219 (2003).
Xu et al., "Bovine Viral Diarrhea Virus NS3 Serine Proteinase: Polyprotein Cleavage Sites, Cofactor Requirements, and Molecular Model of an Enzyme Essential for Pestivirus Replication," J. Virol., vol. 71, No. 7, pp. 5312-5322 (1997).
Yuan et al.' "Expression, Purification, and Partial Characterization of HCV RNA Polymerase," Biochemical and Biophysical Research Communications, vol. 232, No. 1, pp. 231-235 (1997).
Zhong et al., "Identification and characterization of an RNA-Dependent RNA Polymerase Activity within the Nonstructural Protein 5B Region of Bovine Viral Diarrhea Virus," J. Virol., vol. 72, No. 11, pp. 9365-9369 (1998).
Gudmundsson et al., Nucleosides, Nucleotides & Nucleic Acids (2003) 22(10):1953-1961.
McGuigan et al., Bioorg. & Med. Chem. Lett. (2009) 19:4250-4254.
Siddiqui et al., J. Med. Chem. (1999) 42(3): 393-399.
Dumez et al., Arzneim.-Forsch./Drug Res. (2006), 56(2a):136-151.
Gardelli et al., J. Med. Chem. (2009) 52(17): 5394-5407.
Gudmundsson et al., Nucleosides, Nucleotides and Nucleic Acids (2004) 23(12): 1929-1937.
McGuigan et al., Bioorg. & Med. Chem. Lett. (2010) 19: 4850-4854.
Nakayama et al., J. Am. Chem. Soc. (1990) 112(19): 6936-6942.
Wozniak et al., Chem. Soc. Rev. (2003) 32:158-169.
Uchiyama et al., J. Org. Chem. (1993) 58(2): 373-379.
International Search Report and Written Opinion mailed Nov. 7, 2011—International application No. PCT/US2011/030725 (24 pages).
Chawla et al., CRIPS (2004) 5(1): 9-12.
Haleblian, J. Pharm. Sci. (1975) 64(8): 1269-1288.
Office Action issued in Chinese Patent Application No. 201180023066.7, dated Feb. 27, 2014 (13 pages).
Office Action issued in Eurasian Patent Application No. 201290988, dated Jan. 30, 2014 (3 pages).
Valette, G. et al., "Decomposition Pathways and in Vitro HIV Inhibitory Effects of IsoddA Pronucleotides: Toward a Rational Approach for Intracellular Delivery of Nucleoside 5'-Monophosphates," J. Med. Chem., vol. 39, pp. 1981-1990 (1996).
English translation of the Office Action issued in Panama Application No. 89232-01, dated Jun. 5, 2012 (5 pages).
International Preliminary Report on Patentability and Written Opinion issued in International Application No. PCT/US2004/012472, dated Dec. 1, 2005 (8 pages).
International Preliminary Report on Patentability and Written Opinion issued in International Application No. PCT/US2005/025916, dated Jan. 23, 2007 (5 pages).
International Preliminary Report on Patentability and Written Opinion issued in International Application No. PCT/US2005/032406, dated Mar. 10, 2009 (4 pages).
International Preliminary Report on Patentability issued in International Application No. PCT/EP2006/069060, dated Nov. 5, 2008 (6 pages).
International Preliminary Report on Patentability and Written Opinion issued in International Application No. PCT/US2008/058183, dated Apr. 7, 2010 (17 pages).
International Search Report issued in International Application No. PCT/US2009/046619, dated Sep. 23, 2010 (4 pages).
Invitation to Pay Additional Fees and Communication Relating to the Results of the Partial International Search issued in International Application No. PCT1US2009/069475, dated Mar. 5, 2010 (7 pages).
International Search Report issued in International Application No. PCT/US2009/069475, dated May 10, 2010 (7 pages).
International Preliminary Report on Patentability and Written Opinion issued in International Application No. PCT/US2009/069475, dated Jun. 29, 2011 (12 pages).
Invitation to Pay Additional Fees and Communication Relating to the Results of the Partial International Search issued in International Application No. PCT/ US2010/035641, dated Jul. 23, 2010 (7 pages).
International Search Report issued in International Application No. PCT/US2010/035641, dated Sep. 28, 2010 (8 pages).
International Preliminary Report on Patentability and Written Opinion issued in International Application No. PCT/US2010/035641, dated Nov. 22, 2011 (16 pages).

* cited by examiner

STEREOSELECTIVE SYNTHESIS OF PHOSPHORUS CONTAINING ACTIVES

PRIORITY

This application claims priority to U.S. 61/319,513, filed on Mar. 31, 2010 and U.S. 61/319,548, filed on Mar. 31, 2010, the subject matter of which is incorporated by reference in its entirety.

FIELD OF THE INVENTION

Disclosed herein are phosphorus-containing actives, their use as actives for treating diseases, and a stereoselective process for preparing the same. Also disclosed herein are useful synthetic intermediates and processes for preparing the same.

BACKGROUND OF THE INVENTION

The liver is a vital organ whose functions include, among other things, detoxification, protein synthesis, maintaining an adequate supply of glucose and lipids to the surrounding tissues. R. Kahl's Chapter 13 entitled "The Liver," pp. 273-296 in H. Marquardt's *Toxicology* (1999): Academic Press, San Diego, Calif. Chronic liver diseases such as hepatitis B virus and hepatitis C virus, liver cancer and certain metabolic diseases can seriously injure the liver. Serious liver injury can give rise to a loss of any one of certain liver functions, which in turn can lead to liver failure and death of the organism. Certain drugs that may be effective for treating identified liver diseases may cause unwanted and even serious side-effects that limit the drug's usefulness. Therefore, specific liver-targeting is an important consideration in developing a particular drug substance designed to combat certain liver diseases.

M. D. Erion in "Prodrugs for Liver-targeted Drug Delivery," Biotechnology Pharmaceutical Aspects, 1, Volume V, Prodrugs, Part II, Part 5, Pages 541-572, explains that liver-utilization of certain nucleosides and/or nucleoside-analogs can be hampered if the drug substance is a poor substrate for certain phosphorylating enzymes generally known as kinases. The biological activity of some pharmaceutically active agents may be hampered by poor substrate characteristics for one or more of the kinases needed to convert it to the active triphosphate form or alternatively for introduction into a cell that requires treatment. Formation of the monophosphate by a nucleoside kinase is generally viewed as the rate limiting step of the three phosphorylation events. To circumvent the need for the initial phosphorylation step in the metabolism of an active to the triphosphate analog, the preparation of stable phosphate prodrugs has been reported. Nucleoside phosphoramidate prodrugs have been shown to be precursors of the active nucleoside triphosphate and to inhibit viral replication when administered to viral infected whole cells (McGuigan, C., et al., *J. Med. Chem.,* 1996, 39, 1748-1753; Valette, G., et al., *J. Med. Chem.,* 1996, 39, 1981-1990; Balzarini, J., et al., *Proc. National Acad Sci USA,* 1996, 93, 7295-7299; Siddiqui, A. Q., et al., *J. Med. Chem.,* 1999, 42, 4122-4128; Eisenberg, E. J., et al., *Nucleosides, Nucleotides and Nucleic Acids,* 2001, 20, 1091-1098; Lee, W. A., et al., *Antimicrobial Agents and Chemotherapy,* 2005, 49, 1898; Mehellou, Y., et al. ChemMedChem., 2009, 4, 1779-1791); US 2006/0241064; and WO 2007/095269. Erion further proposes strategies for circumventing the kinase-associated problems. For instance, Erion identifies a prodrug variant of adefovir, which is designated chemically as (2R,4S)-2-(2-(6-amino-9H-purin-9-yl)ethoxy)-4-(3-chlorophenyl)-1,3,2-dioxaphosphinane 2-oxide, was designed to deliver an adefovir containing a phosphorus moiety to the liver. Erion discloses other strategies for delivering nucleosides and nucleoside-analogs to the liver, but does not disclose or suggest the phosphorus-containing actives.

Also limiting the utility of actives as viable therapeutic agents is their sometimes poor physicochemical and pharmacokinetic properties. These poor properties can limit the intestinal absorption of an agent and limit uptake into the target tissue or cell. To improve on their properties prodrugs of actives have been employed. It has been demonstrated in certain instances that preparation of nucleoside phosphoramidates improves the systemic absorption of a nucleoside and furthermore, the phosphoramidate moiety of these "pronucleotides" is masked with neutral lipophilic groups to obtain a suitable partition coefficient to optimize uptake and transport into the cell dramatically enhancing the intracellular concentration of the nucleoside monophosphate analog relative to administering the parent nucleoside alone. Enzyme-mediated hydrolysis of the phosphate ester moiety produces a nucleoside monophosphate wherein the rate limiting initial phosphorylation is unnecessary. This concept has been demonstrated for certain compounds disclosed in US 2010/0016251. There, certain 2'-deoxy-2'-α-F-2'-β-C-methyluridine phosphoramidates are capable of being absorbed through the intestinal tract, and then, delivered to the liver where the phosphoramidate moiety is cleaved to produce a 2'-deoxy-2'-α-F-2'-β-C-methyluridine monophosphate. It is conceivable that the liver-directed phosphoramidate approach can be applied to actives other than the above-mentioned 2'-deoxy-2'-α-F-2'-β-C-methyluridine phosphoramidates. Such an approach would leverage the ability of the liver to metabolize the phosphoramidate moiety to the monophosphate and in the case of a non-nucleoside to lose the phosphate group ultimately releasing the active agent.

However, a potential complicating factor is that asymmetrically-substituted phosphoramidates can exist as either enantiomeric or diastereomeric mixtures. These mixtures may be purified to afford enantiomerically- or diastereomerically-enriched compositions, but the additional purification can increase overall costs for production of the phosphoramidate-derivatized active. In an effort to reduce and/or eliminate the potential complicating factor, a methodology has been developed to prepare enantiomerically- or diastereomerically-enriched phosphoramidate reagents, which may then be used as useful starting materials for the preparation of enantiomerically- or diastereomerically-enriched phosphoramidate-containing actives.

SUMMARY OF THE INVENTION

Disclosed herein is a process for preparing a composition comprising an enantiomerically- or a diastereomerically enriched phosphorus-containing active, salt, or pharmaceutically acceptable salt thereof, of formula I:

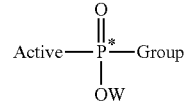

I which comprises reacting a protected or unprotected active with a composition comprising an enantiomerically- or a diastereomerically-enriched compound of formula II:

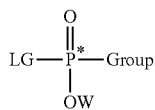

in the presence of a base; wherein Active comprises a functional group capable of forming a bond to P; Group, W, and LG are as defined herein.

Also disclosed herein is a composition comprising an enantiomerically- or diastereomerically-enriched phosphorus-containing active, salt, or pharmaceutically acceptable salt thereof, of formula I:

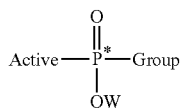

wherein Active comprises a functional group capable of forming a bond to P; Group and W are as defined herein.

Also disclosed herein is a process for preparing an enantiomerically- or a diastereomerically enriched phosphorus-containing active, salt, or pharmaceutically acceptable salt thereof, of formula III:

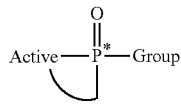

which comprises reacting a protected or unprotected active with a compound of formula IV:

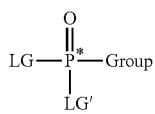

in the presence of a base
wherein Active comprises at least two functional groups capable of forming a bond to P; Group is as defined herein; and each of LG and LG', independent of one another, is a leaving group.

Disclosed herein is a phosphorus-containing active, salt, or pharmaceutically acceptable salt thereof, of formula III:

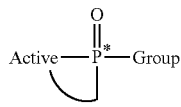

wherein Active comprises at least two functional groups capable of forming a bond to P; and Group is as defined herein.

Also disclosed herein is a composition comprising an enantiomerically- or a diastereomerically-enriched compound, hydrate, solvate, salt, or combinations thereof, represented by the formula II:

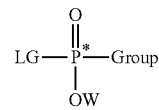

wherein LG, Group, and W are as defined herein.

DETAILED DESCRIPTION OF THE INVENTION

Definitions

Figure 1A:
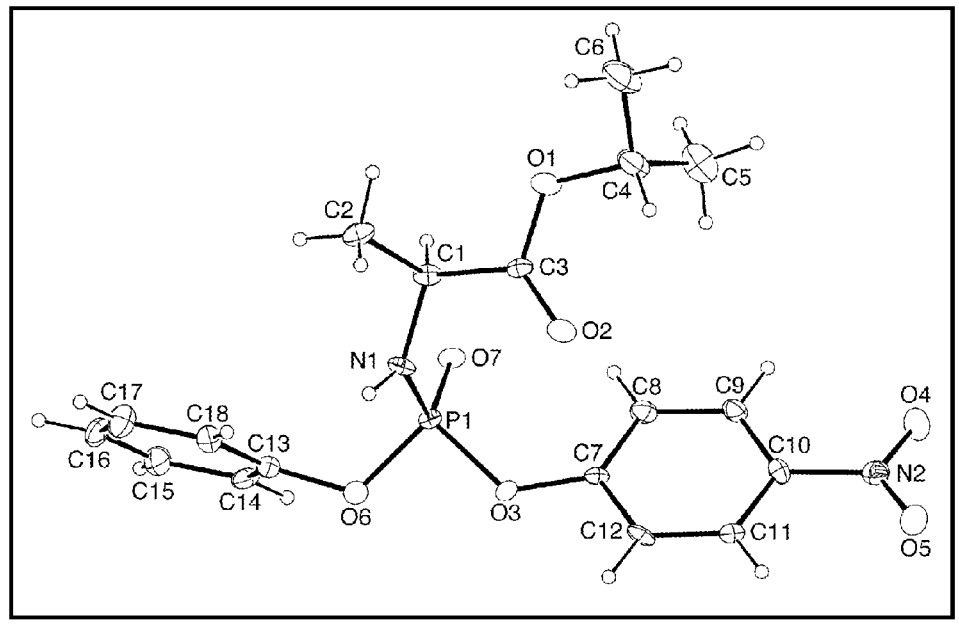
FIG. 1: (A) ORTEP drawing of molecule no. 1 109 of the asymmetric unit with 30% probability thermal ellipsoids. (B) ORTEP drawing of molecule no. 2 109 of the asymmetric unit with 30% probability thermal ellipsoids.

The phrase "a" or "an" entity as used herein refers to one or more of that entity; for example, a compound refers to one or more compounds or at least one compound. As such, the terms "a" (or "an"), "one or more", and "at least one" can be used interchangeably herein.

The terms "optional" or "optionally" as used herein means that a subsequently described event or circumstance may but need not occur, and that the description includes instances where the event or circumstance occurs and instances in which it does not. For example, "optional bond" means that the bond may or may not be present, and that the description includes single, double, or triple bonds.

The term "about" (also represented by ~) means that the recited numerical value is part of a range that varies within standard experimental error.

The term "P*" means that the phosphorus atom is chiral and that it has a corresponding Cahn-Ingold-Prelog designation of "R" or "S" which have their accepted plain meanings.

The terms "enantiomerically-enriched" and "diastereomerically-enriched," as used herein refer to an instance where, due to the chirality at phosphorus, the mole amount of one enantiomer or diastereomer ($R_P$ or $S_P$) exceeds the mole amount of the other enantiomer or disasteremoer ($S_P$ or $R_P$). Recognizing that the phosphorus atom in a compound of formula I, a compound of formula II, a compound of formula III is chiral, one of ordinary skill will understand that a composition, comprised of a compound of formula I, a compound of formula II or a compound of formula III, comprises a mixture of enantiomers (when the substituents Active/Group, ArO, and LG lack chirality) or a mixture of diastereomers (when at least one substituent Active/Group, ArO, and LG possesses chirality).

Thus, "enantiomerically-enriched" or "diastereomerically-enriched" as used herein, embraces a composition having at least about 51 mol % of one enantiomer or one diastereomer ($R_P$ or $S_P$) and at most about 49 mol % of the other enantiomer or the other diastereomer ($S_P$ or $R_P$). Within this meaning, "enantiomerically-enriched" or "diastereomerically-enriched" includes a composition comprised of about 51 mol % to about 100 mol %, and all integers inbetween, of one enantiomer or one diastereomer ($R_P$ or $S_P$) and about 49 mol % to about 0 mol %, and all integers inbetween, of the other enantiomer or the other diastereomer ($S_P$ or $R_P$). Also within this meaning, "enantiomerically-enriched" or "diastereomerically-enriched" includes a composition comprised of about at least about 60 mol % of one enantiomer or one diastereomer to about 40 mol % of the other enantiomer or the other diastereomer, about 70 mol % of one enantiomer or one diastereomer to about 30 mol % of the other enantiomer or the other diastereomer, about 80 mol % of one enantiomer or one diastereomer to about 20 mol % of the other enantiomer or the other diastereomer, about 90 mol % of one enantiomer or one diastereomer to about 10 mol % of the other enantiomer or the other diastereomer, about 95 mol % of one enantiomer or one diastereomer to about 5 mol % of the other enantiomer or the other diastereomer, about 96 mol % of one enantiomer or one diastereomer to about 4 mol % of the other enantiomer or the other diastereomer, about 97 mol % of one enantiomer or one diastereomer to about 3 mol % of the other enantiomer or the other diastereomer, about 98 mol % of one enantiomer or one diastereomer to about 2 mol % of the other enantiomer or the other diastereomer, about 99 mol % of one enantiomer or one diastereomer to about 1 mol % of the other enantiomer or the other diastereomer, about 99.5 mol % of one enantiomer or one diastereomer to about 0.5 mol % of the other enantiomer or the other diastereomer, about 99.8 mol % of one enantiomer or one diastereomer to about 0.2 mol % of the other enantiomer or the other diastereomer, about 99.9 mol % of one enantiomer or one diastereomer to about 0.1 mol % of the other enantiomer or the other diastereomer, and about 99.99 mol % of one enantiomer or one diastereomer to about 0.01 mol % of the other enantiomer or the other diastereomer.

The term "purified," as described herein, refers to the purity of a given compound. For example, a compound is "purified" when the given compound is a major component of the composition, i.e., at least 50% w/w pure. Thus, "purified" embraces at least 50% w/w purity, at least 60% w/w purity, at least 70% purity, at least 80% purity, at least 85% purity, at least 90% purity, at least 92% purity, at least 94% purity, at least 96% purity, at least 97% purity, at least 98% purity, at least 99% purity, at least 99.5% purity, and at least 99.9% purity, wherein "substantially pure" embraces at least 97% purity, at least 98% purity, at least 99% purity, at least 99.5% purity, and at least 99.9% purity.

The term "substantially anhydrous" means that a substance contains at most 10% by weight of water, at most 1% by weight of water, at most 0.5% by weight of water, or at most 0.1% by weight of water.

The term "halo" or "halogen" as used herein, includes chloro, bromo, iodo and fluoro.

The term "blocking group" or "protecting group" which is derived from a "protecting compound," refers to a chemical protecting group which has its plain and ordinary meaning, i.e., at least one protecting or blocking group is bound to at least one functional group (e.g., —OH, —NH$_2$, etc.) that allows chemical modification of an unprotected part of a compound. The group must react selectively in good yield to give a protected substrate that is stable to the projected reactions (see Protective Groups in Organic Synthesis, 3$^{rd}$ ed. T. W. Greene and P. G. M. Wuts, John Wiley & Sons, New York, N.Y., 1999). Examples of groups include, but are not limited to: benzoyl, acetyl, phenyl-substituted benzoyl, tetrahydropyranyl, trityl, DMT (4,4'-dimethoxytrityl), MMT (4-monomethoxytrityl), trimethoxytrityl, pixyl(9-phenylxanthen-9-yl) group, thiopixyl (9-phenylthioxanthen-9-yl) or 9-(p-methoxyphenyl)xanthine-9-yl (MOX), etc.; C(O)-alkyl, C(O)Ph, C(O)aryl, C(O)O(C$_{1-6}$alkyl), C(O)O(C$_{1-6}$alkylene) aryl (e.g., —C(O)OCH$_2$Ph), C(O)Oaryl, CH$_2$O-alkyl, CH$_2$O-aryl, SO$_2$-alkyl, SO$_2$-aryl, a protecting group comprising at least one silicon atom, such as, tert-butyldimethylsilyl, tert-butyldiphenylsilyl, Si(C$_{1-6}$alkyl)$_2$OSi(C$_{1-6}$alkyl)$_2$OH (such as, —Si($^i$Pr)$_2$OSi($^i$Pr)$_2$OH). Acetals, such as MOM or THP and the like are considered possible groups. Fluorinated compounds are also contemplated insofar that they can be attached to the compound and can be selectively removed by passing through a fluorous solid phase extraction media (e.g., FluoroFlash®). A specific example includes a fluorinated trityl analog, trityl analog 1-[4-(1H,1H,2H,2H-perfluorodecyl)phenyl]-1,1-diphenylmethanol. Other fluorinated analogs of trityl, BOC, FMOC, CBz, etc. are also contemplated. Sulfonyl chlorides like p-toluenesulfonyl chloride can react selectively on the 5' position. Esters could be formed selectively such as acetates and benzoates. Dicarboxylic anhydrides such as succinic anhydride and its derivatives can be used to generate an ester linkage with a free carboxylic acid, such examples include, but are not limited to oxalyl, malonyl, succinyl, glutaryl, adipyl, pimelyl, superyl, azelayl, sebacyl, phthalyl, isophthalyl, terephthalyl, etc. The free carboxylic acid increases the polarity dramatically and can also be used as a handle to extract the reaction product into mildly basic aqueous phases such as sodium bicarbonate solutions. The phosphoramidate group is relatively stable in acidic media, so groups requiring acidic reaction conditions, such as, tetrahydropyranyl, could also be used.

The term "protecting compound," as used herein and unless otherwise defined, refers to a compound that contains a "protecting group" and that is capable of reacting with a compound that contains functional groups that are capable of being protected.

The term "leaving group", as used herein, has the same meaning to the skilled artisan (Advanced Organic Chemistry: reactions, mechanisms and structure—Fourth Edition by Jerry March, John Wiley and Sons Ed.; 1992 pages 351-357) and represents a group which is part of and attached to a substrate molecule; in a reaction where the substrate molecule undergoes a displacement reaction (with for example a nucleophile), the leaving group is then displaced. Examples of leaving groups include, but are not limited to: halogen (F, Cl, Br, and I), Cl, Br, or I; tosylate, mesylate, triflate, acetate, trifluoromethylacetate, camphorsulfonate, 2-thioxobenzo[d]thiazol-3(2H)-yl, aryloxide, and aryloxide substituted with at least one electron withdrawing group. The term "electron withdrawing group" is accorded its plain meaning Examples of an aryloxide substituted with at least one electron withdrawing group include, but are not limited to, 2-nitrophenoxide, 4-nitrophenoxide, 2,4-dinitrophenoxide, pentafluorophenoxide, 2-chloro-4-nitrophenoxide; 2,4-dichlorophenoxide; and 2,4,6-trichlorophenoxide, etc. Examples of electron withdrawing groups include, but are not limited to, a halogen (F, Cl, Br, or I), —NO$_2$, —CN, —C(O) (C$_{1-6}$alkyl), —C(O)(aryl), —C(O)O(C$_{1-6}$alkyl), —C(O)O (aryl), etc.

The term "base" embraces the term "basic reagent" and is meant to be a compound that is capable of deprotonating a proton-containing compound, e.g., a Brønsted base. In addition to the examples recited above, further examples of a base include, but are not limited to pyridine, collidine, 2,6-(C$_{1-6}$alkyl)-pyridine, dimethyl-aniline, imidazole, N-methyl-imidazole, pyrazole, N-methyl-pyrazole, triethylamine, diisopropylethylamine, etc.

The term "basic reagent", as used herein, means a compound that is capable of deprotonating a hydroxyl group or an amino group. Examples of basic reagents include, but are not limited to, a ($C_{1-6}$alkyl)oxide (($C_{1-6}$alkyl)OM) in combination with an alcoholic solvent, where ($C_{1-6}$alkyl)oxides include, but are not limited to, MeO⁻, EtO⁻, $^n$PrO⁻, $^i$PrO⁻, $^t$BuO⁻, $^i$AmO-(iso-amyloxide), etc., and where M is an alkali metal cation, such as Li⁺, Na⁺, K⁺, etc. Alcoholic solvents include ($C_{1-6}$alkyl)OH, such as, for example, MeOH, EtOH, $^n$PrOH, $^i$PrOH, $^t$BuOH, $^i$AmOH, etc. Non-alkoxy bases can also be used such as sodium hydride, sodium hexamethyldisilazane, lithium hexamethyldisilazane, lithium diisopropylamide, calcium hydride, sodium carbonate, potassium carbonate, cesium carbonate, DBU, DBN, Grignard reagents, such as ($C_{1-6}$alkyl)Mg(halogen), which include but are not limited to MeMgCl, MeMgBr, $^t$BuMgCl, $^t$BuMgBr, etc.

The term "non-nucleophilic base" means a compound that is capable of acting as a Brønsted base, but has low nucleophilicity. Examples of non-nucleophilic bases include, but are not limited to, potassium carbonate, cesium carbonate, di-isopropylamine, di-isopropylethylamine, triethylamine, quinuclidine, naphthalene-1,8-diamine, 2,2,6,6-tetramethylpiperidine, 1,8-diazabicycloundec-7-ene, 4-dimethylamino-pyridine, pyridine, a 2,6-di-C1-6-alkyl-pyridine, a 2,4,6-tri-C1-6-alkyl-pyridine, 1,5-diazabicyclo[4.3.0]non-5-ene, and 1,4-diazabicyclo[2.2.2]octane.

The term "alkyl" refers to an unbranched or branched chain, saturated, monovalent hydrocarbon residue containing 1 to 30 carbon atoms. The term "$C_{1-M}$alkyl" refers to an alkyl comprising 1 to M carbon atoms, where M is an integer having the following values: 2, 3, 4, 5, 6, 7, 8, 9, 10, 11, 12, 13, 14, 15, 16, 17, 18, 19, 20, 21, 22, 23, 24, 25, 26, 27, 28, 29, or 30. The term "$C_{1-20}$alkyl" as used herein refers to an alkyl comprising 1 to 20 carbon atoms. The term "$C_{1-10}$alkyl" as used herein refers to an alkyl comprising 1 to 10 carbons. The term "$C_{1-6}$alkyl" denotes a straight or branched chain hydrocarbon residue comprising 1 to 6 carbon atoms. Examples of $C_{1-6}$alkyl groups include, but are not limited to, methyl, ethyl, propyl, i-propyl, n-butyl, i-butyl, t-butyl or pentyl, isopentyl, neopentyl, and hexyl. The term "$C_{1-4}$alkyl" refers to an alkyl containing 1 to 4 carbon atoms. Examples of alkyl groups include, but are not limited to, methyl, ethyl, propyl, i-propyl, n-butyl, i-butyl, t-butyl or pentyl, isopentyl, neopentyl, hexyl, heptyl, and octyl. The term (ar)alkyl or (heteroaryl)alkyl indicate the alkyl group is optionally substituted by an aryl or a heteroaryl group respectively.

The terms "alkaryl" or "alkylaryl" refer to an alkyl group with an aryl substituent, such as benzyl. The term "$C_{1-6}$alkaryl" or "$C_{1-6}$alkylaryl" refer to a $C_{1-6}$alkyl group with an aryl substituent, such as benzyl. The terms "aralkyl" or "arylalkyl" refer to an aryl group with an alkyl substituent, such as tolyl, xylyl, mesityl, etc.

The term "cycloalkyl" refers to an unsubstituted or substituted carbocycle, in which the carbocycle contains 3 to 10 carbon atoms; 3 to 8 carbon atoms ($C_{3-8}$cycloalkyl); 3 to 7 carbon atoms ($C_{3-7}$cycloalkyl); 3 to 6 carbon atoms ($C_{3-6}$cycloalkyl). Examples of cycloalkyl groups include, but are not limited to, cyclopropyl, 2-methyl-cyclopropyl, cyclobutyl, cyclopentyl, cycloheptyl, or cyclooctyl. Examples of a $C_{3-7}$cycloalkyl and a $C_{3-6}$cycloalkyl include, but are not limited to, cyclopropyl ($^c$Pr), 2-methyl-cyclopropyl, etc., cyclobutyl ($^c$Bu), 2-methyl-cyclobutyl, 3-methyl-cyclobutyl, etc., cyclopentyl ($^c$Pn), 2-methyl-cyclopentyl, 3-methyl-cyclopentyl, 4-methyl-cyclopentyl, etc., cyclohexyl ($^c$Hx), cycloheptyl ($^c$Hp) etc.

The term "alkenyl" refers to an unsubstituted hydrocarbon chain radical having from 2 to 10 carbon atoms having one or two olefinic double bonds, preferably one olefinic double bond. The term "$C_{2-N}$alkenyl" refers to an alkenyl comprising 2 to N carbon atoms, where N is an integer having the following values: 3, 4, 5, 6, 7, 8, 9, or 10. The term "$C_{2-10}$alkenyl" refers to an alkenyl comprising 2 to 10 carbon atoms. The term "$C_{2-4}$alkenyl" refers to an alkenyl comprising 2 to 4 carbon atoms. Examples include, but are not limited to, vinyl, 1-propenyl, 2-propenyl (allyl) or 2-butenyl (crotyl).

The term "aryl," as used herein, and unless otherwise specified, refers to substituted or unsubstituted phenyl (Ph), biphenyl, or naphthyl, preferably the term aryl refers to substituted or unsubstituted phenyl. The aryl group can be substituted with one or more moieties selected from among hydroxyl, F, Cl, Br, I, amino, alkyl, cycloalkyl, alkylamino, arylamino, alkoxy, alkenyl, aryl, aryloxy, nitro, cyano, sulfonic acid, sulfate, phosphonic acid, phosphate, and phosphonate, either unprotected, or protected as necessary, as known to those skilled in the art, for example, as taught in T. W. Greene and P. G. M. Wuts, "Protective Groups in Organic Synthesis," 3rd ed., John Wiley & Sons, 1999.

The term "aryloxide" ("—OAr") as used herein, and unless otherwise specified, refers to substituted or unsubstituted phenoxide (PhO—), p-phenyl-phenoxide (p-Ph-PhO—), or naphthoxide, preferably the term aryloxide refers to substituted or unsubstituted phenoxide. The aryloxide group can be substituted with one or more moieties selected from among hydroxyl, F, Cl, Br, I, —C(O)($C_{1-6}$alkyl), —C(O)O($C_{1-6}$alkyl), amino, alkyl, cycloalkyl, alkylamino, arylamino, alkoxy, alkenyl, aryl, aryloxy, nitro, cyano, sulfonic acid, sulfate, phosphonic acid, phosphate, and phosphonate, either unprotected, or protected as necessary, as known to those skilled in the art, for example, as taught in T. W. Greene and P. G. M. Wuts, "Protective Groups in Organic Synthesis," 3rd ed., John Wiley & Sons, 1999.

The term "Active" as used herein refers to a compound capable of eliciting a biological response, which comprises at least one functional group capable of forming a bond to P. Examples of Actives include, but are not limited to, nucleosides, nucleoside-analogs, and non-nucleoside compounds.

Examples of nucleoside and nucleoside-analog actives include, but are not limited to:

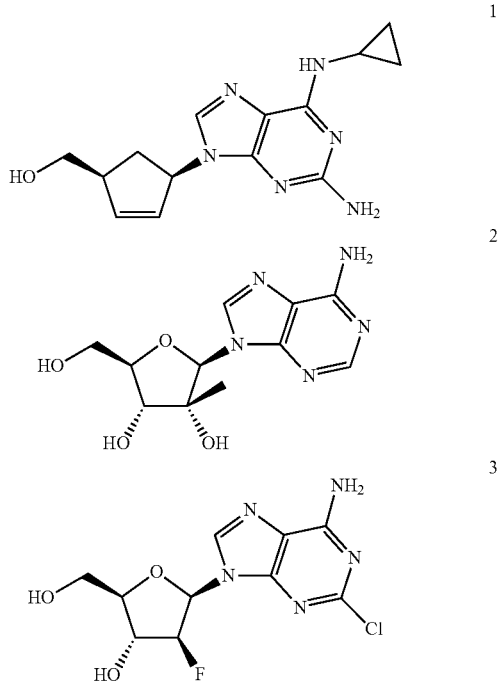

4
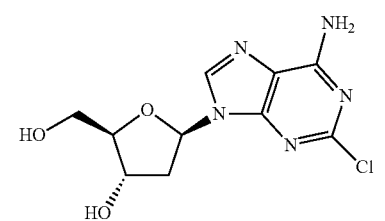
5
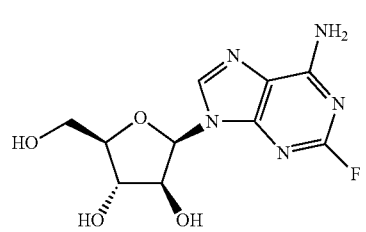
6
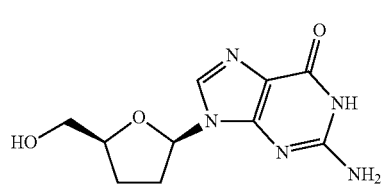
7
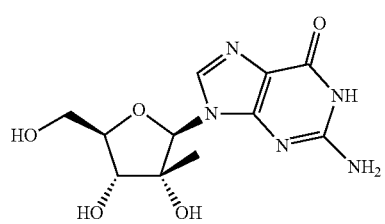
8
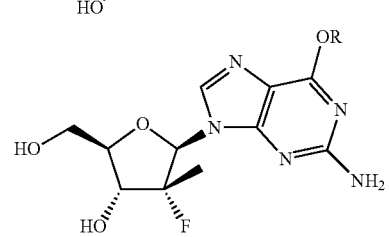
9a, R = Me
9b, R = Et
9c, R = ⁱPr
10
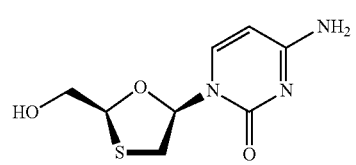
11
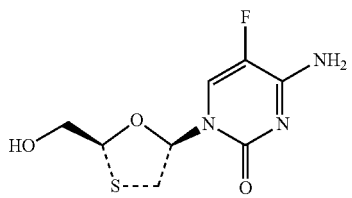
12
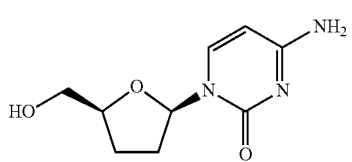
13
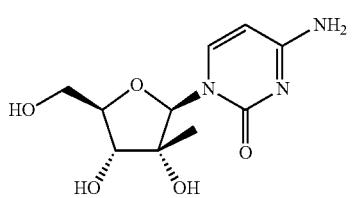
14
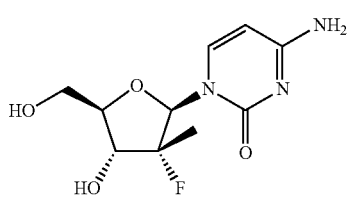
15
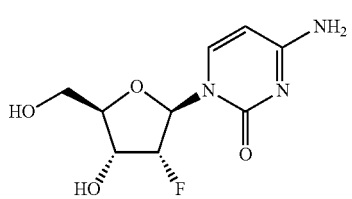
16
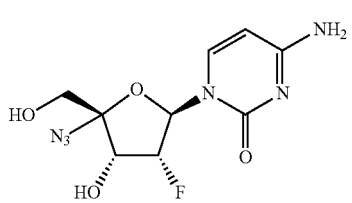
17
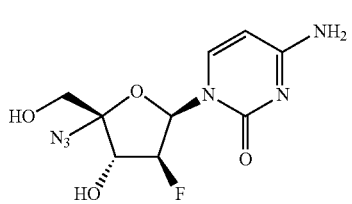
18
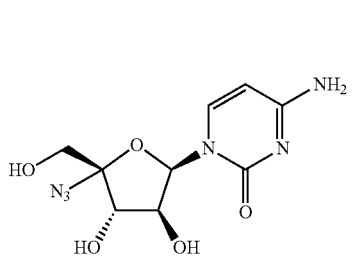

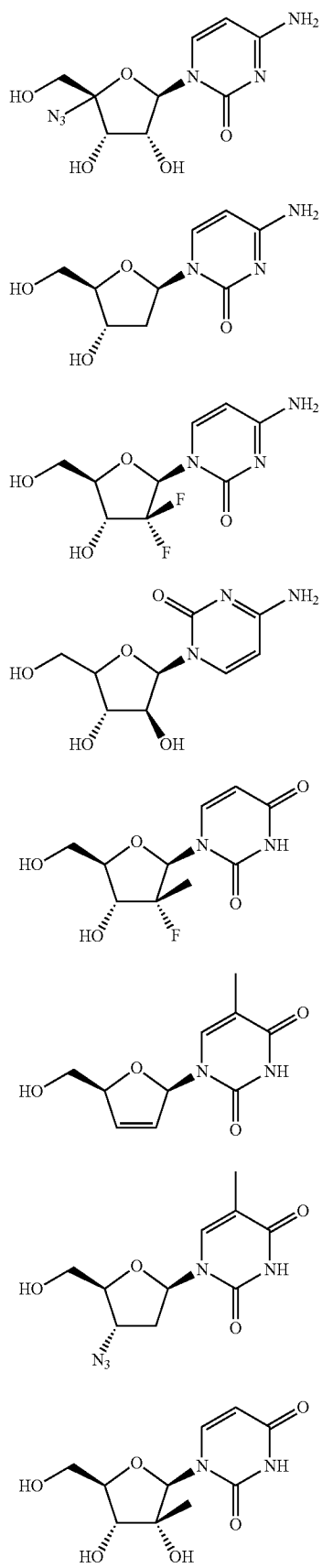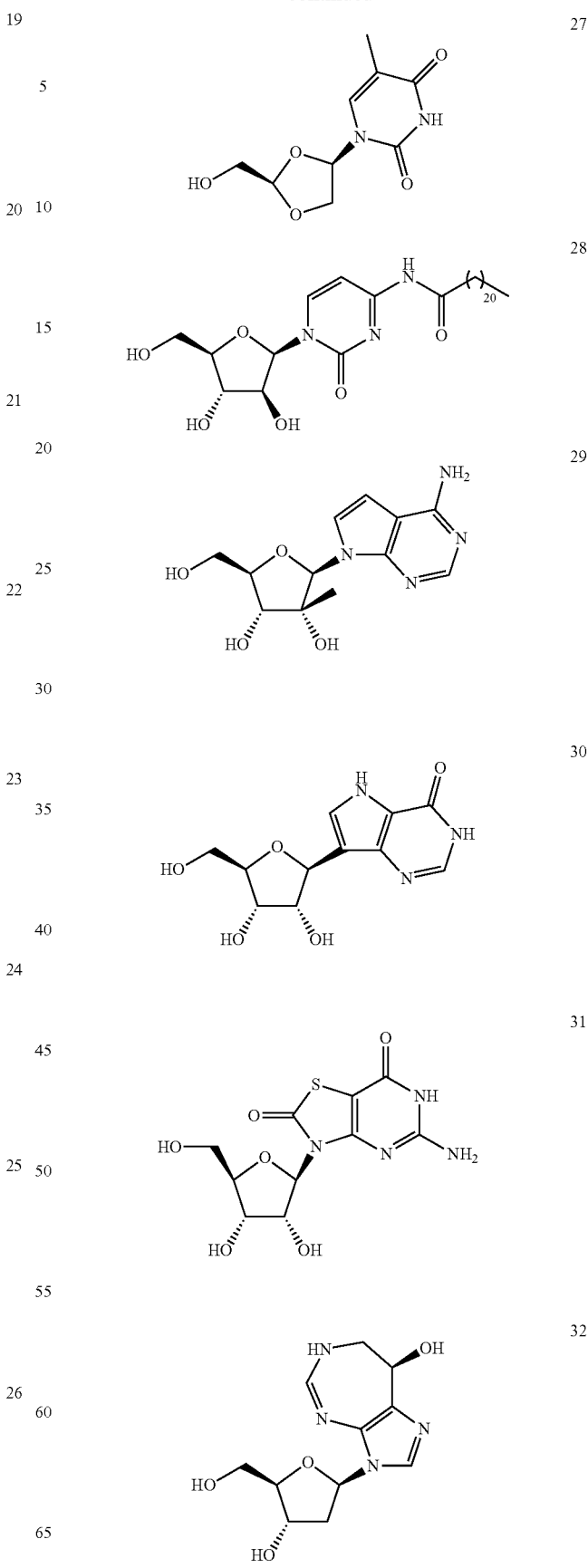

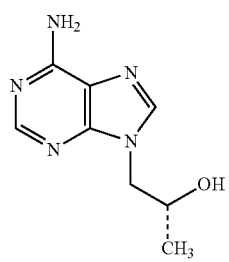
33a
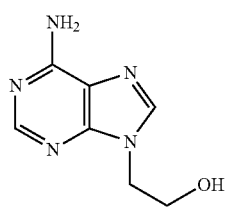
33b
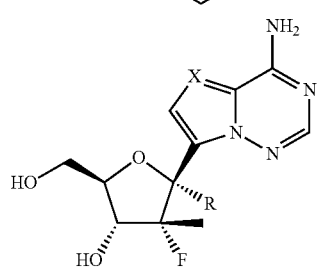
34a: R = H; X = CH
34b: R = CN; X = CH
34c: R = H; X = N
34d: R = CN; X = N
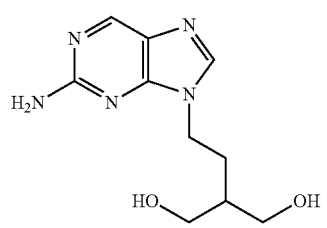
35
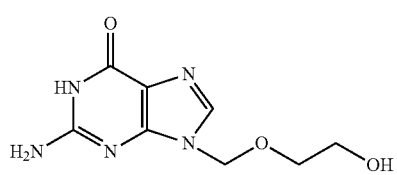
36
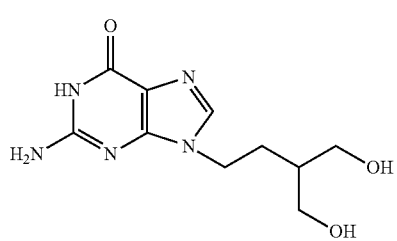
37
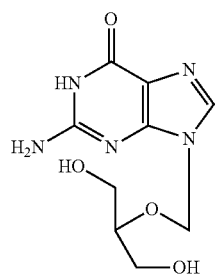
38
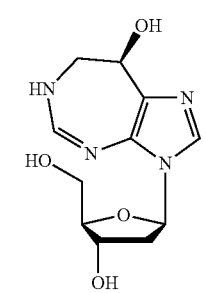
39
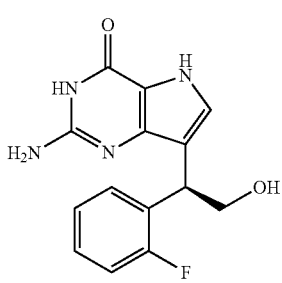
40
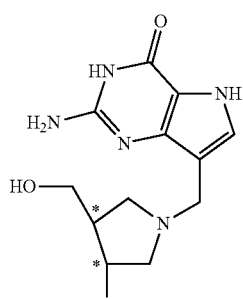
(S,S)-41
(R,R)-41
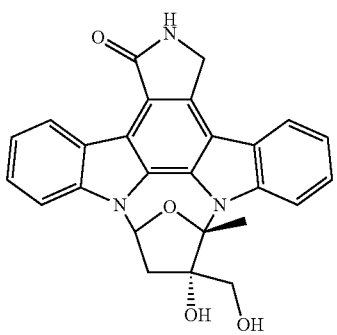
42

43
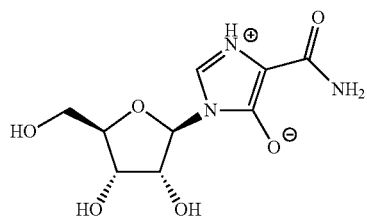
Examples of non-nucleoside actives include, but are not limited to:
44
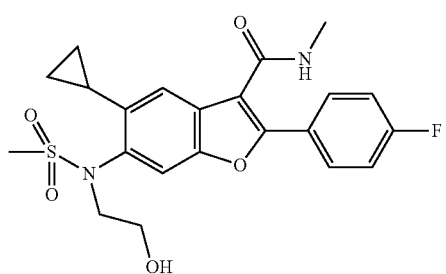
45
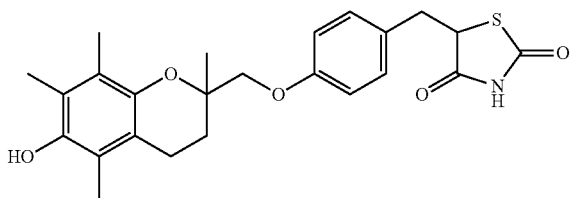
46
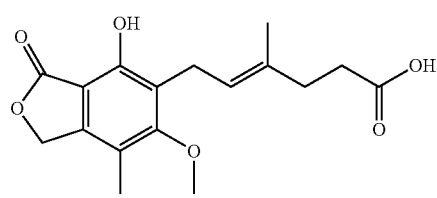
47
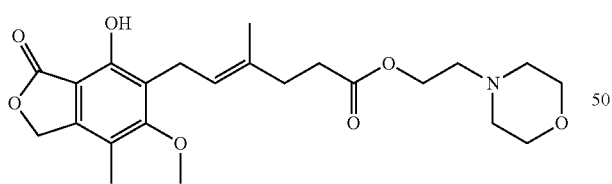
48
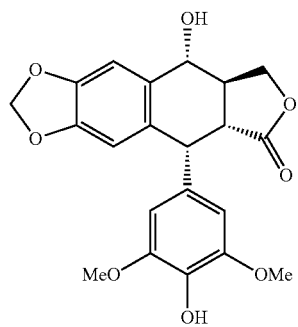
49
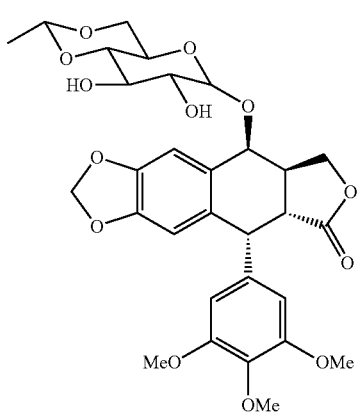
50
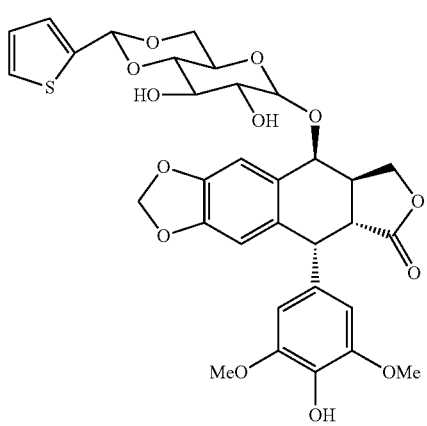
51
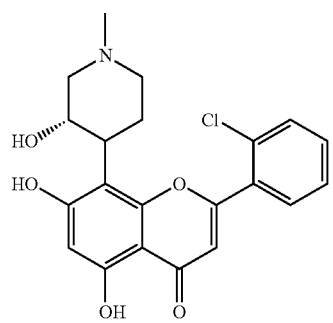
52
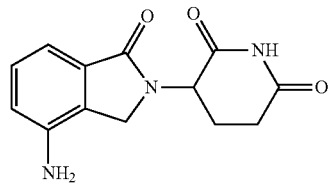
53
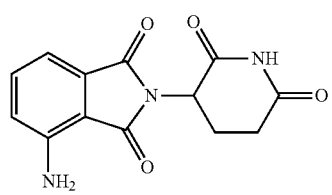

54
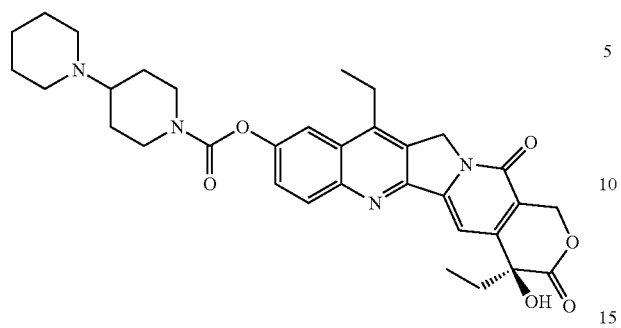
55
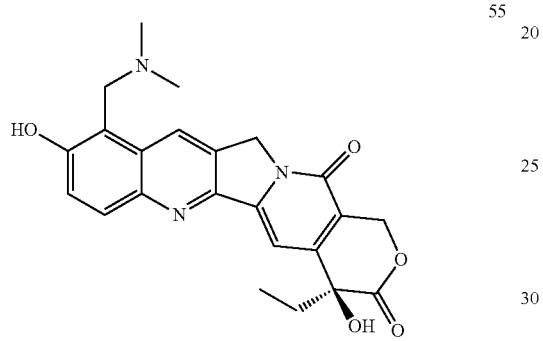
56
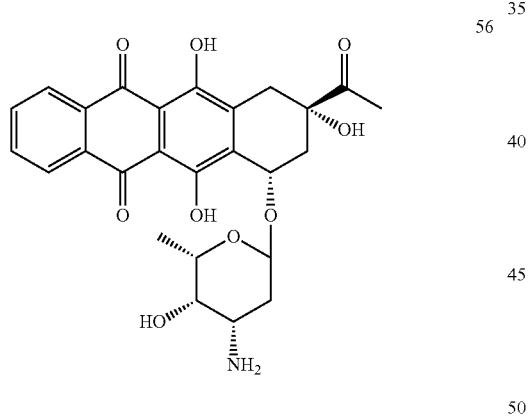
57
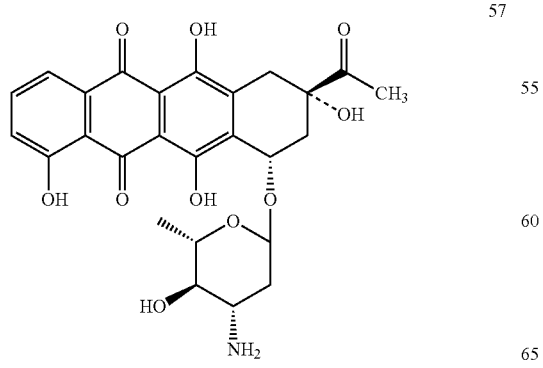
58
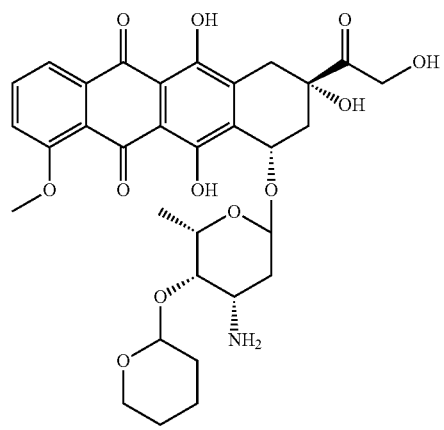
59
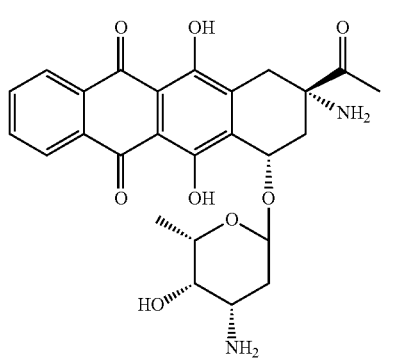
60
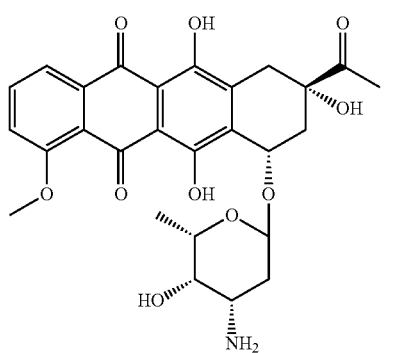
61
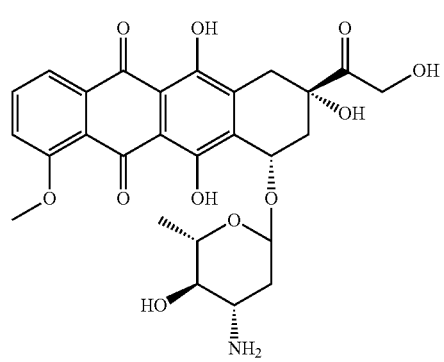

62
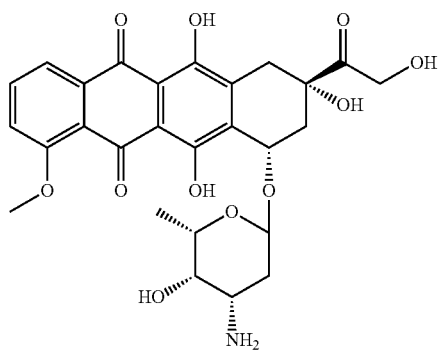
63
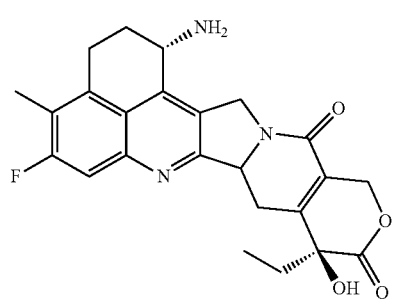
64
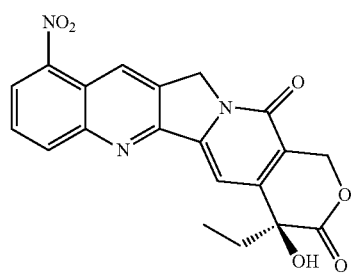
65
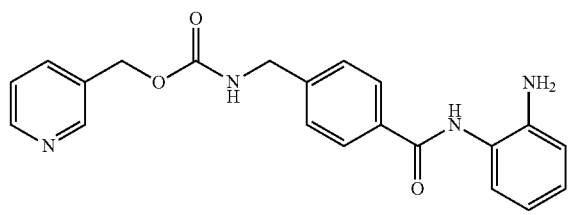
66
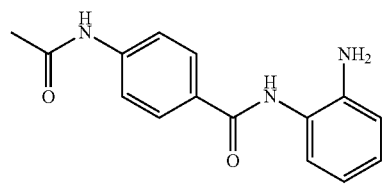
67
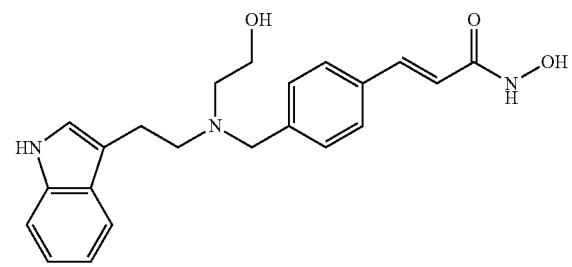
68
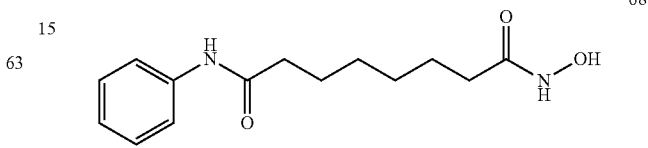
69
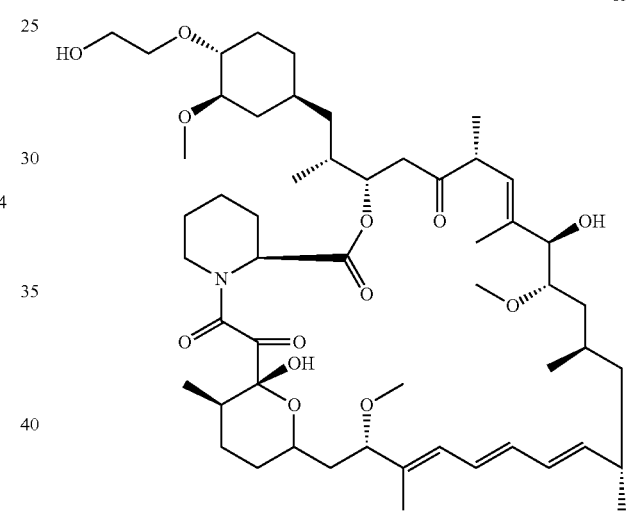
70
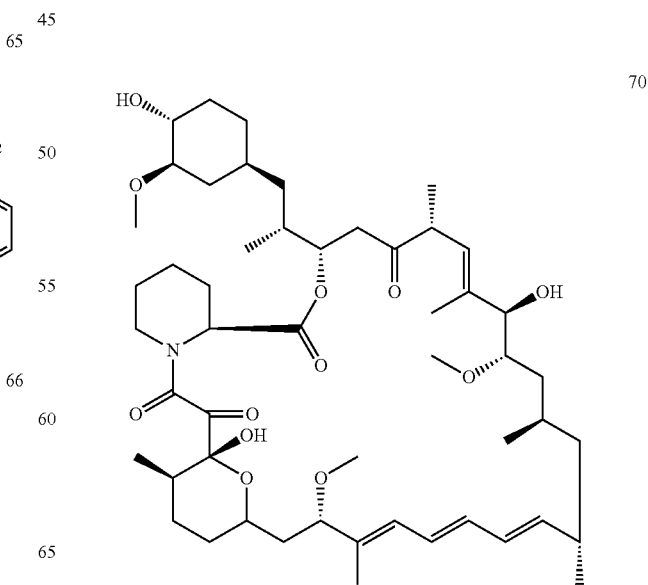

21
-continued
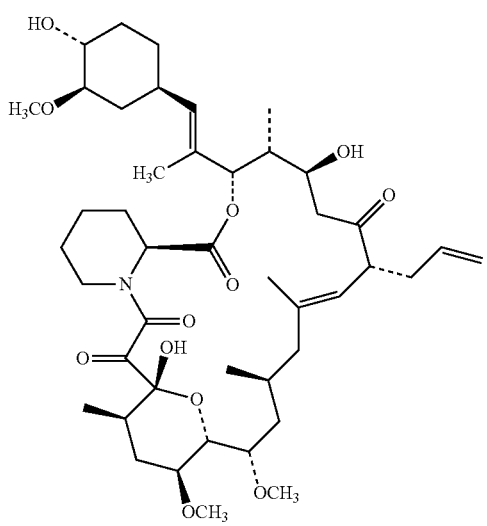
71
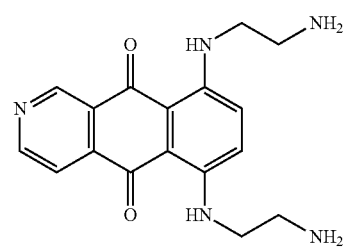
72
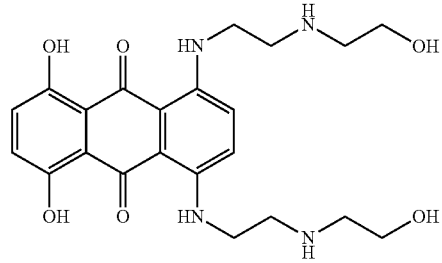
73
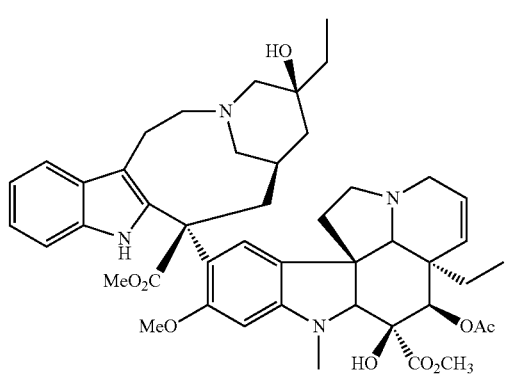
74
22
-continued
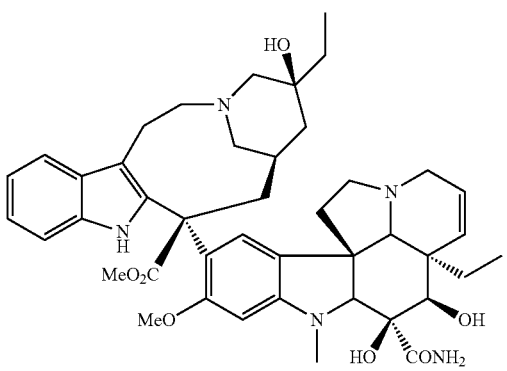
75
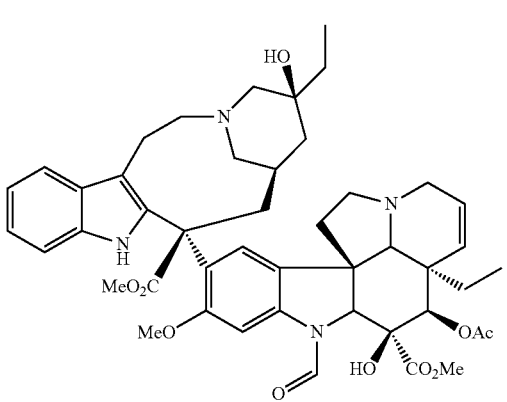
76
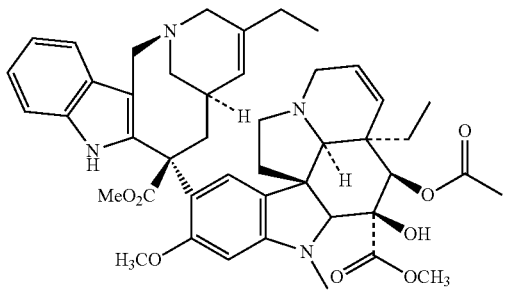
77
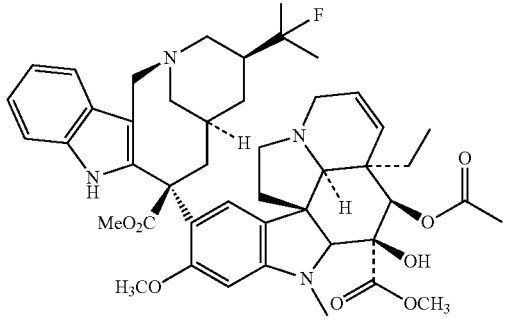
78

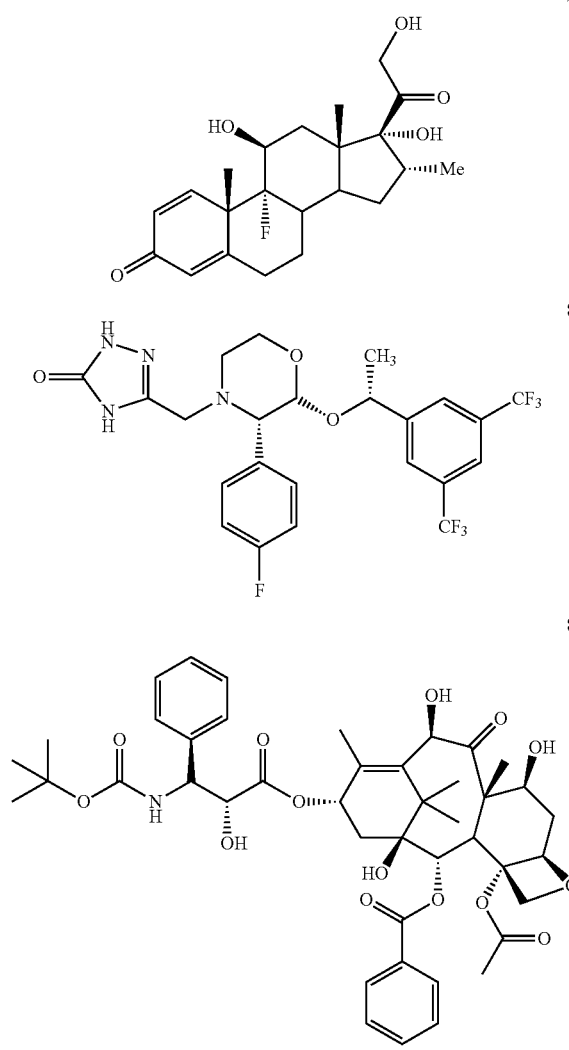
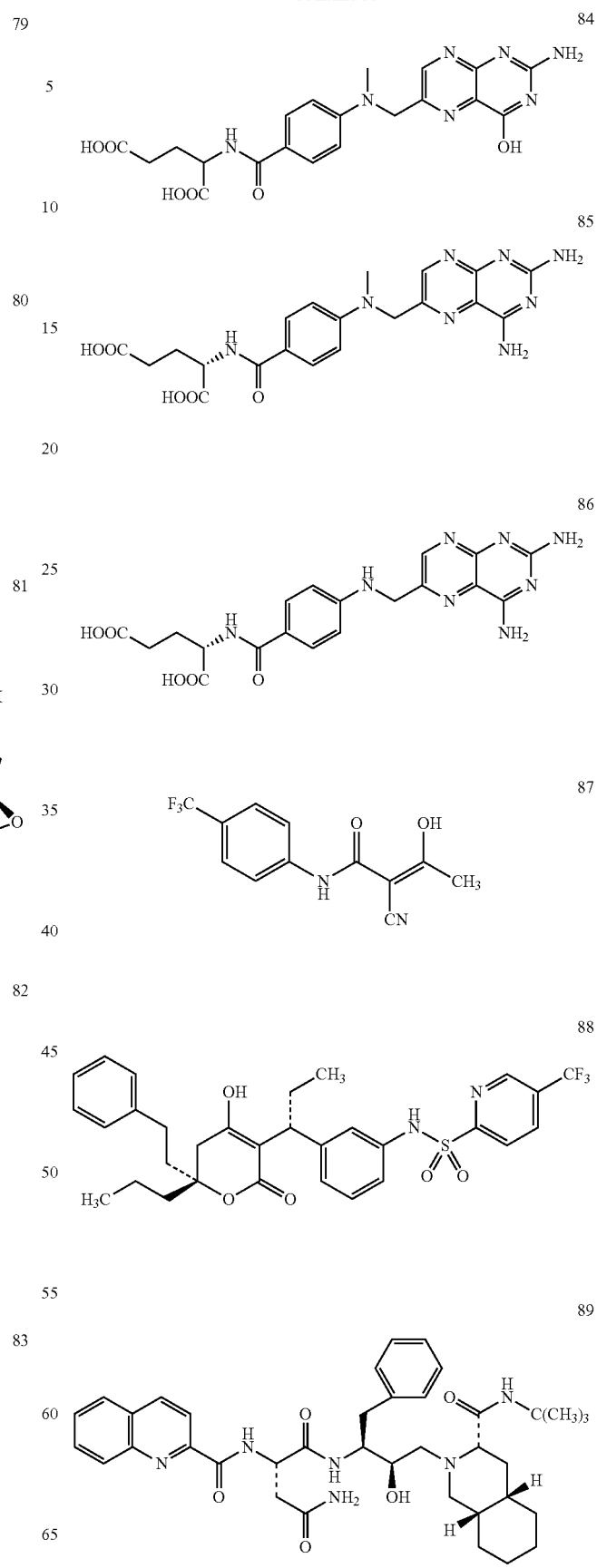

-continued

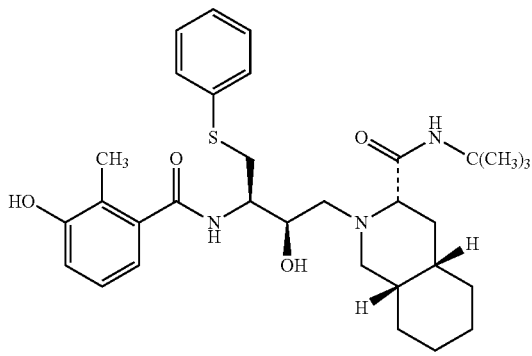

90

The term "protected active" as used herein refers to an active that comprises a blocking (or protecting) group. As a "protected active" is useful for preparing compound I or compound II, it is contemplated that said protected active is an embodiment of the disclosed invention and that said embodiment covers at least the following compounds.

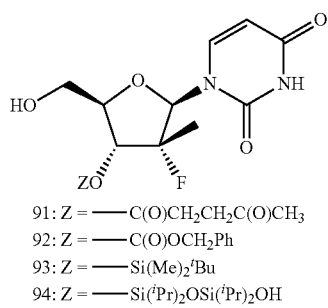

91: Z = ——C(O)CH$_2$CH$_2$C(O)CH$_3$
92: Z = ——C(O)OCH$_2$Ph
93: Z = ——Si(Me)$_2$$^t$Bu
94: Z = ——Si($^i$Pr)$_2$OSi($^i$Pr)$_2$OH

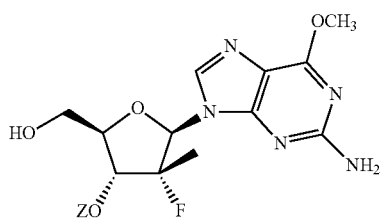

95: Z = ——C(O)CH$_2$CH$_2$C(O)CH$_3$
96: Z = ——C(O)OCH$_2$Ph
97: Z = ——Si(Me)$_2$$^t$Bu
98: Z = ——Si($^i$Pr)$_2$OSi($^i$Pr)$_2$OH

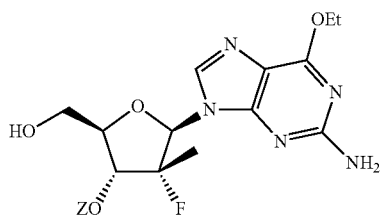

99: Z = ——C(O)CH$_2$CH$_2$C(O)CH$_3$
100: Z = ——C(O)OCH$_2$Ph
101: Z = ——Si(Me)$_2$$^t$Bu
102: Z = ——Si($^i$Pr)$_2$OSi($^i$Pr)$_2$OH

-continued

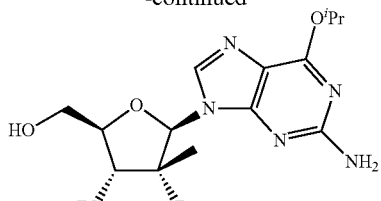

103: Z = ——C(O)CH$_2$CH$_2$C(O)CH$_3$
104: Z = ——C(O)OCH$_2$Ph
105: Z = ——Si(Me)$_2$$^t$Bu
106: Z = ——Si($^i$Pr)$_2$OSi($^i$Pr)$_2$OH

The term "Group" as defined herein is hydrolyzable group meaning that when compound I or compound II is ingested the group is hydrolyzed, either enzymatically or non-enzymatically. The term "group precursor" as used herein is a parent compound, existing as its salt, hydrate, or salt/hydrate thereof, of the Group. Examples of a Group include, but are not limited to, a radical comprising an amine (e.g., benzylamine) or an amine further comprising a chiral center, which includes, but is not limited to an amino acid or an R- or S-α-methylbenzylamine.

The term "amino acid" includes naturally occurring and synthetic α, β, γ, or δ amino acids, and includes but is not limited to, amino acids found in proteins, i.e. glycine, alanine, valine, leucine, isoleucine, methionine, phenylalanine, tryptophan, proline, serine, threonine, cysteine, tyrosine, asparagine, glutamine, aspartate, glutamate, lysine, arginine and histidine. In a certain embodiment, the amino acid is in the L-configuration. Alternatively, the amino acid can be a derivative of alanyl, valinyl, leucinyl, isoleucinyl, prolinyl, phenylalaninyl, tryptophanyl, methioninyl, glycinyl, serinyl, threoninyl, cysteinyl, tyrosinyl, asparaginyl, glutaminyl, aspartoyl, glutaroyl, lysinyl, argininyl, histidinyl, β-alanyl, β-valinyl, β-leucinyl, β-isoleucinyl, β-prolinyl, β-phenylalaninyl, β-tryptophanyl, β-methioninyl, β-glycinyl, β-serinyl, β-threoninyl, β-cysteinyl, β-tyrosinyl, β-asparaginyl, β-glutaminyl, β-aspartoyl, β-glutaroyl, β-lysinyl, β-argininyl or β-histidinyl. When the term amino acid is used, it is considered to be a specific and independent disclosure of each of the alkyl, cycloalkyl, or alkaryl esters of α, β, γ, or δ glycine, alanine, valine, leucine, isoleucine, methionine, phenylalanine, tryptophan, proline, serine, threonine, cysteine, tyrosine, asparagine, glutamine, aspartate, glutamate, lysine, arginine and histidine in the D and L-configurations, as well as acid-addition salts. For example, reference to L-alanine is a specific and independent disclosure not only of the free acid, but of alkyl, cycloalkyl, or alkaryl esters of L-alanine or its acid-addition salts, as well as $C_{1-6}$alkyl, $C_{3-7}$cycloalkyl, and $C_{1-6}$alkaryl esters of L-alanine or its acid addition salts.

A solvent or anti-solvent (as used in reactions, crystallization, etc. or lattice and/or adsorbed solvents) includes at least one of a $C_1$ to $C_8$ alcohol, a $C_2$ to $C_8$ ether, a $C_3$ to $C_7$ ketone, a $C_3$ to $C_7$ ester, a $C_1$ to $C_2$ chlorocarbon, a $C_2$ to $C_7$ nitrile, a miscellaneous solvent, a $C_5$ to $C_{12}$ saturated hydrocarbon, and a $C_6$ to $C_{12}$ aromatic hydrocarbon.

The $C_1$ to $C_8$ alcohol refers to a straight/branched and/or cyclic/acyclic alcohol having such number of carbons. The $C_1$ to $C_8$ alcohol includes, but is not limited to, methanol, ethanol, n-propanol, isopropanol, isobutanol, hexanol, and cyclohexanol.

The $C_2$ to $C_8$ ether refers to a straight/branched and/or cyclic/acyclic ether having such number of carbons. The $C_2$ to $C_8$ ether includes, but is not limited to, dimethyl ether, diethyl ether, di-isopropyl ether, di-n-butyl ether, methyl-t-butyl ether (MTBE), tetrahydrofuran, and dioxane The $C_3$ to $C_7$ ketone refers to a straight/branched and/or cyclic/acyclic ketone having such number of carbons. The $C_3$ to $C_7$ ketone includes, but is not limited to, acetone, methyl ethyl ketone, propanone, butanone, methyl isobutyl ketone, methyl butyl ketone, and cyclohexanone.

The $C_3$ to $C_7$ ester refers to a straight/branched and/or cyclic/acyclic ester having such number of carbons. The $C_3$ to $C_7$ ester includes, but is not limited to, ethyl acetate, propyl acetate, n-butyl acetate, etc.

The $C_1$ to $C_2$ chlorocarbon refers to a chlorocarbon having such number of carbons. The $C_1$ to $C_2$ chlorocarbon includes, but is not limited to, chloroform, methylene chloride (DCM), carbon tetrachloride, 1,2-dichloroethane, and tetrachloroethane.

A $C_2$ to $C_7$ nitrile refers to a nitrile have such number of carbons. The $C_2$ to $C_7$ nitrile includes, but is not limited to, acetonitrile, propionitrile, etc.

A miscellaneous solvent refers to a solvent commonly employed in organic chemistry, which includes, but is not limited to, diethylene glycol, diglyme (diethylene glycol dimethyl ether), 1,2-dimethoxy-ethane, dimethylformamide, dimethylsulfoxide, ethylene glycol, glycerin, hexamethylphsphoramide, hexamethylphosphorous triame, N-methyl-2-pyrrolidinone, nitromethane, pyridine, triethyl amine, and acetic acid.

The term $C_5$ to $C_{12}$ saturated hydrocarbon refers to a straight/branched and/or cyclic/acyclic hydrocarbon. The $C_5$ to $C_{12}$ saturated hydrocarbon includes, but is not limited to, n-pentane, petroleum ether (ligroine), n-hexane, n-heptane, cyclohexane, and cycloheptane.

The term $C_6$ to $C_{12}$ aromatic refers to substituted and unsubstituted hydrocarbons having a phenyl group as their backbone. The term $C_6$ to $C_{12}$ aromatic includes, but is not limited to, benzene, xylene, toluene, chlorobenzene, o-xylene, m-xylene, p-xylene, xylenes, mesitylene, etc.

The term "salts," as described herein, refers to a compound comprising a cation and an anion, which can produced by the protonation of a proton-accepting moiety and/or deprotonation of a proton-donating moiety. It should be noted that protonation of the proton-accepting moiety results in the formation of a cationic species in which the charge is balanced by the presence of a physiological anion, whereas deprotonation of the proton-donating moiety results in the formation of an anionic species in which the charge is balanced by the presence of a physiological cation.

The term "HX," as used herein, refers a Brønsted acid in the form of an acid addition salt to a synthetic reagent. Examples of HX include, but are not limited to, HCl, HBr, p-toluenesulfonic acid, methanesulfonic acid, triflic acid, trifluoroacetic acid, etc.

The phrase "pharmaceutically acceptable salt" means a salt that is pharmaceutically acceptable. Examples of pharmaceutically acceptable salts include, but are not limited to: (1) acid addition salts, formed with inorganic acids such as hydrochloric acid, hydrobromic acid, sulfuric acid, nitric acid, phosphoric acid, and the like; or formed with organic acids such as glycolic acid, pyruvic acid, lactic acid, malonic acid, malic acid, maleic acid, fumaric acid, tartaric acid, citric acid, 3-(4-hydroxybenzoyl)benzoic acid, cinnamic acid, mandelic acid, methanesulfonic acid, ethanesulfonic acid, 1,2-ethanedisulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, lauryl sulfuric acid, gluconic acid, glutamic acid, salicylic acid, muconic acid, and the like or (2) basic addition salts formed with the conjugate bases of any of the inorganic acids listed above, wherein the conjugate bases comprise a cationic component selected from among $Na^+$, $K^+$, $Mg^{2+}$, $Ca^{2+}$, $NH_gR'''_{4-g}{}^+$, in which R''' is a $C_{1-3}$ alkyl and g is a number selected from among 0, 1, 2, 3, or 4. It should be understood that all references to pharmaceutically acceptable salts include solvent addition forms (solvates) or crystal forms (polymorphs) as defined herein, of the same acid addition salt.

The term "preparation" or "dosage form" is intended to include both solid and liquid formulations of the active compound and one skilled in the art will appreciate that an active ingredient can exist in different preparations depending on the desired dose and pharmacokinetic parameters.

The term "excipient" as used herein refers to a compound that is used to prepare a pharmaceutical composition, and is generally safe, non-toxic and neither biologically nor otherwise undesirable, and includes excipients that are acceptable for veterinary use as well as human pharmaceutical use.

Embodiments

A first embodiment is directed to a composition comprising an enantiomerically- or a diastereomerically-enriched phosphorus-containing active, salt, or pharmaceutically acceptable salt thereof, of formula I:

wherein Active comprises a functional group capable of forming a bond to P; Group is as defined herein; and W is an aryl or —$(CH_2)_nSC(O)C(CH_3)_m(CH_2OH)_{3-m}$, where n is 2 or 3 and m is 0, 1, 2, or 3.

A first aspect of the first embodiment is directed to a composition comprising an enantiomerically- or a diastereomerically-enriched phosphorus-containing active, salt, or pharmaceutically acceptable salt thereof, of formula I:

wherein Active comprises a nucleoside, nucleoside-analog, or non-nucleoside compound; Group is as defined herein; and W is an aryl or —$(CH_2)_nSC(O)C(CH_3)_m(CH_2OH)_{3-m}$, where n is 2 or 3 and m is 0, 1, 2, or 3.

A second aspect of the first embodiment is directed to a composition comprising an enantiomerically- or a diastereomerically-enriched phosphorus-containing active, salt, or pharmaceutically acceptable salt thereof, of formula I:

wherein Active comprises a nucleoside, nucleoside-analog, or non-nucleoside and Group is an N-amino-acyl having the following structure

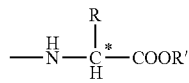

and W is an aryl or —(CH$_2$)$_n$SC(O)C(CH$_3$)$_m$(CH$_2$OH)$_{3-m}$, where n is 2 or 3 and m is 0, 1, 2, or 3.

A third aspect of the first embodiment is directed to a phosphorus-containing active, salt, or pharmaceutically acceptable salt thereof, of formula R$_P$-I-1 or S$_P$-I-1:

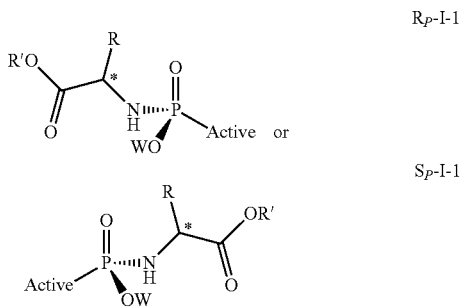

wherein Active comprises a nucleoside, nucleoside-analog, or non-nucleoside; W is an aryl or —(CH$_2$)$_n$SC(O)C(CH$_3$)$_m$(CH$_2$OH)$_{3-m}$, where n is 2 or 3 and m is 0, 1, 2, or 3; R is a substituent for an amino acid as defined herein; and R' is an alkyl or a cycloalkyl. Here, for purposes of illustration, it is assumed that the order of priority from highest to lowest is Active>ArO>P=O>NHCH(R)C(O)OR'.

A fourth aspect of the first embodiment is directed to a phosphorus-containing active, salt, or pharmaceutically acceptable salt thereof, of formula R$_P$-I-1 or S$_P$-I-1, wherein Active comprises a nucleoside, nucleoside-analog, or non-nucleoside; W is an aryl or —(CH$_2$)$_n$SC(O)C(CH$_3$)$_m$(CH$_2$OH)$_{3-m}$, where n is 2 or 3 and m is 0, 1, 2, or 3; R is an alkyl; and R' is an alkyl or a cycloalkyl.

A fifth aspect of the first embodiment is directed to a phosphorus-containing active, salt, or pharmaceutically acceptable salt thereof, of formula R$_P$-I-1 or S$_P$-I-1, wherein Active comprises a nucleoside, nucleoside-analog, or non-nucleoside; W is an aryl or —(CH$_2$)$_n$SC(O)C(CH$_3$)$_m$(CH$_2$OH)$_{3-m}$, where n is 2 or 3 and m is 0, 1, 2, or 3; R is a C$_{1-6}$alkyl; and R' is a C$_{1-6}$alkyl or a C$_{3-7}$cycloalkyl.

A sixth aspect of the first embodiment is directed to a phosphorus-containing active, salt, or pharmaceutically acceptable salt thereof, of formula R$_P$-I-1 or S$_P$-I-1, wherein Active comprises a nucleoside, nucleoside-analog, or non-nucleoside; W is an aryl or —(CH$_2$)$_n$SC(O)C(CH$_3$)$_m$(CH$_2$OH)$_{3-m}$, where n is 2 or 3 and m is 0, 1, 2, or 3; R is a C$_{1-6}$alkyl; and R' is a C$_{1-6}$alkyl or a C$_{3-7}$cycloalkyl; and wherein the stereochemistry of C—R is the same as a naturally occurring amino acid.

A seventh aspect of the first embodiment is directed to a phosphorus-containing active, salt, or pharmaceutically acceptable salt thereof, of formula R$_P$-I-1 or S$_P$-I-1, wherein Active comprises a nucleoside, nucleoside-analog, or non-nucleoside; W is an aryl or —(CH$_2$)$_n$SC(O)C(CH$_3$)$_m$(CH$_2$OH)$_{3-m}$, where n is 2 or 3 and m is 0, 1, 2, or 3; R is selected from among methyl, ethyl, and isopropyl; and R' is a selected from among, methyl, ethyl, isopropyl, neopentyl, cyclobutyl, cyclopentyl, and cyclohexyl; and wherein the stereochemistry of C—R is the same as a naturally occurring amino acid.

An eighth aspect of the first embodiment is directed to a phosphorus-containing active, salt, or pharmaceutically acceptable salt thereof, of formula R$_P$-I-1 or S$_P$-I-1, wherein Active comprises a nucleoside, nucleoside-analog, or non-nucleoside; W is a phenyl naphthalen-1-yl, or —(CH$_2$)$_2$SC(O)C(CH$_3$)$_2$(CH$_2$OH); R is selected from among methyl, ethyl, and isopropyl; and R' is a selected from among, methyl, ethyl, isopropyl, neopentyl, cyclobutyl, cyclopentyl, and cyclohexyl; and wherein the stereochemistry of C—R is the same as a naturally occurring amino acid.

A ninth aspect of the first embodiment is directed to a phosphorus-containing active, salt, or pharmaceutically acceptable salt thereof, of formula R$_P$-I-1 or S$_P$-I-1, wherein Active comprised of a nucleoside selected from among compounds 1-8, 10-13, 15-20, 22, 24-26, 28-32, 39, and 41-43, a nucleoside-analog selected from among compounds 33-38 and 40, or non-nucleoside compound selected from among compounds 44-90; W is a phenyl naphthalen-1-yl, or —(CH$_2$)$_2$SC(O)C(CH$_3$)$_2$(CH$_2$OH); R is selected from among methyl, ethyl, and isopropyl; and R' is a C$_{1-6}$alkyl or a C$_{3-7}$ cycloalkyl; and wherein the stereochemistry of C—R is the same as a naturally occurring amino acid.

A tenth aspect of the first embodiment is directed to a compound having the structure:

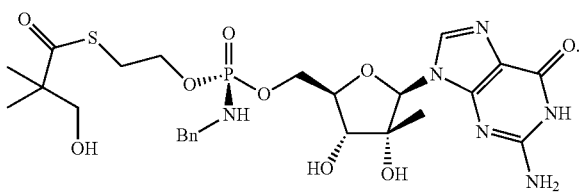 [SMILES: CC(C)(CO)C(=O)SCCO[P@@](=O)(NCc1ccccc1)OC[C@H]1O[C@@H](n2cnc3c(=O)[nH]c(N)nc32)[C@](C)(O)[C@@H]1O]

An eleventh aspect of the first embodiment is directed to a compound having the structure:

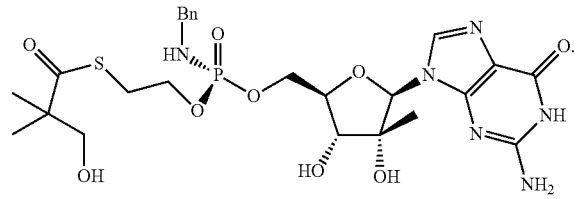 [SMILES: CC(C)(CO)C(=O)SCCO[P@](=O)(NCc1ccccc1)OC[C@H]1O[C@@H](n2cnc3c(=O)[nH]c(N)nc32)[C@](C)(O)[C@@H]1O]

A twelfth aspect of the first embodiment is directed to a compound having the structure:

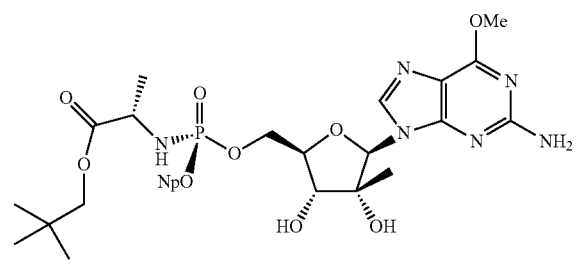

wherein Np represents naphthalen-1-yl.

A thirteenth aspect of the first embodiment is directed to a compound having the structure:

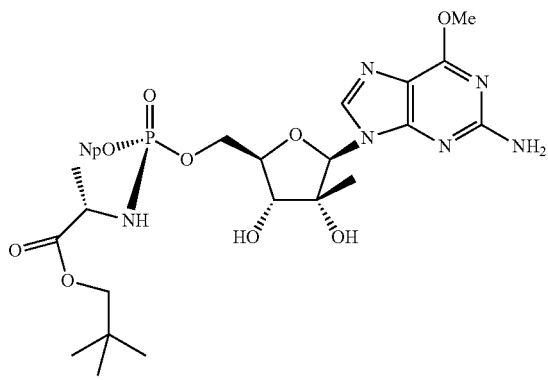

wherein Np represents naphthalen-1-yl.

A fourteenth aspect of the first embodiment is directed to a compound having the structure:

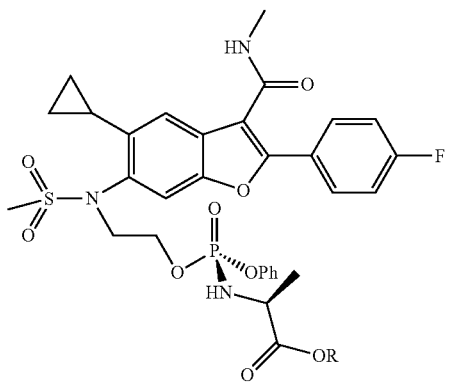

wherein R is a $C_{1-6}$alkyl or a $C_{3-7}$cycloalkyl.

A fifteenth aspect of the first embodiment is directed to a compound having the structure:

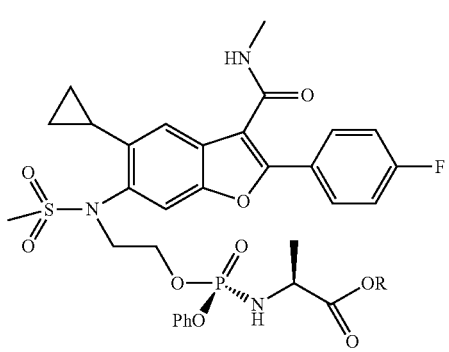

wherein R is a $C_{1-6}$alkyl or a $C_{3-7}$cycloalkyl.

A second embodiment is directed to a process for preparing a composition comprising an enantiomerically- or a diastereomerically enriched phosphorus-containing active, salt, or pharmaceutically acceptable salt thereof, of formula I:

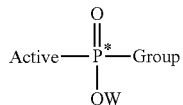

which comprises a) reacting a protected or unprotected Active with a base to form a salt of said active and then reacting said salt with an enantiomerically- or diastereomerically-enriched compound of formula II

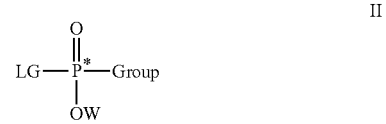

wherein Group is as defined herein, W is an aryl or —$(CH_2)_nSC(O)C(CH_3)_m(CH_2OH)_{3-m}$, where n is 2 or 3 and m is 0, 1, 2, or 3, and LG is a leaving group;

b) optionally deprotecting the compound obtained in step a) and c) optionally subjecting the compound obtained in step a) or the compound obtained in step b) to chromatography, extraction, or crystallization to obtain the desired compound.

A first aspect of the second embodiment is directed to a process for preparing a composition comprising an enantiomerically- or a diastereomerically enriched phosphorus-containing active, salt, or pharmaceutically acceptable salt thereof, of formula I:

which comprises a) reacting a protected or unprotected Active with a basic reagent to form a salt of said active and then reacting said salt with a compound of formula II

wherein the Active is a nucleoside, a nucleoside-analog, or a non-nucleoside; Group is as defined herein; W is an aryl or —$(CH_2)_nSC(O)C(CH_3)_m(CH_2OH)_{3-m}$, where n is 2 or 3 and m is 0, 1, 2, or 3; and LG is a leaving group;

b) optionally deprotecting the compound obtained in step a) and c) optionally subjecting the compound obtained in step a) or the compound obtained in step b) to chromatography, extraction, or crystallization to obtain the desired compound.

A second aspect of the second embodiment is directed to a process for preparing a composition comprising an enantiomerically- or a diastereomerically enriched phosphorus-containing active, salt, or pharmaceutically acceptable salt thereof, of formula I:

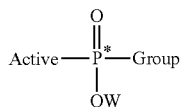

which comprises a) reacting a protected or unprotected Active with a basic reagent to form a salt of said active and then reacting said salt with a compound of formula II

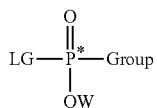

wherein the Active is a nucleoside, a nucleoside-analog, or a non-nucleoside; Group is as defined herein; W is an aryl or $-(CH_2)_nSC(O)C(CH_3)_m(CH_2OH)_{3-m}$, where n is 2 or 3 and m is 0, 1, 2, or 3; and LG is a leaving group;

b) optionally deprotecting the compound obtained in step a) and c) optionally subjecting the compound obtained in step a) or the compound obtained in step b) to chromatography, extraction, or crystallization to obtain the desired compound;

d) obtaining the compound of formula II

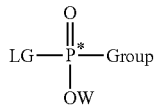

by a process that comprises:

1) reacting $(LG)P(O)(LG')_2$, wherein LG', independent of LG, is a leaving group, with
   (i) a Group-precursor, as defined herein, and a first base to obtain (LG)P(O)(LG')(Group) followed by reacting (LG)P(O)(LG')(Group) with HOW and a second base to obtain a mixture comprising (LG)P(O)(OW)(Group), wherein the first base and the second base are the same or different,
   (ii) HOW and a first base to obtain (LG)P(O)(LG')(OW) followed by reacting (LG)P(O)(LG')(OW) with a Group-precursor and a second base to obtain a mixture comprising (LG)P(O)(OW)(Group), wherein the first base and the second base are the same or different,
   (iii) combining a Group, HOW, and at least one base to obtain a mixture comprising (LG)P(O)(OW)(Group); or
2) reacting $(WO)P(O)(LG')_2$, wherein LG' is a leaving group, with
   (i) a Group-precursor and a first base to obtain (WO)P(O)(LG')(Group) followed by reacting (WO)P(O)(LG')(Group) with a leaving group precursor and a second base to obtain a mixture comprising (LG)P(O)(OW)(Group), wherein the first base and the second base are the same or different, e) subjecting the mixture comprising (LG)P(O)(OW)(Group) to chromatography, extraction, or crystallization to obtain compound II.

Recognizing that the phosphorus atom in (LG)P(O)(OW)(Group) is chiral, one of ordinary skill will understand that the mixture comprising (LG)P(O)(OW)(Group), which is represented by the following structures, comprises a mixture of enantiomers (when the substituents Group, WO, and LG lack chirality) or a mixture of diastereomers (when at least one substituent Group, WO, and LG possesses chirality).

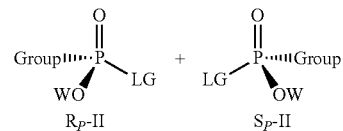

Here, for purposes of assignment of the Cahn-Ingold-Prelog ("CIP") designation of $R_P$ or $S_P$, it is assumed that the order of priority from highest to lowest is LG>WO>P=O>Group. It is expected that one of ordinary skill would be able to deduce the chirality, and thus the CIP designation of $R_P$ or $S_P$, of the phosphorus atom according to the CIP rules based on the particular identity of the functional groups bound to the phosphorus atom. A utility of the disclosed process is that a compound represented by formula II is sufficiently stable so as to allow one to obtain the enantiomeric or diastereomeric mixture of II, and then isolate the desired stereoisomer of II depending on which stereoisomer of I is sought, viz.

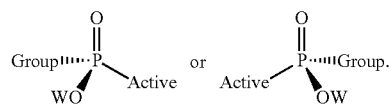

A third aspect of the second embodiment is a process for preparing a composition comprising an enantiomerically- or a diastereomerically enriched phosphorus-containing active, salt, or pharmaceutically acceptable salt thereof, of formula I-1:

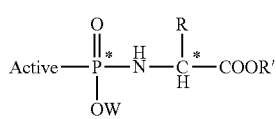

which comprises a) reacting a protected or unprotected Active with a basic reagent to form a salt of said active and then reacting said salt with a compound of formula II-1

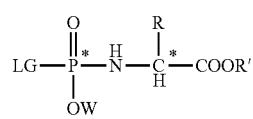

wherein
the Active is a nucleoside, a nucleoside-analog, or a non-nucleoside compound; W is an aryl or $-(CH_2)_nSC(O)C(CH_3)_m(CH_2OH)_{3-m}$, where n is 2 or 3 and m is 0, 1, 2, or 3; LG is a leaving group; R is a radical observed in any one of the naturally occurring amino acids, which includes proline or hydroxy-proline where the fragment N—C—R forms a ring-system, or R is a substituted or unsubstituted alkyl, a substituted or unsubstituted cycloalkyl, a substituted or unsubstituted alkaryl, a substituted or unsubstituted alkenyl, a substituted or unsubstituted alkoxide, a substituted or unsubstituted aryl; and R' is a substituted or unsubstituted alkyl, a substituted or unsubstituted cycloalkyl, a substituted or unsubstituted alkaryl, or a substituted or unsubstituted aryl;

b) optionally deprotecting the compound obtained in step a) and c) optionally subjecting the compound obtained in step a) or the compound obtained in step b) to chromatography, extraction, or crystallization to obtain compound II-1.

A fourth aspect of the second embodiment is a process for preparing a composition comprising an enantiomerically- or a diastereomerically enriched phosphorus-containing active, salt, or pharmaceutically acceptable salt thereof, of formula I-1:

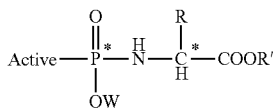

which comprises a) reacting a protected or unprotected Active with a basic reagent to form a salt of said active and then reacting said salt with a compound of formula II-1

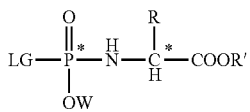

wherein the Active is a nucleoside, a nucleoside-analog, or a non-nucleoside compound; W is an aryl or $-(CH_2)_nSC(O)C(CH_3)_m(CH_2OH)_{3-m}$, where n is 2 or 3 and m is 0, 1, 2, or 3;

LG is a leaving group; R is a radical observed in any one of the naturally occurring amino acids, or R is a substituted or unsubstituted alkyl, a substituted or unsubstituted cycloalkyl, a substituted or unsubstituted alkaryl, a substituted or unsubstituted alkenyl, a substituted or unsubstituted alkoxide, a substituted or unsubstituted aryl; and R' is a substituted or unsubstituted alkyl, a substituted or unsubstituted cycloalkyl, a substituted or unsubstituted alkaryl, or a substituted or unsubstituted aryl;

b) optionally deprotecting the compound obtained in step a) and c) optionally subjecting the compound obtained in step a) or the compound obtained in step b) to chromatography, extraction, or crystallization to obtain the desired compound said aspect further comprising d) obtaining the compound of formula II-1

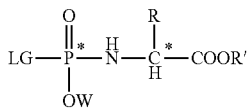

by a process that comprises:

1) reacting $(LG)P(O)(LG')_2$, wherein LG', independent of LG, is a leaving group, with
   (i) $R'O_2CCHRNH_2 \cdot HX$ and a first base to obtain $(LG)P(O)LG'(NHCHRCO_2R')$ followed by reacting $(LG)P(O)(LG')(NHCHRCO_2R')$ with HOW and a second base to obtain a mixture comprising $(LG)P(O)(OW)(NHCHRCO_2R')$, wherein the first base and the second base are the same or different,
   (ii) HOW and a first base to obtain $(LG)P(O)(LG')(OW)$ followed by reacting $(LG)P(O)(LG')(OW)$ with $R'O_2CCHRNH_2 \cdot HX$ and a second base to obtain a mixture comprising $(LG)P(O)(OW)(NHCHRCO_2R')$, wherein the first base and the second base are the same or different, or
   (iii) combining $R'O_2CCHRNH_2 \cdot HX$, HOW, and at least one base to obtain a mixture comprising $(LG)P(O)(OW)(NHCHRCO_2R')$; or 2) reacting $(WO)P(O)(LG')_2$, wherein LG' is a leaving group, with
   (i) $R'O_2CCHRNH_2 \cdot HX$ and a first base to obtain $(WO)P(O)(LG')(NHCHRCO_2R')$ followed by reacting $(WO)P(O)(LG')(NHCHRCO_2R')$ with a leaving group precursor and a second base to obtain a mixture comprising $(LG)P(O)(OW)(NHCHRCO_2R')$, wherein the first base and the second base are the same or different, e) subjecting the mixture comprising $(LG)P(O)(OW)(NHCHRCO_2R')$ to chromatography or crystallizing the mixture to obtain compound II-1.

For the first aspect of the second embodiment, the leaving groups (either LG or LG') are as defined above. In a first sub-aspect, LG is an aryloxide substituted with at least one electron withdrawing group. In a second sub-aspect, LG is selected from among 2-nitrophenoxide, 4-nitrophenoxide, 2,4-dinitrophenoxide, pentafluorophenoxide, 2-chloro-4-nitrophenoxide, 2,4-dichlorophenoxide, and 2,4,6-trichlorophenoxide. In a third sub-aspect, W is an aryl or $-(CH_2)_nSC(O)C(CH_3)_m(CH_2OH)_{3-m}$, where n is 2 or 3 and m is 0, 1, 2, or 3; R is a $C_{1-6}$alkyl; and R' is a $C_{1-6}$alkyl or a $C_{3-7}$cycloalkyl. In a fourth sub-aspect, W is an aryl or $-(CH_2)_nSC(O)C(CH_3)_m(CH_2OH)_{3-m}$, where n is 2 or 3 and m is 0, 1, 2, or 3; R is a $C_{1-6}$alkyl; and R' is a $C_{1-6}$alkyl or a $C_{3-7}$cycloalkyl; and wherein the stereochemistry of C—R is the same as a naturally occurring amino acid. In a fifth sub-aspect, W is an aryl or $-(CH_2)_nSC(O)C(CH_3)_m(CH_2OH)_{3-m}$, where n is 2 or 3 and m is 0, 1, 2, or 3; R is selected from among methyl, ethyl, and isopropyl; and R' is a selected from among, methyl, ethyl, isopropyl, neopentyl, cyclobutyl, cyclopentyl, and cyclohexyl; and wherein the stereochemistry of C—R is the same as a naturally occurring amino acid. In a sixth sub-aspect, W is a phenyl naphthalen-1-yl, or $-(CH_2)_2SC(O)C(CH_3)_2(CH_2OH)$; R is selected from among methyl, ethyl, and isopropyl; and R' is a selected from among, methyl, ethyl, isopropyl, neopentyl, cyclobutyl, cyclopentyl, and cyclohexyl; and wherein the stereochemistry of C—R is the same as a naturally occurring amino acid. In a seventh sub-aspect, $R'O_2CCHRNH_2 \cdot HX$ is substantially anhydrous. In an eighth sub-aspect, R is methyl and R' is isopropyl. In a ninth sub-aspect, R is methyl, R' is isopropyl, HX is HCl.

A fifth aspect of the second embodiment is directed to a process for preparing a compound having the structure:

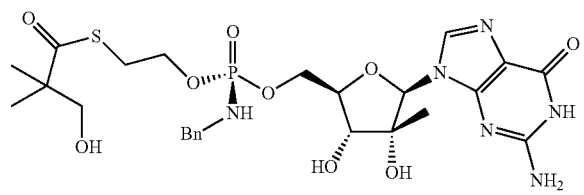 [SMILES: CC(C)(CO)C(=O)SCCO[P@@](=O)(NCc1ccccc1)OC[C@H]1O[C@@H](n2cnc3c(=O)[nH]c(N)nc32)[C@](C)(O)[C@@H]1O]

which comprises:
a) reacting a first compound having the structure

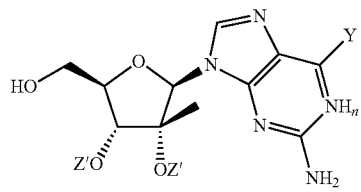

with a basic reagent to form a salt of the first compound, where Z' is hydrogen or a protecting group and Y is =O or =OC$_{1-6}$alkyl, with proviso that ---- is a single bond and n is 1 when Y is =O, and ---- is a double bond and n=0 when Y is —OC$_{1-6}$alkyl;
b) reacting the salt of the first compound with a second compound having the structure,

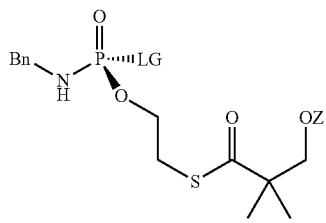

where LG is a leaving group, Z is hydrogen or a protecting group, and Bn is —CH$_2$Ph; and
c) optionally deprotecting. In a first sub-aspect, Z is hydrogen and Z' is hydrogen. In a second sub-aspect, LG is an aryloxide having at least one electron withdrawing group. In a third sub-aspect, LG is an aryloxide selected from among 2-nitrophenoxide, 4-nitrophenoxide, 2,4-dinitrophenoxide, pentafluorophenoxide, 2-chloro-4-nitrophenoxide; 2,4-dichlorophenoxide; and 2,4,6-trichlorophenoxide. In a fourth sub-aspect, the basic reagent is a Grignard reagent. In a fifth sub-aspect, the basic reagent is a t-butylmagnesium halide. In a sixth sub-aspect, the basic reagent is a t-butylmagnesium halide is present in a mole equivalent amount of about 1 to about 2.5 relative to the first compound. In a seventh sub-aspect, the basic reagent is a t-butylmagnesium halide is present in a mole equivalent amount of about 1, about 1.1, about 1.2, about 1.3, about 1.4, about 1.5, about 1.6, about 1.7, about 1.8, about 1.9, about 2.0 about 2.1, about 2.2, about 2.3, about 2.4, or about 2.5 relative to the first compound. In a seventh sub-aspect, the basic reagent is a t-butylmagnesium bromide is present in a mole equivalent amount of about 1, about 1.1, about 1.2, about 1.3, about 1.4, about 1.5, about 1.6, about 1.7, about 1.8, about 1.9, about 2.0 about 2.1, about 2.2, about 2.3, about 2.4, or about 2.5 relative to the first compound.

As in the discussion for formula II above, recognizing that the phosphorus atom in (LG)P(O)(OW)(NHCHRCO$_2$R') is chiral, one of ordinary skill will understand that the mixture comprising (LG)P(O)(OW)(NHCHRCO$_2$R), which is represented by the following structures, comprises a mixture of enantiomers (when the substituents NHCHRCO$_2$R', WO, and LG lack asymmetry thus imparting chirality to said substituent) or a mixture of diastereomers (when at least one substituent NHCHRCO$_2$R', WO, and LG possesses asymmetry thus imparting chirality to said substituent).

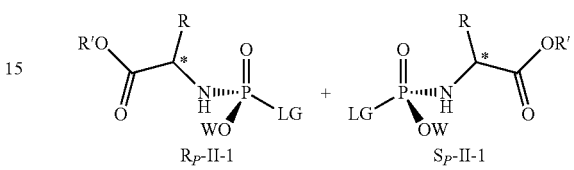

R$_P$-II-1            S$_P$-II-1

Here, for purposes of illustration, it is assumed that the order of priority from highest to lowest is LG>WO>P=O>NHCHRCO$_2$R'.

A sixth aspect of the second embodiment is directed to a process for preparing a compound having the structure

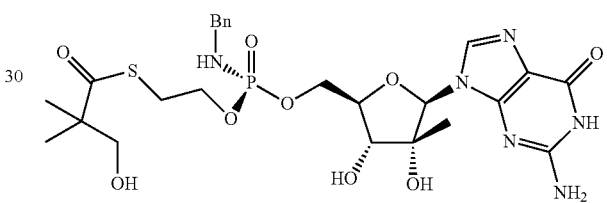

which comprises:
a) reacting a first compound having the structure

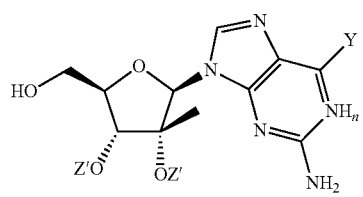

with a basic reagent to form a salt of the first compound, where Z' is hydrogen or a protecting group and Y is =O or =OC$_{1-6}$alkyl, with proviso that ---- is a single bond and n is 1 when Y is =O, and ---- is a double bond and n=0 when Y is —OC$_{1-6}$alkyl;
b) reacting the salt of the first compound with a second compound having the structure

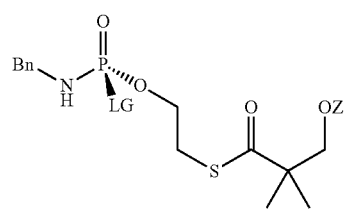

where LG is a leaving group, Z is hydrogen or a protecting group, and Bn is —CH$_2$Ph; and c) optionally deprotecting. In a first sub-aspect, Z is hydrogen and Z' is hydrogen. In a second sub-aspect, LG is an aryloxide having at least one electron withdrawing group. In a third sub-aspect, LG is an aryloxide selected from among 2-nitrophenoxide, 4-nitrophenoxide, 2,4-dinitrophenoxide, pentafluorophenoxide, 2-chloro-4-nitrophenoxide; 2,4-dichlorophenoxide; and 2,4,6-trichlorophenoxide. In a fourth sub-aspect, the basic reagent is a Grignard reagent. In a fifth sub-aspect, the basic reagent is a t-butylmagnesium halide. In a sixth sub-aspect, the basic reagent is a t-butylmagnesium halide is present in a mole equivalent amount of about 1 to about 2.5 relative to the first compound. In a seventh sub-aspect, the basic reagent is a t-butylmagnesium halide is present in a mole equivalent amount of about 1, about 1.1, about 1.2, about 1.3, about 1.4, about 1.5, about 1.6, about 1.7, about 1.8, about 1.9, about 2.0 about 2.1, about 2.2, about 2.3, about 2.4, or about 2.5 relative to the first compound. In an eighth sub-aspect, the basic reagent is a t-butylmagnesium bromide is present in a mole equivalent amount of about 1, about 1.1, about 1.2, about 1.3, about 1.4, about 1.5, about 1.6, about 1.7, about 1.8, about 1.9, about 2.0 about 2.1, about 2.2, about 2.3, about 2.4, or about 2.5 relative to the first compound.

A seventh aspect of the second embodiment is directed to a process for preparing a compound having the structure

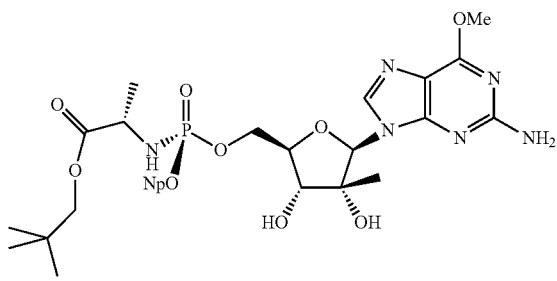

which comprises:
a) reacting a first compound having the structure

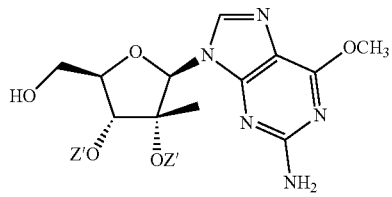

with a basic reagent to form a salt of the first compound, where Z' is hydrogen or a protecting group;
b) reacting the salt of the first compound with a second compound having the structure

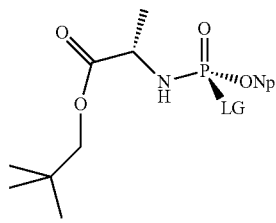

where LG is a leaving group and Np is naphthalen-1-yl; and c) optionally deprotecting. In a first sub-aspect, Z' is hydrogen. In a second sub-aspect, LG is an aryloxide having at least one electron withdrawing group. In a third sub-aspect, LG is an aryloxide selected from among 2-nitrophenoxide, 4-nitrophenoxide, 2,4-dinitrophenoxide, pentafluorophenoxide, 2-chloro-4-nitrophenoxide; 2,4-dichlorophenoxide; and 2,4,6-trichlorophenoxide. In a fourth sub-aspect, the basic reagent is a Grignard reagent. In a fifth sub-aspect, the basic reagent is a t-butylmagnesium halide. In a sixth sub-aspect, the basic reagent is a t-butylmagnesium halide is present in a mole equivalent amount of about 1 to about 2.5 relative to the first compound. In a seventh sub-aspect, the basic reagent is a t-butylmagnesium halide is present in a mole equivalent amount of about 1, about 1.1, about 1.2, about 1.3, about 1.4, about 1.5, about 1.6, about 1.7, about 1.8, about 1.9, about 2.0 about 2.1, about 2.2, about 2.3, about 2.4, or about 2.5 relative to the first compound. In an eighth sub-aspect, the basic reagent is a t-butylmagnesium bromide is present in a mole equivalent amount of about 1, about 1.1, about 1.2, about 1.3, about 1.4, about 1.5, about 1.6, about 1.7, about 1.8, about 1.9, about 2.0 about 2.1, about 2.2, about 2.3, about 2.4, or about 2.5 relative to the first compound.

An eighth aspect of the second embodiment is directed to a process for preparing a compound having the structure

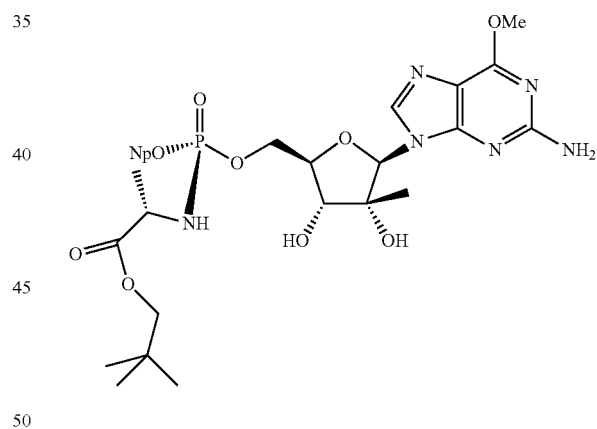

which comprises:
a) reacting a first compound having the structure

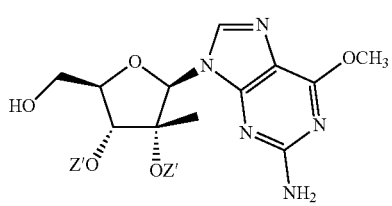

with a basic reagent to form a salt of the first compound, where Z' is hydrogen or a protecting group;

b) reacting the salt of the first compound with a second compound having the structure

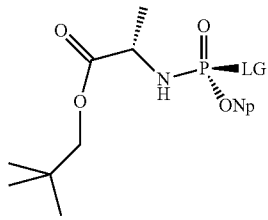

where LG is a leaving group and Np is naphthalen-1-yl; and c) optionally deprotecting. In a first sub-aspect, Z' is hydrogen. In a second sub-aspect, LG is an aryloxide having at least one electron withdrawing group. In a third sub-aspect, LG is an aryloxide selected from among 2-nitrophenoxide, 4-nitrophenoxide, 2,4-dinitrophenoxide, pentafluorophenoxide, 2-chloro-4-nitrophenoxide; 2,4-dichlorophenoxide; and 2,4,6-trichlorophenoxide. In a fourth sub-aspect, the basic reagent is a Grignard reagent. In a fifth sub-aspect, the basic reagent is a t-butylmagnesium halide. In a sixth sub-aspect, the basic reagent is a t-butylmagnesium halide is present in a mole equivalent amount of about 1 to about 2.5 relative to the first compound. In a seventh sub-aspect, the basic reagent is a t-butylmagnesium halide is present in a mole equivalent amount of about 1, about 1.1, about 1.2, about 1.3, about 1.4, about 1.5, about 1.6, about 1.7, about 1.8, about 1.9, about 2.0 about 2.1, about 2.2, about 2.3, about 2.4, or about 2.5 relative to the first compound. In an eighth sub-aspect, the basic reagent is a t-butylmagnesium bromide is present in a mole equivalent amount of about 1, about 1.1, about 1.2, about 1.3, about 1.4, about 1.5, about 1.6, about 1.7, about 1.8, about 1.9, about 2.0 about 2.1, about 2.2, about 2.3, about 2.4, or about 2.5 relative to the first compound.

A ninth aspect of the second embodiment is directed to a process for preparing a compound having the structure

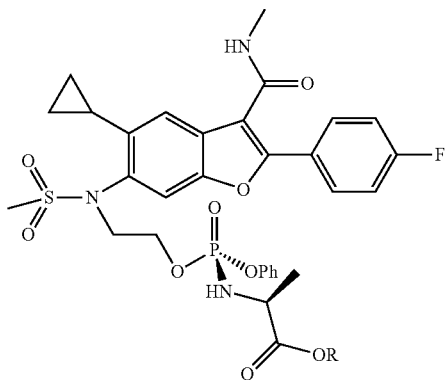

which comprises:
a) reacting a first compound having the structure

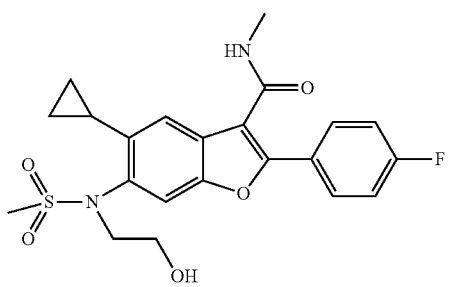 [SMILES: CNC(=O)c1c(-c2ccc(F)cc2)oc2cc(N(CCO)S(C)(=O)=O)c(C3CC3)cc12]

with a basic reagent to form a salt of the first compound, b) reacting the salt of the first compound with a second compound having the structure

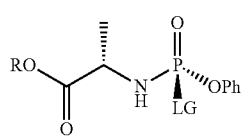

where LG is a leaving group and R is a $C_{1-6}$alkyl or a $C_{3-7}$ cycloalkyl. In a first sub-aspect, LG is an aryloxide having at least one electron withdrawing group. In a second sub-aspect, LG is an aryloxide selected from among 2-nitrophenoxide, 4-nitrophenoxide, 2,4-dinitrophenoxide, pentafluorophenoxide, 2-chloro-4-nitrophenoxide; 2,4-dichlorophenoxide; and 2,4,6-trichlorophenoxide. In a third sub-aspect, the basic reagent is a Grignard reagent. In a fourth sub-aspect, the basic reagent is a t-butylmagnesium halide. In a fifth sub-aspect, the basic reagent is a t-butylmagnesium halide is present in a mole equivalent amount of about 1 to about 2.5 relative to the first compound. In a sixth sub-aspect, the basic reagent is a t-butylmagnesium halide is present in a mole equivalent amount of about 1, about 1.1, about 1.2, about 1.3, about 1.4, about 1.5, about 1.6, about 1.7, about 1.8, about 1.9, about 2.0 about 2.1, about 2.2, about 2.3, about 2.4, or about 2.5 relative to the first compound. In a seventh sub-aspect, the basic reagent is a t-butylmagnesium bromide is present in a mole equivalent amount of about 1, about 1.1, about 1.2, about 1.3, about 1.4, about 1.5, about 1.6, about 1.7, about 1.8, about 1.9, about 2.0 about 2.1, about 2.2, about 2.3, about 2.4, or about 2.5 relative to the first compound.

A tenth aspect of the second embodiment is directed to a process for preparing a compound having the structure

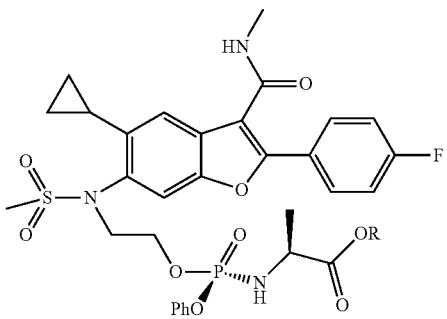

which comprises:
a) reacting a first compound having the structure

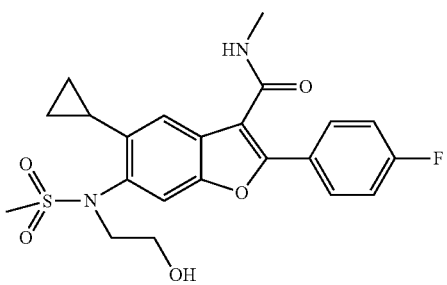 [SMILES: CNC(=O)c1c(-c2ccc(F)cc2)oc2cc(N(CCO)S(C)(=O)=O)c(C3CC3)cc12]

with a basic reagent to form a salt of the first compound, b) reacting the salt of the first compound with a second compound having the structure

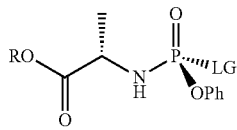

where LG is a leaving group and R is a $C_{1-6}$alkyl or a $C_{3-7}$ cycloalkyl. In a first sub-aspect, LG is an aryloxide having at least one electron withdrawing group. In a second sub-aspect, LG is an aryloxide selected from among 2-nitrophenoxide, 4-nitrophenoxide, 2,4-dinitrophenoxide, pentafluorophenoxide, 2-chloro-4-nitrophenoxide; 2,4-dichlorophenoxide; and 2,4,6-trichlorophenoxide. In a third sub-aspect, the basic reagent is a Grignard reagent. In a fourth sub-aspect, the basic reagent is a t-butylmagnesium halide. In a fifth sub-aspect, the basic reagent is a t-butylmagnesium halide is present in a mole equivalent amount of about 1 to about 2.5 relative to the first compound. In a sixth sub-aspect, the basic reagent is a t-butylmagnesium halide is present in a mole equivalent amount of about 1, about 1.1, about 1.2, about 1.3, about 1.4, about 1.5, about 1.6, about 1.7, about 1.8, about 1.9, about 2.0 about 2.1, about 2.2, about 2.3, about 2.4, or about 2.5 relative to the first compound. In a seventh sub-aspect, the basic reagent is a t-butylmagnesium bromide is present in a mole equivalent amount of about 1, about 1.1, about 1.2, about 1.3, about 1.4, about 1.5, about 1.6, about 1.7, about 1.8, about 1.9, about 2.0 about 2.1, about 2.2, about 2.3, about 2.4, or about 2.5 relative to the first compound.

A third embodiment is directed to a phosphorus-containing active, salt, or pharmaceutically acceptable salt thereof, of formula III:

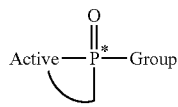

wherein

Active comprises at least two functional groups capable of forming a bond to P; and Group is as defined herein.

A first aspect of the third embodiment is directed to a phosphorus-containing active, salt, or pharmaceutically acceptable salt thereof, of formula III, wherein Active comprises at least two functional groups capable of forming a bond to P and Group is an amino acid.

A second aspect of the third embodiment is directed to a phosphorus-containing active, salt, or pharmaceutically acceptable salt thereof, of formula III, wherein Active is a nucleoside, nucleoside-analog, or non-nucleoside compound comprising at least two functional groups capable of forming a bond to P and Group is an amino acid. Examples of a nucleoside, nucleoside-analog, or non-nucleoside compound comprising at least two functional groups capable of forming a bond to P include, but are not limited to compounds 2, 3, 4, 5, 7, 8, 9a, 9b, 9c, 13, 14, 15-23, 26, 28-32, 34a, 34b, 34c, 34d, 35, 37-39, 41-43, 49-51, 56-57, 59-62, and 79.

A fourth embodiment is directed to a process for preparing a phosphorus-containing active, salt, or pharmaceutically acceptable salt thereof, of formula III:

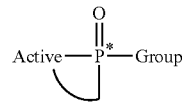

which comprises reacting a protected or unprotected active with a basic reagent to form a salt of said active and then react said salt with a compound of formula IV:

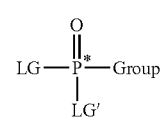

wherein

Active comprises at least two functional groups capable of forming a bond to P;

Group is as defined herein;

and each of LG and LG', independent of one another, is a leaving group.

A first aspect of the fourth embodiment is directed to a phosphorus-containing active, salt, or pharmaceutically acceptable salt thereof, of formula III, wherein Active comprises at least two functional groups capable of forming a bond to P and Group is an amino acid.

A second aspect of the fourth embodiment is directed to a phosphorus-containing active, salt, or pharmaceutically acceptable salt thereof, of formula III, wherein Active is a nucleoside, nucleoside-analog, or non-nucleoside compound comprising at least two functional groups capable of forming a bond to P and Group is an amino acid. Examples of a nucleoside, nucleoside-analog, or non-nucleoside compound comprising at least two functional groups capable of forming a bond to P include, but are not limited to compounds 2, 3, 4, 5, 7, 8, 9a, 9b, 9c, 13, 14, 15-23, 26, 28-32, 34a, 34b, 34c, 34d, 35, 37-39, 41-43, 49-51, 56-57, 59-62, and 79.

A fifth embodiment is directed to a composition comprising an enantiomerically- or diasteromerically-enriched compound, hydrate, solvate, salt, or combinations thereof, represented by the formula II:

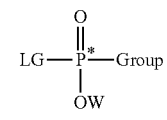

where LG is a leaving group, group is as defined herein, and —W is an aryl or —$(CH_2)_n SC(O)C(CH_3)_m(CH_2OH)_{3-m}$, where n is 2 or 3 and m is 0, 1, 2, or 3.

A first aspect of the fifth embodiment is directed to a compound, its hydrate, solvate, salt, or combinations thereof, represented by the formula $R_P$-II or $S_P$-II.

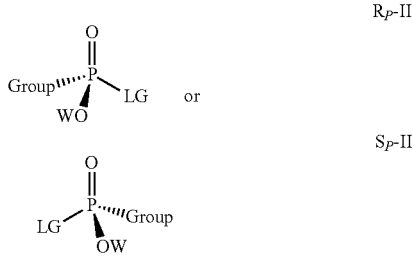

Here, for purposes of assignment of the Cahn-Ingold-Prelog ("CIP") designation of $R_P$ or $S_P$, it is assumed that the order of priority from highest to lowest is LG>WO>P=O>Group. It is expected that one of ordinary skill would be able to deduce the chirality, and thus the CIP designation of $R_P$ or $S_P$, of the phosphorus atom according to the CIP rules based on the particular identity of the functional groups bound to the phosphorus atom. A utility of the a compound represented by formula $R_P$-II or $S_P$-II is that it is sufficiently stable, yet adequately reactive, so as to allow one to obtain the enantiomeric or diastereomeric I or III in substantially pure form by reaction of $R_P$-II or $S_P$-II with a protected or unprotected active, as disclosed herein.

A second aspect of the fifth embodiment is directed to a compound, its hydrate, solvate, salt, or combination thereof, represented by the formula $R_P$-II-1 or $S_P$-II-1

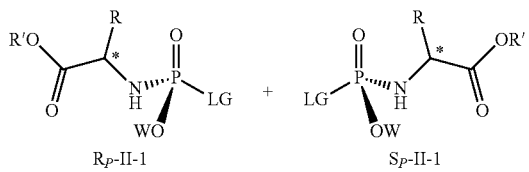

wherein W is an aryl or —(CH$_2$)$_n$SC(O)C(CH$_3$)$_m$(CH$_2$OH)$_{3-m}$, where n is 2 or 3 and m is 0, 1, 2, or 3; LG is a leaving group; R is a radical observed in any one of the naturally occurring amino acids, which includes proline or hydroxy-proline where the fragment N—C—R forms a ring-system or R is a substituted or unsubstituted alkyl, a substituted or unsubstituted cycloalkyl, a substituted or unsubstituted alkaryl, a substituted or unsubstituted alkenyl, a substituted or unsubstituted alkoxide, a substituted or unsubstituted aryl; and R' is a substituted or unsubstituted alkyl, a substituted or unsubstituted cycloalkyl, a substituted or unsubstituted alkaryl, or a substituted or unsubstituted aryl.

A third aspect of the fifth embodiment is directed to a compound, its hydrate, solvate, salt, or combination thereof, represented by the formula $R_P$-II-1 or $S_P$-II-1 wherein LG is an aryloxide substituted with at least one electron withdrawing group, which includes, but is not limited to, 2-nitrophenoxide, 4-nitrophenoxide, 2,4-dinitrophenoxide, pentafluorophenoxide, 2-chloro-4-nitrophenoxide, 2,4-dichlorophenoxide, and 2,4,6-trichlorophenoxide.

A third aspect of the fifth embodiment is directed to a compound, its hydrate, solvate, salt, or combination thereof, represented by the formula $R_P$-II-1 or $S_P$-II-1 wherein LG is an aryloxide substituted with at least one electron withdrawing group, which includes, but is not limited to, 2-nitrophenoxide, 4-nitrophenoxide, 2,4-dinitrophenoxide, pentafluorophenoxide, 2-chloro-4-nitrophenoxide, 2,4-dichlorophenoxide, and 2,4,6-trichlorophenoxide.

A fourth aspect of the fifth embodiment is directed to a compound, its hydrate, solvate, salt, or combination thereof, represented by the formula $R_P$-II-1 or $S_P$-II-1 wherein LG is or an aryloxide substituted with at least one electron withdrawing group, which includes, but is not limited to, 2-nitrophenoxide, 4-nitrophenoxide, 2,4-dinitrophenoxide, pentafluorophenoxide, 2-chloro-4-nitrophenoxide, 2,4-dichlorophenoxide, and 2,4,6-trichlorophenoxide; R is an alkyl; and R' is an alkyl or a cycloalkyl.

A fifth aspect of the fifth embodiment is directed to a compound, its hydrate, solvate, salt, or combination thereof, represented by the formula $R_P$-II-1 or $S_P$-II-1 wherein LG is an aryloxide substituted with at least one electron withdrawing group, which includes, but is not limited to, 2-nitrophenoxide, 4-nitrophenoxide, 2,4-dinitrophenoxide, pentafluorophenoxide, 2-chloro-4-nitrophenoxide, 2,4-dichlorophenoxide, and 2,4,6-trichlorophenoxide; R is a $C_{1-6}$alkyl; and R' is a $C_{1-10}$alkyl or a $C_{3-8}$cycloalkyl.

A sixth aspect of the fifth embodiment is directed to a compound, its hydrate, solvate, salt, or combination thereof, represented by the formula $R_P$-II-1 or $S_P$-II-1 wherein LG is an aryloxide substituted with at least one electron withdrawing group, which includes, but is not limited to, 2-nitrophenoxide, 4-nitrophenoxide, 2,4-dinitrophenoxide, pentafluorophenoxide, 2-chloro-4-nitrophenoxide, 2,4-dichlorophenoxide, and 2,4,6-trichlorophenoxide; R is a $C_{1-6}$alkyl; and R' is a $C_{1-6}$alkyl or a $C_{3-7}$cycloalkyl.

A seventh aspect of the fifth embodiment is directed to a compound, its hydrate, solvate, salt, or combination thereof, represented by the formula $R_P$-II-1 or $S_P$-II-1 wherein LG is an aryloxide or an aryloxide substituted with at least one electron withdrawing group, which includes, but is not limited to, 2-nitrophenoxide, 4-nitrophenoxide, 2,4-dinitrophenoxide, pentafluorophenoxide, 2-chloro-4-nitrophenoxide, 2,4-dichlorophenoxide, and 2,4,6-trichlorophenoxide; R is a $C_{1-6}$alkyl; and R' is a $C_{1-6}$alkyl or a $C_{3-7}$cycloalkyl; and wherein the stereochemistry of C—R is the same as a naturally occurring amino acid.

An eighth aspect of the fifth embodiment is directed to a compound, its hydrate, solvate, salt, or combination thereof, represented by the formula $R_P$-II-1 or $S_P$-II-1 wherein LG is an aryloxide substituted with at least one electron withdrawing group, which includes, but is not limited to, 2-nitrophenoxide, 4-nitrophenoxide, 2,4-dinitrophenoxide, pentafluorophenoxide, 2-chloro-4-nitrophenoxide, 2,4-dichlorophenoxide, and 2,4,6-trichlorophenoxide; R is selected from among methyl, ethyl, and isopropyl; and R' is a selected from among, methyl, ethyl, isopropyl, neopentyl, cyclobutyl, cyclopentyl, and cyclohexyl; and wherein the stereochemistry of C—R is the same as a naturally occurring amino acid.

A ninth embodiment is directed to a compound, hydrate, solvate, salt, or combinations thereof, represented by the formula II:

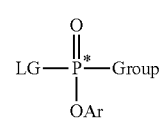

where LG is a leaving group, group is as defined herein, and Ar is an aryl.

A tenth aspect of the fifth embodiment is directed to a compound, its hydrate, solvate, salt, or combinations thereof, represented by the formula $R_P$-II or $S_P$-II.

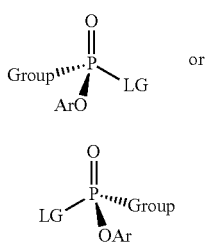

Here, for purposes of assignment of the Cahn-Ingold-Prelog ("CIP") designation of $R_P$ or $S_P$, it is assumed that the order of priority from highest to lowest is LG>ArO>P=O>Group. It is expected that one of ordinary skill would be able to deduce the chirality, and thus the CIP designation of $R_P$ or $S_P$, of the phosphorus atom according to the CIP rules based on the particular identity of the functional groups bound to the phosphorus atom. A utility of the a compound represented by formula $R_P$-II or $S_P$-II is that it is sufficiently stable, yet adequately reactive, so as to allow one to obtain the enantiomeric or diastereomeric I or III in substantially pure form by reaction of $R_P$-II or $S_P$-II with a protected or unprotected active, as disclosed herein.

An eleventh aspect of the fifth embodiment is directed to a compound, its hydrate, solvate, salt, or combination thereof, represented by the formula $R_P$-II-1 or $S_P$-II-1

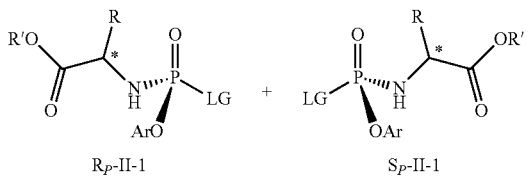

wherein Ar is an aryl; LG is a leaving group; R is a radical observed in any one of the naturally occurring amino acids, which includes proline or hydroxy-proline where the fragment N—C—R forms a ring-system, or R is a substituted or unsubstituted alkyl, a substituted or unsubstituted cycloalkyl, a substituted or unsubstituted alkaryl, a substituted or unsubstituted alkenyl, a substituted or unsubstituted alkoxide, a substituted or unsubstituted aryl; and R' is a substituted or unsubstituted alkyl, a substituted or unsubstituted cycloalkyl, a substituted or unsubstituted alkaryl, or a substituted or unsubstituted aryl.

A twelfth aspect of the fifth embodiment is directed to a compound, its hydrate, solvate, salt, or combination thereof, represented by the formula $R_P$-II-1 or $S_P$-II-1 wherein LG is an aryloxide substituted with at least one electron withdrawing group, which includes, but is not limited to, 2-nitrophenoxide, 4-nitrophenoxide, 2,4-dinitrophenoxide, pentafluorophenoxide, 2-chloro-4-nitrophenoxide, 2,4-dichlorophenoxide, and 2,4,6-trichlorophenoxide.

A thirteenth aspect of the fifth embodiment is directed to a compound, its hydrate, solvate, salt, or combination thereof, represented by the formula $R_P$-II-1 or $S_P$-II-1 wherein LG is an aryloxide substituted with at least one electron withdrawing group, which includes, but is not limited to, 2-nitrophenoxide, 4-nitrophenoxide, 2,4-dinitrophenoxide, pentafluorophenoxide, 2-chloro-4-nitrophenoxide, 2,4-dichlorophenoxide, and 2,4,6-trichlorophenoxide.

A fourteenth aspect of the fifth embodiment is directed to a compound, its hydrate, solvate, salt, or combination thereof, represented by the formula $R_P$-II-1 or $S_P$-II-1 wherein LG is an aryloxide substituted with at least one electron withdrawing group, which includes, but is not limited to, 2-nitrophenoxide, 4-nitrophenoxide, 2,4-dinitrophenoxide, pentafluorophenoxide, 2-chloro-4-nitrophenoxide, 2,4-dichlorophenoxide, and 2,4,6-trichlorophenoxide; R is an alkyl; and R' is an alkyl or a cycloalkyl.

A fifteenth aspect of the fifth embodiment is directed to a compound, its hydrate, solvate, salt, or combination thereof, represented by the formula $R_P$-II-1 or $S_P$-II-1 wherein LG is an aryloxide or an aryloxide substituted with at least one electron withdrawing group, which includes, but is not limited to, 2-nitrophenoxide, 4-nitrophenoxide, 2,4-dinitrophenoxide, pentafluorophenoxide, 2-chloro-4-nitrophenoxide, 2,4-dichlorophenoxide, and 2,4,6-trichlorophenoxide; R is a $C_{1-6}$alkyl; and R' is a $C_{1-10}$alkyl or a $C_{3-7}$cycloalkyl.

A sixteenth aspect of the fifth embodiment is directed to a compound, its hydrate, solvate, salt, or combination thereof, represented by the formula $R_P$-II-1 or $S_P$-II-1 wherein LG is an aryloxide substituted with at least one electron withdrawing group, which includes, but is not limited to, 2-nitrophenoxide, 4-nitrophenoxide, 2,4-dinitrophenoxide, pentafluorophenoxide, 2-chloro-4-nitrophenoxide, 2,4-dichlorophenoxide, and 2,4,6-trichlorophenoxide; R is a $C_{1-6}$alkyl; and R' is a $C_{1-6}$alkyl or a $C_{3-7}$cycloalkyl.

A seventeenth aspect of the fifth embodiment is directed to a compound, its hydrate, solvate, salt, or combination thereof, represented by the formula $R_P$-II-1 or $S_P$-II-1 wherein LG is aryloxide substituted with at least one electron withdrawing group, which includes, but is not limited to, 2-nitrophenoxide, 4-nitrophenoxide, 2,4-dinitrophenoxide, pentafluorophenoxide, 2-chloro-4-nitrophenoxide, 2,4-dichlorophenoxide, and 2,4,6-trichlorophenoxide; R is a $C_{1-6}$alkyl; and R' is a $C_{1-6}$alkyl or a $C_{3-7}$cycloalkyl; and wherein the stereochemistry of C—R is the same as a naturally occurring amino acid.

An eighth aspect of the sixth embodiment is directed to a compound, its hydrate, solvate, salt, or combination thereof, represented by the formula $R_P$-II-1 or $S_P$-II-1 wherein LG is an aryloxide substituted with at least one electron withdrawing group, which includes, but is not limited to, 2-nitrophenoxide, 4-nitrophenoxide, 2,4-dinitrophenoxide, pentafluorophenoxide, 2-chloro-4-nitrophenoxide, 2,4-dichlorophenoxide, and 2,4,6-trichlorophenoxide; R is selected from among methyl, ethyl, and isopropyl; and R' is a selected from among, methyl, ethyl, isopropyl, neopentyl, cyclobutyl, cyclopentyl, and cyclohexyl; and wherein the stereochemistry of C—R is the same as a naturally occurring amino acid.

A sixth embodiment is directed to a process for preparing compound of formula II

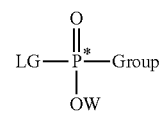

wherein Group is as defined herein, W is an aryl or —$(CH_2)_n SC(O)C(CH_3)_m(CH_2OH)_{3-m}$, where n is 2 or 3 and m is 0, 1, 2, or 3, and LG is a leaving group;

by a process that comprises:

a) reacting (LG)P(O)(LG')$_2$, wherein LG', independent of LG, is a leaving group, with 1) a Group-precursor and a first base to obtain (LG)P(O)(LG')(Group) followed by reacting (LG)P(O)(LG')(Group) with HOW and a second base to obtain a mixture comprising (LG)P(O)(OW)(Group), where the first base and the second base are the same or different, 2) HOW and a first base to obtain (LG)P(O)(LG')(OW) followed by reacting (LG)P(O)(LG')(OW) with a Group and a second base to obtain a mixture comprising (LG)P(O)(OW)(Group), where the first base and the second base are the same or different, 3) combining a Group, HOW, and at least one base to obtain a mixture comprising (LG)P(O)(OW)(Group); or b) reacting (WO)P(O)(LG')$_2$, wherein LG', independent of LG, is a leaving group, with 1) a Group-precursor and a first base to obtain (WO)P(O)(LG')(Group) followed by reacting (WO)P(O)(LG')(Group) with a leaving group precursor and a second base to obtain a mixture comprising (LG)P(O)(OW)(Group), where the first base and the second base are the same or different, and c) subjecting the mixture comprising (LG)P(O)(OW)(Group) to chromatography, extraction, crystallization to obtain compound II.

In a first aspect of the sixth embodiment, LG' is chloride or bromide.

In a second aspect of the sixth embodiment, LG' is chloride.

In a third aspect of the sixth embodiment, LG is an aryloxide substituted with at least one electron withdrawing group.

In a fourth aspect of the sixth embodiment, LG is selected from among 2-nitrophenoxide, 4-nitrophenoxide, 2,4-dinitrophenoxide, pentafluorophenoxide, 2-chloro-4-nitrophenoxide, 2,4-dichlorophenoxide, and 2,4,6-trichlorophenoxide.

A fifth aspect of the sixth embodiment is directed to a process for preparing compound of formula II by a process that comprises:

b) reacting (WO)P(O)(LG')$_2$, wherein LG', independent of LG, is a leaving group, with a Group-precursor and a first base to obtain (WO)P(O)(LG')(Group) followed by reacting (WO)P(O)(LG')(Group) with a leaving group precursor and a second base to obtain a mixture comprising (LG)P(O)(OW)(Group), where the first base and the second base are the same or different, and c) subjecting the mixture comprising (LG)P(O)(OW)(Group) to chromatography, extraction, crystallization to obtain compound II. In a first sub-aspect, LG' is chloride or bromide. In a second sub-aspect, LG' is chloride. In a third sub-aspect, LG is an aryloxide substituted with at least one electron withdrawing group. In a fourth sub-aspect, LG is selected from among 2-nitrophenoxide, 4-nitrophenoxide, 2,4-dinitrophenoxide, pentafluorophenoxide, 2-chloro-4-nitrophenoxide, 2,4-dichlorophenoxide, and 2,4,6-trichlorophenoxide. In a fifth sub-aspect, W is aryl or —(CH$_2$)$_2$SC(O)C(CH$_3$)$_2$(CH$_2$OH). In a sixth sub-aspect, W is phenyl.

A seventh embodiment is directed to a process for preparing compound of formula II-1

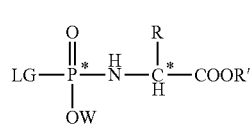

II-1 by a process that comprises:

a) reacting (LG)P(O)(LG')$_2$, wherein LG', independent of LG, is a leaving group, with 1) R'O$_2$CCHRNH$_2$.HX and a first base to obtain (LG)P(O)LG'(NHCHRCO$_2$R') followed by reacting (LG)P(O)(LG')(NHCHRCO$_2$R') with HOW and a second base to obtain a mixture comprising (LG)P(O)(OW)(NHCHRCO$_2$R'), where the first base and the second base are the same or different 2) HOW and a first base to obtain (LG)P(O)(LG')(OW) followed by reacting (LG)P(O)(LG')(OW) with R'O$_2$CCHRNH$_2$.HX and a second base to obtain a mixture comprising (LG)P(O)(OW)(NHCHRCO$_2$R'), where the first base and the second base are the same or different or 3) combining R'O$_2$CCHRNH$_2$.HX, HOW, and at least one base to obtain a mixture comprising (LG)P(O)(OW)(NHCHRCO$_2$R'); or b) reacting (WO)P(O)(LG')$_2$, wherein LG', independent of LG, is a leaving group, with 1) R'O$_2$CCHRNH$_2$.HX and a first base to obtain (WO)P(O)(LG')(NHCHRCO$_2$R') followed by reacting (WO)P(O)(LG')(NHCHRCO$_2$R') with a leaving group precursor and a second base to obtain a mixture comprising (LG)P(O)(OW)(NHCHRCO$_2$R'), e) subjecting the mixture comprising (LG)P(O)(OW)(NHCHRCO$_2$R') to chromatography or crystallizing the mixture to obtain compound II-1.

For the first aspect of the seventh embodiment, the leaving groups (either LG or LG') are as defined above. In a first sub-aspect, LG is an aryloxide substituted with at least one electron withdrawing group. In a second sub-aspect, LG is selected from among 2-nitrophenoxide, 4-nitrophenoxide, 2,4-dinitrophenoxide, pentafluorophenoxide, 2-chloro-4-nitrophenoxide, 2,4-dichlorophenoxide, and 2,4,6-trichlorophenoxide. In a third sub-aspect, W is an aryl or —(CH$_2$)$_n$SC(O)C(CH$_3$)$_m$(CH$_2$OH)$_{3-m}$, where n is 2 or 3 and m is 0, 1, 2, or 3; R is a C$_{1-6}$alkyl; and R' is a C$_{1-6}$alkyl or a C$_{3-7}$cycloalkyl. In a fourth sub-aspect, W is an aryl or —(CH$_2$)$_n$SC(O)C(CH$_3$)$_m$(CH$_2$OH)$_{3-m}$, where n is 2 or 3 and m is 0, 1, 2, or 3; R is a C$_{1-6}$alkyl; and R' is a C$_{1-6}$alkyl or a C$_{3-7}$cycloalkyl; and wherein the stereochemistry of C—R is the same as a naturally occurring amino acid. In a fifth sub-aspect, W is an aryl or —(CH$_2$)$_n$SC(O)C(CH$_3$)$_m$(CH$_2$OH)$_{3-m}$, where n is 2 or 3 and m is 0, 1, 2, or 3; R is selected from among methyl, ethyl, and isopropyl; and R' is a selected from among, methyl, ethyl, isopropyl, neopentyl, cyclobutyl, cyclopentyl, and cyclohexyl; and wherein the stereochemistry of C—R is the same as a naturally occurring amino acid. In a sixth sub-aspect, W is a phenyl naphthalen-1-yl, or —(CH$_2$)$_2$SC(O)C(CH$_3$)$_2$(CH$_2$OH); R is selected from among methyl, ethyl, and isopropyl; and R' is a selected from among, methyl, ethyl, isopropyl, neopentyl, cyclobutyl, cyclopentyl, and cyclohexyl; and wherein the stereochemistry of C—R is the same as a naturally occurring amino acid. In a seventh sub-aspect, R'O$_2$CCHRNH$_2$.HX is substantially anhydrous. In an eighth sub-aspect, R is methyl and R' is isopropyl. In a ninth sub-aspect, R is methyl, R' is isopropyl, HX is HCl.

One of ordinary skill will appreciate that the compounds disclosed herein, such as, I, II, or III, can be separated by traditional extraction, traditional crystallization or traditional chromatographic techniques. Traditional chromatographic techniques include, but are not limited to, chromatography on silica gel (using, e.g., 3-5% methanol in DCM or 4-6% isopropanol in DCM) to produce enhanced levels of one isomer (50-100%) and then crystallize it, if possible. Alternatively, one could use reversed phase chromatography (using, e.g., 1-30% acetonitrile-aqueous mobile phase). Furthermore the compounds can be isolated by supercritical fluid chromatography SFC with carbon dioxide as the main solvent and alcohols such as methanol as a modifier, preferably using the appropriate chiral media, such as, Daicel Chiralpack IA. Alternatively, SMB chromatography may be employed using the appropriate chiral media, such as, Daicel ChiralPack IA, using a mixture of solvents such as hexanes/isopropanol or single solvents such as ethyl acetate. Furthermore, the compound represented by formula II may be purified by crystallization induced dynamic resolution, which is contemplated by the following embodiment.

An eighth embodiment is directed to a process for preparing a compound of formula $R_P$-II-1 or $S_P$-II-1 represented by the structures

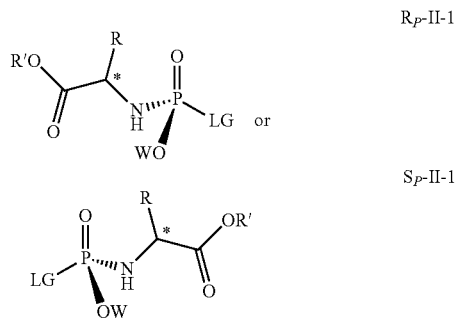

said process comprising:
crystallizing the compound of formula $R_P$-II-1 or $S_P$-II-1 from a composition, comprising
a) a first composition;
b) a leaving group precursor;
c) a non-nucleophilic base; and
d) a liquid composition;
wherein the first composition comprises both $R_P$-II-1 or $S_P$-II-1; and
wherein LG is a leaving group, W is an aryl or —$(CH_2)_n SC(O)C(CH_3)_m (CH_2OH)_{3-m}$, where n is 2 or 3 and m is 0, 1, 2, or 3; R is a $C_{1-6}$alkyl, and R' is a $C_{1-6}$alkyl or a $C_{3-7}$cycloalkyl.

In a first aspect of the eighth embodiment, the mole amount of $R_P$-II-1 and the mole amount of $S_P$-II-1 are the same or different.

In a second aspect of the eighth embodiment, the mole amount of $R_P$-II-1 is greater than the mole amount of $S_P$-II-1 or vice versa.

In a third aspect of the eighth embodiment, the leaving group precursor is 2,4-dinitrophenol, 4-nitrophenol, 2-nitrophenol, 2-chloro-4-nitrophenol, 2,4-dichlorophenol, or pentafluorophenol.

In a fourth aspect of the eighth embodiment, LG is 2-nitrophenoxide, 4-nitrophenoxide, 2,4-dinitrophenoxide, pentafluorophenoxide, 2-chloro-4-nitrophenoxide, 2,4-dichlorophenoxide, or 2,4,6-trichlorophenoxide.

In a fifth aspect of the eighth embodiment, LG is pentafluorophenoxide. In a first sub-aspect, the second leaving group precursor is pentafluorophenol. In a second sub-aspect, the amount of pentafluorophenol ranges from about 0.01 mole equivalents to about 10 mole equivalents relative to the mole amount of $R_P$-II-1 and $S_P$-II-1 and all mole equivalents in between. In a third sub-aspect, the amount of pentafluorophenol ranges from about 0.1 mole equivalents to about 1 mole equivalents relative to the mole amount of $R_P$-II-1 and $S_P$-II-1 and all mole equivalents in between.

In a fifth aspect of the eighth embodiment, the crystallizing occurs at a temperature that ranges from about −10° C. to about +40° C. and all temperature values in between. In a first sub-aspect, the crystallizing occurs at about room temperature.

In a sixth aspect of the eighth embodiment, the non-nucleophilic base is selected from among potassium carbonate, cesium carbonate, di-isopropylamine, di-isopropylethylamine, triethylamine, quinuclidine, naphthalene-1,8-diamine, 2,2,6,6-tetramethylpiperidine, 1,8-diazabicycloundec-7-ene, 4-dimethylamino-pyridine, pyridine, a 2,6-di-$C_{1-6}$-alkyl-pyridine, a 2,4,6-tri-$C_{1-6}$-alkyl-pyridine, and mixtures thereof. In a first sub-aspect, the non-nucleophilic base is triethylamine or 1,8-diazabicycloundec-7-ene. In a second sub-aspect, the non-nucleophilic base is triethylamine.

In a seventh aspect of the eighth embodiment, the non-nucleophilic base is present in an amount that ranges from about 0.01 equivalents mol to about 10 mol equivalents, and all mole equivalents in between, relative to the total mole amount of $R_P$-II-1 and $S_P$-II-1. In a first sub-aspect, the non-nucleophilic base is present in an amount that ranges from about 0.1 mol equivalents to about 1 mol equivalents, and all mole equivalents in between, relative to the total mole amount of $R_P$-II-1 and $S_P$-II-1.

In an eighth aspect of the eighth embodiment, the solubility of $R_P$-II-1 is less than the solubility of $S_P$-II-1 in the liquid composition or vice versa.

In a ninth aspect of the eighth embodiment, the liquid composition comprises at least one of a solvent and an antisolvent. In a first sub-aspect, the liquid composition comprises at least one of a $C_1$ to $C_8$ alcohol, a $C_2$ to $C_8$ ether, a $C_3$ to $C_7$ ketone, a $C_3$ to $C_7$ ester, a $C_1$ to $C_2$ chlorocarbon, a $C_2$ to $C_7$ nitrile, a $C_5$ to $C_{12}$ saturated hydrocarbon, and a $C_6$ to $C_{12}$ aromatic hydrocarbon. In a second sub-aspect, the liquid composition comprises at least one of a $C_2$ to $C_8$ ether, a $C_3$ to $C_7$ ester, a $C_5$ to $C_{12}$ saturated hydrocarbon, and a $C_6$ to $C_{12}$ aromatic hydrocarbon. In a third sub-aspect, the liquid composition comprises at least one of a $C_2$ to $C_8$ ether, a $C_3$ to $C_7$ ester, and a $C_5$ to $C_{12}$ saturated hydrocarbon. In a fourth sub-aspect, the liquid composition comprises at least one of ethyl acetate, t-butyl-methylether, and hexane. In a fifth sub-aspect, the liquid composition comprises ethyl acetate and hexane. In a sixth sub-aspect, the liquid composition comprises t-butyl-methylether and hexane.

In a tenth aspect of the eighth embodiment, the amount of liquid composition ranges from about 1 mL to about 10 mL for every gram of the first composition and all mL/g values in between.

An eleventh aspect of the eighth embodiment further comprises adding crystalline $R_P$-II-1 or $S_P$-II-1 to the composition. A first sub-aspect further comprises adding about 0.1 to about 1 wt. %, and all wt. % values in between, of crystalline $R_P$-II-1 or $S_P$-II-1 to the first composition.

With respect to the eighth embodiment, certain aspects may be disclosed in U.S. patent application Ser. No. 13/076,765, filed on Mar. 31, 2011, which is hereby incorporated by reference.

Dosage, Administration, and Use

In a ninth embodiment, the invention is for the treatment and/or prophylaxis of a disease state by administering a therapeutically effective amount of compound I or compound III to a host in need thereof.

Selected disease states include, but are not limited to, cancer or a diseased state that may arise form the introduction of a viral agent to a host. For instance, one of ordinary skill will recognize that the nucleoside, nucleoside-analog, and non-nucleoside actives depicted above, have been approved by the FDA for the treatment of at least one diseased state. It is contemplated that compound I or compound III would likewise be useful for the treatment of at least one diseased state, the treatment of which has been approved by the FDA. It is contemplated that the process disclosed herein will afford enantiomers or diastereomers of compound I or compound III that will have improved pharmacokinetic parameters relative to the active itself.

It is contemplated that a diseased state may arise from the introduction of a viral agent to a host. Thus, it is contemplated that the compound I or compound III can be used for the treatment and/or prophylaxis of a viral agent. Possible viral agents include, but are not limited to: HIV-1, HIV-2, herpes type 1, herpes type 2, HSV, influenza, HPV, ebolla, XMRV, CMV, RSV, rhinovirus, hepatitis C virus, hepatitis B virus, West Nile virus, yellow fever virus, dengue virus, rhinovirus, polio virus, bovine viral diarrhea virus, Japanese encephalitis virus, Murray Valley encephalitis virus, St. Louis encephalitis virus, or those viruses belonging to the groups of Pestiviruses, hepaciviruses, or flavaviruses.

An aspect of this embodiment is directed to a composition for the treatment of any of the viral agents disclosed herein said composition comprising a pharmaceutically acceptable medium selected from among an excipient, carrier, diluent, and equivalent medium and compound I or compound III.

Compound I or compound III may be formulated in a wide variety of oral administration dosage forms and carriers. Oral administration can be in the form of tablets, coated tablets, hard and soft gelatin capsules, solutions, emulsions, syrups, or suspensions. Compound I or compound III is efficacious when administered by suppository administration, among other routes of administration. The most convenient manner of administration is generally oral using a convenient daily dosing regimen which can be adjusted according to the severity of the disease and the patient's response to the antiviral medication.

Compound I or compound III, as well as its salts, together with one or more conventional excipients, carriers, or diluents, may be placed into the form of pharmaceutical compositions and unit dosages. The pharmaceutical compositions and unit dosage forms may be comprised of conventional ingredients in conventional proportions, with or without additional active compounds and the unit dosage forms may contain any suitable effective amount of the active ingredient commensurate with the intended daily dosage range to be employed. The pharmaceutical compositions may be employed as solids, such as tablets or filled capsules, semisolids, powders, sustained release formulations, or liquids such as suspensions, emulsions, or filled capsules for oral use; or in the form of suppositories for rectal or vaginal administration. A typical preparation will contain from about 0.1% to about 99% active compound or compounds (w/w).

Compound I or compound III can be administered alone but will generally be administered in admixture with one or more suitable pharmaceutical excipients, diluents or carriers selected with regard to the intended route of administration and standard pharmaceutical practice.

A pharmaceutically acceptable salt form of an active ingredient may also initially confer a desirable pharmacokinetic property on the active ingredient which were absent in the non-salt form, and may even positively affect the pharmacodynamics of the active ingredient with respect to its therapeutic activity in the body.

Solid form preparations include, for example, powders, tablets, pills, capsules, suppositories, and dispersible granules. A solid carrier may be one or more substances which may also act as diluents, flavoring agents, solubilizers, lubricants, suspending agents, binders, preservatives, tablet disintegrating agents, or an encapsulating material. In powders, the carrier generally is a finely divided solid which is a mixture with the finely divided active component. In tablets, the active component generally is mixed with the carrier having the necessary binding capacity in suitable proportions and compacted in the shape and size desired. Suitable carriers include but are not limited to magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. Solid form preparations may contain, in addition to the active component, colorants, flavors, stabilizers, buffers, artificial and natural sweeteners, dispersants, thickeners, solubilizing agents, and the like. Examples of solid formulations are exemplified in EP 0524579; US 2002/0142050; US 2004/0224917; US 2005/0048116; US 2005/0058710; US 2006/0034937; US 2006/0057196; US 2006/0188570; US 2007/0026073; US 2007/0059360; US 2007/0077295; US 2007/0099902; US 2008/0014228; U.S. Pat. No. 6,267,985; U.S. Pat. No. 6,294,192; U.S. Pat. No. 6,383,471; U.S. Pat. No. 6,395,300; U.S. Pat. No. 6,569,463; U.S. Pat. No. 6,635,278; U.S. Pat. No. 6,645,528; U.S. Pat. No. 6,923,988; U.S. Pat. No. 6,932,983; U.S. Pat. No. 7,060,294; and U.S. Pat. No. 7,462,608, each of which is incorporated by reference.

Liquid formulations also are suitable for oral administration include liquid formulation including emulsions, syrups, elixirs and aqueous suspensions. These include solid form preparations which are intended to be converted to liquid form preparations shortly before use. Examples of liquid formulation are exemplified in U.S. Pat. Nos. 3,994,974; 5,695,784; and 6,977,257. Emulsions may be prepared in solutions, for example, in aqueous propylene glycol solutions or may contain emulsifying agents such as lecithin, sorbitan monooleate, or acacia. Aqueous suspensions can be prepared by dispersing the finely divided active component in water with viscous material, such as natural or synthetic gums, resins, methylcellulose, sodium carboxymethylcellulose, and other well known suspending agents.

Compound I or compound III may be independently formulated for administration as suppositories. A low melting wax, such as a mixture of fatty acid glycerides or cocoa butter is first melted and the active component is dispersed homogeneously, for example, by stirring. The molten homogeneous mixture is then poured into convenient sized molds, allowed to cool, and to solidify.

Compound I or compound III may be independently formulated for vaginal administration. Pessaries, tampons, creams, gels, pastes, foams or sprays containing in addition to the active ingredient such carriers as are known in the art to be appropriate. Certain of these formulations may also be used in conjunction with a condom with or without a spermicidal agent.

Suitable formulations along with pharmaceutical carriers, diluents and excipients are described in *Remington: The Science and Practice of Pharmacy* 1995, edited by E. W. Martin, Mack Publishing Company, 19th edition, Easton, Pa., which is hereby incorporated by reference. A skilled formulation scientist may modify the formulations within the teachings of the specification to provide numerous formulations for a particular route of administration without rendering the compositions of the present invention unstable or compromising their therapeutic activity.

Additionally, compound I may be independently formulated in conjunction with liposomes or micelles. As to liposomes, it is contemplated that the purified compounds can be formulated in a manner as disclosed in U.S. Pat. Nos. 4,797,285; 5,013,556; 5,077,056; 5,077,057; 5,154,930; 5,192,549; 5,213,804; 5,225,212; 5,277,914; 5,316,771; 5,376,380; 5,549,910; 5,567,434; 5,736,155; 5,827,533; 5,882,679; 5,891,468; 6,060,080; 6,132,763; 6,143,321; 6,180,134; 6,200,598; 6,214,375; 6,224,903; 6,296,870; 6,653,455; 6,680,068; 6,726,925; 7,060,689; and 7,070,801, each of which is incorporated by reference. As to micelles, it is contemplated that the purified compounds can be formulated in a manner as disclosed in U.S. Pat. Nos. 5,091,188 and 5,145,684 both of which are incorporated by reference.

A tenth embodiment is directed to a use of compound I or compound III in the manufacture of a medicament for the treatment of any one of the diseased states contemplated herein.

The term "medicament" means a substance used in a method of treatment and/or prophylaxis of a subject in need thereof, wherein the substance includes, but is not limited to, a composition, a formulation, a dosage form, and the like, comprising compound I or compound III. It is contemplated that the use of compound I or compound III in the manufacture of a medicament, for the treatment of any one of the diseased states contemplated herein. A medicament includes, but is not limited to, any one of the compositions contemplated by the ninth embodiment of the present invention.

An eleventh embodiment is directed to a method of treatment and/or prophylaxis in a subject in need thereof said method comprises administering a therapeutically effective amount of compound I or compound III to the subject for the treatment of any one of the diseased states contemplated herein.

It is intended that a subject in need thereof is one that has any diseased state disclosed herein, which may be the result of an infection by any of the viral agents disclosed herein, which includes, but is not limited to, HIV-1, HIV-2, herpes type 1, herpes type 2, HSV, influenza, HPV, ebolla, XMRV, CMV, RSV, rhinovirus, hepatitis C virus, hepatitis B virus, West Nile virus, yellow fever virus, dengue virus, rhinovirus, polio virus, bovine viral diarrhea virus, Japanese encephalitis virus, Murray Valley encephalitis virus, St. Louis encephalitis virus, or those viruses belonging to the groups of Pestiviruses, hepaciviruses, or flavaviruses or a viral agent causing symptoms equivalent or comparable to any of the above-listed viruses.

The term "subject" means a mammal, which includes, but is not limited to, cattle, pigs, sheep, chicken, turkey, buffalo, llama, ostrich, dogs, cats, and humans, preferably the subject is a human. It is contemplated that in the method of treating a subject thereof of the fifth embodiment can be compound I or compound III, either alone or in combination with another compound falling within the scope of compound I or compound III.

The term "therapeutically effective amount" as used herein means an amount required to reduce symptoms of the disease in an individual. The dose will be adjusted to the individual requirements in each particular case. That dosage can vary within wide limits depending upon numerous factors such as the severity of the disease to be treated, the age and general health condition of the patient, other medicaments with which the patient is being treated, the route and form of administration and the preferences and experience of the medical practitioner involved. For oral administration, a daily dosage of between about 0.001 and about 10 g, including all values in between, such as 0.001, 0.0025, 0.005, 0.0075, 0.01, 0.025, 0.050, 0.075, 0.1, 0.125, 0.150, 0.175, 0.2, 0.25, 0.5, 0.75, 1, 1.5, 2, 2.5, 3, 3.5, 4, 4.5, 5, 5.5, 6, 6.5, 7, 7.5, 8, 8.5, 9, and 9.5, per day should be appropriate in monotherapy and/or in combination therapy. A particular daily dosage is between about 0.01 and about 1 g per day, including all incremental values of 0.01 g (i.e., 10 mg) in between, a preferred daily dosage about 0.01 and about 0.8 g per day, more preferably about 0.01 and about 0.6 g per day, and most preferably about 0.01 and about 0.25 g per day, each of which including all incremental values of 0.01 g in between. Generally, treatment is initiated with a large initial "loading dose" to rapidly reduce or eliminate the virus following by a decreasing the dose to a level sufficient to prevent resurgence of the infection. One of ordinary skill in treating diseases described herein will be able, without undue experimentation and in reliance on personal knowledge, experience and the disclosures of this application, to ascertain a therapeutically effective amount of the compounds of the present invention for a given disease and patient.

Therapeutic efficacy can be ascertained from tests of liver function including, but not limited to protein levels such as serum proteins (e.g., albumin, clotting factors, alkaline phosphatase, aminotransferases (e.g., alanine transaminase, aspartate transaminase), 5'-nucleosidase, γ-glutaminyltranspeptidase, etc.), synthesis of bilirubin, synthesis of cholesterol, and synthesis of bile acids; a liver metabolic function, including, but not limited to, carbohydrate metabolism, amino acid and ammonia metabolism. Alternatively the therapeutic effectiveness may be monitored by measuring HCV-RNA. The results of these tests will allow the dose to be optimized.

A first aspect of the eleventh embodiment is directed to a method for the treatment of any one of the diseased states contemplated herein by administering to a subject (or host) in need thereof said method comprises administering to the subject a therapeutically effective amount of compound I or compound III and a therapeutically effective amount of another antiviral agent; wherein the administration is concurrent or alternative. It is understood that the time between alternative administration can range between 1-24 hours, which includes any sub-range in between including, 2, 3, 4, 5, 6, 7, 8, 9, 10, 11, 12, 13, 14, 15, 16, 17, 18, 19, 20, 21, 22, and 23 hours.

Examples of "another antiviral agent" include, but are not limited to: HCV NS3 protease inhibitors (see EP 1881001, US 2003187018, US 2005267018, WO 2003006490, WO 200364456, WO 2004094452, WO 2005028502, WO 2005037214, WO 2005095403, WO 2007014920, WO 2007014921, WO 2007014922, WO 2007014925, WO 2007014926, WO 2007015824, WO 2008010921, and WO 2008010921); HCV NS5B Inhibitors (see US 2004229840, US 2005/0098125, US 2005154056, US 20060194749, US 20060241064, US 20060293306, US 2006040890, US 2006040927, US 2006166964, US 2007275947, U.S. Pat. No. 6,784,166, US20072759300, WO 2002057287, WO 2002057425, WO 2003010141, WO 2003037895, WO 2003105770, WO 2004000858, WO 2004002940, WO 2004002944, WO 2004002977, WO 2004003138, WO 2004041201, WO 2004065367, WO 2004096210, WO 2005021568, WO 2005103045, WO 2005123087, WO 2006012078, WO 2006020082, WO 2006065335, WO 2006065590, WO 2006093801, WO 200702602, WO 2007039142, WO 2007039145, WO 2007076034, WO 2007088148, WO 2007092000, and WO2007095269); HCV NS4 Inhibitors (see WO 2005067900 and WO 2007070556); HCV NS5a Inhibitors (see US 2006276511, WO 2006035061, WO 2006100310, WO 2006120251, WO 2006120252); Toll-like receptor agonists (see WO 2007093901); and other inhibitors (see WO 2000006529, WO 2003101993, WO 2004009020, WO 2004014313, WO 2004014852, and WO 2004035571); and compounds disclosed in U.S. patent application Ser. No. 12/053,015, filed Mar. 21, 2008 (US 2010-0016251 the contents of which are incorporated by reference), interferon-α, interferon-β, pegylated interferon-α, ribavirin, levovirin, viramidine, another nucleoside HCV polymerase inhibitor, a HCV non-nucleoside polymerase inhibitor, a HCV protease inhibitor, a HCV helicase inhibitor or a HCV fusion inhibitor.

In contemplated applications where HIV is the viral agent to be treated, nonlimiting examples of antiviral agents that can be used in combination with compound I or compound III include, but are not limited to the following: Invirase® (Saquinavir), Fortovase® (Saquinavir), Norvir® (Ritonavir), Crixivan® (Indinavir), Viracept® (Nelfinavir), Agenerase® (Amprenavir), Kaletra® (Lopinavir), Retrovir® (Zidovudine), Epivir® (Lamivudine), Combivir® (lamivudine and zidovudine), Triazivir® (abacavir sulfate, lamivudine, and zidovudine), Ziagen® (Abacavir), Hivid® (Zalcitabine), Videx® (Didanosine), Videx® EC, Zerit® (Stavudine), Viread® (Tenofovir), Covincil™, Viramune® (Nevirapine), Rescriptor® (Delavirdine), Sustiva® (Efavirenz), Droxia® (hydroxyurea), Fuzeon® (Enfuvirtide), Atazanavir® (Atazanavir), Proleukin® (Interleukin-2), Remune® (HIV-1 Immunogen), Procrit® (Erythropoietin), Darunavir® (Darunavir), and Serostim® (synthetic growth hormone).

When compound I or compound III is administered in combination with another antiviral agent the activity may be increased over the parent compound. When the treatment is combination therapy, such administration may be concurrent or sequential with respect to that of the nucleoside derivatives. "Concurrent administration" as used herein thus includes administration of the agents at the same time or at different times. Administration of two or more agents at the same time can be achieved by a single formulation containing two or more active ingredients or by substantially simultaneous administration of two or more dosage forms with a single active agent.

It will be understood that references herein to treatment extend to prophylaxis as well as to the treatment of existing conditions. Furthermore, the term "treatment" of a HCV infection, as used herein, also includes treatment or prophylaxis of a disease or a condition associated with or mediated by HCV infection, or the clinical symptoms thereof.

EXAMPLES

The specifically identified actives may be commercially available. Alternatively, the specifically identified actives can be prepared according to procedures known in the art, as illustrated by the following information.

| Active (CAS RN) | Biological Activity and/or Synthetic Methods |
|---|---|
| 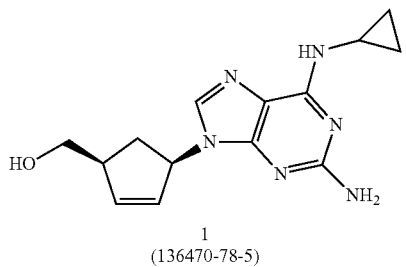 [SMILES: Nc1nc(NC2CC2)c2ncn([C@H]3C=C[C@@H](CO)C3)c2n1]<br>1<br>(136470-78-5) | Compound 1, abacivir, is a nucleoside reverse transcriptase inhibitor (NRTI). The preparation of abacivir is described in EP 349242 and U.S. Pat. No. 5,034,394. The asymmetric synthesis is described in Crimmins et al. *J. Org. Chem.* (1996) 61, 4192. |
| 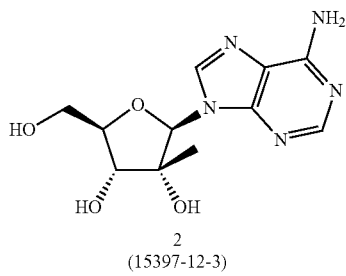 [SMILES: C[C@@]1(O)[C@H](O)[C@@H](CO)O[C@H]1n1cnc2c(N)ncnc21]<br>2<br>(15397-12-3) | Compound 2, 2'-C-methyladenosine, and Compound 7, 2'-C-methylguanosine, have been found to be potent nucleoside inhibitors of HCV RNA replication in vitro, see, for example, Eldrup et al., *J. Med. Chem.* (2004) 47, 5284-5297. For example, U.S. Pat. No. 3,480,613, discloses synthesis of 2'-C-methylpurines and pyrimidines. For example, compound 2, 2'-C-methyladenosine, is prepared in Example 34 by refluxing a suspension of chloromercuri-6-benzamidopurine in xylene with 2,3,5-tri-O-benzoyl-2-C-methyl-D-ribofuranosyl chloride. The resultant 9-(2,3,5-tri-O-benzoyl-2-C-methyl-β-D-ribofuranosyl)-6-benzoamidopurine is treated with sodium methoxide in methanol to return 59% 2-C-methyladenosine. Compound 7, 2'-C-methylguanosine, can be prepared by a similar synthetic route. Preparation of starting intermediate 2,3,5-tri-O-benzoyl-2-C-methyl-D-ribofuranosyl chloride is also described in Jenkens et al., *J. Org. Chem.* (1968), 33(6), 2490-2494. 2-C-methyl-D-ribono-1,4-lactone is completely benzoylated and the benzoyl derivative is reduced with bis-(3-methyl-2-butyl)borane which produces a mixture of 2,3,5-tri-O-benzoyl-2-C-methyl-α(and (β)-D-ribofuranose and 3,5-di-O-benzoyl-2-C-methyl-α(and β)-D-ribofuranose. This mixture is benzoylated to give a mixture of α and β tetrabenzoates which is converted into 2,3,5-tri-O-benzoyl-2-C-methyl-β-D-ribofuranosyl chloride. See also, U.S. Pat. No. 3,480,613 and Walton et al. *J. Am. Chem. Soc.* (1966), 88(19), 4524-4525. |

| Active (CAS RN) | | Biological Activity and/or Synthetic Methods |
|---|---|---|
| 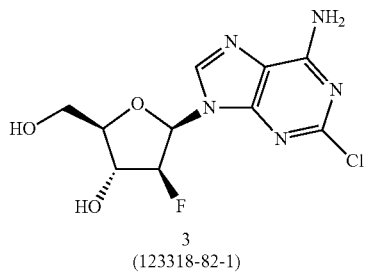 [SMILES: Nc1nc(Cl)nc2c1ncn2[C@@H]1O[C@H](CO)[C@@H](O)[C@@H]1F]<br>3<br>(123318-82-1) | | Compound 3, clofarabine, is a antimetabolite that inhibits DNA synthesis and resists deamination by adenosine deaminase. The preparation of compound 3 is described in: (Watanabe et al EP 219829 and U.S. Pat. No. 4,918,179; Montgomery et al., *J. Med. Chem.* (1992) 35, 397; and an improved synthesis is described in Bauta et al. *Org. Process Res. Dev.* (2004) 8, 889. |
| 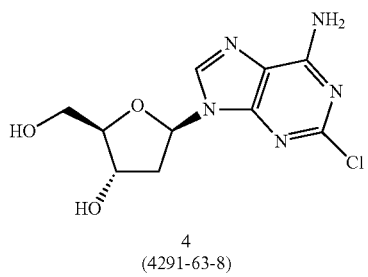 [SMILES: Nc1nc(Cl)nc2c1ncn2[C@H]1C[C@H](O)[C@@H](CO)O1]<br>4<br>(4291-63-8) | | Compound 4, cladribine, is a substituted purine nucleoside with antileukemic activity. Compound 4 is prepared as intermediate in synthesis of 2-deoxynucleosides, see, e.g., Venner, *Ber.* (1960) 93, 140; Ikehara et al. *J. Am. Chem. Soc.* (1963) 85, 2344; Ikehara et al. *J. Am. Chem. Soc.* (1965) 87, 606. Christensen et al., *J. Med. Chem.* (1972) 15, 735 discloses the synthesis and biological activity, while the following disclose a stereospecific synthesis: Kazimierczuk et al., *J. Am. Chem. Soc.* (1984) 106, 6379; R. K. Robins, G. R. Revankar, EP 173059; and U.S. Pat. No. 4,760,137. |
| 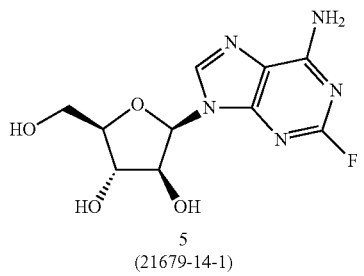 [SMILES: Nc1nc(F)nc2c1ncn2[C@@H]1O[C@H](CO)[C@@H](O)[C@@H]1O]<br>5<br>(21679-14-1) | | Compound 5, fludarabine is an adenosine deaminase-resistant purine nucleoside antimetabolite. The preparation of compound 5 is described in Montgomery et al. *J. Med. Chem.* (1969) 12, 498, while improved syntheses are disclosed in Montgomery et al., *J. Heterocycl. Chem.* (1979) 16, 157 and U.S. Pat. No. 4,210,745. |
| 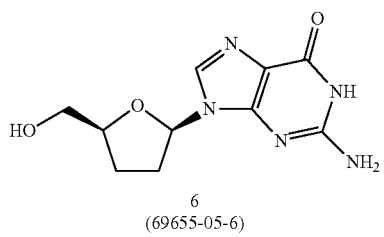 [SMILES: Nc1nc2c(ncn2[C@H]2CC[C@@H](CO)O2)c(=O)[nH]1]<br>6<br>(69655-05-6) | | Compound 6, didanosine, is a hypoxanthine nucleoside with antiviral activity and is a metabolic product of dideoxyadenosine. The synthesis of compound 6 is disclosed in EP 206497 and Webb et al., *Nucleosides Nucleotides* (1988) 7, 147. |
| 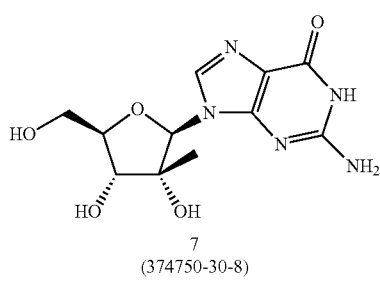 [SMILES: C[C@@]1(O)[C@H](O)[C@@H](CO)O[C@H]1n1cnc2c(=O)[nH]c(N)nc21]<br>7<br>(374750-30-8) | | Compound 7 (aka, INX-08032), 2'-C-methylguanosine, a nucleoside inhibitor of HCV RNA replication in vitro, may also be obtained by the route of Eldrup et al., *J. Med. Chem.* (2004) 47, 2283-2295. For example, as shown in Scheme 1, p. 2284, treatment of 2-C-methyl-1,2,3,5-tetra-O-benzoyl-D-ribose with 2-amino-6-chloropurine, DBU and trimethylsilyl triflate in acetonitrile returns the benzoyl-protected 2-amino-6-chloropurine derivative. Stereocontrol is achieved by transient 1,2-acyloxonium ion formation. Deprotection of this derivative with methanolic ammonia yields 2-amino-6-chloro-9-(2-C-methyl-b-D-ribofuranosyl)purine(15). The 6-chloropurine can be converted to 2'-C-methylguanosine by treatment with 2-mercaptoethanol and sodium methoxide in methanol which results in substitution of the 6-chloro substituent with hydroxide. See also, WO 2001/090121; WO 2004/058792; and Eldrup et al. *J. Med. Chem.* (2004), 47(9), 2283-2295. |

| Active (CAS RN) | Biological Activity and/or Synthetic Methods |
|---|---|
| 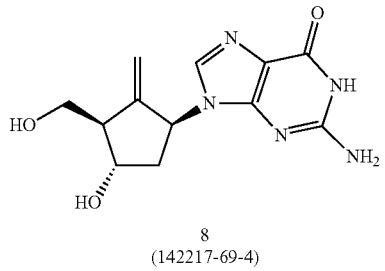 [SMILES: C=C1[C@H](CO)[C@@H](O)C[C@@H]1n1cnc2c(=O)[nH]c(N)nc21]<br>8<br>(142217-69-4) | Compound 8, [1S-(1α,3α,4β)]-2-amino-1,9-dihydro-9-[4-hydroxy-3-(hydroxymethyl)-2-methylenecyclopentyl]-6H-purin-6-one, Entecavir, is a deoxyguanine nucleoside analog that inhibits hepatitis B virus (HBV) DNA polymerase. Entecavir can be prepared as disclosed in U.S. Pat. No. 5,206,244 to Zahler et al. For example, according to Zahler, Example 1, (1S-trans)-2-(Phenylmethoxy)methyl-3-cyclopenten-1-ol is treated with t-butyl hydroperoxide and vanadyl acetate in dry dichloromethane to give the epoxide [1S-(1α,2α,3β,5α)]-2-[(Phenylmethoxy)-methyl]-6-oxa-bicyclo[3.1.0]hexan-3-ol. The free hydroxy group of the epoxide intermediate is protected by introduction of a benzyl group with sodium hydride in THF followed by benzyl bromide and tetrabutyl-ammonium iodide to give the fully protected epoxide, [1S-(1α,2α,3β,5α)-3-(Phenylmethoxy)-2-[(phenylmeth oxy)methyl]-6-oxabicyclo-[3.1.0]hexane. The protected epoxide can then be reacted with O-benzylguanine to give the guanine substituted cyclopentanol 1S-(1α,2(3,3α,5β)-5-[2-Amino-6-(phenyl-methoxy)-9H-purin-9-yl]-3-(phenylmethoxy)-2-[(phenylmethoxy)methyl]cyclopentanol. The amino group of the guanine can then be protected with trityl or substituted trityl to give the protected guanine. The protected guanine cyclopentanol intermediate is then oxidized to the protected guanine cyclopentanone intermediate. Improvements to the synthetic route of Zahler et al. are described in WO 98/09964 to Bisacchi and Sundeen. The protected guanine substituted cyclopentanol intermediate, e.g., 1S-(1α,2β,3α,5β)-5-[2-Amino-6-(phenyl-methoxy)-9H-purin-9-yl]-3-(phenylmethoxy)-2-[(phenylmethoxy)methyl]cyclopentanol, can be converted to the cyclopentanone via Dess-Martin periodinane oxidation. Subsequent methylenation of the cyclopentanone by use of Nysted reagent (e.g. Example 2), Tebbe reagent (e.g., Example 3), or a reagent prepared from zinc powder, diiodomethane, lead powder or lead chloride, and titanium chloride, results in Compound 8, [1S-(1α,3α,4β)]-2-amino-1,9-dihydro-9-[4-hydroxy-3-(hydroxymethyl)-2-methylenecyclopentyl]-6H-Purin-6-one, in an improved yield. |
| 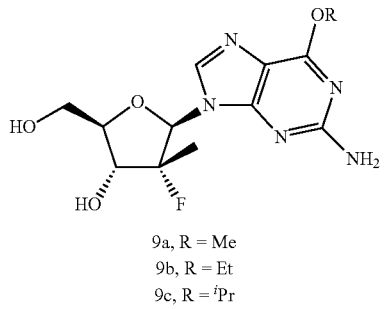<br>9a, R = Me<br>9b, R = Et<br>9c, R = $^i$Pr | Compounds 9a, 9b and 9c can be prepared, for example, by the synthetic route of Du et al., WO 2009/152095. The compounds have utility, for example, in the preparation of nucleoside cyclic phosphates and can be useful in inhibiting RNA- dependent RNA viral replication and are useful as inhibitors of HCV NS5B polymerase, as inhibitors of HCV replication and for treatment of hepatitis C infection in mammals. For example, compound 9a, (2R,3R,4R,5R)-5-(2-amino-6-methoxy-9H-purin-9-yl)-4-fluoro-2-(hydroxy methyl)-4-methyltetrahydrofuran-3-ol, can be prepared as follows. The lactone, ((2R,3R,4R)-3-(benzoyloxy)-4-fluoro-4-methyl-5-oxotetrahydrofuran-2-yl)methyl benzoate, can be obtained by the route disclosed in at page 5 in U.S. Published application No. 2008/0139802. The lactone can be reduced to the corresponding lactol, ((2R,3R,4R,5R)-3-(benzoyloxy)-4-fluoro-5-hydroxy-4-methyltetrahydrofuran-2-yl)methyl benzoate, by treatment with lithium tri-tert-butoxyaluminohydride in THF. The lactol can be converted to the alpha-bromosugar, ((2R,3R,4R,5R)-3-(benzoyloxy)-5-bromo-4-fluoro-4-methyltetrahydrofuran-2-yl)methyl benzoate, by treatment with triphenylphosphine in dichloromethane, then carbon tetrabromide. Following the general purine coupling method of Bauta et al., WO 2003/011877, the alpha-bromosugar can be coupled with the potassium salt of 6-chloro-2-amino-purine in t-butanol in acetonitrile to return (2R,3R,4R,5R)-5-(2-amino-6-chloro-9H-purin-9-yl)-2-(benzoyloxymethyl)-4-fluoro-4-methyltetrahydrofuran-3-yl benzoate. Conversion to unprotected 2-amino-6-substituted purine, compound 9a, (2R,3R,4R,5R)-5-(2-amino-6-methoxy-9H-purin-9-yl)-4-fluoro-2-(hydroxy methyl)-4-methyltetrahydrofuran-3-ol, can be accomplished by suspension in dry methanol and treatment with sodium methoxide. |

| Active (CAS RN) | Biological Activity and/or Synthetic Methods |
|---|---|
| 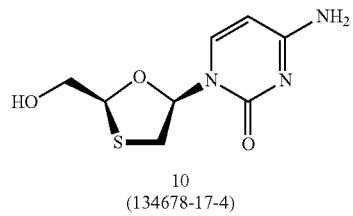<br>10<br>(134678-17-4) | Compound 10, lamivudine, is a reverse transcriptase inhibitor. The synthesis of compound 10 is disclosed in WO 9117159 C.A. 117, 111989 (1991), while the enantiomer synthesis is disclosed in Beach et al., *J. Org. Chem.* (1992) 57, 2217 and Humber et al., *Tetrahedron Lett.* (1992) 33, 4625((−)-enantiomer). |
| 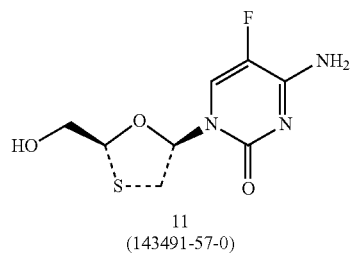<br>11<br>(143491-57-0) | Compound 11, emtricitabine, is a reverse transcriptase inhibitor. The preparation of compound 11 is disclosed in WO 92/14743; U.S. Pat. No. 5,538,975 and Jeong et al., *J. Med. Chem.* (1993) 36, 181. |
| 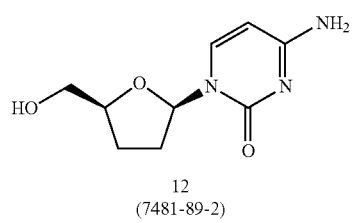 [SMILES: Nc1ccn([C@H]2CC[C@@H](CO)O2)c(=O)n1]<br>12<br>(7481-89-2) | Compound 12, zalcitabine, is a pyrimidine nucleoside analog with antiviral activity. The synthesis of compound 12 is disclosed in Horwitz et al., *J. Org. Chem.* (1967) 32, 817 (1967); Marumoto et al. *Chem. Pharm. Bull.* (1974) 22, 128 (1974); and Lin et al., *J. Med. Chem.* (1987) 30, 440. |
| 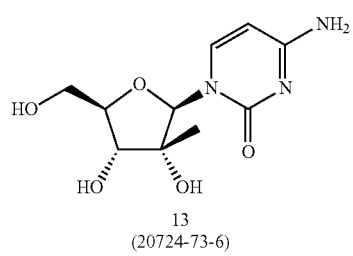 [SMILES: C[C@@]1(O)[C@H](O)[C@@H](CO)O[C@H]1n1ccc(N)nc1=O]<br>13<br>(20724-73-6) | Compound 13, 2'-C-methylcytidine, is known to possess antiviral activity. For example, it has antiviral activity against foot-and-mouth disease virus (FMDV), a member of the Picornaviridae. Goris et al., *Antiviral Res.* 2007, 73(3): 161-168. Compound 13 can be prepared, for example, by the method of Walton, GB 1209654. Walton, Example 2, page 4, discloses 2,3,5-tri-O-benzoyl-2-C-methyl-β-D-ribofuranosyl chloride in dry toluene can be treated with 2,4 - dimethoxy-5-fluoropyrimidine to give the protected pyrimidinone, 1-(2',3',5'-tri-O-benzoyl-2'-C-methyl-β-D-ribofuranosyl)-4 methoxy-2(1H)-pyrimidinone. The protected pyrimidinone can be treated in methanol saturated with ammonia in a sealed tube to return 2'-C-Methylcytidine, compound 13. |
| 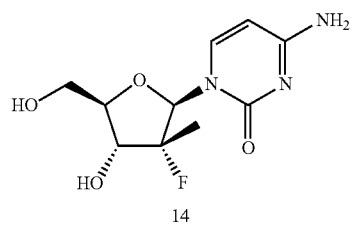 [SMILES: C[C@@]1(F)[C@H](O)[C@@H](CO)O[C@H]1n1ccc(N)nc1=O]<br>14 | Compound 14, PSI-6130, can be converted to its phosphate nucleotide where it is capable of inhibiting HCV NS5B polymerase. The synthesis of compound 14 is disclosed in U.S. Pat. No. 7,429,572. |
| 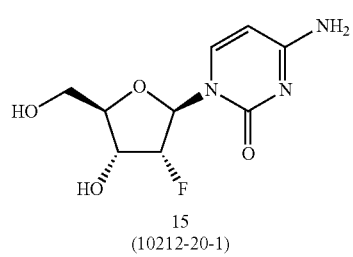 [SMILES: Nc1ccn([C@@H]2O[C@H](CO)[C@@H](O)[C@H]2F)c(=O)n1]<br>15<br>(10212-20-1) | Compound 15, 2'-deoxy-2'-fluorocytidine, inhibits growth in various lymphoblastic cell lines in culture. Brox et al. *Cancer Res.* (1974) 34, 1838-1842. Compound 15 can be prepared, for example, by the technique of Kanai et al., JP 47016483, or Shannahoff and Sanchez, *J. Org. Chem.*, 1973, 38(3), 593-8. For example, Shannahoff and Sanchez. at page 595, 6b, treats 2,2'-anhydrocytidine with anhydrous DMF to return 2'-deoxy-2'-fluorocytidine. |

| Active (CAS RN) | Biological Activity and/or Synthetic Methods |
|---|---|
| 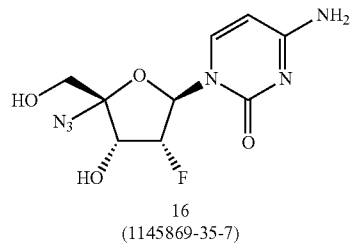 [SMILES: [N-]=[N+]=N[C@]1(CO)O[C@@H](n2ccc(N)nc2=O)[C@H](F)[C@@H]1O]<br>16<br>(1145869-35-7) | Compound 16, 4'-C-azido-2'-deoxy-2'-fluorocytidine, and Compound 17, 4-amino-1-(4-C-azido-2-deoxy-2-fluoro-β-D-arabinofuranosyl)-2(1H)-pyrimidinone, can be prepared by the route of WO 2009/067409, Sofia and Du. These compounds possess antiviral activity, e.g., with activity against HCV NS5B polymerase. For example, compound 16 can be prepared as compound 30, page 65, in an analogous fashion to that shown in Scheme 4, page 57, and for compounds 26-28, pages 62-64. Intermediate 2'-deoxy-2'-C-fluoro-4'-C-azido-5'-C-deoxy-5'-C-iodouridine can be prepared from starting nucleoside, 2'-C-fluoro-2'-deoxyuridine, by treatment with $I_2/Ph_3P$ and elimination catalyzed by NaOMe followed by azido-iodination with $NCl/NaN_3$. The free 3'-C-hydroxy of 2'-C-deoxy-2'-C-fluoro-4'-C-azido-5'-C-deoxy-5'-C-iodouridine is protected by treatment with benzoyl chloride to form the fully protected iodide. The fully protected iodide is treated with m-chloroperbenzoic acid/m-chlorobenzoic acid to replace the iodo group with a chlorobenzoate moiety. The chlorobenzoate uridine is treated with a mixture of $POCl_3$ and triazole with triethylamine; then sodium methoxide/methanol, followed by ammonia in dioxane to return compound 16, 4'-C-azido-2'-deoxy-2'-fluorocytidine. |
| 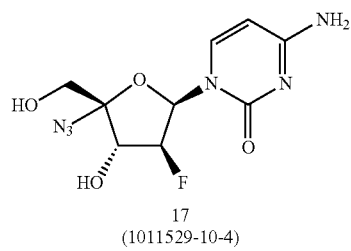 [SMILES: [N-]=[N+]=N[C@]1(CO)O[C@@H](n2ccc(N)nc2=O)[C@@H](F)[C@@H]1O]<br>17<br>(1011529-10-4) | Compound 17 exhibits anti-HCV properties. The preparation of compound 17 is disclosed in WO 2009/067409 WO 2009/009951; and Smith et al. *J. Med. Chem.* (2009) 52(9), 2971-2978. |
| 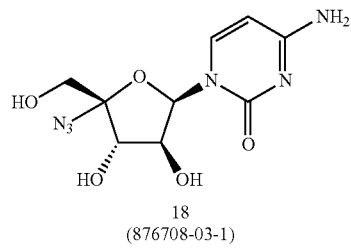 [SMILES: [N-]=[N+]=N[C@]1(CO)O[C@@H](n2ccc(N)nc2=O)[C@@H](O)[C@@H]1O]<br>18<br>(876708-03-1) | Compound 18, 4-amino-1-(4-C-azido-β-D-arabinofuranosyl-2(1H)-pyrimidinone, can be prepared by the techniques disclosed in U.S. Pat. No. 7,378,402, Martin et al. This compound possesses antiviral activity, e.g., activity against HCV NS5B polymerase. For example, Compound 18 can be prepared as in Martin, Example 2. Briefly, 4'-azidouridine, diphenylcarbonate with sodium bicarbonate is heated to return 2'-anhydrouridine which is treated with ethanol and aqueous sodium hydroxide to return 4'-azidoarabinouridine which is converted to compound 18 by conventional methods. For example, conversion of uridines to cytidines by the addition of triazoles is cited in Martin, col. 18. Specifically, as in Example 2, the 4'-azidoarabinouridine can be treated with acetic anhydride, pyridine, DMAP; then triazole, TEA and $POCl_3$ to return 4-Amino-1-((2R,3S,4S,5R)-5-azido-3,4-dihydroxy-5-hydroxymethyl-tetrahydro-furan-2yl)-1H-pyrimidin-2-one, compound 18. See also, Smith et al., *J. Med. Chem.* (2009), 52(1), 219-223. |
| 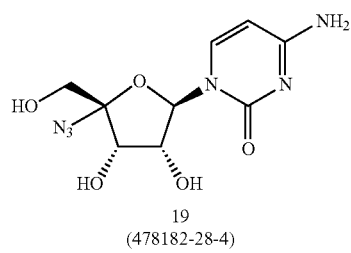 [SMILES: [N-]=[N+]=N[C@]1(CO)O[C@@H](n2ccc(N)nc2=O)[C@H](O)[C@@H]1O]<br>19<br>(478182-28-4) | Compound 19, 4'-azidocytidine, is an inhibitor of Hepatitis C Virus (HCV) RNA replication, and can be prepared by the route disclosed in WO 2005/000864, Connolly et al. Connolly, Examples 1-7, provides various routes to 4'-azidocytidine starting from uridine. For example, uridine is treated with triphenylphosphine, imidazole, and iodine to return 5'-deoxy-5'-iodouridine, as in Example 1. Treatment with sodium methoxide/methanol, followed by acetic anhydride to yield the 5-methylene nucleoside, 1-((2R, 3R,4S)-3,4-dihydroxy-5-methylene-tetrahydrofuran-2-yl)-1H-pyrimidine-2,4-dione, which is treated with benzyl triethylammonium azide and iodine; then N-methylmorpholine, DMAP and benzoyl chloride to return the 2',3'-dibenzoyl-protected 4'-azido-5'-deoxy-4'-iodouridine which is treated with a peracid, an acid and a phase-transfer catalyst to interconvert the uridine to a cytosine and return Compound 19. See also, Smith et al., *Bioorg. Med. Chem. Lett.* (2007), 17(9), 2570-2576; WO 2005/000864; and WO 2002/100415 |

| Active (CAS RN) | Biological Activity and/or Synthetic Methods |
|---|---|
| 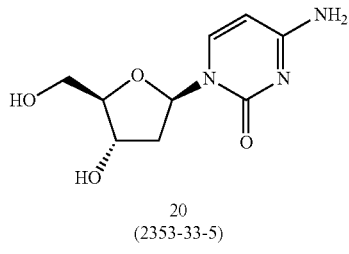 [SMILES: Nc1ccn([C@H]2C[C@H](O)[C@@H](CO)O2)c(=O)n1]<br>20<br>(2353-33-5) | Compound 20, decitabine, is a pyrimidine analog that inhibits DNA methylation and induces differentiation of leukemic cells. The preparation of compound 20 is disclosed in: Pliml et al. *Collect. Czech. Chem. Commun.* (1964) 29, 2576; Piskala et al. *Nucleic Acid Chemistry* Part 1 (Wiley, New York, 1978) pp 443-449; and Ben-Hattar et al. *Nucleosides Nucleotides* (1987) 6, 393. |
| 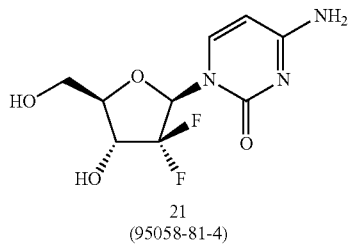<br>21<br>(95058-81-4) | Compound 21, 2',2'-difluoro-2'-deoxycytidine, Gemcitabine, is an antineoplastic and can be prepared by the route disclosed in U.S. Pat. No. 4,808,614, Hertel et al. Hertel prepares protected 2-desoxy 2,2-difluorocarbohydrates for preparation of antiviral nucleosides. Example 8 provides 1-(2-oxo-4-amino-1H-pyrimidin-1-yl)-2-desoxy-2,2-difluororibose by reaction of bis(trimethylsilyl)-N-acetylcytosine with 3,5-bis(t-butyldimethylsilyloxy)-1-methanesulfonyloxy-2-desoxy-2,2-difluororibose, from Example 2. See also, GB 2136425; U.S. Pat. No. 4,808,614; Hertel et al., *J. Org. Chem.* (1988) 53(11), 2406-9; and Chou et al., *Synthesis* (1992), (6), 565-570. |
| 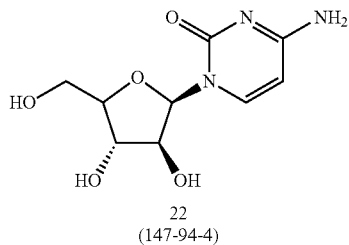 [SMILES: Nc1ccn([C@@H]2OC(CO)[C@@H](O)[C@@H]2O)c(=O)n1]<br>22<br>(147-94-4) | Compound 22, 1-(β-D-Arabinofuranosyl)cytosine, aracytidine, is an antineoplastic and may be prepared by the route disclosed in U.S. Pat. No. 3,116,282, Hunter. For example, Hunter Example 25 utilizes 1-(2,3,5-tri-O-acetyl-p-arabinofuranosyl)uracil with phosphorus pentasulfide and pyridine to prepare 1-(2,3,5-tri-O-acetyl-β-D-arabinofuranosyl)-4-thiouracil, which is treated with methanol and anhydrous ammonia in a bomb to prepare 1-β-D-arabinofuranosylcytosine. |
| 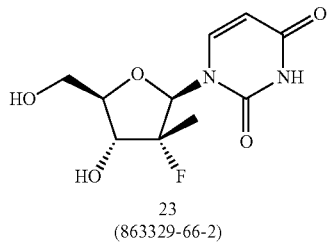 [SMILES: C[C@@]1(F)[C@H](O)[C@@H](CO)O[C@H]1n1ccc(=O)[nH]c1=O]<br>23<br>(863329-66-2) | Compound 23, PSI-6206, disclosed and claimed in U.S. Pat. No. 7,429,572, where the phosphate nucleotide form is known to possess antiviral activity. An improved process for preparation of compound 23 is disclosed in US 2010/016252, Sofia et al. Sofia prepares the uridine derivative from the corresponding cytidine derivative. Example 4 protects 2'-deoxy-2'-fluoro-2'-C-methylcytidine with pyridine and benzoyl chloride. The resultant tribenzoyl cytidine is refluxed in acetic acid to return 3',5'-dibenzoyl-2'-Deoxy-2'-fluoro-2'-C-methyluridine which is treated in methanolic ammonia to give Compound 22, 2'-deoxy-2'-fluoro-2'-C-methyluridine. See also Clark et al. *J. Med. Chem.* (2005), 48(17), 5504-5508. |
| 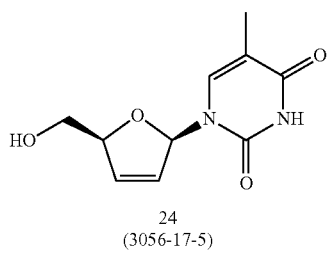 [SMILES: Cc1cn([C@H]2C=C[C@@H](CO)O2)c(=O)[nH]c1=O]<br>24<br>(3056-17-5) | Compound 24, stavudine, possesses antiretroviral activity and can be produced by the route disclosed in U.S. Pat. No. 5,130,421, Starrett et al. For example as shown in Scheme1, Route A, and col. 15-17, thymidine is treated with pyridine and methanesulfonyl chloride to produce 3',5'-di-O-(methanesulfonyl)thymidine which is treated with sodium hydroxide to return 1-(3,5-Anhydro-2-deoxy-beta-D-threo-pentofuranosyl)thymine. See also Horwitz et al. *J. Org. Chem.* (1966), 31, 205. |

-continued

| Active (CAS RN) | Biological Activity and/or Synthetic Methods |
|---|---|
| 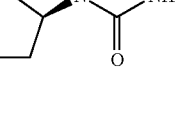<br>25<br>(30516-87-1) | Compound 25, zidovudine, is a pyrimidine nucleoside analog; reverse transcriptase inhibitor. The preparation of compound 25 is disclosed in: Horwitz et al., *J. Org. Chem.* (1964) 29, 2076 (1964); Glinski et al., *J. Org. Chem.* (1973) 38, 4299; U.S. Pat. No. 4,724,232; and Chu et al., *Tetrahedron Lett.* (1988) 29, 5349. |
| 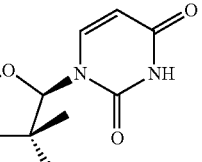<br>26<br>(31448-54-1) | Compound 26, 2'-C-Methyluridine, is a potent inhibitor of hepatitis C virus (HCV) RNA replication. Murakami et al., *Antimicrob. Agents Chemother.* (2008) 52(2): 458-64. 2'-C-Methyluridine can be prepared by the method of GB1209654, Walton, particularly Example 1, page 4. |
| 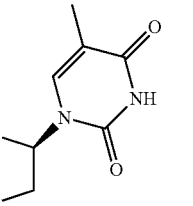<br>27<br>(136982-89-3) | Compound 27, 1-[(2R,4R)-2-(hydroxymethyl)-1,3-dioxolan-4-yl]-5-methyl- 2,4(1H,3H)-Pyrimidinedione, possesses antiviral activity against human immunodeficiency virus (HIV), and can be prepared by the method disclosed in U.S. Pat. No. 5,925,643, Chu et al. A synthetic route to Compound 27 is shown in Chu Figure 2, Examples 1 and 2, col. 7-10. See also, Evans et al. *Tetrahedron: Asymmetry* (1993), 4(11), 2319-2322 and WO 92/10497. |
| 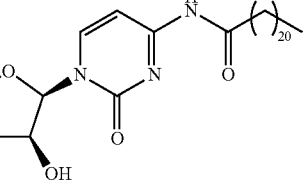<br>28<br>(55726-47-1) | Compound 28, enocitabine, is a derivative of cytarabine having antitumor activity. The preparation of compound 28 is disclosed in DE 2426304 and U.S. Pat. No. 3,991,045. |
| 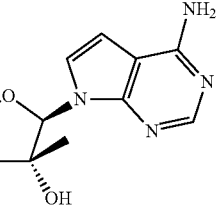<br>29<br>(443642-29-3) | Compound 29, 7-Deaza-2'-C-methyladenosine, is known to be an inhibitor of HCV RNA replication in vitro, and can be prepared as described in, for example, Eldrup et al. *J. Med. Chem.* (2004) 47, 5284-5297. Eldrup Scheme 1, shows a synthetic route to compound 9 at pages 5293-5294. Starting with 3,5-bis-O-(2,4-dichlorophenylmethyl)-1-O-methyl-β-D-ribofuranose, the 2-hydroxyl group can be oxidized to the 2-oxoribofuranose using Dess-Martin periodinane in dichloromethane. Subsequent stereospecific addition of a methyl group on the β face of the ribofuranose to give 3,5-bis-O-(2,4-dichlorophenylmethyl)-2-C-methyl-1-O-methyl-α-D-ribofuranose can be accomplished by reaction with methylmagnesium bromide in diethyl ether. The ribofuranose can next be converted to the corresponding 1-bromo compound (with hydrogen bromide/acetic acid in dichloromethane) and then reacted with the sodium salt of 4-chloro-1H-pyrrolo[2,3-d]pyrimidine to yield the β anomer. The removal of the dichlorophenylmethyl protection groups can be performed using boron trichloride in dichloromethane to give the 4-chloro ribonucleoside. This compound can be converted to the desired 4-amino derivative, Compound 29, by ammonolysis at elevated temperature. See also WO 2003/068244; WO 2002/057425; and WO 2002/057287. |

| Active (CAS RN) | Biological Activity and/or Synthetic Methods |
|---|---|
| 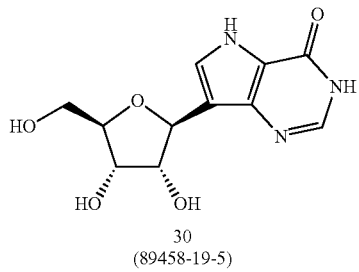 [SMILES: O=c1[nH]cnc2c([C@@H]3O[C@H](CO)[C@@H](O)[C@H]3O)c[nH]c12]<br>30<br>(89458-19-5) | Compound 30, 9-Deazainosine, 1,5-dihydro-7-β-D-ribofuranosyl-4H-Pyrrolo[3,2-d]pyrimidin-4-one, finds utility in e.g., potential treatment of visceral leishmaniasis. Berman et al. *Antimicrob. Agents Chemother.* (1987) 31(1), 111-113. Compound 31 can be prepared by the route disclosed in WO 2007/002191, Chand et al. Chand compound 3-4 is disclosed at page 7, and Scheme 3, page 21. |
| 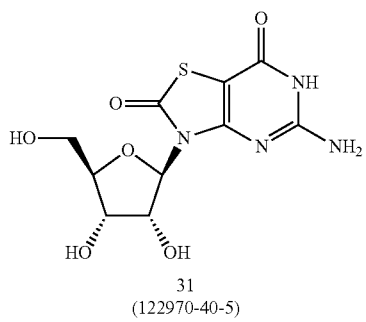 [SMILES: Nc1nc2c(sc(=O)n2[C@@H]2O[C@H](CO)[C@@H](O)[C@H]2O)c(=O)[nH]1]<br>31<br>(122970-40-5) | Compound 31, 7-Thia-8-oxoguanosine, 5-amino-3-β-D-ribofuranosyl-thiazolo[4,5-d]pyrimidine-2,7(3H,4H)-dione, possesses antitumor, antiviral and immune system enhancing properties. Compound 32 can be produced by the method disclosed in U.S. Pat. No. 5,041,426, Robins and Cottam. Synthesis of Robins compound 7 is disclosed in Examples 1 and 2, col. 8-9. See also U.S. Pat. No. 4,880,784. |
| 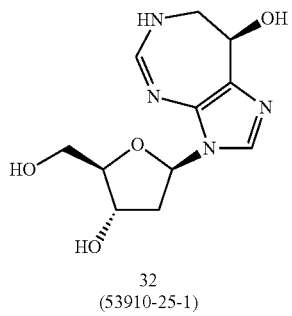 [SMILES: OC[C@H]1O[C@@H](n2cnc3c2N=CNC[C@H]3O)C[C@@H]1O]<br>32<br>(53910-25-1) | Compound 32, 2'-Deoxycoformycin, (8R)-3-(2-deoxy-β-D-erythropentofuranosyl)-3,4,7,8-tetrahydro-, Imidazo[4,5-d][1,3]diazepin-8-ol, pentostatin, is an adenosine deaminase inhibitor with antineoplastic utility originally isolated from *Steptomyces antibioticus*. Woo et al., *J. Heterocyclic Chem.*, (1974) 11, 641; Showalter et al. *J. Med. Chem.* (1982) 47, discloses a multigram synthetic route for pentostatin. See also Baker et al. *J. Heterocyclic Chem.* (1983) 20(3), 629-634; Showalter, et al. *J. Med. Chem.* (1983), 26(10), 1478-1482; and Chan et al. *J. Org. Chem.* (1982), 47(18), 3457-3464. |
| 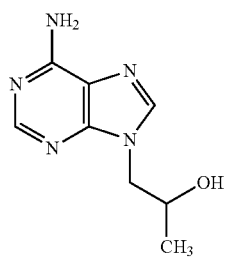<br>33a | Compound 33a, (R)-9-(2-hydroxypropyl)adenine, is a precursor for tenofovir, which is a reverse transcriptase inhibitor. General procedures for preparing compound 33 are disclosed in Rosenberg et al. *Collect. Czech. Chem. Commun.* (1988) 53, 2753; Holy et al., *Collect. Czech. Chem. Commun.* (1995) 60, 1390; and Schultze et al., *Tetrahedron Lett.* (1998) 39, 1853. |
| 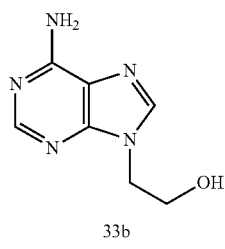 [SMILES: Nc1ncnc2c1ncn2CCO]<br>33b | Compound 33b, 9-(2-hydroxyethyl)adenine, is a precursor for adefovir, which is a useful for the treatment of chronic hepatitis B in patients ≥ 12 years of age. Procedures for preparing compound 34 are disclosed in EP 206459; U.S. Pat. No. 4,808,716; and Holy et al. *Collect. Czech. Chem. Commun.* (1987) 52, 2801. |

| Active (CAS RN) | Biological Activity and/or Synthetic Methods |
|---|---|
| 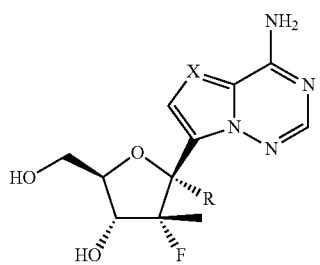<br>34a: R = H; X = CH<br>34b: R = CN; X = CH<br>34c: R = H; X = N<br>34d: R = CN; X = N | Compounds 34a-d may be useful for the treatment of HCV. Procedures for preparing compounds 34a-d are disclosed in US 2011/0070194. |
| 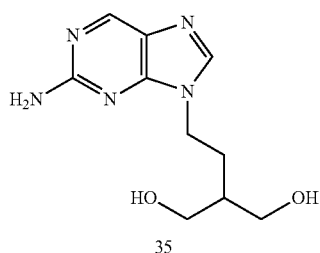 [SMILES: Nc1ncc2ncn(CCC(CO)CO)c2n1]<br>35 | Compound 35, which is the precursor "famciclovir," is referred to chemically as 2-(2-Amino-9H-purin-9-yl)ethyl]-1,3-propanediol. Synthetic procedures for preparing compound 35 can be found in U.S. Pat. No. 5,246,937. |
| 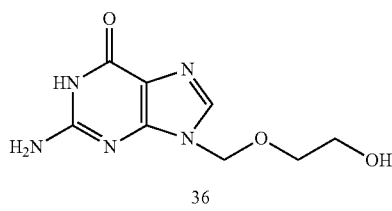<br>36<br>(59277-89-3) | Compound 36, acyclovir, is an orally active acyclic nucleoside with inhibitory activity towards several herpes viruses. The preparation of compound 36 can be found in: DE 2539963; U.S. Pat. No. 4,199,574; and Matsumoto et al., *Chem. Pharm. Bull.* (1988) 36, 1153. |
| 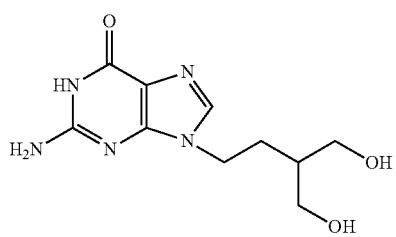<br>37<br>(39809-25-1) | Compound 37, is the carba analog of ganciclovir, which shows activity against several herpes viruses. The preparation of compound 37 is disclosed in Pandit et al., *Synth. Commun.* (1972) 2, 345; U.S. Pat. No. 5,075,445; Harnden et al., *J. Med. Chem.* (1987) 30, 1636; and Hannah et al., *J. Heterocycl. Chem.* (1989) 26, 1261. |
| 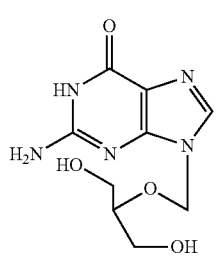<br>38<br>(82410-32-0) | Compound 38, ganciclovir, is a nucleoside analog structurally related to acyclovir. The preparation of compound 38 is described in: U.S. Pat. No. 4,355,032; Ogilvie et al., *Can. J. Chem.* (1982) 60, 3005; Ashton et al., *Biochem. Biophys. Res. Commun.* (1982) 108, 1716; and Martin et al., *J. Med. Chem.* (1983) 26, 759. |

-continued

| Active (CAS RN) | Biological Activity and/or Synthetic Methods |
|---|---|
| 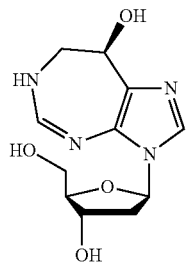<br>39<br>(53910-25-1) | Compound 39, pentostatin, is an adenosine deaminase inhibitor. Compound 39 can be isolated from *Streptomyces antibioticus* (see also DE 2517596 and U.S. Pat. No. 3,923,785) or may be synthesized as disclosed in Chan et al. *J. Org. Chem.* (1982) 47, 3457. |
| 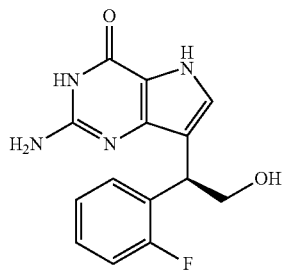<br>40<br>(216754-03-9) | Compound 40, 2-amino-7-[(1R)-1-(2-fluorophenyl)-2-hydroxyethyl]-3,5-dihydro-4H-Pyrrolo[3,2-d]pyrimidin-4-one, PNP45, a phosphorylase inhibitor, can be prepared by the route of Prashad et al. *J. Org. Chem.* (2002) 67, 6612-6617. For example, Prashad Scheme 1, page 6613, and examples 1-10, pages 6614-6617, disclose an eight step route to compound 41. See also WO 98/54185. |
| 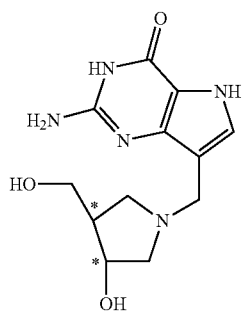<br>(S,S)-41<br>(R,R)-41<br>(S,S)-41 (942201-43-6)<br>(R,R)-41 (548486-61-9) | (S,S)-41, 2-amino-3,5-dihydro-7-[[(3S,4S)-3-hydroxy-4-(hydroxymethyl)-1-pyrrolidinyl]methyl]-4H-Pyrrolo[3,2-d]pyrimidin-4-one, possesses utility as a phosphorylase (PNP), methylthioadenosine phosphorylase (MTAP), 5'-methylthioadenosine nucleosidase (MTAN) and/or a nucleoside hydrolase inhibitor. Compound (S,S)-41 can also be prepared by the route disclosed in WO 2007/069923, Furneaux et al.. Furneaux Scheme 1 and Examples 1-8, pages 18-22 disclose synthesis of the (3S,4S)-4-(hydroxymethyl)pyrrolidin-3-ol; Scheme 2 and Example 10 disclose condensation with a deazapurine base.<br>(R,R)-41, 2-amino-3,5-dihydro-7-[[(3R,4R)-3-hydroxy-4-(hydroxymethyl)-1-pyrrolidinyl]methyl]-Pyrrolo[3,2-d]pyrimidin-4-one, possesses utility as a phosphorylase (PNP) inhibitor and can be prepared by the route disclosed in WO 2004/0698856, Evans et al. Evans compound 23, and synthetic route thereto is disclosed at pages 11-13, and page 19. |
| 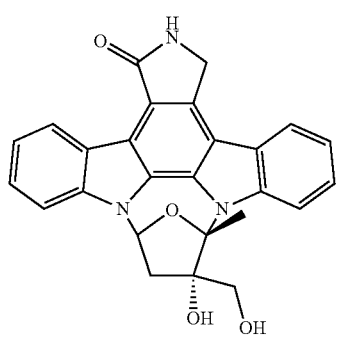<br>42<br>(111358-88-4) | Compound 42, (9S,10S,12R)2,3,9,10,11,12-hexahydro-10-hydroxy-10-(hydroxymethyl)-9-methyl-12-Epoxy-1H-diindolo[1,2,3-fg:3',2',1'-kl]pyrrolo[3,4-i][1,6]benzodiazocin-1-one, is known to inhibit protein kinase C and exhibit antitumor activity, and can be produced by the methods disclosed in U.S. Pat. No. 4,923,986, Murakata et al. Murakata discloses the synthesis of compound 1-18 at columns 7-24. Step 32 and the preceding steps disclose synthesis of compound 43, at columns 45-49. See also WO 88/07045. |

-continued

| Active (CAS RN) | Biological Activity and/or Synthetic Methods |
|---|---|
| 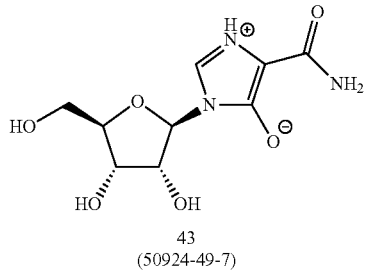<br>43<br>(50924-49-7) | Compound 43, mizoribine, is a nucleoside antibiotic produced by *Eupenicillium brefedianum* with cytotoxic and immunosuppressive activity. Compound 43 can be isolated (BE 799805; U.S. Pat. No. 3,888,843; Mizuno et al. *J. Antibiot.* (1974) 27, 775) or synthesized (Hayashi et al. *Chem. Pharm. Bull.* (1975) 23, 245; and Fukukuwa et al. *Chem. Pharm. Bull.* (1984) 32, 1644. |
| 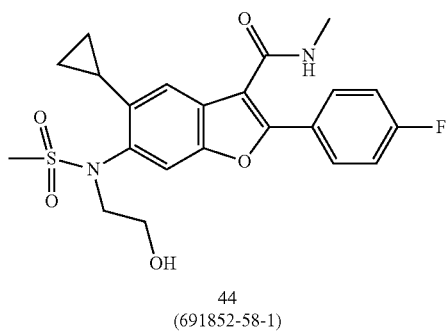 [SMILES: CNC(=O)c1c(-c2ccc(F)cc2)oc2cc(N(CCO)S(C)(=O)=O)c(C3CC3)cc12]<br>44<br>(691852-58-1) | Compound 44, HCV 796/Nesbuvir (5-cyclopropyl-2-(4-fluorophenyl)-6-[(2-hydroxyethyl)(methylsulfonyl)amino]-N-methyl-3-Benzofurancarboxamide), is a known HCV inhibitor, and a synthetic route is disclosed in WO 2008/024843, at Example 1, pages 15 to 19, (cf. Compound 44). See also U.S. Pat. No. 7,265,152 and WO 2004/041201. |
| 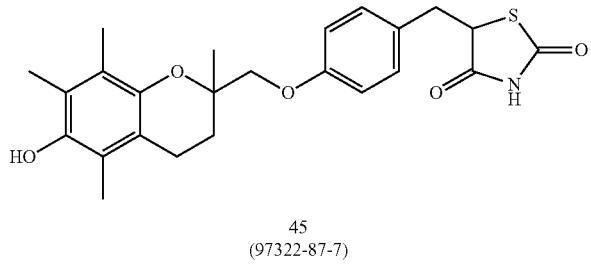 [SMILES: Cc1c(C)c2c(c(C)c1O)CCC(C)(COc1ccc(CC3SC(=O)NC3=O)cc1)O2]<br>45<br>(97322-87-7) | Compound 45, Depotox/Rezulin (5-[[4-[(3,4-dihydro-6-hydroxy-2,5,7,8-tetramethyl-2H-1-benzopyran-2-yl)methoxy]phenyl]methyl]-2,4-Thiazolidinedione), is an oral hypoglycemic agent which improves insulin sensitivity and decreases hepatic glucose production. Yoshioka et al., *J. Med. Chem.* (1989) 32(2), 421-428, , discloses synthesis of compound 45, as compound 27, Chart VI, page 422, Table II, and Scheme II, page 423, and protocols on pages 426-427. See also U.S. Pat. No. 5,104,888 and U.S. Pat. No. 4,572,912. |
| 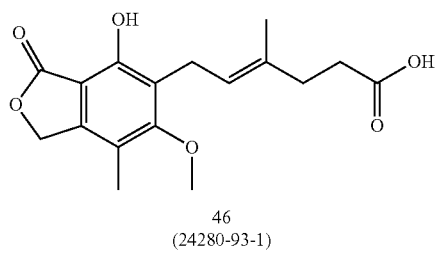 [SMILES: COc1c(C)c2c(c(O)c1C/C=C(\C)CCC(=O)O)C(=O)OC2]<br>46<br>(24280-93-1) | Compound 46, Mycophenolic acid ((4E)-6-(1,3-dihydro-4-hydroxy-6-methoxy-7-methyl-3-oxo-5-isobenzofuranyl)-4-methyl-4-Hexenoic acid), is an antibiotic produced by *Penicillium brevi-compactum, P. stoloniferum* and related spp. Selectively inhibits lymphocyte proliferation by blocking inosine monophosphate dehydrogenase (IMPDH), an enzyme involved in the de novo synthesis of purine nucleotides. A total synthesis of mycophenolic acid is disclosed in Birch and Wright, *Aust. J. Chem.* (1969) 22, 2635-2644. See also, Oxford et al. *Biochemical Journal* (1933), 27, 1473-1478; Clutterbuck et al. *Biochemical Journal* (1933), 27, 654-667; and Clutterbuck et al. *Biochemical Journal* (1932), 26, 1441-1458. |
| 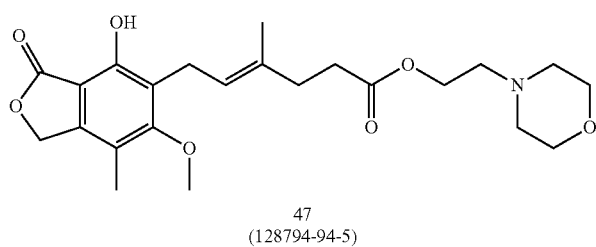 [SMILES: COc1c(C)c2c(c(O)c1C/C=C(\C)CCC(=O)OCCN1CCOCC1)C(=O)OC2]<br>47<br>(128794-94-5) | Compound 47, Mycophenolate mofetil ((4E)-6-(1,3-dihydro-4-hydroxy-6-methoxy-7-methyl-3-oxo-5 -isobenzofuranyl)-4-methyl-4-Hexenoic acid 2-(4-morpholinyl)ethyl ester), which possesses immunosuppressant properties, can be obtained by the methods of U.S. Pat. No. 4,753,935 to Nelson. Nelson describes two preferred synthetic routes for conversion of mycophenolic acid into the morpholinoethyl ester, Compound 47, as provided in Examples1-3, Col 9-11. The one route involves conversion into an acid halide, followed by condensation with morpholinoethanol to the end product. A second route involves conversion directly into the end product using a carbodiimide reaction. |

-continued

| Active (CAS RN) | Biological Activity and/or Synthetic Methods |
|---|---|
| 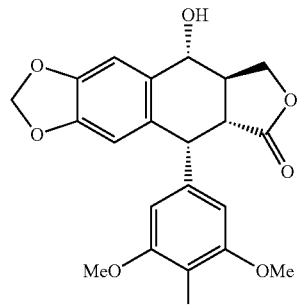<br>48<br>(518-28-5) | Compound 48, podophyllotoxin. Synthesized as described in:<br>Gensler et al. *J. Am. Chem. Soc.* (1962) 84, 1748;<br>Kaneko et al. *Tetrahedron Lett.* (1987) 28, 517;<br>Andrews et al., *J. Am. Chem. Soc.* (1988) 110, 7854;<br>Bush et al. *Chem. Commun.* (1993) 1200. |
| 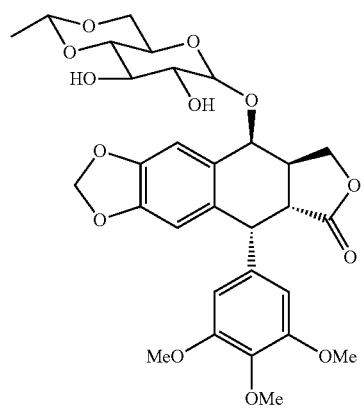<br>49<br>(33419-42-0) | Compound 49, (−)-Etoposide ((5R,5aR,8aR,9S)-9-[(4,6-O-(1R)-Ethylidene-β-D-glucopyranosyl)oxy]-5,8,8a,9-tetrahydro-5-(4-hydroxy-3,5-dimethoxyphenyl)furo[3',4':6,7]naphtho[2,3-d]-1,3-dioxol-6(5aH)-one; 4'-demethylepipodophyllotoxin 9-[4,6-O-ethylidene-β-D-glucopyranoside]), is a DNA topoisomerase II inhibitor useful as an antineoplastic. A synthetic route is provided in CA 956939, Kuhn et al. Synthesis is generally described at pages 1-6, and specifically at examples 1 and 2, pages 8-16. See also, JP 58-219196; Arnold et al. *Lancet* (1981), 2(8252), 912-914; and U.S. Pat. No. 3,524,844. |
| 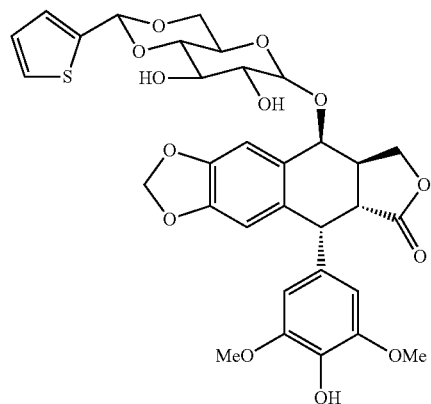<br>50<br>(29767-20-2) | Compound 50, teniposide, is a semi-synthetic derivative of podophyllotoxin. The synthesis of compound 50 is disclosed in ZA 6607585 and U.S. Pat. No. 3,524,844. |

-continued

| Active (CAS RN) | Biological Activity and/or Synthetic Methods |
|---|---|
| 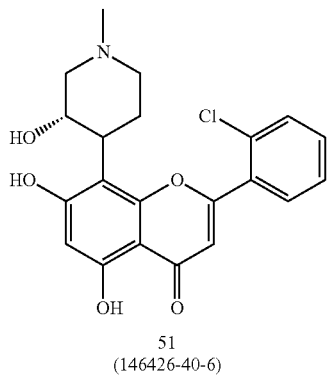 [SMILES: CN1CCC(c2c(O)cc(O)c3c(=O)cc(-c4ccccc4Cl)oc23)[C@H](O)C1]<br>51<br>(146426-40-6) | Compound 51, alvocidib, can be prepared, for example, by the route of Kim, WO 98/13344. For example, by the route of Kim, e.g. Examples 1-2, resolution of a mixture of (±)-1-methyl-4-(2,4,6-trimethoxyphenyl)-3-piperidinone can be performed with dibenzoyl-D-tartaric acid in MeOH give the tartarate salt which can be dissolved in a mixture of dichloromethane and 0.5N aqueous NaOH. The organic phase can be separated and worked up to give the (R)-piperidone. The R-piperidone can be subjected to reduction with diisobutylaluminum hydride, the resulting 3-piperidinol intermediate which can be C-acetylated and partially demethylated with acetic anhydride and $BF_3$-etherate in dichloromethane to give (3S-cis)-4-(3-acetyl-2-hydroxy-4,6-dimethoxyphenyl)-1-methyl-3-piperidinol. The piperidinol can be cyclocondensed with methyl 2-chlorobenzoate in presence of NaH in DMF to return (3S-cis)-2-(2-chlorophenyl)-8-(3-hydroxy-1-methyl-4-piperidinyl)-5,7-dimethyoxy-4H-1-benzopyran-4-one. The benzopyran-4-one can be subjected to methoxy ether cleavage with $BBr_3$ in 1,2-dichloroethane to give compound 51, 2-(2-chlorophenyl)-5,7-dihydroxy-8-[(3S,4R)-3-hydroxy-1-methyl-4-piperidinyl]-4H-1-benzopyran-4-one. See also WO 97/42949. |
| 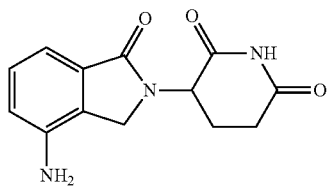<br>52<br>(191732-72-6) | Compound 52, lenalidomide, is an immunomodulatory drug substance, the preparation of which is disclosed in U.S. Pat. No. 5,635,517. |
| 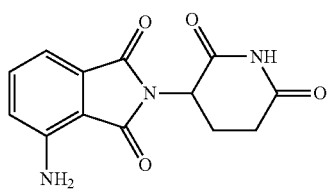<br>53<br>(50-35-1) | Compound 53, thalidomide, is a selective inhibitor of tumor necrosis factor α (TNF-α), which was formerly used as sedative/hypnotic. GB 768821 discloses a procedure for preparing thalidomide. |
| 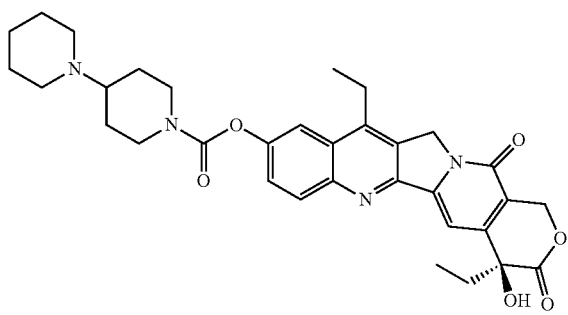<br>54<br>(97682-44-5) | Compound 54, irinotecan, is a DNA topoisomerase I inhibitor and a semisynthetic derivative of camptothecin. Compound 54 is prepared according to any one of the following procedures: JP 85 19790; U.S. Pat. No. 4,604,463; and Sawada et al., *Chem. Pharm. Bull.* (1991) 39, 1446. |

-continued

| Active (CAS RN) | Biological Activity and/or Synthetic Methods |
|---|---|
| 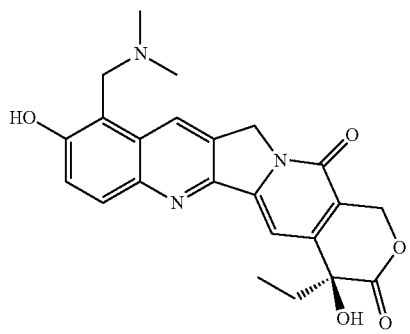<br>55<br>(123948-87-8) | Compound 55, topotecan, is a DNA topoisomerase I inhibitor and a semisynthetic analog of camptothecin. Procedures for preparing topotecan are described in any one of: EP 321122; U.S. Pat. No. 5,004,758; and Kingsbury et al. *J. Med. Chem.* (1991)34, 98. |
| 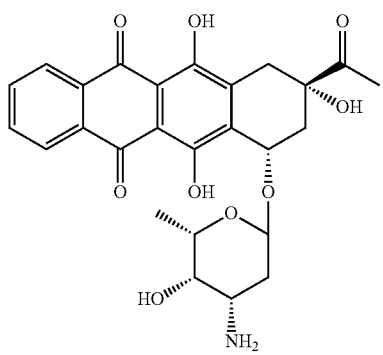<br>56<br>(58957-92-9) | Compound 56, Idarubicin, 1-Demethoxydaunorubicin, 4-Demethoxydaunomycin, (7S,9S)-9-Acetyl-7-[(3-amino-2,3,6-trideoxy-α-L-lyxo-hexopyranosyl)oxy]-7,8,9,10-tetrahydro-6,9,11-trihydroxy-5,12-naphthacenedione; (1S,3S)-3-acetyl-1,2,3,4,6,11-hexahydro-3,5,12-trihydroxy-6,11-dioxo-1-naphthacenyl-3-amino-2,3,6-trideoxy-α-L-lyxo-hexopyranoside, is an orally active anthracycline and an analog of daunorubicin with utility as an antineoplastic. Preparation of Compound 56 is disclosed in U.S. Pat. No. 4,046,878, Patelli et al., specifically at columns 3 and 4. See also, Arcamone et al. *Experientia* (1978) 34(10), 1255-1257; BE 842930; and U.S. Pat. No. 4,046,878. |
| 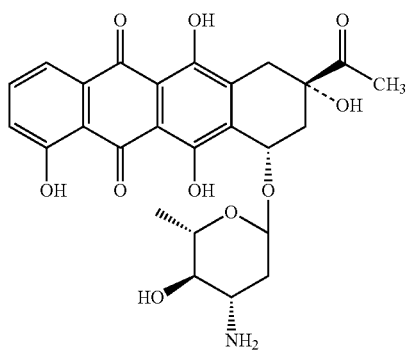<br>57<br>(50935-04-1) | Compound 57, carubicin, is an anthracycline antitumor antibiotic, related to daunorubicin and doxorubicin, which can be isolated from *Actinomadura carminat* (Gauze et al. *Antibiotiki* (1973) 18, 675; Brazhnikova et al., *J. Antibiot.* (1974) 27, 254; and SU 508076 (see C.A. 86, 15215 (1977)). |

| Active (CAS RN) | Biological Activity and/or Synthetic Methods |
|---|---|
| 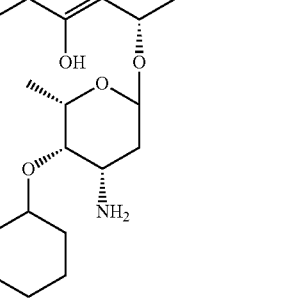<br>58<br>(72496-41-4) | Compound 58, pirarubicin, is an antineoplastic agent that is structurally related to doxorubicin. See Umezawa et al. *J. Antibiot.* (1979) 32, 1082; EP 14853; and U.S. Pat. No. 4,303,785 (for the preparation of the (2″R)- and (2″S)- diastereomers. |
| 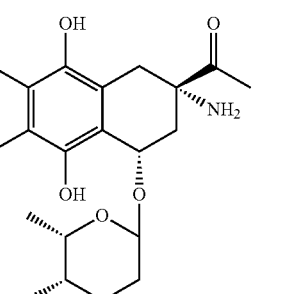<br>59<br>(110267-81-7) | Compound 59, amrubicin, is a synthetic anthracycline antibiotic; inhibits DNA topoisomerase II. Procedures for preparing comound 59 are disclosed in: EP 107486; U.S. Pat. No. 4,673,668; and Ishizumi et al. *J. Org. Chem.* (1987) 52, 4477. |
| 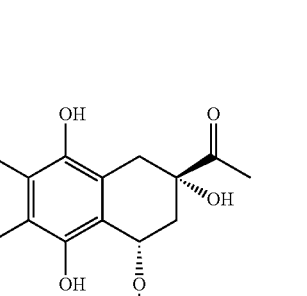<br>60<br>(20830-81-3) | Compound 60, daunorubicin, (8S,10S)-8-Acetyl-10-[(3-amino-2,3,6-trideoxy-α-L-lyxo-hexopyranosyl)oxy]-7,8,9,10-tetrahydro-6,8,11-trihydroxy-1-methoxy-5,12-naphthacenedione, is an anthracycline antibiotic with utility as an antineoplastic. Preparation is described in GB985598 to Rhone-Poulenc, particularly at pages 16 to 20. See also, GB 985598; Di Marco et al. *Nature* (1964) 201(4920), 706-707; Acton et al., *J. Med. Chem.* (1974) 17, 659. |

| Active (CAS RN) | Biological Activity and/or Synthetic Methods |
|---|---|
| 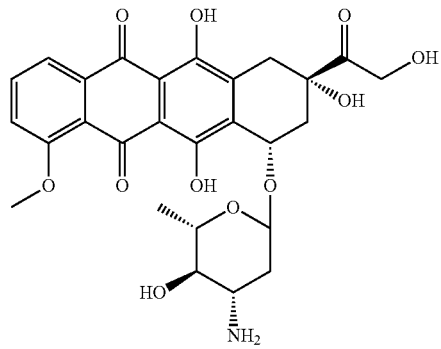<br>61<br>(56420-45-2) | Compound 61, epirubicin, is an analog of the anthracycline antibiotic doxorubicin differing only in the position of the C-4 hydroxy group of the sugar moiety. Compound 61 procedures are disclosed in any one of DE 2510866; U.S. Pat. No. 4,058,519; Arcamone et al. *J. Med. Chem.* (1975) 18, 703; and Penco, *Process Biochem.* (1980) 15(5), 12 (1980). Purification procedures are described in BE 898506 and GB 2133005. |
| 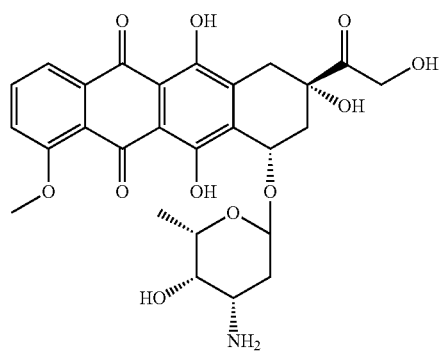<br>62<br>(23214-92-8) | Compound 62, doxorubicin, is an anthracycline antibiotic that interferes with topoisomerase II function. Compound 62 can be isolated from *Streptomyces peucetius* var*caesius* (see ZA 6802378; U.S. Pat. No. 3,590,028; and Arcamone et al. *Biotechnol. Bioeng.* (1969) 11, 1101. |
| 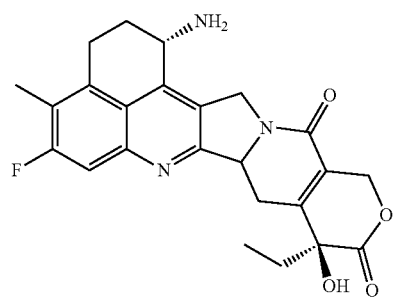<br>63<br>(171335-80-1) | Compound 63, exatecan, (1S,9S)-1-Amino-9-ethyl-5-fluoro-1,2,3,9,12,15-hexahydro-9-hydroxy-4-methyl-10H,13H-benzo[de]pyrano[3',4':6,7]indolizino[1,2-b]quinoline-10,13-dione, is a topoisomerase I inhibitor with utility as an anticancer drug and is a synthetic analogue of camptothecin, preparation of the compound and methansulfonate salt is provided in U.S. Pat. No. 6,552,197, Kamihara et al. Examples 1 and 2, and columns 8-10 disclose synthetic protocols. See also EP 495432; EP 737686; and U.S. Pat. No. 6,552,197. |
| 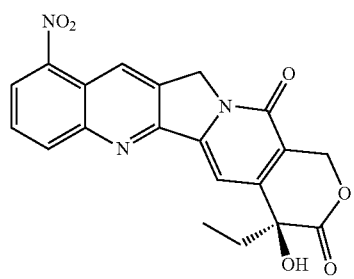<br>64<br>(91421-42-0) | Compound 64, 9-Nitro-20(S)-camptothecin, Orathecin, Rubitecan, (4S)-4-Ethyl-4-hydroxy-10-nitro-1H-pyrano[3',4':6,7]indolizino[1,2-b]quinoline-3,14(4H,12H)-dione; 9-nitrocamptothecin; 9-nitro-(20S)-camptothecin, is a DNA topoisomerase inhibitor that has utility as an anticancer drug, and is a prodrug of 9-aminocamptothecin. Preparation of Compound 64 is disclosed in Sawada et al., *Chem. Pharm. Bull.* (1991) 39(12) 3183-3188. Sawada equivalent compound Compound 5a is shown in Chart 1, page 3184 and synthesis thereof on page 3185. See also, Wani et al. *J. Med. Chem.* (1986) 29(11), 2358-2363. |

| Active (CAS RN) | Biological Activity and/or Synthetic Methods |
|---|---|
| 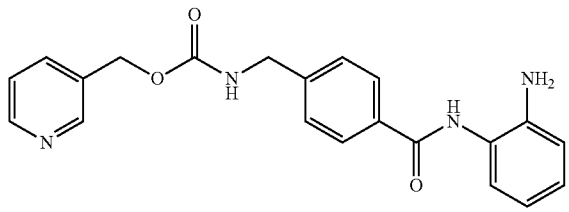<br>65<br>(209783-80-2) | Compound 65, entinostat, N-[[4-[[(2-aminophenyl)amino]carbonyl]phenyl]methyl]-Carbamic acid 3-pyridinylmethyl ester, a histone deacetylase inhibitor with anticancer activity, is disclosed in U.S. Pat. No. 6,320,078, Suzuki et al.; particularly Examples 1, 4 and 5, columns 13-15 and U.S. Pat. No. 6,174,905. |
| 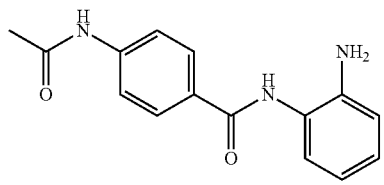<br>66<br>(112522-64-2) | Compound 66, Acetyldinaline, 4-(acetylamino)-N-(2-aminophenyl)benzamide, with utility as an oral anticancer agent, is disclosed in U.S. Pat. No. 5,137,918, Weiershausen et al.; specifically Example 1, Col. 6. See also, EP 0 242 851 A1. |
| 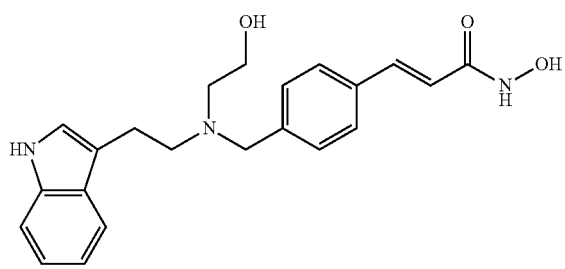<br>67<br>(404951-53-7) | Compound 67, dacinostat, (2E)-N-hydroxy-3-[4-[[(2-hydroxyethyl)[2-(1H-indol-3-yl)ethyl]amino]methyl]phenyl]-2-propenamide, is a histone deacetylase inhibitor with utility as an anticancer agent, and is disclosed in Remiszewski et al., *J. Med. Chem.* (2003) 46, 4609-4624. The Remiszewski compound 9 is disclosed in Table 2, page 4614, and preparation is disclosed at pages 4617-4618. See also, WO 2003/066885. |
| 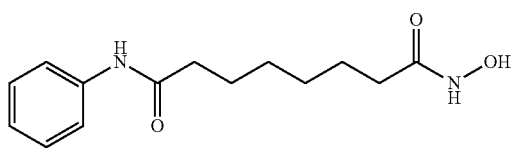<br>68<br>(149647-78-9) | Compound 68, Vorinostat, SAHA, suberoylanilide hydroxamic acid, N1-hydroxy-N8-phenyl-octanediamide, a histone deacetylase inhibitor with utility as an antineoplastc, is disclosed in WO 95/31977, Breslow et al. The Beslow synthesis is disclosed in General procedure D, pages 56-57. See also, U.S. Pat. No. 5,369,108 and Stowell et al. *J. Med. Chem.* (1995) 38(8), 1411-1413. |

| Active (CAS RN) | Biological Activity and/or Synthetic Methods |
|---|---|
| 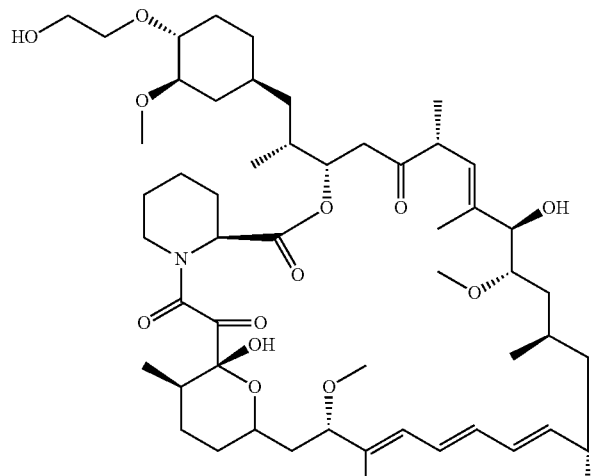<br>69<br>(159351-69-6) | Compound 69, everolimus, 42-O-(2-hydroxyethyl)-Rapamycin, with utility as an immunosuppressant, is disclosed in WO 94/09010, Cottons and Sedrani. Cottons Example 8 at pages 21 and 22 discloses synthesis of Compound 69. See also, U.S. Pat. No. 6,620,325 and Sorbera et al. *Drugs of the Future* (1999) 24(1), 22-29. |
| 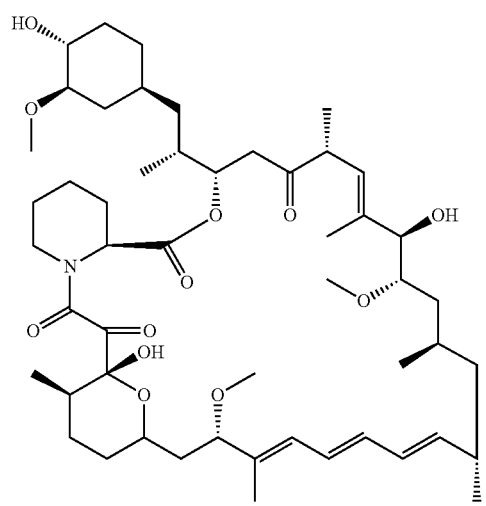<br>70<br>(53123-88-9) | Compound 70, sirolimus/rapamycin, is a triene macrolide antibiotic with immunomodulatory properties isolated from *Streptomyces hygroscopicus*. Preparation and characterization is described in U.S. Pat. No. 3,929,992, Sehgal et al, specifically at columns 5 to 11. The triene fungicide rapamycin is prepd. by culturing *Streptomyces hygroscopicus* in an aq. medium. Thus, *S. hygroscopicus* NRRL 5491 is inoculated in a starter medium of soybean flour 4, glucose 2, $(NH_4)_2SO_4$ 0.3, and $CaCO_3$ 0.15% and after a 2nd stage in the same medium, transferred to 160 l. containing soybean flour 3, glucose 2, $(NH_4)_2SO_4$ 0.1, $KH_2PO_4$ 0.5%, and antifoamer. Incubation is at 25° with aeration and agitation. After 2 days, 1.5% glucose is added each day. Fermentation is stopped at 4-5 days, when the titer is .apprx. 60 mg/l. Rapamycin is purified by solvent extraction of the mycelium, adsorption to silica gel, and crystallization from ether. See also, Fretz et al. *J. Am. Chem. Soc.* (1991) 113(4), 1409-1411 and U.S. Pat. No. 3,929,992. |

| Active (CAS RN) | Biological Activity and/or Synthetic Methods |
|---|---|
| 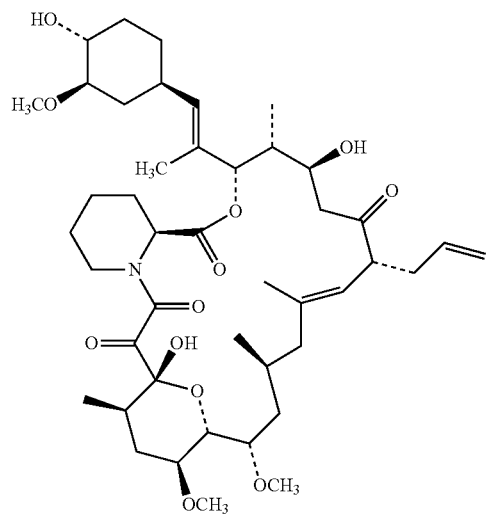<br>71<br>(104987-11-3) | Compound 71, tacrolimus, is a potent immunosuppressant and can be isolated from *Streptomyces tsukubaensis* no. 9993 (see EP 184162 and Kino et al., *J. Antibiot.* (1987) 40, 1249) or may be synthesized (Jones et al. *J. Am. Chem. Soc.* (1989) 111, 1157.). |
| 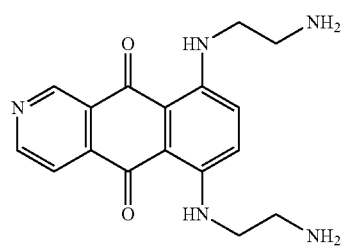<br>72<br>(144510-96-3) | Compound 72, pixantrone, is an aza-anthracenedione analog which intercalates DNA and inhibits topoisomerase II and is structurally similar to mitoxantrone. Compound 72 can be prepared based on the procedure disclosed in EP 503537 or in the procedure disclosed in Krapcho et al. *J. Med. Chem.* (1994) 37, 828. |
| 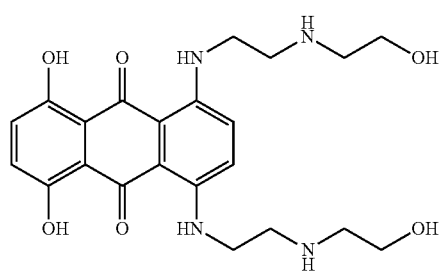<br>73<br>(65271-80-9) | Compound 73, mitoxantrone, is an immunosuppressive and cytostatic anthracenedione having antitumor activity. Compound 73 is prepared by any one of the procedures disclosed in: Zee-Cheng et al. *J. Med. Chem.* (1978) 21, 291; Murdock et al. *J. Med. Chem.* (1979) 22, 1024; DE 2835661 and U.S. Pat. No. 4,197,249. |

| Active (CAS RN) | | Biological Activity and/or Synthetic Methods |
|---|---|---|
| 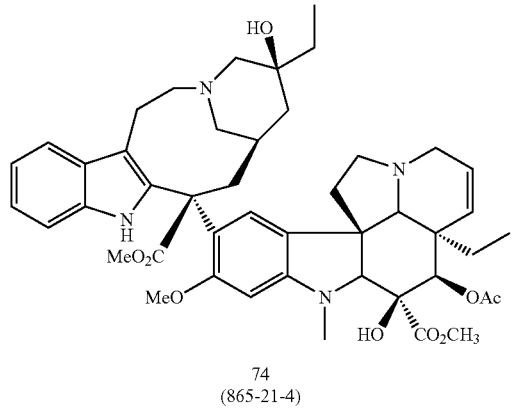<br>74<br>(865-21-4) | | Compound 74, Vinblastine, Vincaleukoblastine, is an antitumor alkaloid isolated from periwinkle, *Vinca rosea* Linn., *Apocynaceae*; inhibits microtubule assembly. Prepration is disclosed in U.S. Pat. No. 3,097,137, Beer et al; see Examples 1-2, columns 4-5. Identification: Noble et al., *Ann. N.Y. Acad. Sci.* (1958) 76, 882-894. Isolation and characterization: Gorman et al., *J. Am. Chem. Soc.* (1959) 81, 4745 and 4754; U.S. Pat. No. 3,097,137. Structure: N. Neuss et al., *J. Am. Chem. Soc.* 86, 1440 (1964). |
| 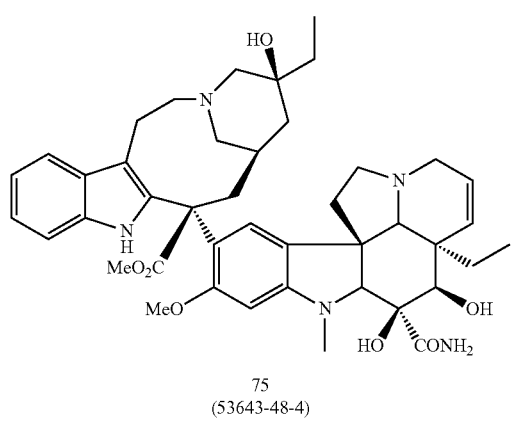<br>75<br>(53643-48-4) | | Compound 75, Vindesine, Vincaleukoblastine, 3-(Aminocarbonyl)-$O^4$-deacetyl-3-de(methoxycarbonyl)vincaleukoblastine; desacetylvinblastine amide, is a synthetic derivative of vinblastine and has utility as an antineoplastic. Preparation of compound 130 is disclosed in U.S. Pat. No. 4,203,898. Preparation is shown, e.g., in Cullinan Examples Column 16-18. See also Barnett et al. J. Med. Chem. (1978) 21(1), 88-96. |
| 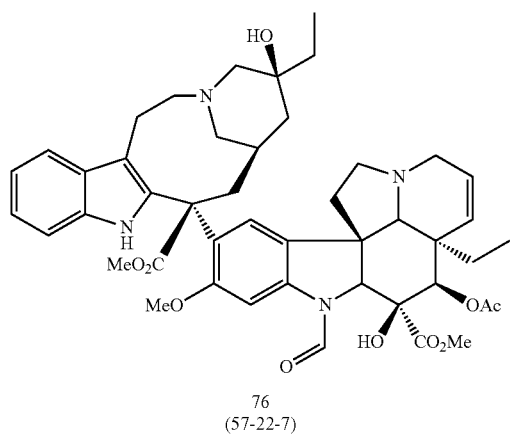<br>76<br>(57-22-7) | | Compound 76, For (+) vincristine, this Antitumor alkaloid is isolated from *Vinca rosea* Linn. (*Catharanthus roseus* G. Don), *Apocynaceae*: Svoboda, *Lloydia* (1961) 24, 173 with the structure disclosed in Neuss et al., *J. Am. Chem. Soc.* (1964) 86, 1440. See also, Moncrief et al. *J. Am. Chem. Soc.* (1965) 87, 4963. |

| Active (CAS RN) | Biological Activity and/or Synthetic Methods |
|---|---|
| 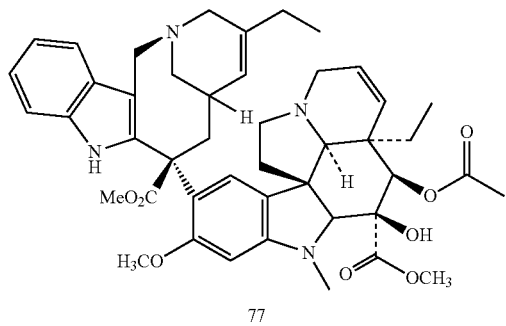<br>77 | Compound 77, Nor-5'-anhydrovinblastine, Vinorelbine, (2β,3β,4β,5α,12R,19α)-4-(Acetyloxy)-6,7-didehydro-15-[(2R,6R,8S)-4-ethyl-1,3,6,7,8,9-hexahydro-8-(methoxycarbonyl)-2,6-methano-2H-azecino[4,3-b]indol-8-yl]-3-hydroxy-16-methoxy-1-methylaspidospermidine-3-carboxylic acid methyl ester; 3',4'-didehydro-4'-deoxy-C'-norvincaleukoblastine, has utility as an antineoplastic. Preparation is described in U.S. Pat. No. 4,307,100. |
| 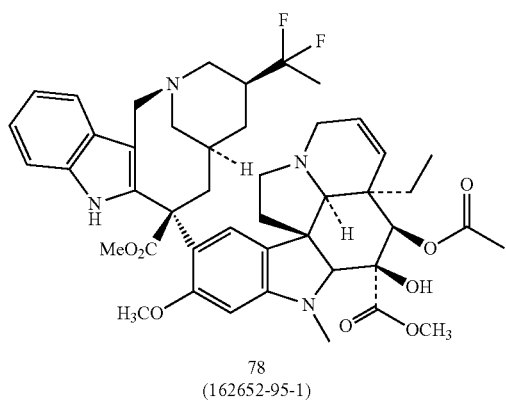<br>78<br>(162652-95-1) | Compound 78, vinflunine, is a semisynthetic Vinca alkaloid with microtubule destabilizing and antiangiogenic activity. Compound 78 can be prepared by any one of FR 2707988; U.S. Pat. No. 5,620,985; and Fahy et al. *J. Am. Chem. Soc.* (1997) 119, 8576. |
| 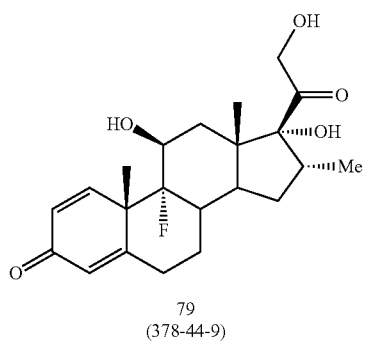<br>79<br>(378-44-9) | Compound 79, betamethasone, anti-inflammatory and immunosuppressive agent, which can be prepared according to any one of the following procedures: Taub et al. *J. Am. Chem. Soc.* (1958) 80, 4435; Oliveto et al. *J. Am. Chem. Soc.* (1958) 80 6688; Taub et al. *J. Am. Chem. Soc.* (1960) 82, 4012; U.S. Pat. No. 3,053,865; and U.S. Pat. No. 3,104,246. |
| 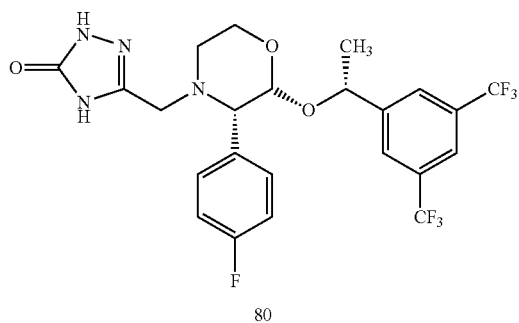<br>80 | Compound 80, aprepitant, having selective neurokinin-1 (NK-1) receptor antagonist activity and is useful as an anti-emetic. Prepared according to the procedures found in WO 95/16679; U.S. Pat. No. 5,719,147; Hale et al., *J. Med. Chem.* (1998) 41, 4607; and Brands et al. *J. Am. Chem. Soc.* (2003) 125, 2129. |

| Active (CAS RN) | Biological Activity and/or Synthetic Methods |
|---|---|
| 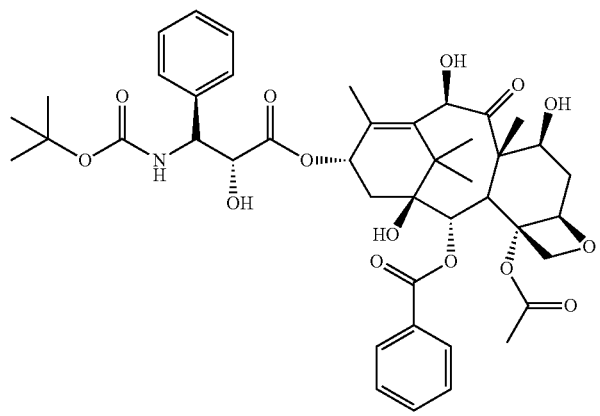<br>81<br>(114977-28-5) | Compound 81, docetaxel, is a semisynthetic derivative of paclitaxel prepared using a natural precursor, 10-deacetylbaccatin III, extracted from the needles of the European yew tree, *Taxus baccata* L., *Taxaceae*. Compound 81 is an antimitotic agent that promotes the assembly of microtubules and inhibits their depolymerization to free tubulin. Compound 81 is prepared according to any of the following: EP 253738; U.S. Pat. No. 4,814,470; and *Tetrahedron* (1989) 45, 4177. |
| 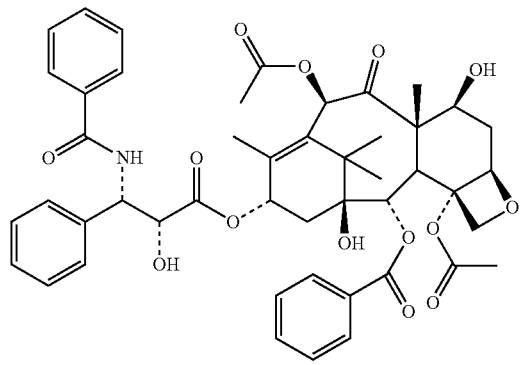<br>82<br>(33069-62-4) | Compound 82, paclitaxel, an antiproliferative agent useful for treating breast cancer, which was first isolated, as the l-form, from the bark of the Pacific yew tree, *Taxus brevifolia*, *Taxaceae*; promotes the assembly of microtubules and inhibits the tubulin disassembly process. The isolation and structure of compound 82 is disclosed in Wani et al. *J. Am. Chem. Soc.* (1971) 93, 2325. Compound 82 can also be prepared according to Holton et al. *J. Am. Chem. Soc.* (1994) 116, 1597, 1599 or Nicolaou et al. *Nature* (1994) 367, 630. |
| 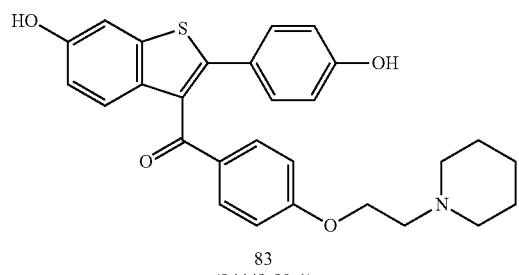<br>83<br>(84449-90-1) | Compound 83, raloxifene, is a nonsteroidal, selective estrogen receptor modulator (SERM), which is prepared by any one of the procedures disclosed in: EP 62503; U.S. Pat. No. 4,418,068; and Jones et al. *J. Med. Chem.* (1984) 27, 1057. |
| 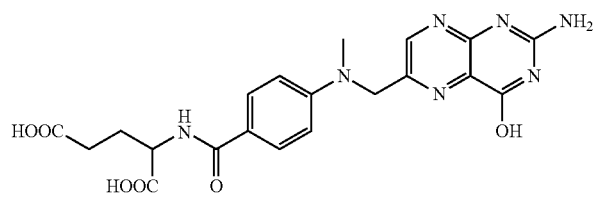<br>84<br>(2410-93-7) | Compound 84, methopterin, the preparation of which is disclosed in Cosulich et al. *J. Am. Chem. Soc.* (1948) 70, 1922 and U.S. Pat. No. 2,563,707. |

| Active (CAS RN) | Biological Activity and/or Synthetic Methods |
|---|---|
| 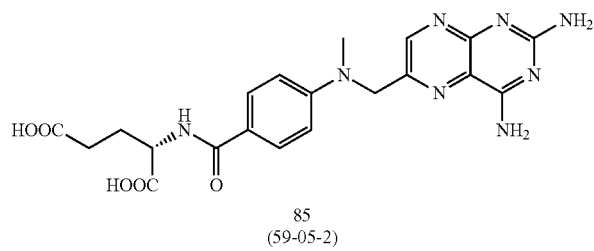 [SMILES: CN(Cc1cnc2nc(N)nc(N)c2n1)c1ccc(C(=O)N[C@@H](CCC(=O)O)C(=O)O)cc1]<br>85<br>(59-05-2) | Compound 85, methotrexate, is a folic acid antagonist, which is useful in the treatment of cancer. Prepared according to the procedures described in: Seeger et al. *J. Am. Chem. Soc.* (1949) 71, 1753; and U.S. Pat. No. 2,512,572. |
| 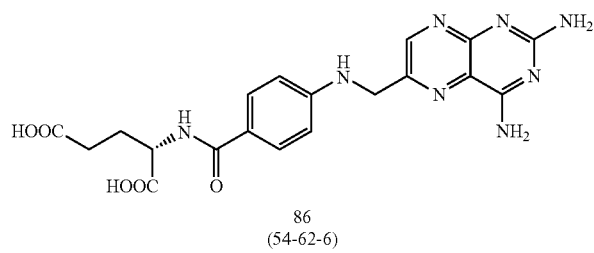 [SMILES: Nc1nc(N)c2nc(CNc3ccc(C(=O)N[C@@H](CCC(=O)O)C(=O)O)cc3)cnc2n1]<br>86<br>(54-62-6) | Compound 86, aminopterin, is an antineoplastic drug with immunosuppressive properties used in chemotherapy. Prepd from 2,4,5,6-tetraminopyrimidine sulfate, 2,3-dibromopropionaldehyde and p-aminobenzoylglutamic acid: Seeger et al. *J. Am. Chem. Soc.* 69, 2567 (1947); from 6-(bromomethyl)-2,4-diaminopteridine HBr: Piper, Montgomery, *J. Heterocycl. Chem.* (1974) 11, 279. |
| 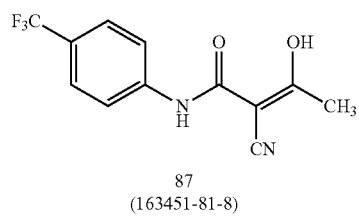 [SMILES: C/C(O)=C(\C#N)C(=O)Nc1ccc(C(F)(F)F)cc1]<br>87<br>(163451-81-8) | Compound 87, teriflumide, is a disease modifying antirheumatic drug that is prepared as described in WO 91/17748 and U.S. Pat. No. 5,494,911. |
| 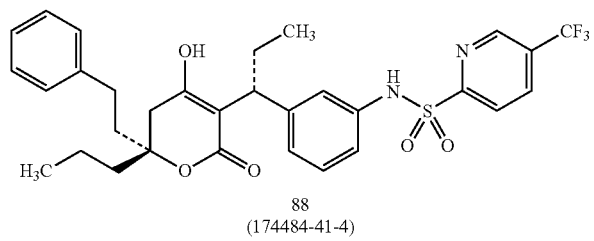<br>88<br>(174484-41-4) | Compound 88, tipranavir, is a non-peptidic HIV protease inhibitor that is prepared according to: WO 95/30670; U.S. Pat. No. 5,852,195; Turner et al. *J. Med. Chem.* (1998) 41, 3467; and Fors et al. *J. Org. Chem.* (1998) 63, 7348. |
| 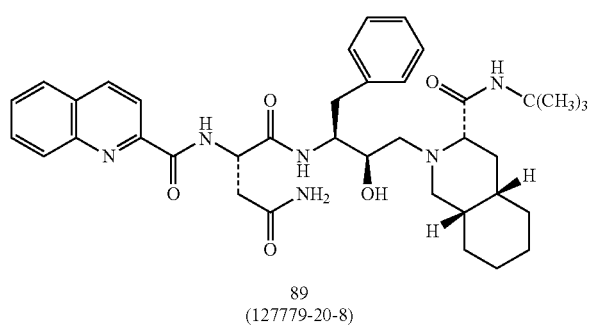 [SMILES: CC(C)(C)NC(=O)[C@@H]1C[C@@H]2CCCC[C@@H]2CN1C[C@@H](O)[C@H](Cc1ccccc1)NC(=O)[C@H](CC(N)=O)NC(=O)c1ccc2ccccc2n1]<br>89<br>(127779-20-8) | Compound 89, saquinavir, is a selective HIV protease inhibitor that is prepared according to any one of the following: EP 432695; U.S. Pat. No. 5,196,438; and Parkes et al., *J. Org. Chem.* (1994) 59, 3656. |

| Active (CAS RN) | Biological Activity and/or Synthetic Methods |
|---|---|
| 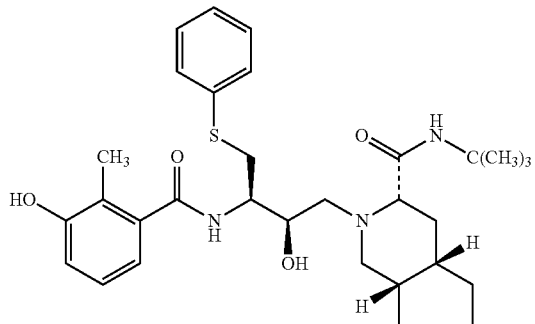<br>90<br>(159989-64-7) | Compound 90, nelfinavir, is an HIV protease inhibitor that is prepared according to the procedures described in WO 95/09843 and U.S. Pat. No. 5,484,926. |

Not to be limited by way of example, the following examples serve to facilitate a better understanding of the claimed invention.

P. D. Howes et al. *Nucleosides, Nucleotides & Nucleic Acids* 2003, Vol. 22, Nos. 5-8, pp. 687-689 ("Howes") discloses 2'- and 5'-phosphoramidates obtained by a reaction with t-butylmagnesium chloride. There, Howes discloses that when a 3'-deoxy-cytidine nucleoside is reacted with (S)-2-[chloro-phenoxy-phosphorylamino]propionic acid methyl ester in the presence of 1.2 equivalents of t-butylmagnesium chloride, selective phosphorylation on the 2'-position occurred, but that with an additional equivalent of t-butyl-magnesium chloride selective phosphorylation on the 5'-position occurred. This disclosure should be contrasted to that which is disclosed in Howes' Scheme 1.

Generally, a compound of formula I, derived, e.g., from any of the actives disclosed herein, can be obtained upon reaction with a compound of formula II. The following examples, are not intended to limit the scope of the disclosed and claimed subject matter, but serve only to better illustrate the embodiments disclosed herein.

Preparation of a Phosphoramidate Nucleotide.

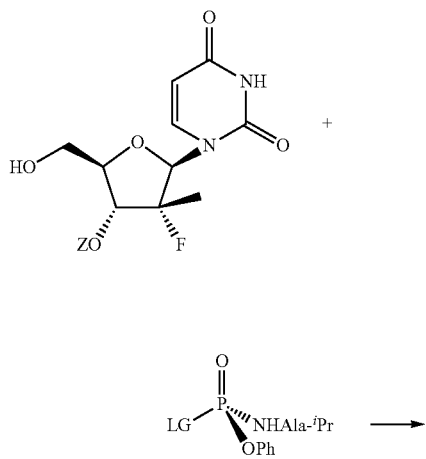

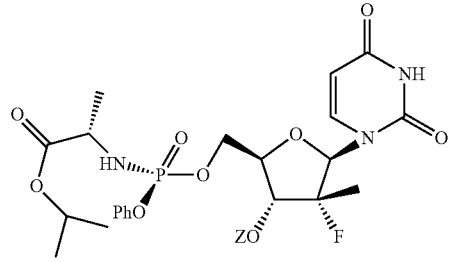

In order to prepare the uridine nucleoside shown above (Z=H, but for illustrative purposes, Z can also be a blocking group (cf. compounds 91-94)), one could take advantage of an advanced tribenzoylated cytidine intermediate (107) in the synthesis of certain 3',5'-diacylated analogs (108) of 23 (see below) already produced efficiently on a pilot plant scale (see WO 2006/031725 or US 2006/0122146, both of which are incorporated by reference in their entirety). The following method was found to be scalable and cost-efficient.

3',5'-O-dibenozyl-2'-deoxy-2'-fluoro-2'-C-methyl-$N^4$-benzoylcytidine (107) is obtained by a method disclosed in WO 2006/031725 (US 2006/0122146) and WO 2008/045419 (US 2008/0139802) the subject matter of which is hereby incorporated by reference in its entirety. 107 is treated with 70% aqueous acetic acid to form 3',5'-O-dibenozyl-2'-deoxy-2'-fluoro-2'-C-methyl-uridine (108). The benzoyl esters can be hydrolyzed by a number of methods as well, e.g., alkoxides in alcoholic solvent, such as sodium methoxide in methanol, potassium carbonate in methanol, or ethanol analogs, alkylamines such as methylamine in methanol, butylamine etc. Methanolic ammonia was chosen for the larger scale work. The uridine product (23) can be purified by crystallization to afford a 70% yield from the tribenzoylated cytidine (107).

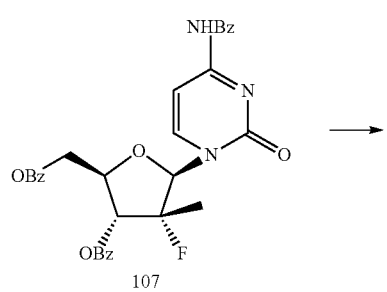

107

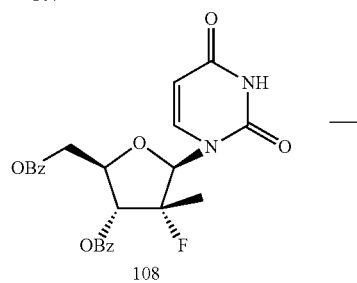

108

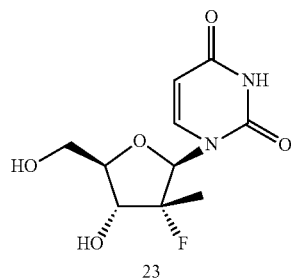

23

Example 1

Preparation of 2'-deoxy-2'-fluoro-2'-C-methyluridine (23)

In a 10 L flask, was added 3',5'-O-dibenozyl-2'-deoxy-2'-fluoro-2'-C-methyl-N4-benzoylcytidine 107 (500 g, 0.874 mol) and 70% aqueous acetic acid (7.5 L). The solution was heated to reflux (110° C.) for 20 h. TLC indicated a complete reaction (Rf 0.6 in 5% methanol in dichloromethane (DCM)). The mixture was cooled to ambient temperature and diluted with water (2 L). After stirring for 2 h, the resulting precipitate was collected by filtration and the solid was rinsed with water (5 L) and dried in the atmosphere at ambient temperature for 12 h to afford 360 g (88%). This dibenzoyluridine intermediate, 108, was used directly in the next step by adding it all to freshly prepared methanolic ammonia (5.4 L, ca 25%) at 0° C. This temperature was maintained for 3 h and then allowed to warm to 15° C. for 24 h. TLC indicated a complete reaction (Rf 0.4 in 10% methanol in DCM). The reaction mixture was filtered through a Celite bed and concentrated under reduced pressure to give the crude product (216 g). The crude product was stirred with ethyl acetate (325 mL) for 3 h at ambient temperature. The resulting solid was collected by filtration and washed with ethyl acetate (216 mL). The solid was dried under vacuum at ambient temperature for 4 h to afford 160 g (78%) of the desired product, 23, in 98.7% HPLC purity. $^1$H-NMR (DMSO-$d_6$) δ 11.44 (br s, 1H, NH), 7.95 (d, 1H, C-6H), 5.97 (d, 1H, C-1'H), 5.64 (d, 1H, C-5H), 3.84-3.77 (m, 3H, C-5'-Ha, C-3'H. C-4'H), 3.63-3.60 (m, 1H, C5'-Hb), 1.23 (d, 3H, C-2'-CH$_3$). ES-MS M−1 259.

Example 2

Preparation of 110

To a stirred solution of 1-((2R,3R,4R,5R)-3-Fluoro-4-hydroxy-5-hydroxymethyl-3-methyl-tetrahydro-furan-2-yl)-1H-pyrimidine-2,4-dione 23 (32 mg, 0.12 mmol) in dry THF (1 mL) was added a 1M solution of tButylmagnesium chloride (0.26 mL, 0.26 mmol, 2.1 equiv)) at room temperature over a period of 3 min. After 30 min, a solution of (S)-2-[(R)-(4-nitro-phenoxy)-phenoxy-phosphorylamino]propionic acid isopropyl ester (109) in THF (0.5 mL) was added drop wise over a period of 3 min. The mixture was allowed to stir at room temperature for 42 h and then quenched with saturated aqueous NH$_4$Cl (10 mL). The mixture was partitioned between ethyl acetate and water. The combined organic extract was dried over anhydrous sodium sulfate and concentrated. The residue was chromatographed using 0-4% methanol/dichloromethane gradient to give 110 as foamy solid (29 mg, 44.5% yield).

110 Data:

$^1$H-NMR (CDCl$_3$) δ 8.63 (br s, 1H, NH), 7.47 (d, 1H, C6-H), 7.30 (m, 2H, o-aromatic), 7.26-7.18 (m, 3H, m,p-aromatic), 6.18 (br d, 1H, C1'-H), 5.70 (d, 1H, C5-H), 5.02 (sept, CH—(CH$_3$)$_2$), 4.53 (m, 2H, C-5'-H$_2$), 4.11 (d, 1H, C3'-H), 3.97 (m, 3H, C3'-OH, C4'-H, ala-CH—CH₃), 3.77 (br s, 1H, ala-NH), 1.39 (d, 3H, C2'-CH₃), 1.37 (d, 3H, ala-CH₃), 1.24 (d, 6H, CH—(CH₃)₂).

Example 3

Preparation of (S)-2-[(4-nitro-phenoxy)-phenoxy-phosphorylamino]propionic acid isopropyl ester

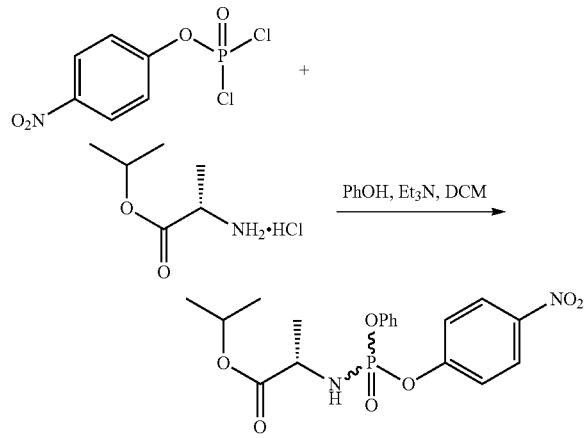

To a stirred solution of 4-nitrophenyl phoshorodichloridate 12.8 g, 50 mmol) in dichloromethane (100 mL) was added a solution of phenol and triethylamine (7.7 mL, 55 mmol) in dichloromethane (100 mL) at −78° C. over a period of 20 min. The mixture was stirred at this temperature for 30 min and then transferred to another round bottom flask containing L-alanine isopropyl ester hydrochloride (8.38 g, 50 mmol) in dichloromethane (100 mL) at 0° C. To the mixture was added second lot of triethylamine (14.6 mL, 105 mmol) over a period of 15 min. The mixture was stirred at 0° C. for 1 h and then the solvent was evaporated. The residue was triturated with ethyl acetate (150 mL) and the white solid was filtered off. The filtrate was concentrated under reduced pressure to give pale yellow oil. The crude compound was chromatographed using 0-20% ethyl acetate/hexanes gradient to give product (17 g, 83% yield) as a mixture of diastereomers in about 1:1 ratio. ³¹P NMR (162 MHz, CDCl₃): δ −2.05, −2.10; ¹H NMR (400 MHz, CDCl₃): δ 8.22 (d, J=9.2 Hz, 2H), 7.41-7.33 (m, 4H), 7.26-7.18 (m, 3H), 5.05-4.96 (m, 1H), 4.14-4.05 (m, 1H), 3.93-3.88 (m, 1H), 1.38 (d, J=6.8 Hz, 3H), 1.22 (dd, J=6.2 & 3.0 Hz, 6H); MS (ESI) m/z 407 (M−1)⁺.

Crystallization of (S)-2-[(S)-(4-nitro-phenoxy)-phenoxy-phosphorylamino]propionic acid isopropyl ester (109)

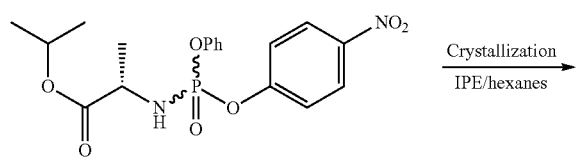

-continued

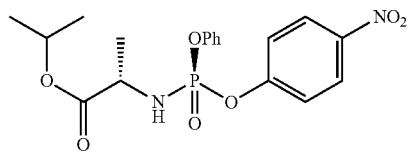

109

(S)-2-[(4-Nitro-phenoxy)-phenoxy-phosphorylamino]-propionic acid isopropyl ester (3.4 g) was dissolved in IPE (6 mL). To the above solution were added hexanes (1 mL) while hand shaking until the solution was turbid. Few drops of IPE were then added to the mixture to get a clear solution. The mixture was gently stirred at room temperature for 20 h. A white and fine crystalline solid obtained was filtered, washed with 1:1 mixture of IPE/hexanes and dried to give white fluffy solid (820 mg, 24% yield) mp 52 (shrinks) 62-66 (melts). ³¹P NMR (162 MHz, CDCl₃): δ −2.05; ¹H NMR (400 MHz, CDCl₃): δ 8.22 (d, J=9.2 Hz, 2H), 7.41-7.33 (m, 4H), 7.26-7.18 (m, 3H), 5.05-4.96 (m, 1H), 4.14-4.05 (m, 1H), 3.93-3.88 (m, 1H), 1.38 (d, J=6.8 Hz, 3H), 1.22 (dd, J=6.2 & 3.0 Hz, 6H); MS (ESI) m/z 407 (M−1)⁺. The stereochemistry of 109 has been confirmed by single crystal X-ray crystallography, as evidenced by the ORTEP representation presented below (where P═O projects away from the viewer).

X-Ray Crystallography of 109

109, $C_{18}H_{21}N_2PO_7$, crystallizes in the monoclinic space group P2₁ (systematic absences 0k0: k=odd) with a=5.3312(4)Å, b=15.3388(8)Å, c=23.7807(13)Å, β=92.891(3)°, V=1942.2(2)Å³, Z=4, and $d_{calc}$=1.397 g/cm³. X-ray intensity data were collected on a Bruker APEXII CCD area detector employing graphite-monochromated Mo—Kα radiation (λ=0.71073 Å) at a temperature of 100(1)K. Preliminary indexing was performed from a series of thirty-six 0.5° rotation frames with exposures of 30 seconds. A total of 3608 frames were collected with a crystal to detector distance of 70.00 mm, rotation widths of 0.5° and exposures of 20 seconds:

| scan type | 2θ | ω | φ | χ | frames |
|---|---|---|---|---|---|
| φ | −35.50 | 279.40 | 27.32 | 48.96 | 725 |
| φ | 24.50 | 22.31 | 35.56 | 69.08 | 692 |
| ω | −13.00 | 321.68 | 247.79 | 69.08 | 95 |
| φ | 34.50 | 204.08 | 28.21 | −92.80 | 293 |
| φ | −30.50 | 310.60 | 214.10 | 54.21 | 361 |
| φ | 32.00 | 304.67 | 24.47 | 50.72 | 722 |
| φ | −35.50 | 122.14 | 316.59 | −78.84 | 720 |

Rotation frames were integrated using SAINT (Bruker (2009) SAINT. Bruker AXS Inc., Madison, Wis., USA.) producing a listing of unaveraged F² and σ(F²) values which were then passed to the SHELXTL (Bruker (2009) SHELXTL. Bruker AXS Inc., Madison, Wis., USA.) program package for further processing and structure solution on a Dell Pentium 4 computer. A total of 6909 reflections were measured over the ranges 1.58≤θ≤25.09°, −6≤h≤6, −18≤k≤18, −28≤l≤28 yielding 6909 unique reflections (Rint=0.0581). The intensity data were corrected for Lorentz and polarization effects and for absorption using SADABS (Sheldrick, G. M. (2007) SADABS. University of Gottingen, Germany.) (minimum and maximum transmission 0.6093, 0.7452).

The structure was solved by direct methods (SHELXS-97 (Sheldrick, G. M. (2008) Acta Cryst. A64, 112-122)). Refinement was by full-matrix least squares based on $F^2$ using SHELXL-97 (Sheldrick, G. M. (2008) Acta Cryst. A64, 112-122). All reflections were used during refinement. The weighting scheme used was $w=1/[\sigma^2(F_o^2)+(0.0000P)^2+14.0738P]$ where $P=(F_o^2+2F_c^2)/3$. Non-hydrogen atoms were refined anisotropically and hydrogen atoms were refined using a riding model. Refinement converged to R1=0.0847 and wR2=0.1899 for 6173 observed reflections for which F>4σ(F) and R1=0.0963 and wR2=0.1963 and GOF=1.119 for all 6909 unique, non-zero reflections and 512 variables ($R1=\Sigma||F_o|-|F_c||/\Sigma|F_o|$; $wR2=[\Sigma w(F_o^2-F_c^2)^2/\Sigma w(F_o^2)^2]^{1/2}$; $GOF=[\Sigma w(F_o^2-F_c^2)^2/(n-p)]^{1/2}$; where n=the number of reflections and p=the number of parameters refined). The maximum Δ/σ in the final cycle of least squares was 0.000 and the two most prominent peaks in the final difference Fourier were +0.402 and −0.559 e/Å³.

Figure 1B:
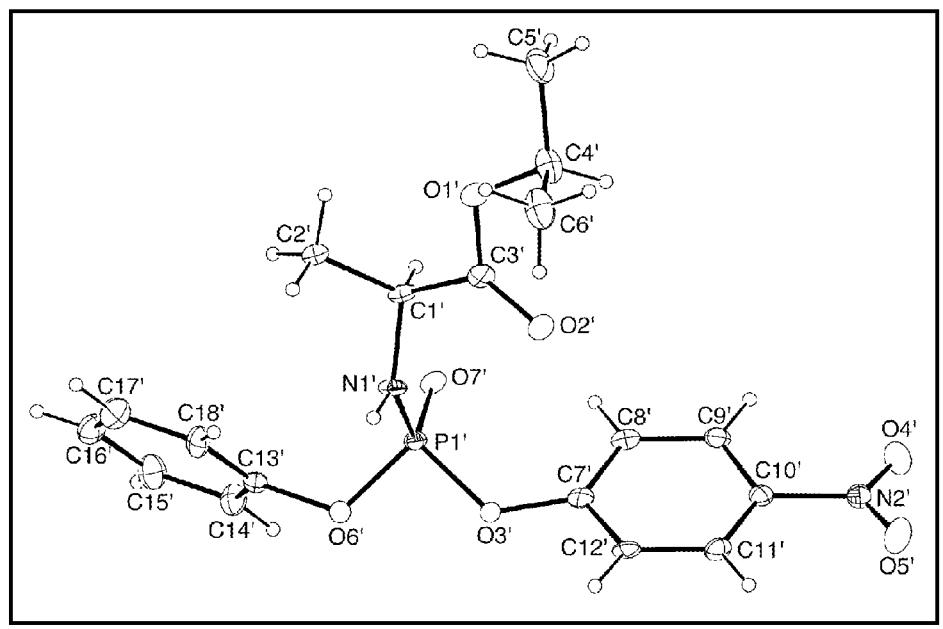

Table 1 lists cell information, data collection parameters, and refinement data. Final positional parameters are given in Tables 2 and 3. FIGS. 1A and 1B are ORTEP ("ORTEP-II: A Fortran Thermal Ellipsoid Plot Program for Crystal Structure Illustrations". C. K. Johnson (1976) ORNL-5138) representations of the two molecules in the asymmetric unit with 30% probability thermal ellipsoids displayed.

TABLE 1

Summary of Structure Determination of 109

| | |
|---|---|
| Empirical formula | $C_{18}H_{21}N_2PO_7$ |
| Formula weight | 408.34 |
| Temperature | 100(1) K |
| Wavelength | 0.71073 Å |
| Crystal system | monoclinic |
| Space group | $P2_1$ |
| Cell constants: | |
| a | 5.3312(4) Å |
| b | 15.3388(8) Å |
| c | 23.7807(13) Å |
| β | 92.891(3)° |
| Volume | 1942.2(2) Å³ |
| Z | 4 |
| Density (calculated) | 1.397 Mg/m³ |
| Absorption coefficient | 0.185 mm⁻¹ |
| F(000) | 856 |
| Crystal size | 0.40 × 0.10 × 0.08 mm³ |
| Theta range for data collection | 1.58 to 25.09° |
| Index ranges | −6 ≤ h ≤ 6, −18 ≤ k ≤ 18, −28 ≤ l ≤ 28 |
| Reflections collected | 6909 |
| Independent reflections | 6909 [R(int) = 0.0581] |
| Completeness to theta = 25.09° | 99.6% |
| Absorption correction | Semi-empirical from equivalents |
| Max. and min. transmission | 0.7452 and 0.6093 |
| Refinement method | Full-matrix least-squares on $F^2$ |
| Data/restraints/parameters | 6909/1/512 |
| Goodness-of-fit on $F^2$ | 1.119 |
| Final R indices [I > 2 sigma(I)] | R1 = 0.0847, wR2 = 0.1899 |
| R indices (all data) | R1 = 0.0963, wR2 = 0.1963 |
| Absolute structure parameter | 0.1(2) |
| Largest diff. peak and hole | 0.402 and −0.559 e · Å⁻³ |

Example 4

Preparation of 110 with 91 as a Synthetic Intermediate

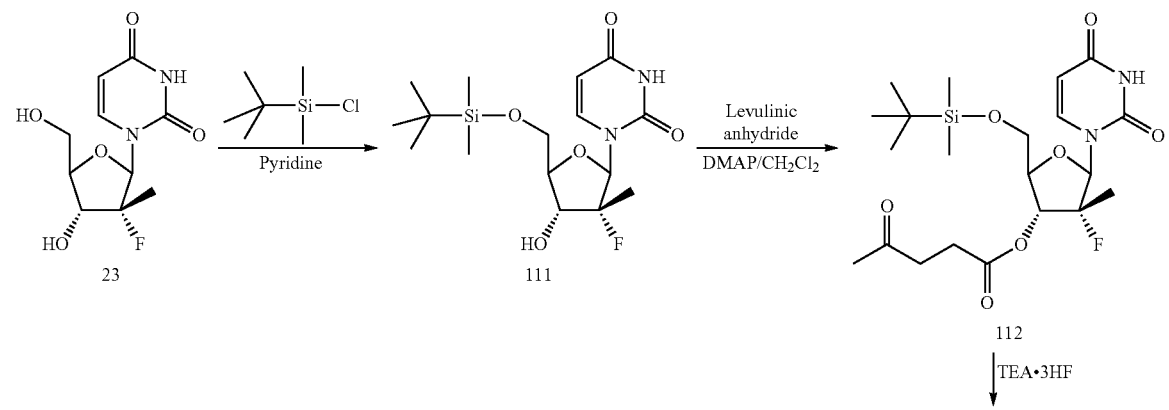

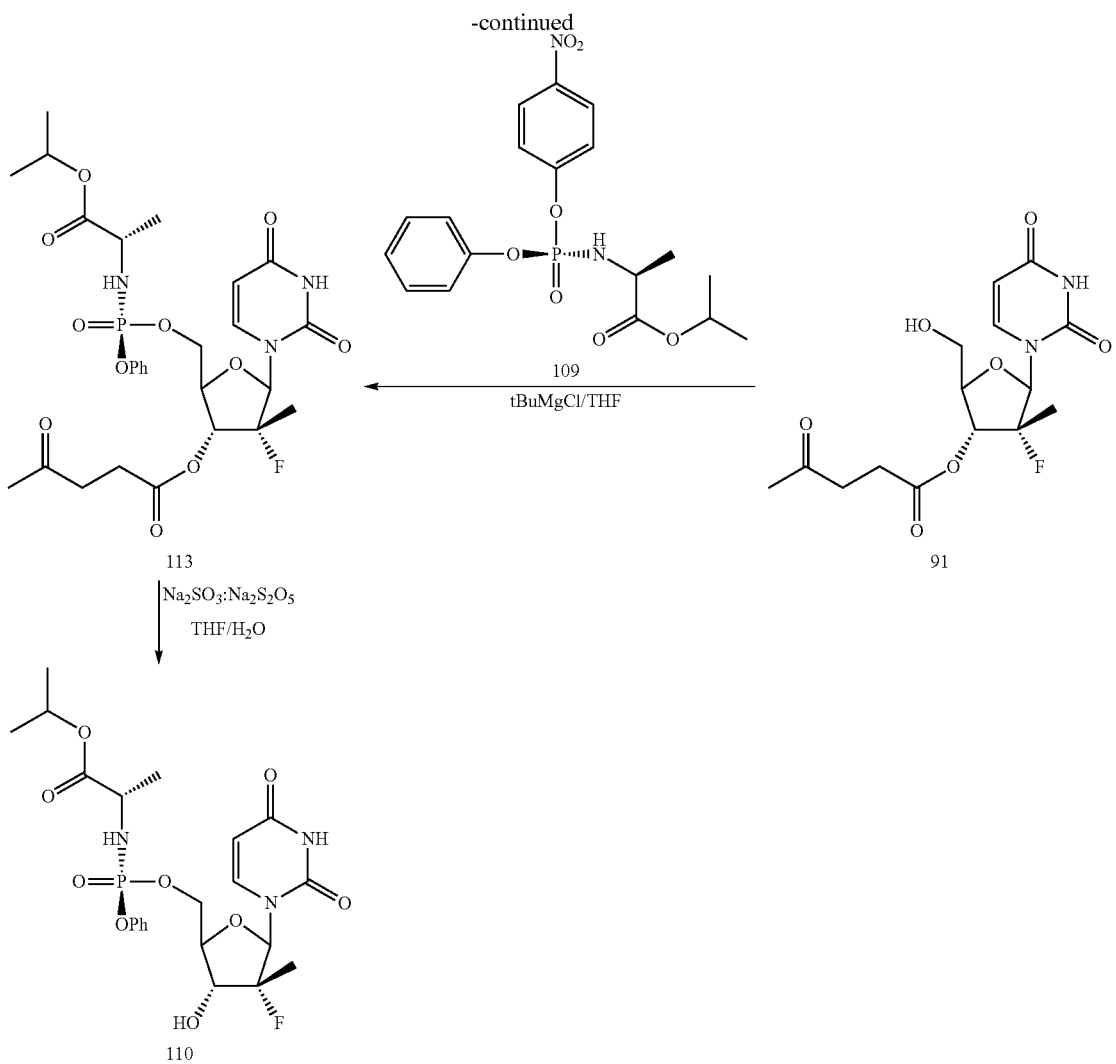

a) Synthesis of 5'-O-tert-Butyldimethylsilyl-2'-deoxy-2'-fluoro-2'-C-methyluridine (111)

To a stirred solution of 2'-deoxy-2'-fluoro-2'-C-methyluridine (23, 81.1 g, 312 mmol) in dry pyridine (750 mL) was added drop-wise a solution of TBDMSCl (103.19 g, 685.6 mmol) in dry pyridine (500 mL) over a period of 45 min at ambient temperature. The reaction was allowed to stir at ambient temperature for 24 h. Methanol (85 mL) was added to the reaction mixture and it was allowed to stir for 10 min and then the solvents were distilled off under reduced pressure. Hot water (45° C.) (1 L) was added to the reaction mass and the mixture extracted with ethyl acetate (2×500 mL), washed with water (1×500 mL). The organic layer was dried over anhydrous sodium sulfate. Ethyl acetate was distilled off and the residue obtained was co-evaporated with toluene (2×500 mL) to give crude 111 as a white foam. Yield=116.9 g (quantitative).

$^1$H NMR: CDCl$_3$ (300 MHz): δ 0.1 (s, 6H), 0.91 (s, 9H), 1.22 (d, 3H, J=21 Hz), 2.50 (s, 2H), 3.75-4.05 (m, 4H), 5.54 (d, 1H, J=9 Hz), 5.73 (s, 1H), 6.0 (d, 1H, J=18 Hz), 7.81 (d, 1H, J=9 Hz), 8.57 (br, s, 1H), 11.1 (s, 1H).

b) Synthesis of 5'-O-(tert-Butyldimethylsilyl)-3'-O-levulinyl-2'-deoxy-2'-fluoro 2'-C-methyl-uridine (112)

To a stirred solution of nucleoside 111 (116.9 g, 312.1 mmol) in DCM (1 L) was added DMAP (30.5 g, 249.7 mmol) and this was allowed to stir at RT for 20 min. A soln. of levulinic anhydride (133.6 g, 642.3 mmol) in DCM (200 mL) was added to the mixture and allowed to stir for 24 h. TLC of the mixture indicated completion of reaction. Cold water (500 mL) was added and the mixture stirred for 20 min. Layers were separated and the organic layer was washed with sat. sodium bicarbonate solution (2×250 mL), dried over anhydrous sodium sulfate and then the solvent was distilled under reduced pressure to give yellow oil. Crude yield: 197.6 g (135%). The material was used as is for the next step.

112 Data:

$^1$H NMR: CDCl$_3$ (300 MHz) δ 0.11 (s, 6H), 0.94 (s, 9H), 1.34 (d, 3H, J=21 Hz), 2.22 (s, 3H), 2.6-2.89 (m, 4H), 3.72 (m, 1H), 4.01 (d, 1H, J=12 Hz), 4.23 (d, 1H, J=9 Hz), 5.33 (dd, 1H, J=15 Hz), 5.73 (d, 1H, J=6 Hz), 6.26 (d, 1H, J=15 Hz), 8.12 (d, 1H, J=12 Hz), 8.72 (br, s, 1H).

c) Synthesis of 3'-O-levulinyl-2'-deoxy-2'-fluoro 2'-C-methyl-uridine (91)

Crude 112 (197.6 g, 312.1 mmol-assumed) was dissolved in DCM (1 L) to which was added TEA.3HF (50.3 g, 312.1 mmol) and allowed to stir overnight at ambient temperature. TLC of the mixture indicated about 50% completion of reaction. Another equivalent of TEA.3HF (50.3 g, 312.1 mmol) was added and the reaction mixture was allowed to stir for 6 h. TLC at this point indicated about 10% of unreacted starting material. Another 0.25 eq of TEA.3HF (12.5 g, 78.0 mmol) was added and the reaction mixture was allowed to stir overnight. Reaction mixture was concentrated to dryness to give yellow oil. Crude from all the batches was purified by column chromatography on silica gel (0-2% MeOH in DCM) to give 124.1 g of 3'-levulinate as a white foam solid (90% purified yield over three steps from 2'-deoxy-2'-fluoro-2'-C-methyluridine).

91 Data:
$^1$H NMR: $CDCl_3$ (400 MHz) δ 1.55 (d, 3H, CH3, J=20 Hz), 2.36 (s, 3H, CH3), 2.8-3.03 (m, 5H, CH2CH3), 3.91-3.96 (dd, 1H, CH"), 4.2-4.25 (m, 1H, CH'), 4.34 (dd, 1H, CH, J=8 Hz), 5.25 (dd, 1H, J=16 Hz), 5.93 (d, 1H, J=8 Hz), 8.20 (d, 1H, J=8 Hz), 9.18 (s, 1H).

d) Stereoselective synthesis of (S)-2-{[(1R,4R,5R)-5-(2,4-Dioxo-3,4-dihydro-2H-pyrimidin-1-yl)-4-(R)-fluoro-3-(4-oxopentanoyl)-4-methyl-tetrahydro-furan-2-ylmethoxy]-phenoxy-phosphorylamino}-propionic acid (S)-isopropyl ester (113): (Synonym: (2R,3R,4R,5R)-5-(2,4-dioxo-3,4-dihydropyrimidin-1(2H)-yl)-4-fluoro-2-((((R)—(((S)-1-isopropoxy-1-oxopropan-2-yl)amino)(phenoxy)phosphoryl)oxy)methyl)-4-methyltetrahydrofuran-3-yl 4-oxopentanoate)

To a solution of the nucleoside (91, 1.00 mmol, 358 mg) in 5 ml anhydrous THF that was cooled to 0° C. was added tBuMgCl (1.7 M in THF, 2 eq) and allowed it to warm to ambient temperature and stirred for half hour. To this mixture was added the reagent (ca 97% chiral purity) (S)-2-[(S)-(4-nitro-phenoxy)-phenoxy-phosphorylamino]propionic acid isopropyl ester (109) (408 mg, 1.00 mmol, 1.00 eq.) in one lot and allowed it to stir at ambient temperature. After 16 h, there was ~30% starting material left. The reaction mixture was quenched with saturated NH$_4$Cl solution 10 ml, and the aqueous phase was extracted with ethyl acetate (3×25 ml). The combined organic layer was washed with brine and dried over anhydrous sodium sulfate and evaporated to dryness to give a pale yellow foam (500 mg). This was purified by silica gel chromatography using 2-5% methanol in methylene chloride to give the product as a white foam (275 mg) of about 97% P chiral purity and unreacted starting material (162 mg). Based on consumed starting material, the yield was 76%.

113 Data:
$^{31}$P NMR (162 MHz): 3.7 ppm; $^1$H NMR (400 MHz): δ 1.22 (dd, 6H, J=6.4 Hz), 1.37 (s, 3H), 1.58 (s, 3H), 2.18 (s, 3H), 2.63-2.9 (m, 4H), 4.0 (d, 1H, J=8 Hz), 4.2-4.33 (m, 1H), 4.57 (d, 1H, J=8 Hz), 4.96-5.00 (sept, 1H), 5.2 (dd, 1H, J=9 Hz), 5.42 (d, 1H, J=8 Hz), 6.19 (d, 1H, J=18 Hz), 7.15-7.35 (m, 5H), 7.5 (d, 1H, J=5.6 Hz), 8.2 (br, s, 1H).

e) Synthesis of (S)-2-{[(1R,4R,5R)-5-(2,4-Dioxo-3,4-dihydro-2H-pyrimidin-1-yl)-4-(R)-fluoro-3-hydroxy-4-methyl-tetrahydro-furan-2-ylmethoxy]-phenoxy-phosphorylamino}-propionic acid (S)-isopropyl ester (110)

A solution of sodium sulfite was prepared by adding $Na_2S_2O_3$ (1.51 g) and $Na_2S_2O_5$ (0.57 g) in water (25 mL). To a solution of the levulinate (113, 250 mg, 0.40 mmol) in anhydrous THF (2.5 mL) was added 1.0 ml of the sodium sulfite solution. This was allowed to stir at room temperature for 4 h. The reaction mixture was poured in to water (15 mL) and extracted with ethyl acetate (3×25 mL) dried and evaporated to give quantitatively a white solid product with about 97% P chiral purity which matched the physical and spectral properties of 110 produced directly from the unprotected nucleoside.

Example 5

Preparation of 117 with 96 as a Synthetic Intermediate

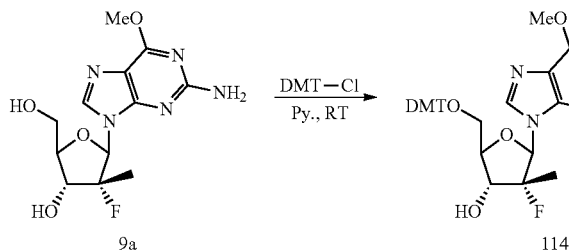

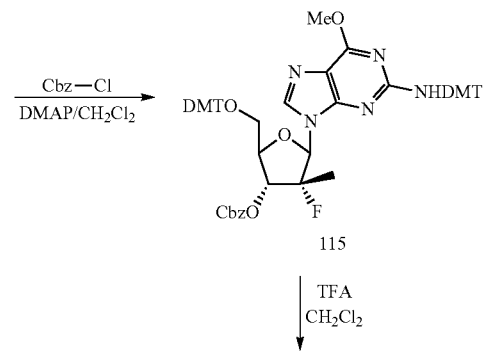

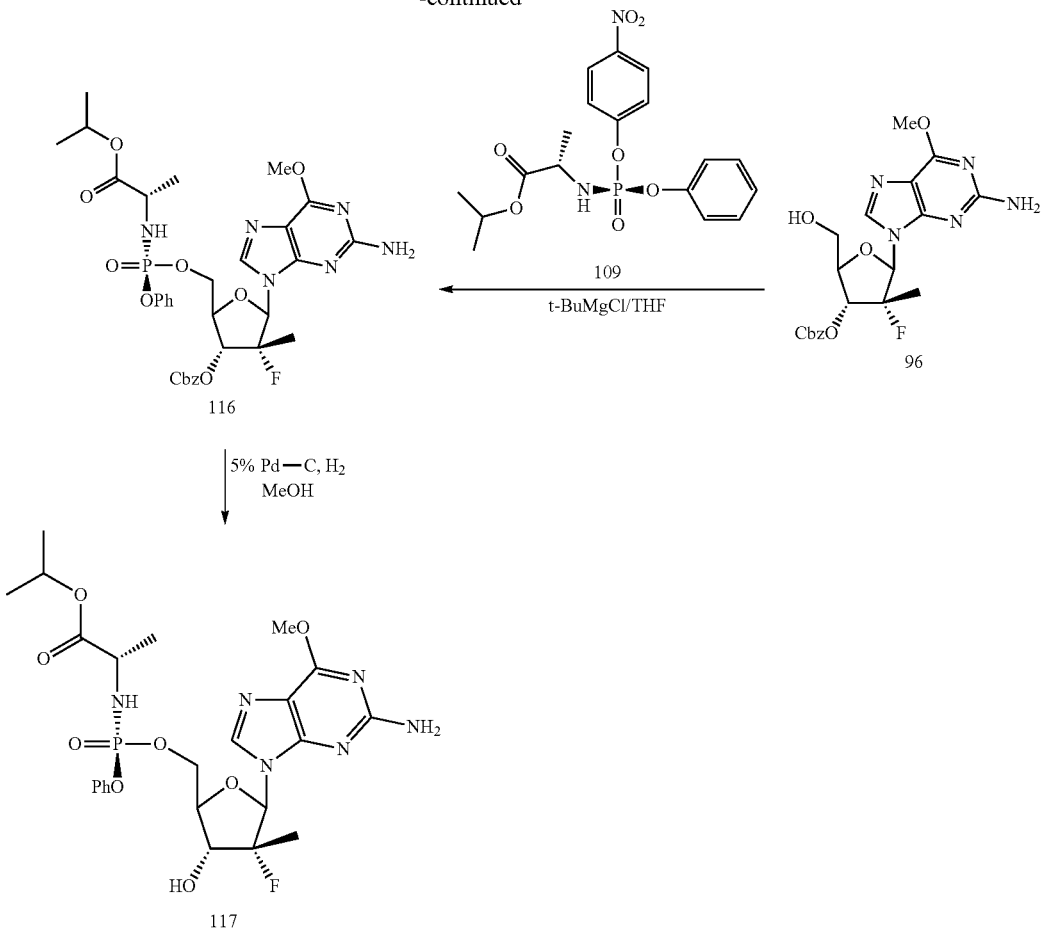

a) Synthesis of (2R,3R,4R,5R)-2-((bis(4-methoxyphenyl)(phenyl)methoxy)methyl)-5-(2-((bis(4-methoxyphenyl)(phenyl)methyl)amino)-6-methoxy-9H-purin-9-yl)-4-fluoro-4-methyltetrahydrofuran-3-ol (114)

To a solution of (2R,3R,4R,5R)-5-(2-amino-6-methoxy-9H-purin-9-yl)-4-fluoro-2-(hydroxymethyl)-4-methyltetrahydrofuran-3-ol (9a, 4 g, 12.8 mmol) in anhydrous pyridine (100 mL) cooled at 0° C. was added DMT-Cl portion-wise under nitrogen. The brown solution was stirred at ambient temperature for 24 hours. The mixture was concentrated under reduced pressure to remove most of solvent and sat. NaHCO₃ (20 mL) was added. The mixture was diluted with water (150 mL) and EtOAc (120 mL). The organic layer was separated and washed with water (5×120 mL), brine and dried over Na₂SO₄. After removal of solvent, the residue was purified via column chromatography (20% EA in hexanes to 80% EA in hexanes) to afford 11.6 g of product, 114, as a white foam solid (quantitative yield).

114 Data:
$^1$H-NMR (DMSO-$d_6$): δ 7.94 (s, 1H), 7.39-7.37 (m, 3H), 7.26-7.14 (m, 17H), 6.84-6.80 (m, 8H), 5.58 (s, 1H), 4.04 (br, 1H), 3.71-3.70 (m, 14H), 3.68 (m, 1H), 3.48 (br, 2H), 3.20 (d, 1H), 0.88 (br, 3H).

b) Synthesis of benzyl ((2R,3R,4R,5R)-2-((bis(4-methoxyphenyl)(phenyl)methoxy)methyl)-5-(2-((bis(4-methoxyphenyl)(phenyl)methyl)amino)-6-methoxy-9H-purin-9-yl)-4-fluoro-4-methyltetrahydrofuran-3-yl) carbonate (115)

To a solution of nucleoside 114 (2.52 g, 2.75 mmol) in anhydrous DCM (8 mL) was added DMAP (1.01 g, 8.2 mmol) and the solution was cooled at 0° C. in an ice-water bath. Cbz-Cl (0.77 g, 4.2 mmol) was added via a syringe to the mixture and resulted in a cloudy reaction mixture. The mixture was stirred at room temperature for 24 hours and sat. NaHCO₃ (10 mL) was added. The mixture was partitioned in DCM and water. The organic layer was dried over Na₂SO₄ and concentrated to a white foam solid. The residue was purified via column chromatography (10-60% EtOAc in hexanes) to afford 2.74 g product, 115, as a white foam solid (yield, 95%).

115 Data:
$^1$H-NMR (CDCl₃): δ 7.87 (s, 1H), 7.41-7.16 (m, 24H), 6.79-6.75 (m 8H), 6.28 (s, 1H), 5.65 (br, 1H), 5.15 (s, 2H), 4.28 (d, 1H), 3.79-3.71 (m, 15H), 3.55-3.52 (m, 1H), 3.39-3.36 (m, 1H), 0.93 (br, 3H).

c) Synthesis of (2R,3R,4R,5R)-5-(2-amino-6-methoxy-9H-purin-9-yl)-4-fluoro-2-(hydroxymethyl)-4-methyltetrahydrofuran-3-ylbenzyl carbonate (96)

A 1 vol % of TFA solution in DCM (50 mL) was added to a flask loaded with 115 (2.69 g, 2.56 mmol). The mixture was stirred at room temperature for 2 h and it was complete. Sat. NaHCO$_3$ (20 mL) was added and the mixture was partitioned in water and DCM. The organic layer was concentrated and solid residue was purified by column chromatography (silica gel, 0-5% 2-PrOH in DCM) to afford 1.01 g of product, 96, as a white foam solid (yield 88%).

96 Data:

$^1$H-NMR (CDCl$_3$): δ 7.82 (s, 1H), 7.39-7.33 (m, 5H), 6.02 (d, 1H, J=19.2 Hz), 5.77 (dd, 1H, J=20.8, 8.8 Hz), 5.32-5.30 (m, 1H), 5.20 (s, 2H), 5.04 (s, 2H), 4.34 (d, 1H, J=8.8 Hz), 4.15 (m, 1H), 4.04 (s, 3H), 3.85-3.79 (m, 1H), 1.21 (d, 3H, J=22.8 Hz).

d) Synthesis of S$_P$-(2S)-isopropyl 2-(((((2R,3R,4R,5R)-5-(2-amino-6-methoxy-9H-purin-9-yl)-3-(((benzyloxy)carbonyl)oxy)-4-fluoro-4-methyltetrahydrofuran-2-yl)methoxy)(phenoxy)phosphoryl)amino) propanoate (116)

To a solution of the nucleoside 96 (150 mg, 0.34 mmol) in 1.5 mL of anhydrous THF was added a solution of t-BuMgCl in THF (1.0 M, 0.41 mL) at 0° C. The cloudy mixture was stirred at ambient temperature for 1 h and then a solution of phosphoramidate reagent (ca 95% chiral purity) (S)-2-[(S)-(4-nitrophenoxy)phenoxyphosphorylamino]propionic acid isopropyl ester (109) (162 mg, 0.4 mmol) in 1.5 mL of THF was added to the mixture via a syringe drop-wise. The mixture was stirred at ambient temperature for 20 h and ca 29% of starting material remained. The reaction was quenched by adding sat. NH$_4$Cl (4 mL) and 20 mL of EtOAc was added. After separation, organic layer was washed with water (3×25 mL), brine and dried over Na$_2$SO$_4$. After removal of solvent, the oil residue was checked by $^1$H-NMR and $^{31}$P-NMR. The ratio of two isomers was ca. 12.5:1. The major isomer, $^1$H-NMR (CDCl$_3$): δ 7.73 (s, 1H); $^{31}$P-NMR (CDCl$_3$): δ 4.02.

e) Synthesis of S$_P$-(2S)-isopropyl 2-(((((2R,3R,4R,5R)-5-(2-amino-6-methoxy-9H-purin-9-yl)-4-fluoro-3-hydroxy-4-methyltetrahydrofuran-2-yl)methoxy) (phenoxy)phosphoryl)amino)propanoate (117)

To a solution of crude phosphoramidate 116 in MeOH (2.5 mL) was added 5% Pd on charcoal (40 mg). The atmosphere in the flask was exchanged with hydrogen twice. The mixture was stirred at ambient temperature under one atmosphere of hydrogen for 1 h. The mixture was filtered through a short pad of Celite and the filtrate was concentrated. The crude residue was checked by $^1$H-NMR and $^{31}$P-NMR and ratio of two isomers was ca. 17:1 favored the desired S$_P$ isomer (117) and also matched the Sp isomer by thin layer chromatography. $^{31}$P-NMR (DMSO-d$_6$): δ 4.91.

The following exemplified embodiments are directed to various phosphoramidate reagents having differing leaving groups.

Example 6

Synthesis of (S)-2-{(S)-[(1R,4R,5R)-5-(2-Amino-6-methoxy-purin-9-yl)-4-(R)-fluoro-3-hydroxy-4-methyl-tetrahydro-furan-2-ylmethoxy]-phenoxy-phosphorylamino}-propionic acid isopropyl ester monohydrate (117) via (S)-isopropyl 2-((((S)-(perfluorophenoxy)(phenoxy)phosphoryl)amino)propanoate (118) and isolation by chromatography and crystallization

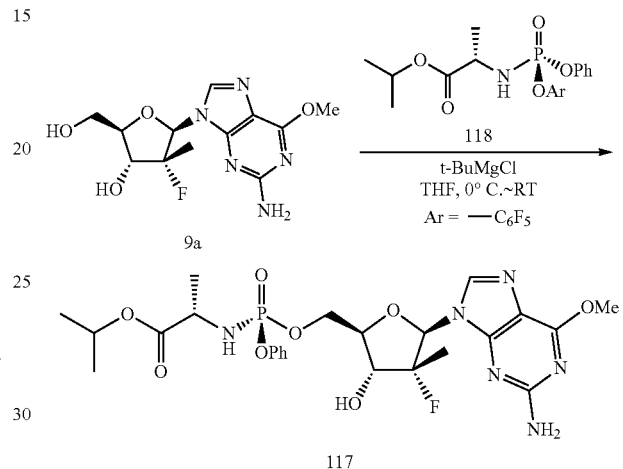

a) Preparation of (S)-2-[(2,3,4,5,6-pentafluoro-phenoxy)-phenoxy-phosphorylamino]propionic acid isopropyl ester and isolation of (S)-2-[(S)-(2,3,4,5,6-pentafluoro-phenoxy)-phenoxy-phosphorylamino] propionic acid isopropyl ester (118) via crystallization-induced dynamic resolution in a single crop To a 1 L of dry three-necked flask fitted with a low-temperature thermometer and a mechanical stirrer was loaded phenyl phosphorodichloridate (25 g, 118.5 mmol). Anhydrous dichloromethane (125 mL) was added and the solution was cooled to 0° C. The alanine ester salt (oven dried) (19.86 g, 1 eq) was added quickly under N$_2$ while agitated. The solution was cooled to ca −50° C. (internal temperature (in an acetone/dry ice bath under N$_2$). A solution of triethylamine (25.2 g, 2.1 eq) in DCM (125 mL) was added dropwise via an addition funnel over 0.5 h at −50° C. and the resulting white slurry was stirred at about −50° C. for 0.5 h. The mixture was allowed to warm up to 0° C. over 1.5 h and then a pre-mixed cooled solution of pentafluorophenol (21.82 g, 1 eq) and TEA (13.2 g, 1.1 eq) (caution: heat released while mixing pentafluorophenol and TEA) in 75 mL of DCM was added over 0.5 h at 0° C. via an addition funnel. The mixture was stirred at 0° C. for additional 4 h.

The mixture was filtered through a Buchner funnel and the collected solid triethylamine hydrochloride was rinsed with DCM (3×40 mL). The filtrate was checked by $^{31}$P-NMR (ratio ca 1.14:1 favored the S$_P$-diastereomer (118)—downfield peak) and was divided into two parts of equal weight. One of them was concentrated under reduced pressure. The white solid residue (31 g) was triturated in a mixture of EtOAc and hexanes (150 mL, 20:80, v/v) at RT for 17 h allowing time for dynamic resolution of the less soluble S$_P$-diastereomer. The white slurry was filtered and solid was rinsed with 20% EtOAc in hexanes (2×25 mL). The solid (22.58 g) was checked by $^1$H-NMR and $^{31}$P-NMR and it contained product as one isomer contaminated with triethylamine hydrochloride salt. The solid was dissolved and partitioned in 310 mL of EtOAc and 100 mL of water. After separation of the organic layer, the aqueous layer was back-extracted with EtOAc (50 mL). The combined organic layer was washed with water (3×80 mL), brine (50 mL) and dried over MgSO$_4$. The solution was concentrated under reduced pressure and then dried under high vacuum at RT to a constant weight to furnish 17.36 g of product as a white solid from the one half of the reaction. The yield is 64%. The mother liquor from above was concentrated to a gummy residue (7.89 g) that contained the reagents with a ratio of 1:1.2 (118/R$_P$-diastereomer) based on $^{31}$P-NMR. (The absolute structure of 118 was confirmed by single crystal X-ray crystallography, see e.g., U.S. Ser. No. 13/076, 552, filed Mar. 31, 2011, incorporated by reference.)

b) Preparation of 117 from 118 and 9a

To a 250 mL of dry three-necked round flask was added 5.06 g (16.15 mmol) of the purine nucleoside (9a). The solid was suspended in 40 mL of anhydrous THF and cooled in an ice-water bath. The Grignard reagent (1 M solution in THF) was added dropwise via a syringe and a clear solution was formed. The mixture was stirred at 0° C. for 30 minutes and a solution of 118 (8.32 g, 18.35 mmol) in 40 mL of THF was added via an addition funnel over 50 minutes. After finishing addition, the reaction mixture was stirred at room temperature for 3 hours. The reaction was quenched by adding 20 mL of sat NH$_4$Cl at 0° C. The mixture was diluted with 100 mL of ethyl acetate. Two layers were separated and aqueous layer was extracted with 50 mL of ethyl acetate. Organic layer was combined and washed with water (60 mL), sat sodium bicarbonate (2×60 mL), water (60 mL), brine (40 mL), and dried over sodium sulfate. Solvent was removed under reduced pressure to afford an amorphous solid residue.

To the crude residue 7 mL of ethyl acetate was added and followed by 26 mL of anisole. The mixture was stirred until a solution was formed. Water (320 mg) was added and 20 mg of crystal seeds of product (117) was added. The mixture was cooled at −5° C. overnight. White solid was formed and collected by filtration. Solid was rinsed with pre-cooled mixture of heptane and TBME (1:1, 3×2 mL) and weighed 3.3 g after drying. The mother liquor was concentrated under reduced pressure and the residue was purified via column chromatography (5~7% 2-propanol in DCM). Product was obtained as a white amorphous solid (4.5 g).

Solids from above were combined (7.8 g) and mixed with 7.7 mL of ethyl acetate. To the slurry, 31 mL of anisole was added and the mixture was stirred until a uniformed solution was formed. To the solution 160 mg of water was added and followed by 20 mg of crystal seeds of product (117). The mixture was stirred slowly at room temperature and white solid precipitated. The mixture was kept at −5° C. for 2 hours and solid was collected via filtration. Solid was rinsed with pre-cooled mixture of heptane and TBME (1:1, 4×5 mL) and dried in vacuo. Product weighed 6.69 g (69% yield).

Example 7

Synthesis 117 by Reaction with 118 and 9a and Isolation by Crystallization Only

To a 250 mL of dry three-necked round flask were loaded 5 g (15.96 mmol) of the nucleoside (9a) and 40 mL of anhydrous THF. The suspension was cooled in an ice-water bath and 20 mL of the Grignard reagent (1 M solution in THF, 20 mmol) was added via a syringe over 10 minutes. The clear reaction mixture was stirred at 0° C. for half hour and then a solution of the phosphorus reagent (118) in 40 mL of THF was added via an addition funnel in 2 hours. The reaction was allowed to warm up to ambient temperature slowly and stirred for overnight. The mixture was cooled to 0° C. and 50 mL of 1 N diluted HCl was added. Most of THF was removed under reduced pressure and the mixture was diluted with 200 mL of ethyl acetate. The organic layer was separated and aqueous layer was extracted with 30 mL of ethyl acetate. The combined organic layer was washed with water (60 mL), sat'd. sodium bicarbonate (2×50 mL), 5% sodium carbonate (70 mL), water (50 mL), and brine (50 mL). Organic solution was dried over magnesium sulfate and solvent was removed under reduced pressure to afford an amorphous solid residue.

The crude residue was dissolved in 41 mL of anisole at room temperature. To the solution, 24 mL of xylenes was added and followed by 410 mg of water. The mixture was stirred slowly at room temperature and crystal seeds of 117 (10 mg) were added. White solid precipitated and the mixture was kept at −5° C. for 2 hours. Solid was collected via filtration and rinsed with a pre-cooled mixture of heptane and TBME (1:1, 3×2 mL). Solid weighed 5.83 g after drying. The mother liquor was concentrated to dryness under reduced pressure. The residue was dissolved in 7.2 mL of anisole and 10.7 mL of xylenes was added. To the solution, 178 mg of water was added and 5 mg of crystal seeds of 117 were added. The mixture was slowly stirred at room temperature for overnight. White solid was formed and collected via filtration. Solid was rinsed with a pre-cooled mixture of heptane and HBME (1:1. 3×1 mL) and weighed 1.17 g.

Solids obtained above were combined (7.0 g) and added 7 mL of ethyl acetate. After addition of 27 mL of anisole, a clear solution was formed. To the solution, 200 mg of water was added and then added 5 mg of crystal seeds of 117. The mixture was stirred at ambient temperature and white solid precipitated. The mixture was kept at −5° C. for overnight. Crystalline solid was collected by filtration and rinsed with a pre-cooled mixture of heptane and TBME (1:1, 3×5 mL). The resultant product (117) weighed 5.66 g with purity of 98.3% by HPLC.

The above solid was purified again via crystallization from a combination of 5.6 mL ethyl acetate and 22.6 mL of anisole. After filtration and drying, 4.48 g (47%) of product was obtained and purity was 99.18% by HPLC. Spectral ($^1$H- and $^{31}$P-NMR, MS) and physical properties (HPLC retention, melting point and appearance) matched an authentic sample.

Example 8

Synthesis of (S)-2-{(S)-[(1R,4R,5R)-5-(2-Amino-6-methoxy-purin-9-yl)-4-(R)-fluoro-3-hydroxy-4-methyl-tetrahydro-furan-2-ylmethoxy]-phenoxy-phosphorylamino}-propionic acid isopropyl ester (117) via (S)-isopropyl 2-(((S)-(2,4-dinitrophenoxy)(phenoxy)phosphoryl)amino)propanoate (119)

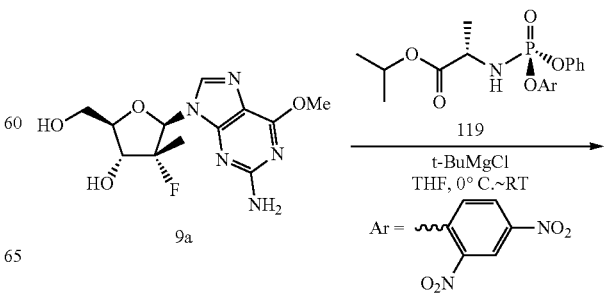

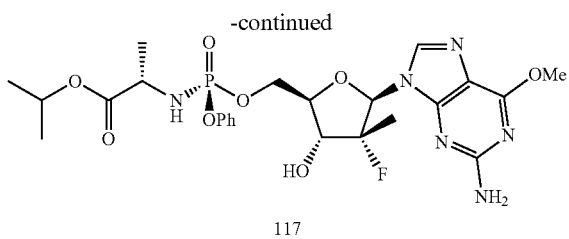

117 a) Preparation of (2S)-isopropyl 2-(((2,4-dinitrophenoxy)(phenoxy)phosphoryl)amino)propanoate diastereomeric mixture and isolation of the single isomer (2S)-isopropyl 2-(((S)-(2,4-dinitrophenoxy)(phenoxy)phosphoryl)amino)propanoate (119) by crystallization

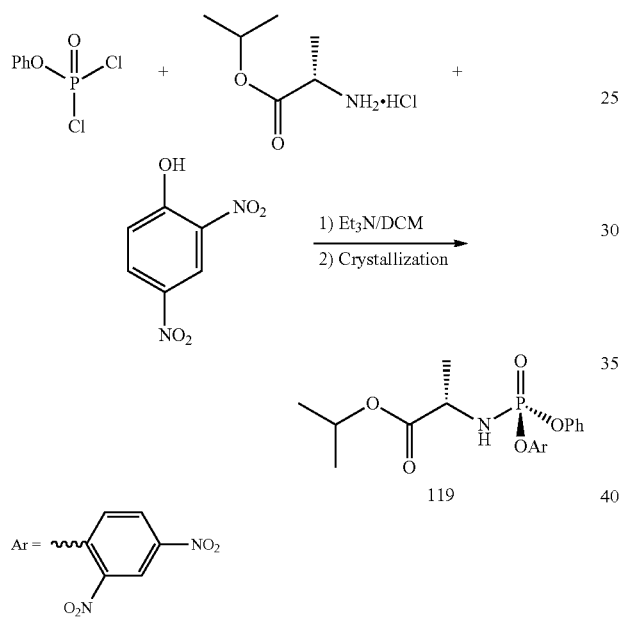

Phenyl phosphorodichloridate (10.0 g, 47.4 mmol) was dissolved in 60 mL of dry DCM and subsequently cooled to −78° C. A premixed solution of 2,4-dinitrophenol (8.72 g, 47.4 mmol) and triethylamine (7.27 mL, 52.1 mmol) in 20 mL of DCM was slowly added at −78° C. over a period of 30 min. The reaction was brought to 0° C. and stirred for 2.5 h at this temperature before (L)-alanine isopropyl ester (7.95 g, 47.4 mmol) was added as a solid in one batch. Stirring for 40 min at 0° C. was then followed by addition of more triethylamine (13.9 mL, 99.54 mmol) and additional stirring for 3 h at 0° C. or until judged complete by TLC (ethyl acetate/hexane=1/3). The reaction mixture was subsequently evaporated under reduced pressure, residue redissolved in MTBE (100 mL), solids filtered off and filtrate evaporated to dryness to give yellow syrup. NMR of the crude sample indicated mixture of 2 isomers in the ratio of 1:1. A mixture of EtOAc:Hexanes (1:1) (50 ml) was added and mixture allowed to stir for 15 h. The white solid thus formed was filtered off and rinsed with EtOAc:Hexanes (1:1) (20 mL) and dried under vacuum to give 6.0 g (28%) of 119a single isomer.

119 Data:
$^1$H NMR (CDCl$_3$, 400 MHz) δ: 8.82-8.81 (m, 1H), 8.43-8.40 (m, 1H), 7.89-7.86 (m, 1H), 7.36-7.32 (m, 2H), 7.23-7.19 (m, 3H), 4.96 (hepta, 1H), 4.19-4.08 (m, 2H), 1.42 (d, 3H), 1.20 (d, 6H). $^{31}$P NMR (CDCl$_3$, 162 MHz) δ: −1.82.

b) Preparation of 117 from 119 and 9a

To a 50 mL of dry round-bottomed flask were added 80 mg (0.255 mmol) of 9a and 1 mL of anhydrous THF. The suspension was cooled in an ice water bath and 0.33 mL of Grignard reagent was added via a syringe under nitrogen. A clear solution was formed and stirred at 0° C. for half hour. A solution of 119 (133 mg, 0.294 mmol) in 1.5 mL of THF was added via a syringe. The orange-colored, clear, reaction mixture was checked by TLC in 20 minutes at 0° C. and the reaction was almost complete. Product was formed as well as the 3',5'-bisphosphoramidate by-product. The reaction was quenched by adding sat NH$_4$Cl after one and half hour. The mixture was diluted with 20 mL of ethyl acetate. Organic layer was separated and aqueous layer was extracted with ethyl acetate (20 mL). The combined organic layer was washed with water (50 mL), sat sodium bicarbonate (2×40 mL), sat sodium carbonate (40 mL), water (40 mL), and brine (30 mL). The light yellow color organic layer was dried over sodium sulfate. The solution was concentrated under reduced pressure and an amorphous solid residue resulted was purified via column chromatography. The bis-phosphoramidate by-product was eluted out at 1% methanol in DCM as a foam solid (32.4 mg) and 117 was eluted out at 3% methanol in DCM (74 mg, 0.127 mmol, 49.6%).

Example 9

Synthesis of (S)-2-{[(1R,4R,5R)-5-(2-Amino-6-methoxy-purin-9-yl)-4-(R)-fluoro-3-hydroxy-4-methyl-tetrahydro-furan-2-ylmethoxy]-phenoxy-phosphorylamino}-propionic acid isopropyl ester diastereomeric mixture (120) via (2S)-isopropyl 2-(((2-nitrophenoxy)(phenoxy)phosphoryl)amino)propanoate (121)

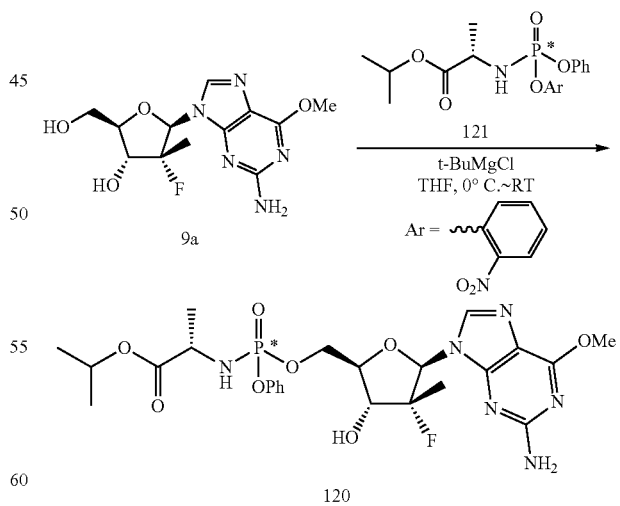

a) Preparation of 121

To a solution of phenyl phosphorodichloridate (30 g, 142.2 mmol) in dichloromethane (150 mL) at −70° C. under nitrogen atmosphere was added drop wise a pre-prepared mixture of o-Nitro phenol (19.76 g, 142.2 mmol) and triethylamine (19.8 mL, 142.2 mmol) in dichloromethane (150 mL) through addition funnel for 1 h at above temperature. Stirring was continued for additional 2 h and was slowly brought to 0° C. L-alanine isopropyl ester hydrochloride salt (26.2 g, 156.3 mmol) was added as solid and then followed by triethylamine (43.7 mL, 313.4 mmol) in dichloromethane (150 mL) drop wise at 0° C. for 20 min. and the reaction mass was continued stirring at the same temperature for additional one hour. The reaction mixture was filtered and concentrated and was finally purified by column chromatography (20% EtOAc/hexanes) on a silica gel to yield 121 as diastereomeric mixture (14.4 g, 25%).

121 Data:

$^1$H NMR (CDCl$_3$, 400 MHz) δ: 7.94-7.90 (m, 1H), 7.67-7.63 (m, 1H), 7.57-7.54 (m, 1H), 7.33-7.26 (m, 3H), 7.23-7.14 (m, 3H), 5.04-4.89 (m, 1H), 4.21-4.04 (m, 2H), 1.38 (d, 3H, isomer I), 1.33 (d, 3H, isomer II), 1.23-1.17 (m, 6H). $^{31}$P NMR (CDCl$_3$, 162 MHz) δ: −1.55 (isomer I), −1.76 (isomer II).

b) Preparation of 120 from 121 and 9a

To a 50 mL of dry round-bottomed flask were added 80 mg (0.255 mmol) of 9a and 1 mL of anhydrous tetrahydrofuran. The suspension was cooled in an ice-water bath and a solution of Grignard reagent (1 M in THF, 0.32 mmol) was added via a syringe. The clear solution thus formed was stirred at 0° C. for half hour and then a solution of 121 (120 mg, 0.296 mmol, mixture of isomers) in 1 mL of THF was added dropwise at 0° C. The mixture was stirred at room temperature for 44 hours and quenched by addition of 1 N diluted HCl. After aqueous work-up as usual, the crude residue was purified via column chromatography (silica gel, 3% methanol in DCM) to afford 33.9 mg (0.058 mmol, 22.8%) of 120 as a 1:1 mixture of two isomers.

Example 10

Synthesis of (S)-2-{[(1R,4R,5R)-5-(2-Amino-6-methoxy-purin-9-yl)-4-(R)-fluoro-3-hydroxy-4-methyl-tetrahydro-furan-2-ylmethoxy]-phenoxy-phosphorylamino}-propionic acid isopropyl ester diastereomeric mixture (120) via diastereomeric mixture of (2S)-isopropyl 2-(((2,4-dichlorophenoxy)(phenoxy)phosphoryl)amino)propanoate (122)

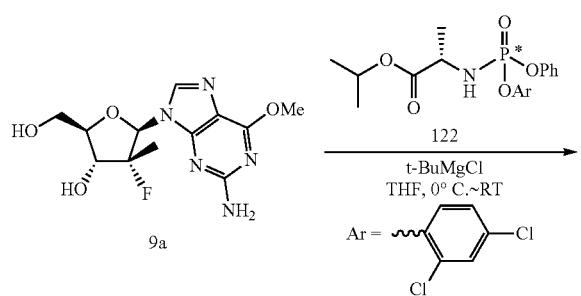

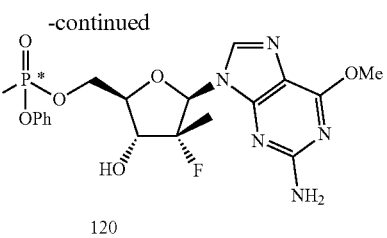

a) Preparation of (2S)-isopropyl 2-(((2,4-dichlorophenoxy)(phenoxy)phosphoryl)amino)propanoate diastereomeric mixture (122)

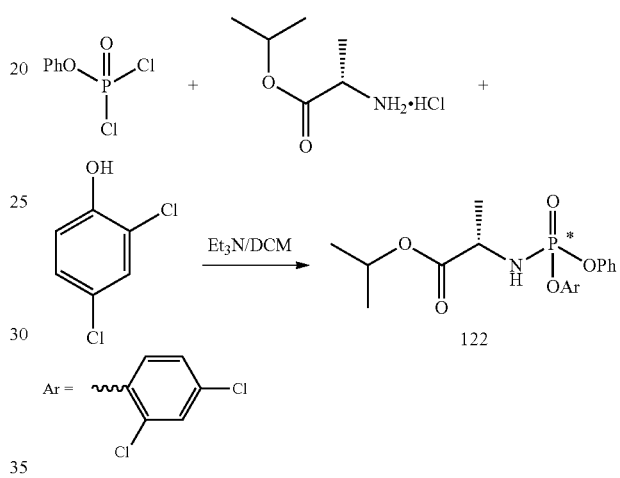

Phenyl phosphorodichloridate (10.0 g, 47.4 mmol) was dissolved in 60 mL of dry DCM and subsequently cooled to −78° C. Slow addition of a preformed mixture of 2,4-dichlorophenol (7.73 g, 47.4 mmol) and triethylamine (7.27 mL, 52.1 mmol) in 20 mL of DCM was followed by stirring at above temperature for 30 min. The reaction was brought to 0° C. and stirred for 2.5 h at this temperature before (L)-alanine isopropyl ester (7.95 g, 47.4 mmol) was added as a solid in one batch. Stirring for 40 min at 0° C. was then followed by addition of more triethylamine (13.9 mL, 99.54 mmol) and additional stirring for 3 h at 0° C. or until judged complete by TLC (ethyl acetate/hexane=1/3). The reaction mixture was subsequently evaporated under reduced pressure and finally submitted to column chromatography (ethyl acetate in hexane) on silica gel to yield the product 122 (mixture of two isomers) in 66% yield (13.6 g) as viscous colorless oil.

122 Data:

$^1$H NMR (CDCl$_3$, 400 MHz) δ: 7.47-7.44 (m, 1H), 7.42-7.39 (m, 1H), 7.35-7.30 (m, 2H), 7.24-7.15 (m, 3H), 5.05-4.94 (m, 1H), 4.19-4.08 (m, 1H), 3.96-3.89 (m, 1H), 1.41-1.35 (m, 1H), 1.24-1.19 (m, 6H). $^{31}$P NMR (CDCl$_3$, 162 MHz) δ: −1.52 (one isomer), −1.54 (the other isomer).

b) Preparation of Diastereomeric Mixture of 120 from 122 and 9a

To a dry 50 mL of round-bottomed flask were added 181 mg (0.58 mmol) of 9a and 1.5 mL of anhydrous THF. The suspension was cooled in an ice-water bath. Grignard reagent (1 M solution in THF, 0.72 mmol) was added via a syringe dropwise over 5 minutes at 0° C. The clear solution was stirred at room temperature for half hour before a solution of 122 (276 mg, 0.66 mmol) in 1.5 mL of THF was added over 10 minutes. The reaction was allowed to warm up to ambient temperature and stirred for 22 hours. Reaction was not complete and less than half of starting material was consumed. The reaction was quenched after additional three days by adding sat NH₄Cl (5 mL). The mixture was diluted with 20 mL of ethyl acetate. After work-up, the residue was purified via column chromatography (silica gel, 4% 2-propanol in DCM) to afford 63.1 mg (0.108 mmol, 19%) of 120 as a mixture of two diastereomers. From column, 29.6 mg (0.094 mmol) of starting nucleoside was recovered.

Example 11

Synthesis of (S)-2-{[(1R,4R,5R)-5-(2-Amino-6-methoxy-purin-9-yl)-4-(R)-fluoro-3-hydroxy-4-methyl-tetrahydro-furan-2-ylmethoxy]-phenoxy-phosphorylamino}-propionic acid isopropyl ester diastereomeric mixture (120) via (2S)-isopropyl 2-(((2-chloro-4-nitrophenoxy)(phenoxy)phosphoryl)amino)propanoate (123)

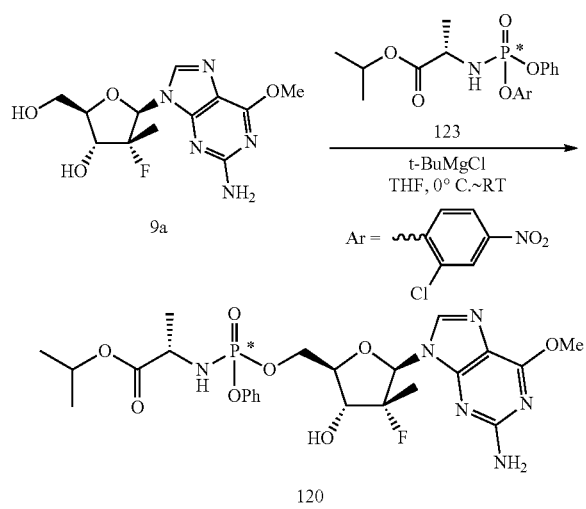

a) Preparation of 123 and Isolation of (124, S$_P$-Diastereomer) and 125 (R$_P$-Diastereomer))

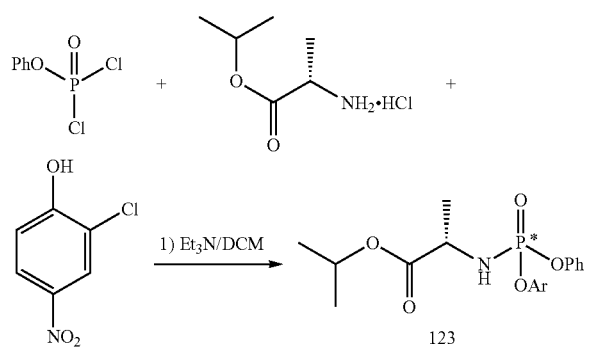

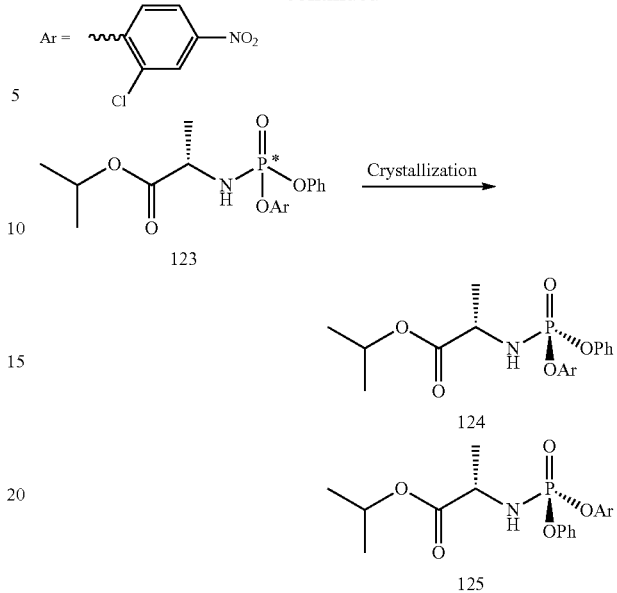

Phenyl phosphorodichloridate (10.0 g, 47.3 mmol) was dissolved in 50 mL of dry DCM and subsequently cooled to 0° C. After addition of solid (L)-alanine isopropyl ester HCl salt (7.94 g, 47.3 mmol), the reaction mixture was cooled to −70° C. and then treated with triethylamine (13.8 mL, 94.6 mmol) dissolved in 50 mL of dry DCM. The resulting mixture was stirred for 30 min at this temperature before being allowed to warm to 0° C. Subsequently, a preformed solution of 2-chloro-4-nitrophenol (8.2 g, 47.3 mmol) and triethylamine (6.6 mL, 47.3 mmol) dissolved in 20 mL of dry DCM was added over 5-10 min and was continued stirring for additional 2 h. The solution was filtered and the filtrate was concentrated under reduced pressure. The resulting residue was suspended in 50 mL of TBME and stirred for 10 min at room temperature. Subsequent filtration removed more triethylamine hydrochloride and yielded a filtrate that was again stripped of its solvent under reduce pressure. Column chromatography (dichloromethane) yielded the desired product (12.2 g, 27.6 mmol) as solid. The product was recrystallized using EtOAc/hexane (2:3) for two times to isolate 125 (5.2 g, 25% yield) and upon cooling the mother liquor to −5° C. 124 was obtained (1.5 g, 7% yield).

124 Data:
¹H NMR (CDCl₃, 400 MHz) δ: 8.33 (m, 1H), 8.13-8.10 (m, 1H), 7.73-7.71 (m, 1H), 7.36-7.33 (m, 2H), 7.25-7.18 (m, 3H), 5.00 (hepta, 1H), 4.19-4.10 (m, 1H), 4.02-3.97 (m, 1H), 1.43 (d, 3H), 1.23-1.21 (m, 6H).
³¹P NMR (CDCl₃, 162 MHz) δ: −1.97.

125 Data: ¹H NMR (CDCl₃, 400 MHz) δ: 8.32-8.31 (m, 1H), 8.13-8.10 (m, 1H), 7.73-7.71 (m, 1H), 7.38-7.34 (m, 2H), 7.28-7.19 (m, 3H), 5.02 (hepta, 1H), 4.21-4.11 (m, 1H), 4.01-3.95 (m, 1H), 1.40 (d, 3H), 1.25-1.22 (m, 6H).
³¹P NMR (CDCl₃, 162 MHz) δ: −2.02.

b) Preparation of 120 from 123 and 9a

To a dry 50 mL of round-bottomed flask were added 181 mg (0.58 mmol) of 9a and 1.5 mL of anhydrous THF. The suspension was cooled in an ice-water bath under nitrogen. Grignard reagent (1 M solution in THF, 0.72 mmol) was added via a syringe and a clear solution was formed. The mixture was stirred at ambient temperature for half hour and then cooled to 0° C. again. A solution of 123 (292 mg, 0.66 mmol) in 1.5 mL of THF was added via a syringe over 10 minutes at 0° C. The resulting orange color reaction solution was stirred at room temperature for overnight (19 h) and reaction was almost complete as checked by TLC. The reaction was quenched by addition of sat NH₄Cl (5 mL) and diluted with 20 mL of ethyl acetate and 10 mL of water. Two layers were separated and aqueous layer was extracted with 20 mL of EtOAc. Organic layer was washed with water (20 mL), sat sodium bicarbonate (2×30 mL), 5% sodium carbonate (30 mL), water (20 mL), and brine (20 mL). Organic solution was dried over sodium sulfate and concentrated to a yellow color solid residue. The residue was purified via column chromatography (silica gel, 3% methanol in DCM) to afford 279 mg (0.48 mmol, 83%) of 120.

Example 12

Synthesis of (S)-2-{(R)-[(1R,4R,5R)-5-(2-Amino-6-methoxy-purin-9-yl)-4-(R)-fluoro-3-hydroxy-4-methyl-tetrahydro-furan-2-ylmethoxy]-phenoxy-phosphorylamino}-propionic acid isopropyl ester (126) via (2S)-isopropyl 2-(((R)-(2-chloro-4-nitrophenoxy)(phenoxy)phosphoryl)amino)propanoate (125) and 9a To a 50 mL of dry round-bottomed flask were charged 70 mg (0.223 mmol) of 9a and 1 mL of anhydrous THF. The flask was cooled in an ice-water bath and Grignard reagent (1 M solution in THF, 0.32 mL) was added dropwise at 0° C. After stirred at 0° C. for half hour, a solution of the (125) (129 mg, 0.29 mmol) in 1 mL of THF was added via a syringe. A clear brown color solution was formed and gradually warmed up to ambient temperature. After overnight (19 h) at room temperature, the reaction was quenched by adding 1 N of diluted HCl at 0° C. The mixture was diluted with ethyl acetate (20 mL) and water (10 mL). After separation of two layers, aqueous layer was extracted with EtOAc (10 mL). Organic layer was washed with water (10 mL), sat sodium bicarbonate (3×15 mL), water (10 mL), brine (10 mL), and dried over sodium sulfate. After concentration, the solid residue was purified via column chromatography (silica gel, 3% methanol in DCM) to afford 100 mg (0.17 mmol, 77%) of 126 as a white solid and single isomer.

Example 13

Synthesis of (S)-2-{[(1R,4R,5R)-5-(2-Amino-6-methoxy-purin-9-yl)-4-(R)-fluoro-3-hydroxy-4-methyl-tetrahydro-furan-2-ylmethoxy]-phenoxy-phosphorylamino}-propionic acid isopropyl ester diastereomeric mixture (120) via diastereomeric mixture (2S)-isopropyl 2-((phenoxy(2-thioxobenzo[d]thiazol-3(2H)-yl)phosphoryl)amino)propanoate (127)

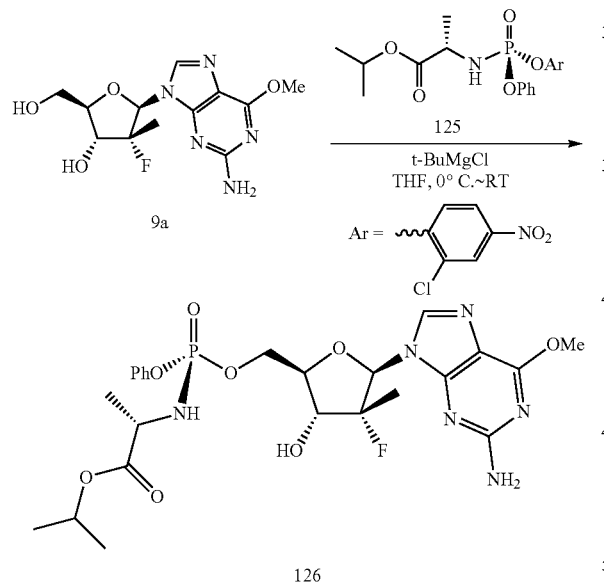

a) Preparation of 127

Phenyl phosphorodichloridate (6.37 g, 30.19 mmol) was dissolved in 40 mL of dry DCM and subsequently cooled to 0° C. After addition of solid (L)-alanine isopropyl ester (5.06 g, 30.19 mmol), the reaction mixture was cooled to −78° C.

and then treated with triethylamine (8.84 mL, 63.3 mmol) dissolved in 20 mL of dry DCM. The resulting mixture was stirred for 30 min at this temperature before being allowed to warm to 0° C. Subsequently, a preformed solution of benzo[d]thiazole-2(3H)-thione (5.05 g, 30.19 mmol) and triethylamine (4.63 mL, 33.21 mmol) dissolved in 20 mL of dry DCM was added over 5-10 min whereupon the mixture was allowed to warm to RT over night. The cloudy mixture was then cooled back to 0° C. and filtered to remove all solids. The filtrate was stripped of all solvent under reduced pressure. The resulting residue was suspended in 50 mL of TBME and stirred for 1 h at RT. Subsequent filtration removed more triethylamine hydrochloride and yielded a filtrate that was again stripped of its solvent under reduce pressure. Column chromatography (DCM) yielded 127 (3:1, isomer I/isomer II) in 15% (1.97 g) yield as viscous oil.

127 Data:

$^1$H NMR (CDCl$_3$, 300 MHz) δ: 8.63-8.59 (m, 1H), 7.37-7.27 (m, 7H), 7.18-7.14 (m, 1H), 6.05-5.97 (m, 1H), 5.04 (hepta, 1H, isomer II), 4.91 (hepta, 1H, isomer I), 4.37-4.24 (m, 1H), 1.45-1.42 (d, 3H, isomer I), 1.41-1.39 (d, 3H, isomer II), 1.26-1.22 (m, 6H), 1.09-1.02 (m, 6H). $^{31}$P NMR (CDCl$_3$, 121 MHz) δ: −0.43 (isomer I), −1.29 (isomer II).

b) Preparation of 120 from 127 and 9a

To a dry round-bottomed flask were added 120 mg (0.38 mmol) of 9a and 1.5 mL of anhydrous THF. The mixture was cooled to 0° C. and 0.5 mL of Grignard reagent (0.5 mmol) was added dropwise. The clear solution was stirred at 0° C. for half hour. A solution of 127 (197 mg, 0.45 mmol) in 1.5 mL of THF was added via a syringe. The resulting mixture was allowed to warm up to room temperature and stirred for overnight (19 h). TLC showed reaction was not complete and product was found together with bis-phosphoramidate by-product. Reaction was quenched by addition of 1 N of diluted HCl at 0° C. and mixture was diluted with 20 mL of ethyl acetate. After work-up, as noted above, an oily residue was obtained and it was purified via column chromatography (silica gel, 3% methanol in DCM) to afford 78.6 mg (0.13 mmol, 35%) of 120. From column, 36.4 mg of bis-phosphoramidate by-product was isolated.

Based on the results in the reactions for preparing compounds 117, 120, and 126, an unexpected correlation was observed between a lower pKa of the leaving group and increased reactivity. Increased reactivity was desirable in the sense that it allowed completion of the reaction in a shorter time period and usually in a higher yield, but very high reactivity also led to less discrimination of substitution on the desired 5'-hydroxyl versus continued reaction with the 3'-hydroxyl. For substrates not containing a competing secondary hydroxyl group or a protected secondary hydroxyl, this would not be a concern.

While this chiral phosphoramidate synthesis method was developed primarily for the Pharmasset nucleotide compounds, 110 and 117, it has broader utility. The methodology can be used to react with any primary or secondary hydroxyl to form chiral phosphoramidates. The examples that follow demonstrate this.

Example 14

Synthesis of racemic S-(2-(((benzylamino)(perfluorophenoxy)phosphoryl)oxy)ethyl)2,2-dimethyl-3-(trityloxy)-propanethioate (128)

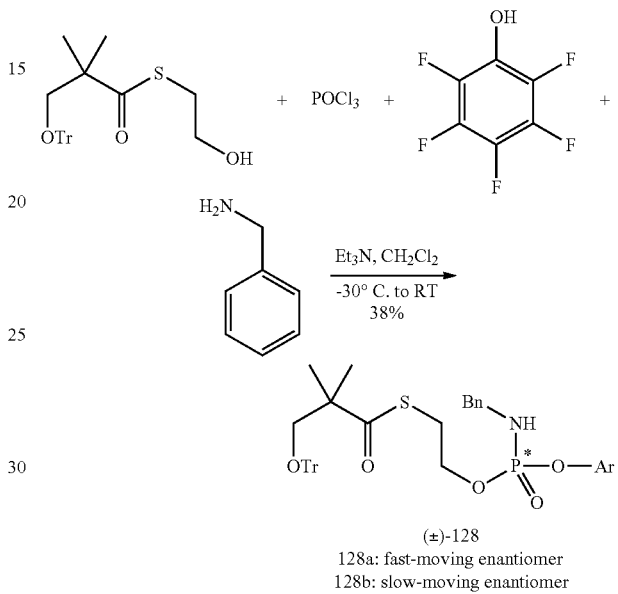

Tr = CPh$_3$
Ar = C$_6$F$_5$

To a stirred solution of POCl$_3$ (0.72 mL, 7.85 mmol) in dichloromethane (24 mL) was added a solution of S-(2-hydroxyethyl) 2,2-dimethyl-3-(trityloxy)propanethioate ((±)-128, 3.3 g, 7.85 mmol) and triethylamine in dichloromethane (16 mL) at −30° C., over a period of 35 min. The mixture was stirred at this temperature for 1 h and then was added a solution of pentafluorophenol (1.44 g, 7.85 mmol) and triethylamine in dichloromethane (16 mL) over a period of 30 min at −30° C. The mixture was stirred at this temperature for 30 min and then warmed to room temperature over 30 min. After stirring for 1 h at room temperature the mixture was cooled to −30° C., and then was added a solution of benzylamine (BnNH$_2$, 0.86 mL, 7.85 mmol) and triethylamine over a period of 5 min. The mixture was stirred at this temperature for 30 min and slowly allowed to warm to 0° C. over a period of 3 h. The solvent was evaporated and the residue was suspended in ethyl acetate (50 mL). The white solids were filtered, washed with ethyl acetate (10 mL) and the filtrate was concentrated under reduced pressure. The residue was chromatographed using 0-30% EtOAc/hexanes gradient to give pure racemic product (128) as colorless syrup (2.25 g, 38% yield).

128 Data:

$^1$H NMR (CDCl$_3$, 400 MHz): δ 7.42-7.39 (m, 6H), 7.31-7.28 (m, 10H), 7.23-7.19 (m, 4H), 4.26 (dd, J=14.8, 6.8 Hz, 2H), 4.20 (dd, J=10.4, 6.8 Hz, 2H), 3.28-3.19 (m, 3H), 3.16 (s, 2H), 1.21 (s, 3H), 1.20 (s, 3H). $^{31}$P NMR (CDCl$_3$, 162 MHz): δ 5.11 (using H$_3$PO$_4$ as external reference set to 0 ppm)

In Example 14, the S-(2-hydroxyethyl) 3-hydroxy-2,2-dimethylpropanethioate is protected with a trityl (—CPh₃) protecting group. It is contemplated that the reaction can be conducted without a protecting group, as shown in the following equation.

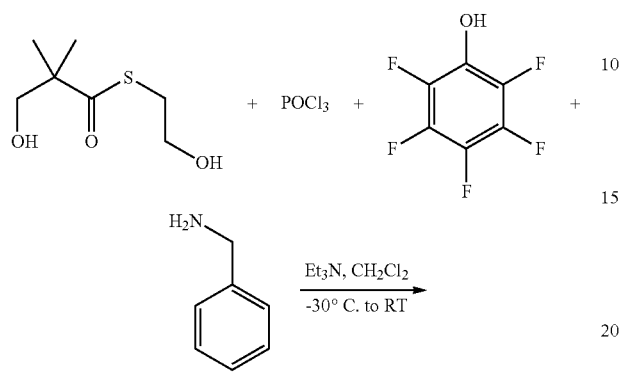

Example 15

Separation of the enantiomers of S-(2-(((benzylamino)(perfluorophenoxy)phosphoryl)oxy)ethyl)2,2-dimethyl-3-(trityloxy)-propanethioate by SFC 1.9 g of (±)-128 was subjected to SFC using a ChiralPak AS-H (2×15 cm) column and eluted with 45% 8:2 isopropanol:ethanol in carbon dioxide at 100 bar with a flow rate of 70 mL/min (UV: 220 nm). An injection loading of 1.75 mL of sample at a concentration of 16 mg/mL in isopropanol was used. The two enantiomers were collected separately and the appropriate fractions of the multiple runs were combined and concentrated under reduced pressure to give 870 mg (100% ee) of the fast moving enantiomer and 430 mg (98.3% ee) of slow moving enantiomer (Analytical method: ChiralPak AS-H (25×0.45 cm), Mobile phase: 40% 80:2 isopropanol:ethanol in carbon dioxide, Pressure: 100 bar, Flow rate: 3 mL/min, UV: 220 nm). The ¹H and ³¹P NMR of the individual enantiomers were identical to the racemic sample. For fast moving enantiomer (128a): $[\alpha]_D^{25}$ (c=1.02 in MeOH): +6.9±0.1. For slow moving enantiomer (128b): $[\alpha]_D^{25}$ (c=1.02 in MeOH): −7.0±0.1. Absolute stereochemistry at phosphorous center was not determined.

Example 16

Synthesis of 131a and 132a from 129 and 128a (Fast-Moving Enantiomer)

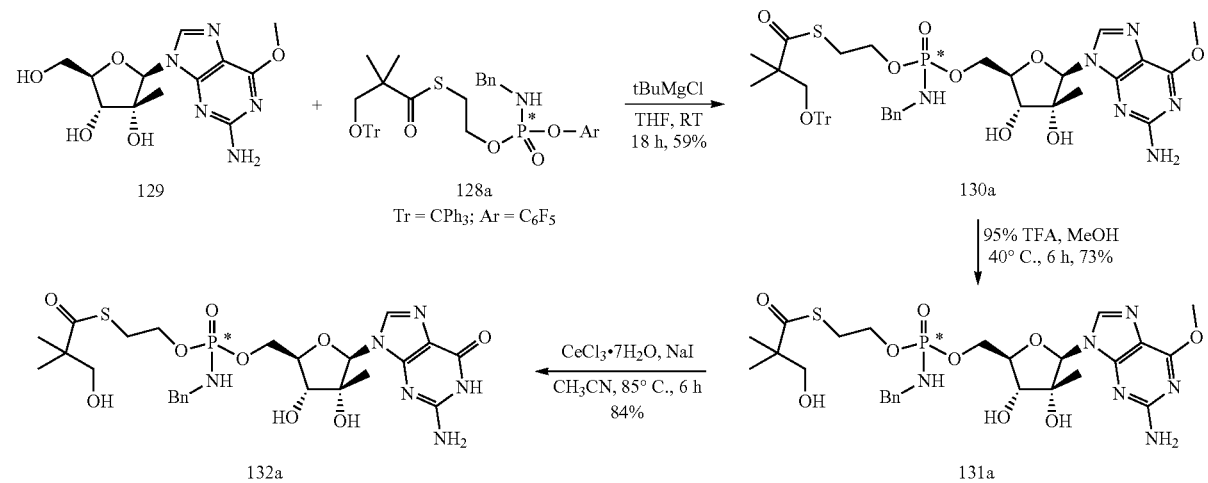

Note: 129 was prepared according to literature procedures: Eldrup et al., *J. Med Chem.* 2004, 47, 2283. and McGuigan et al., *J. Med. Chem.* 2010, 53, 4949.

a) Synthesis of 130a

To a stirred solution of 129 (172 mg, 0.55 mmol) in dry THF (5.6 mL) was added a 1.7M solution of tert-butylmagnesium chloride in THF (1.0 mL, 1.71 mmol) over a period of 8 min at room temperature (23° C.). The white suspension was stirred at this temperature for 30 min and then was added a solution of 128a (500 mg, 0.66 mmol) in THF (1.5 mL) over a period of 5 min. The mixture was stirred at this temperature for 18 h. The reaction mixture was quenched with methanol (1 mL), solvent was evaporated under reduced pressure and the residue was chromatographed using 0-5% methanol/DCM gradient to give pure product (130a) as a foamy solid (240 mg, 59% yield).

130a Data:
¹H NMR (CDCl₃, 400 MHz): δ 7.77 (s, 1H), 7.40-7.38 (m, 6H), 7.29-7.18 (m, 14H), 5.95 (s, 1H), 5.26 (bs, 2H), 4.62 (bs, 1H), 4.50-4.45 (m, 1H), 4.43 (bs, 1H), 4.41 (bs, 1H), 4.32-

4.26 (m, 1H), 4.21-4.17 (m, 1H), 4.13-3.95 (m, 4H), 4.02 (s, 3H), 3.58-3.50 (m, 1H), 3.17-3.08 (m, 2H), 3.14 (s, 2H), 1.18 (s, 3H), 1.17 (s, 3H), 0.96 (s, 3H). $^{31}$P NMR (CDCl$_3$, 162 MHz): δ 9.80 (using H$_3$PO$_4$ as external reference set to 0 ppm). MS (ESI): m/z 883.0 [M+H]$^+$.

b) Synthesis of 131a

To a stirred solution of 130a (205 mg, 0.23 mmol) in methanol (2.0 mL) was added 95% aqueous trifluoroacetic acid (0.5 mL) and the mixture was stirred at 40° C. for 6 h. The solvent was evaporated and the residue was chromatographed using 0-8% methanol/CH$_2$Cl$_2$ gradient to give pure product (131a) as white foam (108 mg, 73% yield).
131a Data:
$^1$H NMR (CD$_3$OD, 400 MHz): δ 8.02 (s, 1H), 7.32-7.25 (m, 4H), 7.21-7.19 (m, 1H), 5.97 (s, 1H), 4.36-4.31 (m, 2H), 4.22 (d, J=8.8 Hz, 1H), 4.16-4.14 (m, 1H), 4.10-3.95 (m, 4H), 4.05 (s, 3H), 3.55 (s, 2H), 3.15 (dd, J=13.6, 6.8 Hz, 1H), 3.07 (dd, J=14.0, 6.8 Hz, 1H), 1.16 (s, 6H), 0.97 (s, 3H). $^{31}$P NMR (CD$_3$OD, 162 MHz): δ 11.05 (using H$_3$PO$_4$ as external reference set to 0 ppm). MS (ESI): m/z 641.0 [M+H]$^+$.

c) Synthesis of 132a

To a stirred solution of 131a (92 mg, 0.14 mmol) in acetonitrile (1.5 mL) was added cerium trichloride heptahydrate (80 mg, 0.22 mmol) followed by sodium iodide (22 mg, 0.14 mmol) at room temperature. The mixture was heated at 85° C. for 6 h. The solvent was evaporated and the residue was chromatographed using 0-20% methanol/DCM gradient to give pure product (132a) as a white solid (76 mg, 84% yield).
132a Data:
$^1$H NMR (CD$_3$OD, 400 MHz): δ 8.01 (bs, 1H), 7.45 (d, J=7.2 Hz, 2H), 7.31 (t, J=7.2 Hz, 2H), 7.22 (t, J=7.2 Hz, 1H), 6.01 (bs, 1H), 4.56-4.24 (m, 6H), 4.19 (bs, 2H), 3.54 (s, 2H), 3.24 (q, J=6.0 Hz, 2H), 1.16 (s, 6H), 1.08 (s, 3H). $^{31}$P NMR (CD$_3$OD, 162 MHz): δ 14.94 (using H$_3$PO$_4$ as external reference set to 0 ppm). MS (ESI): m/z 627.0 [M+H]$^+$.

Example 17

Synthesis of 131b and 132b from 129 and 128b (Slow-Moving Enantiomer)

a) Synthesis of 130b

To a stirred solution of 129 (103 mg, 0.33 mmol) in dry THF (3.5 mL) was added a 1.7M solution of tert-butylmagnesium chloride in THF (0.602 mL, 1.02 mmol) over a period of 5 min at room temperature. The white suspension was stirred at this temperature for 30 min and then was added a solution of 128b (300 mg, 0.397 mmol) in THF (1 mL) over a period of 5 min. The mixture was stirred at this temperature for 18 h. The reaction mixture was quenched with methanol, solvent was evaporated under reduced pressure and the residue was chromatographed using 0-5% methanol/DCM gradient to give pure product (130b) as white foam (105 mg, 36% yield).
130b Data:
$^1$H NMR (CDCl$_3$, 400 MHz): δ 7.74 (s, 1H), 7.40-7.38 (m, 6H), 7.29-7.18 (m, 14H), 5.94 (s, 1H), 5.35 (bs, 2H), 4.85 (bs, 1H), 4.55-4.45 (m, 2H), 4.28-4.17 (m, 3H), 4.15-3.96 (m, 4H), 4.03 (s, 3H), 3.62-3.52 (m, 1H), 3.14 (s, 2H), 3.11 (d, J=6.8 Hz, 2H), 1.18 (s, 6H), 0.94 (s, 3H). $^{31}$P NMR (CDCl$_3$, 162 MHz): δ 9.83 (using H$_3$PO$_4$ as external reference set to 0 ppm). MS (ESI): m/z 883.0 [M+H]$^+$.

b) Synthesis of 131b

To a stirred solution of 130b (85 mg, 0.10 mmol) in methanol (1.0 mL) was added 95% aqueous trifluoroacetic acid (0.3 mL) and the mixture was stirred at 40° C. for 6 h. The solvent was evaporated and the residue was chromatographed using 0-8% methanol/CH$_2$Cl$_2$ gradient to give pure product (131b) as white solid (45 mg, 73% yield).
131b Data:
$^1$H NMR (CD$_3$OD, 400 MHz): δ 7.98 (s, 1H), 7.33-7.30 (m, 2H), 7.27-7.23 (m, 2H), 7.20-7.18 (m, 1H), 5.96 (s, 1H), 4.40 (ddd, J=11.6, 5.6, 2.2 Hz, 1H), 4.36-4.32 (m, 1H), 4.22-4.15 (m, 2H), 4.10-3.96 (m, 4H), 4.06 (s, 3H), 3.55 (s, 2H), 3.10 (t, J=6.6 Hz, 2H), 1.17 (s, 6H), 0.95 (s, 3H). $^{31}$P NMR (CD$_3$OD, 162 MHz): δ 11.16 (using H$_3$PO$_4$ as external reference set to 0 ppm). MS (ESI): m/z 641.0 [M+H]$^+$.

c) Synthesis of 132b

To a stirred solution of 131b (36 mg, 0.056 mmol) in acetonitrile (1 mL) was added cerium trichloride heptahy-

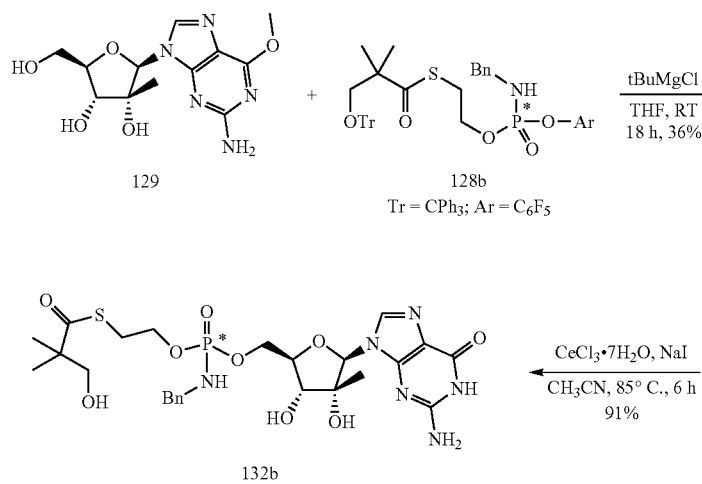

132b

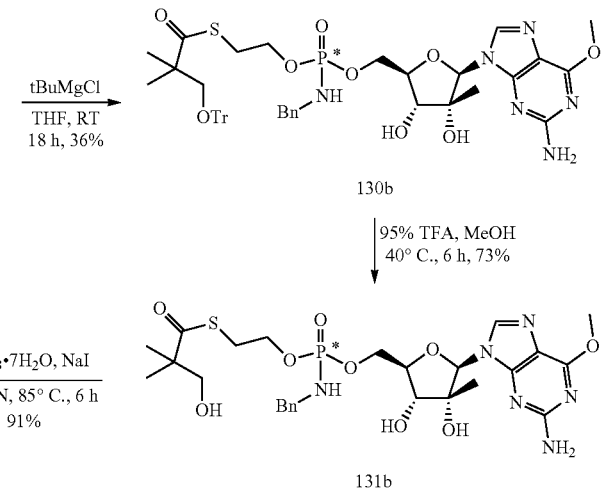

131b drate (31 mg, 0.084 mmol) followed by sodium iodide (8.4 mg, 0.056 mmol) at room temperature. The mixture was heated at 85° C. for 4 h. The solvent was evaporated and the residue was chromatographed using 0-20% methanol/DCM gradient to give pure product (132b) as a white solid (32 mg, 91% yield).

132b Data:

$^1$H NMR (CD$_3$OD, 400 MHz): δ 8.09 (bs, 1H), 7.41 (d, J=7.6 Hz, 2H), 7.28 (t, J=7.6 hz, 2H), 7.19 (t, J=7.6 Hz, 1H), 6.02 (bs, 1H), 4.58-4.52 (m, 1H), 4.48-4.42 (m, 1H), 4.36-4.18 (m, 6H), 3.55 (s, 2H), 3.21 (bt, J=6.0 Hz, 2H), 1.17 (s, 3H), 1.16 (s, 3H), 1.07 (s, 3H). $^{31}$P NMR (CD$_3$OD, 162 MHz): δ 14.57 (using H$_3$PO$_4$ as external reference set to 0 ppm). MS (ESI): m/z 627 [M+H]$^+$.

Example 18

Synthesis of (S)-isopropyl 2-(((S)-(((2R,3R,4R,5R)-5-(2-amino-6-methoxy-9H-purin-9-yl)-3,4-dihydroxy-4-methyltetrahydrofuran-2-yl)methoxy)(phenoxy)phosphoryl)amino)propanoate (133)

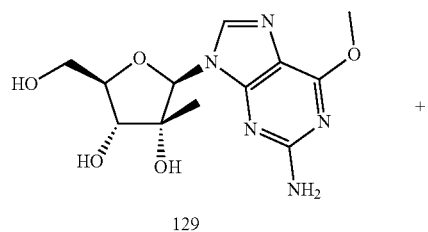

129

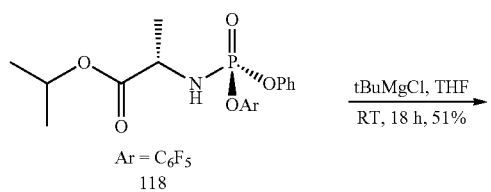

Ar = C$_6$F$_5$
118

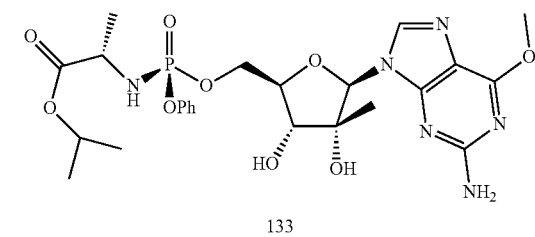

133

To a stirred solution of 129 (208 mg, 0.67 mmol) in dry THF (4 mL) was added a 1.7M solution of tert-butylmagnesium chloride in THF (1.22 mL, 2.07 mmol) over a period of 5 min at 21° C. The white suspension was stirred at this temperature for 30 min and was added a solution of 118 (see Example 6) (360 mg, 0.8 mmol) in THF (5 mL) over a period of 15 min using a syringe pump. The mixture was stirred at 21° C. for 18 h and then quenched with methanol. The solvent was evaporated and the residue was chromatographed using 0-6% methanol/dichloromethane gradient to give pure product 133 as a white solid (196 mg, 51% yield).

133 Data:

$^1$H NMR (DMSO-d$_6$, 400 MHz): δ 7.93 (s, 1H), 7.34 (t, J=7.4 Hz, 2H), 7.19 (d, J=8.4 Hz, 2H), 7.15 (t, J=7.4 Hz, 1H), 6.51 (s, 1H), 5.97 (dd, J=12.8, 10.0 Hz, 1H), 5.83 (s, 1H), 5.38-5.37 (m, 1H), 5.22 (s, 1H), 4.78 (septet, J=6.4 Hz, 1H), 4.35 (dd, J=11.0, 6.2 Hz, 1H), 4.26 (quintet, J=5.8 Hz, 1H), 4.03 (bs, 2H), 3.94 (s, 3H), 3.80-3.74 (m, 1H), 1.19 (d, J=6.8, 3H), 1.09 (d, J=6.4 Hz, 3H), 1.07 (d, J=6.4 Hz, 3H), 0.79 (s, 3H). MS (ESI): m/z 581.0 [M+H]$^+$.

Example 19

Synthesis of (S)-isopropyl 2-(((S)-(((2R,3R,4R,5R)-5-(2-amino-6-oxo-1H-purin-9(6H)-yl)-3,4-dihydroxy-4-methyltetrahydrofuran-2-yl)methoxy)(phenoxy)phosphoryl)amino)propanoate (134)

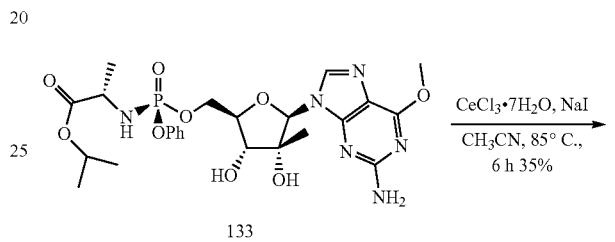

133

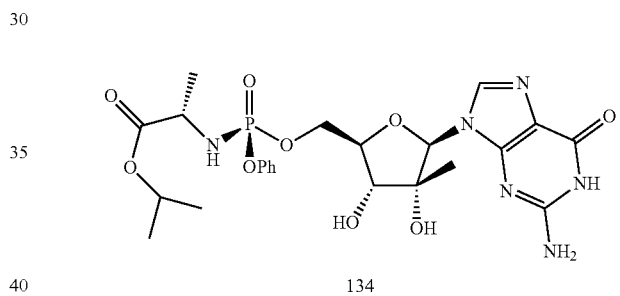

134

To a stirred solution of 133 (160 mg, 0.28 mmol) was added cerium(III)chloride heptahydrate (154 mg, 0.414 mmol) and sodium iodide (41 mg, 0.276 mmol) at room temperature (21° C.). The mixture was heated at 85° C. for 6 h. The solvent was evaporated and the residue was chromatographed using 0-15% methanol/dichloromethane gradient to give pure product 134 as a white solid (55 mg, 35% yield).

134 Data:

$^1$H NMR (DMSO-d$_6$, 400 MHz): δ 10.63 (bs, 1H), 7.76 (s, 1H), 7.34 (t, J=8.0 Hz, 2H), 7.20 (d, J=8.0 Hz, 2H), 7.15 (t, J=7.2 Hz, 1H), 6.53 (bs, 2H), 5.99 (dd, J=12.8, 10.4 Hz, 1H), 5.73 (s, 1H), 5.65 (d, J=6.4 Hz, 1H), 5.19 (s, 1H), 4.79 (septet, J=6.4 Hz, 1H), 4.33 (dd, J=11.0, 6.4 Hz, 1H), 4.24 (quintet, J=5.8 Hz, 1H), 4.03-3.93 (m, 2H), 3.82-3.72 (m, 1H), 1.19 (d, J=6.8 Hz, 3H), 1.09 (t, J=10.8 Hz, 6H), 0.80 (s, 3H). MS (ESI): m/z 566.9 [M+H]$^+$.

Compound 44 is a non-nucleoside NS5B inhibitor of Hepatitis C with a free primary hydroxyl. A chiral phosphoramidate has the advantage of making a single enantiomer and uniform physical properties to aid in development. Com-

Example 20

HCV-796 chiral phosphoramidate derivative: Synthesis of (S)-isopropyl 2-(((S)-(2-(N-(5-cyclopropyl-2-(4-fluorophenyl)-3-(methylcarbamoyl)benzofuran-6-yl)methylsulfonamido)ethoxy)(phenoxy)phosphoryl)amino)propanoate (135)

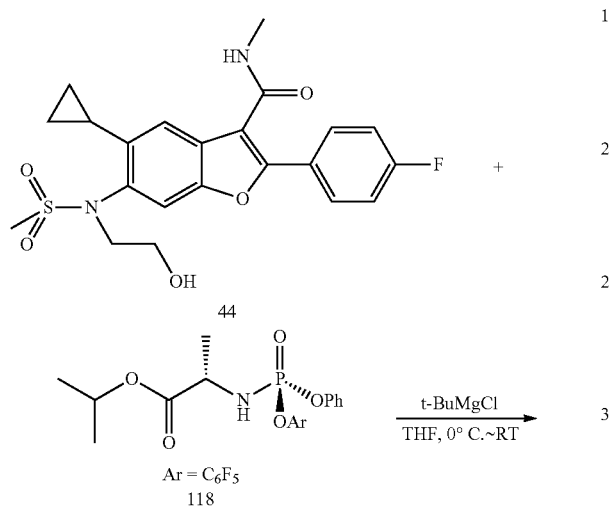

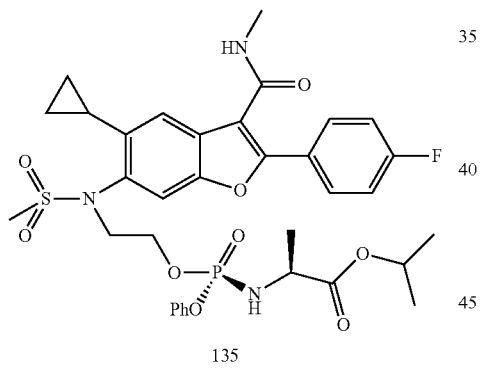

To a dry 50 mL of round-bottomed flask were added 50 mg (0.11 mmol) of 44 and 1 mL of anhydrous tetrahydrofuran. The clear solution was cooled to 0° C. in an ice-water bath. Grignard reagent (1 M solution in THF, 0.18 mmol) was added via a syringe slowly and the mixture was stirred at 0° C. for half hour. A solution of the 118 (71 mg, 0.16 mmol) in 1 mL of THF was added dropwise at 0° C. The mixture was stirred at room temperature for 14 hours. The reaction was complete and sat'd NH$_4$Cl was added. The mixture was diluted with ethyl acetate and water. Organic layer was separated and aqueous layer was extracted with EtOAc. The combined organic layer was washed with water (8 mL), sat. sodium bicarbonate (2×10 mL), 1 M sodium carbonate (8 mL), water (8 mL), brine (8 mL), and dried over sodium sulfate. After removal of solvent, the solid residue was purified via column chromatography (silica gel, 1% MeOH in DCM) to afford 76 mg (0.11 mmol, 95%) of product 135 as a white amorphous solid.

135 Data:
$^1$H NMR (CDCl$_3$) δ 7.89-7.84 (m, 2H), 7.54-7.50 (m, 1H), 7.33-7.26 (m, 3H), 7.22-7.11 (m, 5H), 5.94-5.90 (m, 1H), 4.98 (heptd, 1H), 4.29-4.08 (m, 3H), 4.00-3.75 (m, 2H), 3.68-3.62 (m, 1H), 3.05-3.01 (m, 3H), 2.97 (d, 3H), 2.28-2.21 (m, 1H), 1.32 (d, 3H), 1.23-1.19 (m, 6H), 1.05-1.01 (m, 2H), 0.97-0.92 (m, 1H), 0.65-0.61 (m, 1H).

Example 21

Synthesis of (2S)-neopentyl 2-(((((2R,3R,4R,5R)-5-(2-amino-6-methoxy-9H-purin-9-yl)-3,4-dihydroxy-4-methyltetrahydrofuran-2-yl)methoxy)(naphthalen-1-yloxy)phosphoryl)amino)propanoate

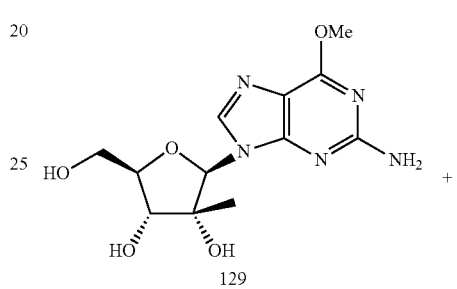

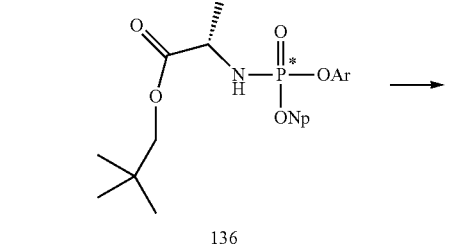

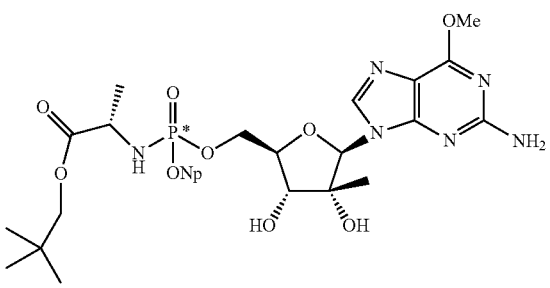

Ar = C$_5$F$_6$; Np = naphth-1-yl a) Preparation of (2S)-neopentyl 2-(((naphthalen-1-yloxy)(perfluorophenoxy)phosphoryl)amino)propanoate (136), as its diastereomeric mixture, chiral separation into two pure diastereomers 136a (fast-moving diastereomer) and 136b (slow-moving diastereomer)

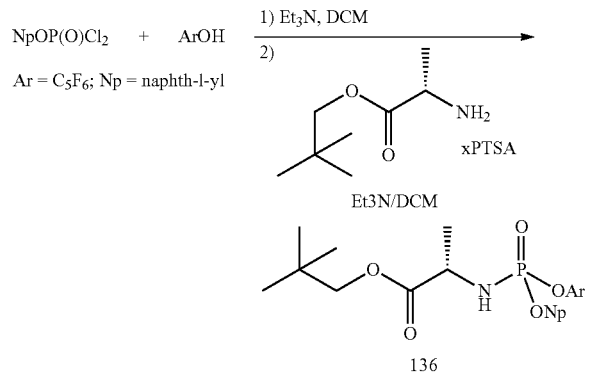

α-Naphthyl phosphorodichloridate (10.0 g, 38.46 mmol) was dissolved in 40 mL of dry dichloromethane and subsequently cooled to 0° C. After addition of solid (L)-alanine neopentyl ester p-toluenesulfonic acid salt (12.7 g, 38.46 mmol), the reaction mixture was cooled to −70° C. and then treated with triethylamine (11.2 mL, 77.0 mmol) dissolved in 50 mL of dry DCM. The resulting mixture was stirred for 30 min at this temperature before being allowed to warm to 0° C. Subsequently, a preformed solution of pentafluorophenol (7.07 g, 38.46 mmol) and triethylamine (5.9 mL, 42.32 mmol) dissolved in 20 mL of dry DCM was added over 5-10 min and was continued stirring for additional 2 h. The solution was filtered and the filtrate was concentrated under reduced pressure. The resulting residue was suspended in 50 mL of TBME and stirred for 10 min at room temperature. Subsequent filtration removed more triethylamine hydrochloride and yielded a filtrate that was again stripped of its solvent under reduced pressure. Column chromatography (dichloromethane) yielded the desired product (14.7 g, 72% yield) as solid diastereomeric mixture.

136 Data:
$^1$H NMR (CDCl$_3$, 400 MHz) δ: 8.13-8.10 (m, 1H), 7.88-7.86 (m, 1H), 7.72-7.70 (m, 1H), 7.62-7.52 (m, 3H), 7.44-7.40 (m, 1H), 4.32-4.27 (m, 1H), 4.14-4.09 (m, 1H), 3.90-3.73 (m, 2H), 1.47 (d, 3H), 0.93 (s, 9H, isomer I), 0.90 (s, 9H, isomer II). $^{31}$P NMR (CDCl$_3$, 162 MHz) δ −0.54, −0.59.

1.9 g of 136 was separated by supercritical fluid chromatography (SFC) using a ChiralPak AD-H column (2×15 cm), and eluting with 20% isopropanol/CO$_2$, 100 bar, 65 mL/min, 220 nm, injection volume of 0.3 mL, 33 mg/mL methanol to yield 930 mg of 136a (fast-moving diastereomer) (>99% ee) and 930 mg of 136b (slow-moving diastereomer) (>99% ee).

136a NMR data: $^1$H NMR (CDCl$_3$, 400 MHz) δ, ppm: 8.12 (d, J=8.0 Hz, 1H), 7.87 (d, J=7.2 Hz), 7.71 (d, J=8.0 Hz, 1H), 7.62-7.53 (m, 3H), 7.42 (t, J=8.0 Hz, 1H), 4.35-4.20 (m, 2H), 3.89 (d, J=10.4 Hz, 1H), 3.81 (d, J=10.4 Hz, 1H), 1.47 (d, J=6.9 Hz, 3H), 0.93 (s, 9H); $^{31}$P NMR (CDCl$_3$, 162 MHz) δ, ppm: 10.87 (s).

136b NMR data: $^1$H NMR (CDCl$_3$, 400 MHz) δ, ppm: 8.16 (d, J=8.0 Hz, 1H), 7.87 (d, J=7.2 Hz), 7.71 (d, J=8.0 Hz, 1H), 7.62-7.53 (m, 3H), 7.40 (t, J=8.0 Hz, 1H), 4.35-4.22 (m, 1H), 4.19-4.10 (m, 1H), 3.85 (d, J=10.4 Hz, 1H), 3.78 (d, J=10.4 Hz, 1H), 1.47 (d, J=6.9 Hz, 3H), 0.93 (s, 9H); $^{31}$P NMR (CDCl$_3$, 162 MHz) δ, ppm: 10.91 (s).

b) Preparation of 137a from 136a (Fast-Moving Diastereomer) and 129

To a dry 10 mL one-neck round bottom flask equipped with an rubber septum, magnetic stir bar and nitrogen inlet/outlet was charged 0.1050 g of 129 (prepared based on an adaptation of literature methods; see Eldrup et al., *J. Med Chem.* 2004, 47, 2283. and McGuigan et al., *J. Med. Chem.* 2010, 53, 4949) and 1.6 mL of anhydrous THF under nitrogen. The slurry was cooled in to 0° C. 1.0 mL of t-butyl magnesium chloride solution (1 M in THF) was added via a syringe over 2-3 mins. The slurry was stirred at 0-5° C. for 20 mins. To this was added a solution of 0.186 g of (2S)-neopentyl 2-(((naphthalen-1-yloxy)(perfluorophenoxy)phosphoryl)amino)-propanoate, 136b (fast-moving diastereomer) in 1 mL of anhydrous THF.

The reaction was allowed to warm up to 20° C. and stirred at 20° C. for 2 hours at which point HPLC indicated complete consumption of 136. The reaction was quenched by the addition of 1 mL of 1 N HCl followed by removing THF by rotary evaporation. The mixture was diluted with 9 mL of EtOAc and 2 mL of water and transferred to a separatory funnel. The bottom aqueous layer was extracted with 2 mL of EtOAc and the combined organic layers were washed with water (1×2 mL), saturated NaHCO$_3$ (2×1.5 mL), 1 M Na$_2$CO$_3$ (2×1.5 mL), and water (2×2.0 mL). The organic layer was dried over MgSO$_4$, filtered, and concentrated via rotary evaporation to furnish the crude product as a white foam, which was purified by flash column chromatography to yield 0.0808 grams (36% yield) of (S)-neopentyl 2-(((((2R,3R,4R,5R)-5-(2-amino-6-methoxy-9H-purin-9-yl)-3,4-dihydroxy-4-methyltetrahydrofuran-2-yl)methoxy)(naphthalen-1-yloxy)phosphoryl)amino)propanoate, 137a, as a white foam.

137a Data:
UPLC-MS: m+1=659; $^1$H NMR (CDCl$_3$, 400 MHz) δ, ppm: 8.12-8.10 (m, 1H), 7.80-7.79 (m, 1H), 7.64-7.62 (m, 2H), 7.62-7.46 (m, 2H), 7.35 (t, J=8 Hz, 1H), 5.90 (s, 1H), 5.34 (br s, 2H), 4.87-4.82 (m, 2H), 4.49-4.42 (m, 2H), 4.40-4.23 (m, 2H), 4.15-4.05 (m, 2H), 4.02 (s, 3H), 3.78 (d, J=10 Hz, 1H), 3.64 (d, J=10 Hz, 1H), 2.30 (br s), 2.09 (br s), 1.34 (d, J=7.0 Hz, 3H), 0.89 (s, 3H), 0.85 (s, 9H); $^{31}$P NMR (CDCl$_3$, 162 MHz) δ, ppm: 4.09 (s).

c) Preparation of 137b from 136b (Slow-Moving Diastereomer) and 129

To a dry 10 mL one-neck round bottom flask equipped with an rubber septum, magnetic stir bar and nitrogen inlet/outlet was charged 0.1079 g of 129 and 2.0 mL of anhydrous THF under nitrogen. The slurry was cooled in to 0° C. 1.0 mL of t-butyl magnesium chloride solution (1 M in THF) was added via a syringe over 2-3 mins. The slurry was stirred at 0-5° C. for approx. 20 mins. To this was added a solution of 0.2642 g of 136b (slow-moving diastereomer) in 1.5 mL of anhydrous THF.

The reaction was allowed to warm up to 20° C. and stirred at 20° C. for 2 hours at which point HPLC indicated complete consumption of 136. The reaction was quenched by the addition of 1 mL of 1 N HCl followed by removing THF by rotary evaporation. The mixture was diluted with 9 mL of EtOAc and 2 mL of water and transferred to a separatory funnel. The bottom aqueous layer was extracted with 2 mL of EtOAc and the combined organic layers were washed with water (1×2 mL), saturated NaHCO$_3$ (2×1.5 mL), 1 M Na$_2$CO$_3$ (2×1.5 mL), and water (2×2.0 mL). The organic layer was dried over MgSO$_4$, filtered, and concentrated via rotary evaporation to furnish the crude product as a white foam, which was purified by flash column chromatography to yield 0.0724 grams (32% yield) of 137b as a white foam.

137b Data:
UPLC-MS: m+1=659; $^1$H NMR (CDCl$_3$, 400 MHz) δ, ppm: 8.12-8.10 (m, 1H), 7.82-7.79 (m, 1H), 7.70 (s, 1H), 7.64-7.62 (m, 1H), 7.61-7.46 (m, 2H), 7.38-7.33 (m, 1H), 5.90 (s, 1H), 5.32 (br s, 2H), 4.70-4.66 (m, 2H), 4.58 (br s, 1H), 4.48-4.10 (m, 6H), 4.05 (s, 3H), 3.78 (d, J=10 Hz, 1H), 3.64 (d, J=10 Hz, 1H), 2.43 (br s), 2.12 (br s), 1.35 (d, J=7.0 Hz, 3H), 0.89 (s, 3H), 0.85 (s, 9H); $^{31}$P NMR (CDCl$_3$,162 MHz) δ, ppm: 4.47 (s).

Example 22

Synthesis of (S)-2-{(S)-[(2R,3R,4R,5R)-5-(4-amino-pyrrolo[2,3-d]pyrimidin-7-yl)-3,4-dihydroxy-4-methyl-tetrahydro-furan-2-ylmethoxy]-phenoxy-phosphorylamino}-propionic acid isopropyl ester (139)

layers, the aqueous layer was extracted with EtOAc (10 mL). Combined organic layer was washed with water (10 mL), sat NaHCO$_3$ (2×10 mL), brine (10 mL), and dried over Na$_2$SO$_4$. Removal of solvent afforded a sticky oil residue. The residue was purified via column chromatography (silica gel, 5% MeOH in DCM) to furnish product as a white amorphous solid (129 mg, 0.23 mmol, 66%).

139 Data:
$^1$H NMR (CDCl$_3$, 400 MHz) δ: 8.27 (s, 1H), 7.30-7.22 (m, 4H), 7.13-7.08 (m, 2H), 6.35 (d, 1H), 6.31 (s, 1H), 5.82 (s, 2H), 4.96 (hepta, 1H), 4.63-4.58 (m, 1H), 4.54-4.50 (m, 1H), 4.45-4.40 (m, 1H), 4.23-4.21 (m, 1H), 4.05-3.95 (m, 2H), 1.33 (d, 3H), 1.18-1.13 (m, 6H), 0.74 (s, 3H). $^{31}$P NMR (CDCl$_3$, 162 MHz) δ: 4.14.

Example 23

Synthesis of (2S)-neopentyl 2-(((((2R,3R,4R,5R)-5-(2-amino-6-methoxy-9H-purin-9-yl)-4-fluoro-3-hydroxy-4-methyltetrahydrofuran-2-yl)methoxy)(naphthalen-1-yloxy)phosphoryl)amino)propanoate (140)

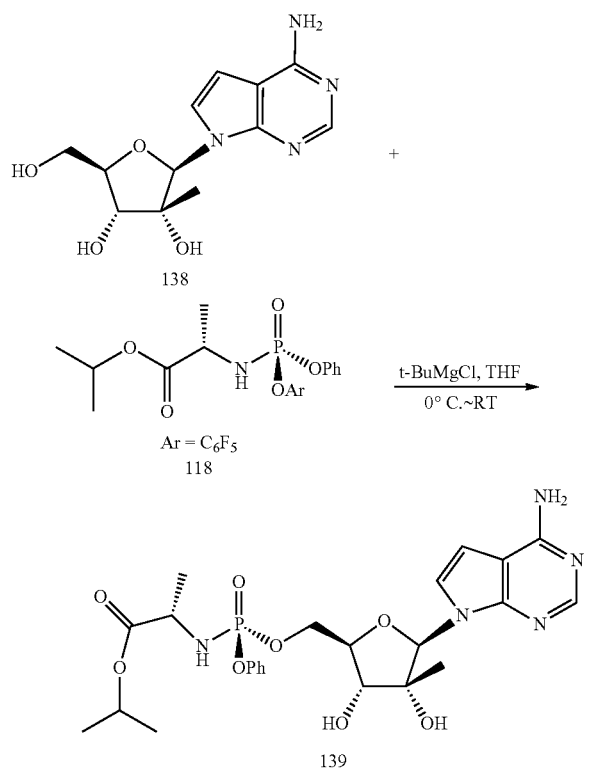

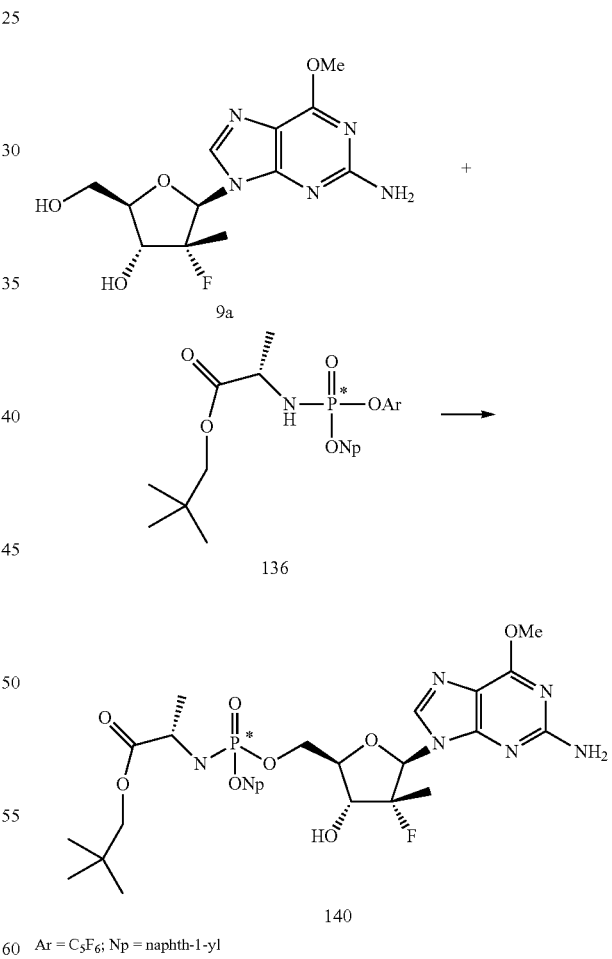

Ar = C$_5$F$_6$; Np = naphth-1-yl

To a 50 mL of dry round-bottomed flask were added the nucleoside 138 (prepared as disclosed in U.S. Pat. No. 6,777,395) (100 mg, 0.36 mmol) and 1.5 mL of anhydrous THF. The white suspension was cooled to 0° C. in an ice-water bath. Grignard reagent (1 M solution in THF, 1.2 mL) was added via a syringe dropwise. The resulting cloudy mixture was stirred at 0° C. for 30 min before a solution of the phosphorus reagent in 1.5 mL of THF was added via a syringe drop wise at 0° C. The resulting clear reaction solution was allowed to warm up to room temperature and stirred for 22 hours. The reaction was quenched by adding sat NH$_4$Cl. The mixture was diluted with ethyl acetate (40 mL). After separation of two To a dry 100 mL one-neck round bottom flask equipped with an rubber septum, magnetic stir bar and nitrogen inlet/outlet was charged 2.0 g of 9a and 12 mL of anhydrous THF under nitrogen. The slurry was cooled in to 0° C. 8.0 mL of t-butyl magnesium chloride solution (1 M in THF) was added via a syringe over 10 mins. The slurry was stirred at 0-5° C. for 30 mins. To this was added a solution of 3.90 g of 136 in 20 mL of anhydrous THF.

The reaction was allowed to warm up to 20° C. and stirred at 20° C. for 4 hours at which point HPLC indicated complete consumption of 136. The reaction was quenched by the addition of 20 mL of 1 N HCl followed by removing THF by rotary evaporation. The mixture was diluted with 100 mL of EtOAc and 12 mL of water and transferred to a separatory funnel. The bottom aqueous layer was extracted with 12 mL of EtOAc and the combined organic layers were washed with water (1×24 mL), saturated $NaHCO_3$ (2×20 mL), 1 M $Na_2CO_3$ (3×20 mL), and water (2×20 mL). The organic layer was dried over $MgSO_4$, filtered, and concentrated via rotary evaporation to furnish the crude product as a white foam, which was purified by flash column chromatography to yield 2.59 grams (63% yield) of (2S)-neopentyl 2-(((((2R,3R,4R,5R)-5-(2-amino-6-methoxy-9H-purin-9-yl)-4-fluoro-3-hydroxy-4-methyltetrahydrofuran-2-yl)methoxy)(naphthalen-1-yloxy)phosphoryl)amino)propanoate (140) as an off-white foam.

140 Data:

UPLC-MS: m+1=661; $^1$H NMR ($CDCl_3$, 400 MHz) δ, ppm: 8.13-8.09 (m, 1H), 7.82-7.78 (m, 1H), 7.63-7.59 (m, 1H), 7.53-7.46 (m, 3H), 7.37-7.32 (m, 1H), 6.00 (dd, J=19, 6 Hz, 1H), 5.21 (br s, 2H), 4.86-4.78 (m, 1H), 4.74-4.65 (m, 1H), 4.52-4.46 (m, 1H), 4.30-4.20 (m, 1H), 4.12-4.06 (m, 1H), 4.02 (d, J=3 Hz, 3H), 3.77 (dd, J=6, 10 Hz, 1H), 3.63 (dd, J=6, 10 Hz, 1H), 1.38 (t, J=6 Hz, 3H), 1.08 (dd, J=19, 6 Hz, 3H), 0.85 (s, 9H); $^{31}$P NMR ($CDCl_3$, 162 MHz) δ, ppm: 5.45 (s), 4.93 (s)

The above-recited examples can be modified by one of ordinary skill without undue experimentation in order to obtain compositions containing enantiomerically- or diastereomerically-enriched compositions comprised of a compound of formula I, a compound of formula II, or a compound of formula III. The above-recited examples can be modified by one of ordinary skill without undue experimentation in order to obtain compositions containing enantiomerically- or diastereomerically-enriched compositions comprised of a compound of formula I or a compound of formula III where the active is comprised of any one of the compounds 1-90 (less one or more hydrogen atoms).

Preparation of Compounds Falling within the Scope of Compound III

It is contemplated that a compound represented by formula III can be prepared by the following scheme,

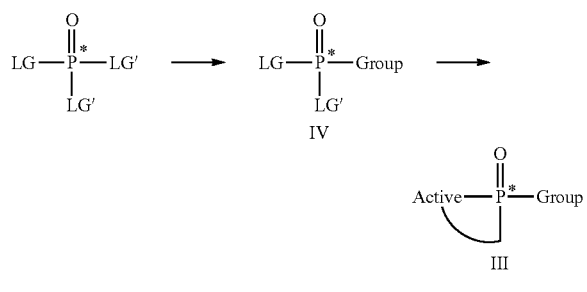

as disclosed in WO 2008/079206 (US 2010/0022468)

Biological Activity

HCV Inhibition Assay.

Clone A or ET-lunet cells were seeded at a density of 1500 or 3000 cells per well in a 96-well plate, respectively. Test compounds serially diluted in culture medium without G418 were added to cells so that the final DMSO concentration was 0.5%. Plates were incubated at 37° C. in a 5% $CO_2$ atmosphere for 4 days. Inhibition of HCV RNA replication was determined by real time PCR (RT-PCR) or by measuring the levels of luminescence expressed via the luciferase reporter gene encoded within the ET replicon. Briefly, for the RT-PCR assay, total RNA was extracted using the RNeasy-96 kit as recommended by the manufacturer (Qiagen, Valencia, Calif.), reversed transcribed into cDNA, and amplified using primer and probe mix for HCV 5'-NTR RNA and human ribosomal RNA (rRNA) in a one-step RT-PCR reaction as described previously (Stuyver, L. J. et al. Antiviral Chem. Chemother. (2006) 17, 79-87). A relative quantification method was used to determine the extent of inhibition. The threshold cycle ($C_t$) of rRNA was subtracted from the $C_t$ of HCV RNA ($\Delta C_t$). The average $\Delta C_t$ of the DMSO cell controls was then subtracted from the $\Delta C_t$ of the compound treated sample ($\Delta\Delta C_t$). Percent inhibition was determined by using the following equation: %=(1−($2^{-\Delta\Delta C_t}$))×100. For the luciferase-based replicon assay, luminescence was measured by using a Victor3 plate reader (Perkin-Elmer, Boston, Mass.) following the addition of Bright-Glo reagent as recommended by the manufacturer (Promega, Madison, Wis.). Percent inhibition of HCV replication was determined by comparing the change in luminescence of the drug treated wells versus the DMSO cell controls. $EC_{50}$ and $EC_{90}$ values, the concentrations at which 50% and 90% inhibition were achieved, were determined using the GraphPad Prism software (San Diego, Calif.).

Cell Cytotoxicity Assays.

Each compound (serially diluted from 100 µM) was added to Huh7 (2×10$^3$ cells/well), HepG2 (2×10$^3$ cells/well), BxPC3 (2×10$^3$ cells/well), or CEM (5×10$^3$ cells/well) cells and allowed to incubate for 8 days at 37° C. A medium only control was used to determine the minimum absorbance value and an untreated cell. At the end of the growth period, MTS dye from the CellTiter 96 Aqueous One Solution Cell Proliferation Assay kit (Promega) was added to each well and the plate was incubated for an additional 2 hours. The absorbance at 490 nm was read with a Victor3 plate reader (Perkin Elmer) using the medium only control wells as blanks. The 50% inhibition value ($CC_{50}$) was determined by comparing the absorbance in wells containing cells and test compound to untreated cell control wells.

| Compound | $EC_{90}$ (µM) | $CC_{50}$ (µM) |
| --- | --- | --- |
| 110 | 0.22 | >20 |
| 117 | 0.13 | >20 |
| 140 | 0.0035 | >20 |
| 137 | 0.0017 | >1 |
| 137a | 0.0037 | 0.93 |
| 137b | 0.0036 | 1.84 |
| 133 | 0.078 | 4.14 |
| 134 | 0.56 | >20 |
| 132 | 0.30 | >10 |
| 132a | 0.30 | >20 |

-continued

| Compound | EC$_{90}$ (μM) | CC$_{50}$ (μM) |
|---|---|---|
| 132b | 0.35 | >20 |
| 131a | 0.093 | >20 |
| 131b | 0.186 | >20 |
| 44 | 0.020 | >10[a] |
| 135 | 0.081 | >20 |
| 138 | 5.56[b] | 800[a] |
| 139 | 0.020 | >10 |

[a]MTT Assay;
[b]PCR

This application claims priority to U.S. 61/319,513, filed on Mar. 31, 2010 and U.S. 61/319,548, filed on Mar. 31, 2010, the subject matter of which is incorporated by reference in its entirety.

The subject matter of U.S. patent application Ser. No. 12/053,015 filed on Mar. 21, 2008; Ser. No. 12/783,680, filed May 20, 2010, Ser. No. 13/076,552, filed on Mar. 31, 2011, and Ser. No. 13/076,718, filed on Mar. 31, 2011 is hereby incorporated by reference in its entirety. The subject matter of U.S. Provisional Patent Application No. 61/179,923, filed May 20, 2009, 61/319,513, filed Mar. 31, 2010, and 61/319,548, filed on Mar. 31, 2010 is incorporated by reference in its entirety. The essential subject matter of all cited references is hereby incorporated by reference. In the event that the meaning of an incorporated term conflicts with the meaning of a term defined herein, the meaning of the term contained in the present disclosure controls over the meaning of the incorporated term.

The invention claimed is:

1. A process for preparing an enantiomerically- or a diastereomerically enriched phosphorus-containing active, salt, or pharmaceutically acceptable salt thereof, of formula I-1:

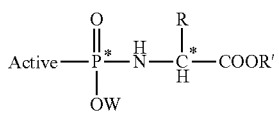

I-1 which comprises the steps of:
(a) reacting a protected or unprotected Active with a base to form a salt of said active and then reacting said salt with an enantiomerically- or a diastereomerically enriched compound of formula II-1

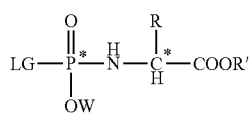

II-1 wherein the Active is a nucleoside, a nucleoside-analog, or a non-nucleoside;

wherein the nucleoside is selected from

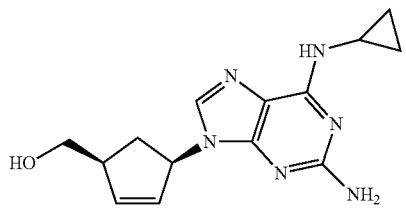

1

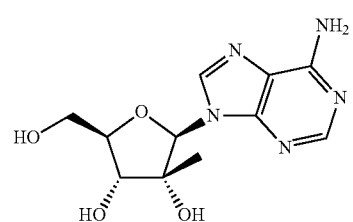

2

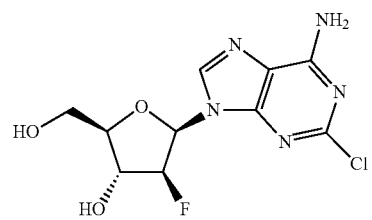

3

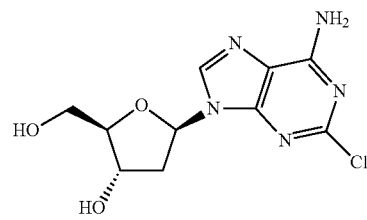

4

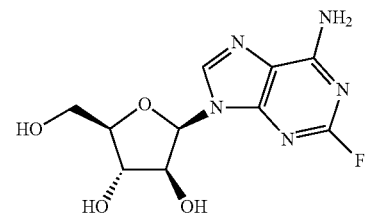

5

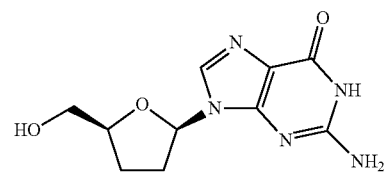

6

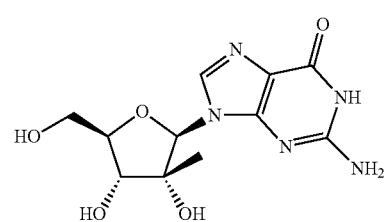

7

8
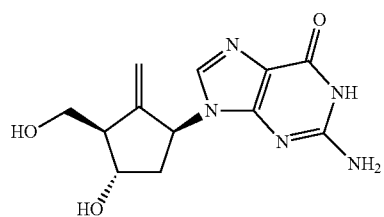
10
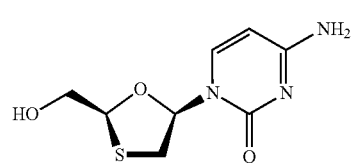
11
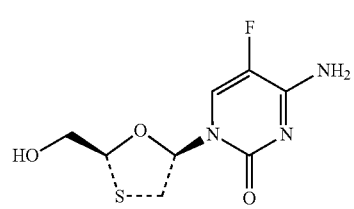
12
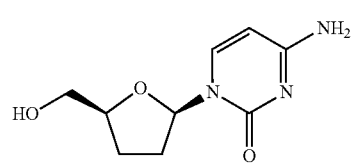
13
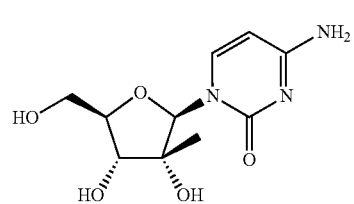
15
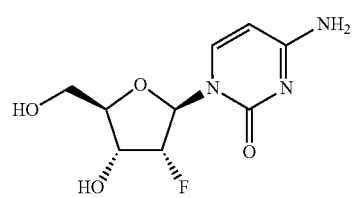
16
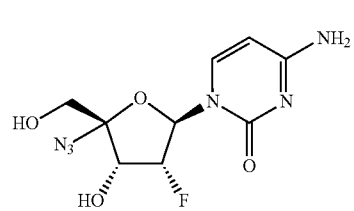
17
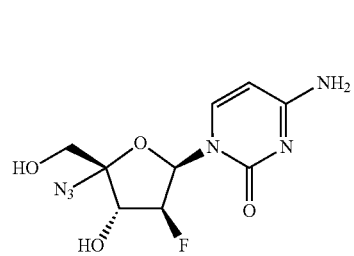
18
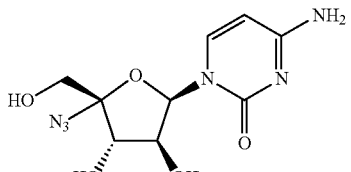
19
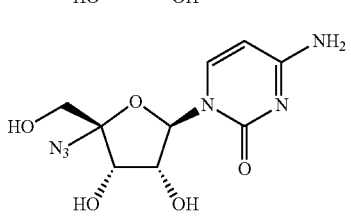
20
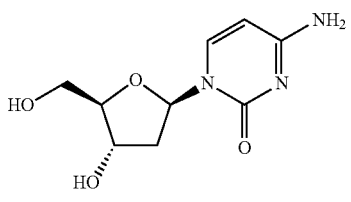
22
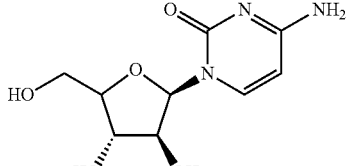
24
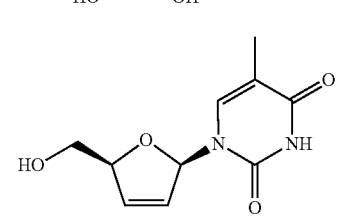
25
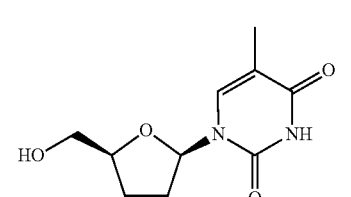
26
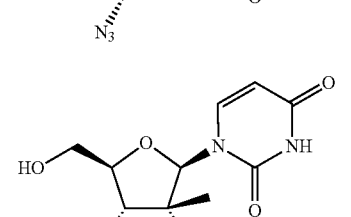
28
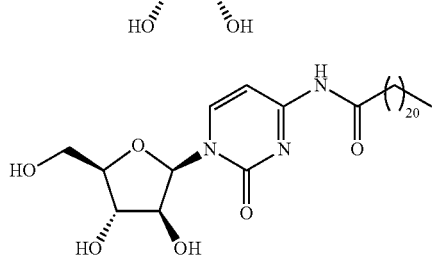

149
-continued
29
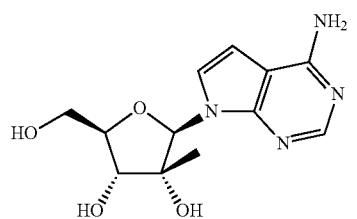
30
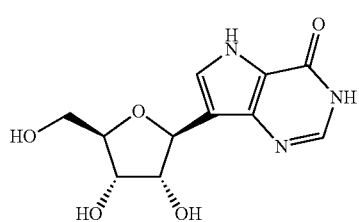
31
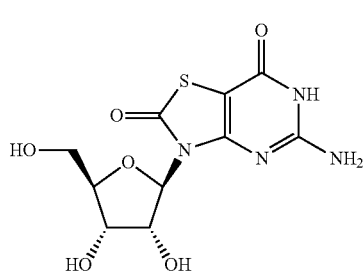
32
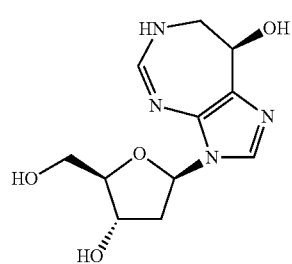
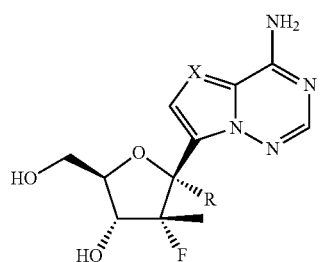
34a: R = H; X = CH
34b: R = CN; X = CH
34c: R = H; X = N
34d: R = CN; X = N
39
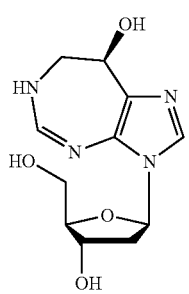
150
-continued
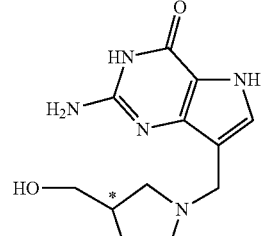
(S,S)-41
(R,R)-41
42
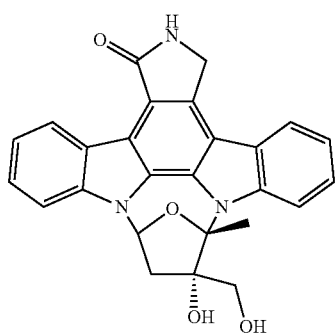
43
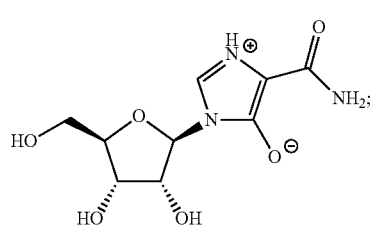
wherein the nucleoside-analog is selected from
33a
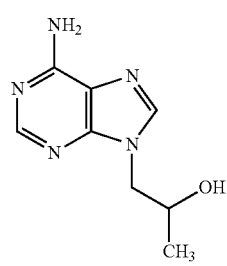
33b
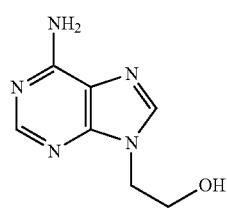

-continued
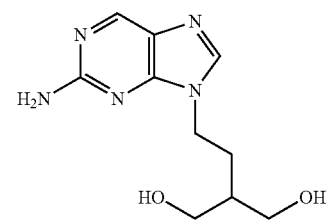
35
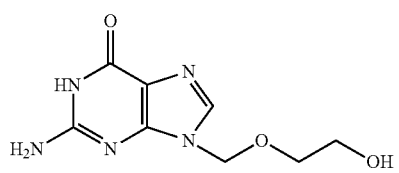
36
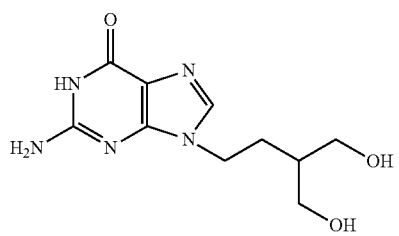
37
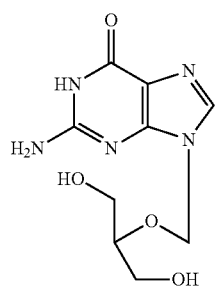
38
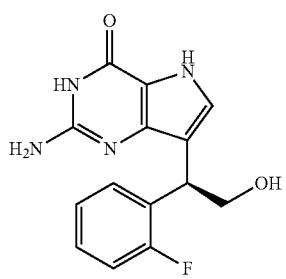
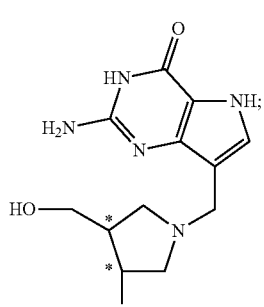
(S,S)-41
(R,R)-41
wherein the non-nucleoside is selected from
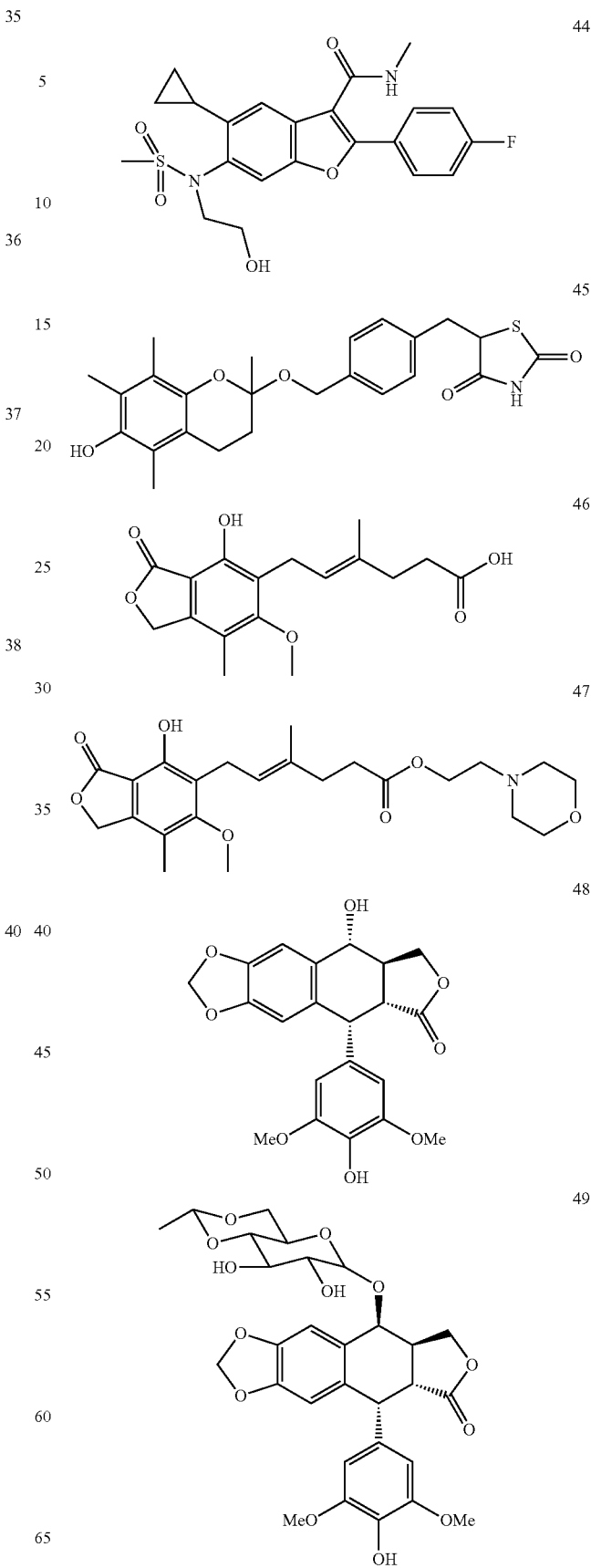

153
-continued
| | |
|---|---|
| 50 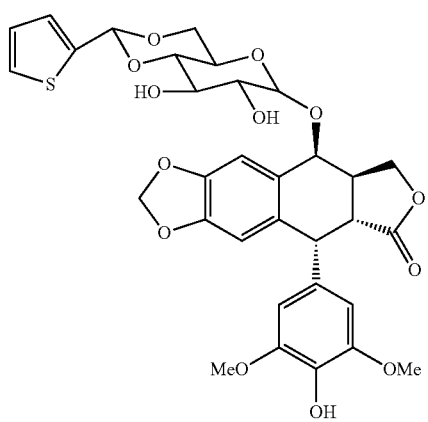 | 55 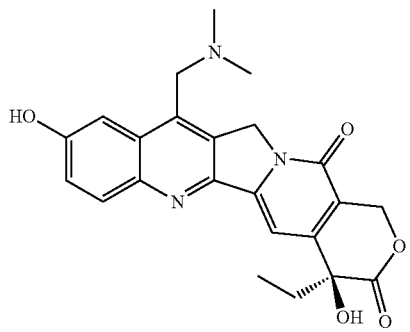 |
| 51 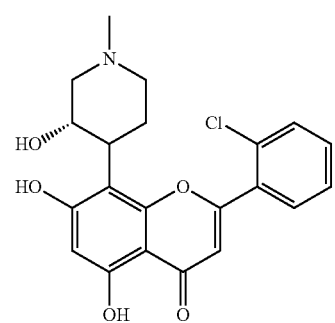 | 56 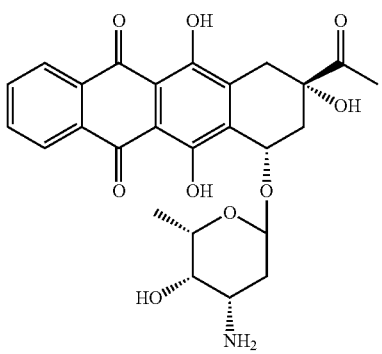 |
| 52 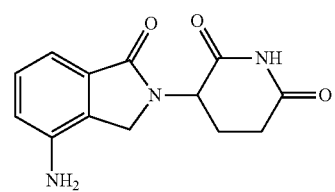 | 57 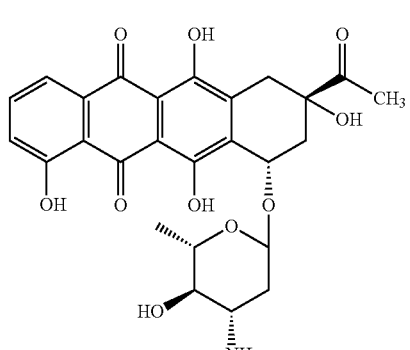 |
| 53 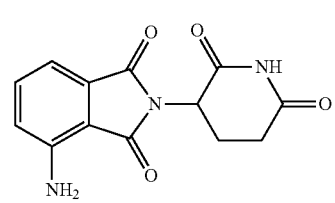 | 58 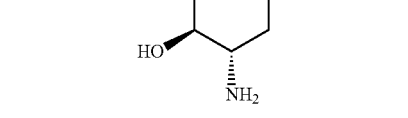 |
| 54 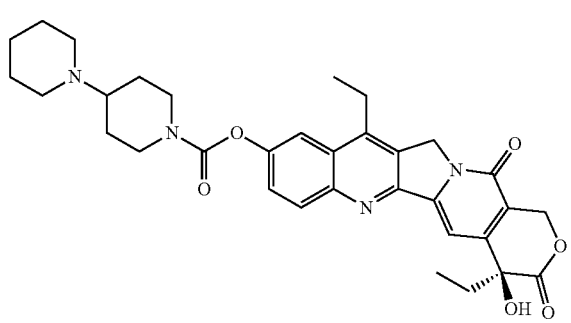 | |
154
-continued

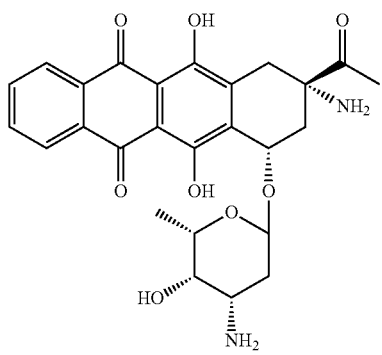
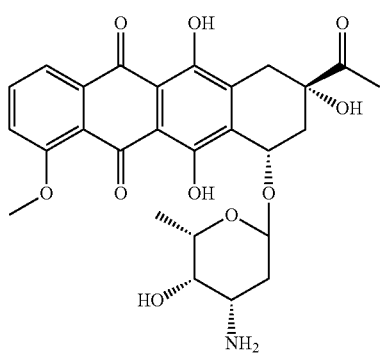
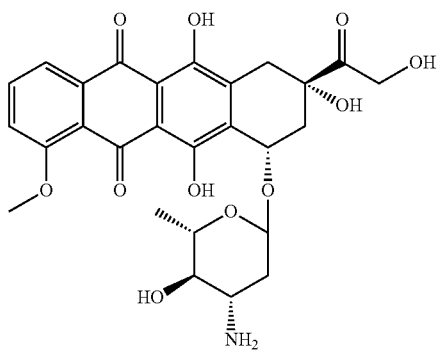
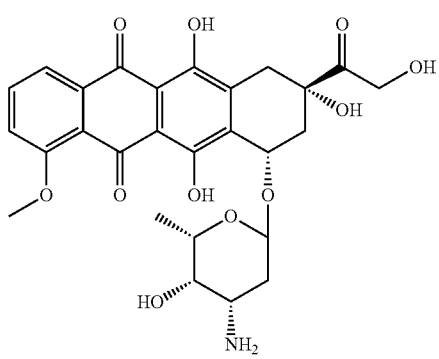
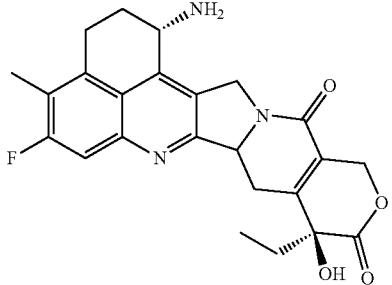
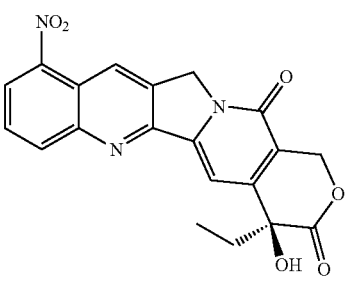
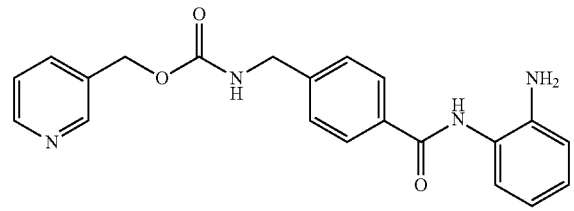
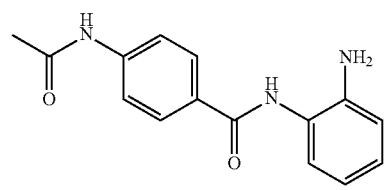
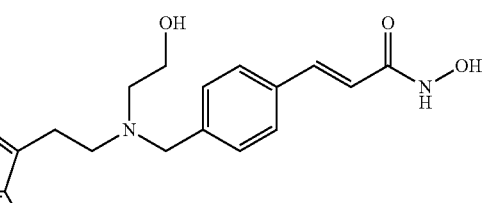
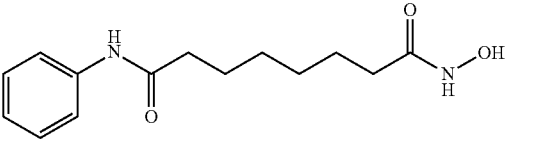

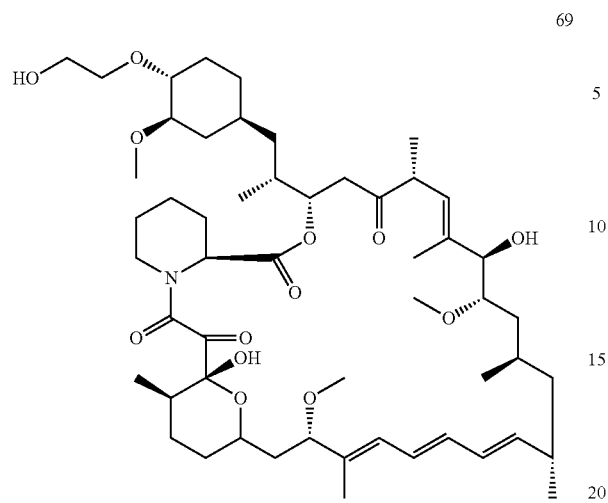
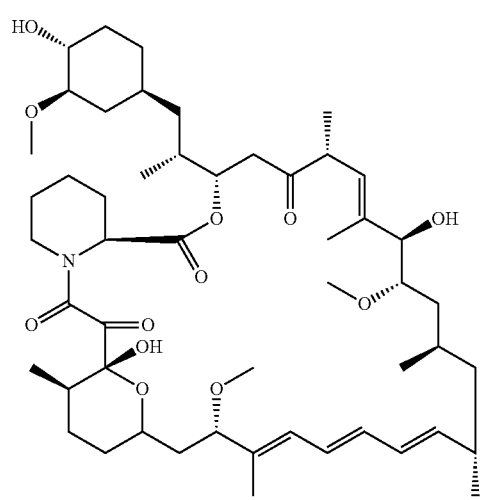
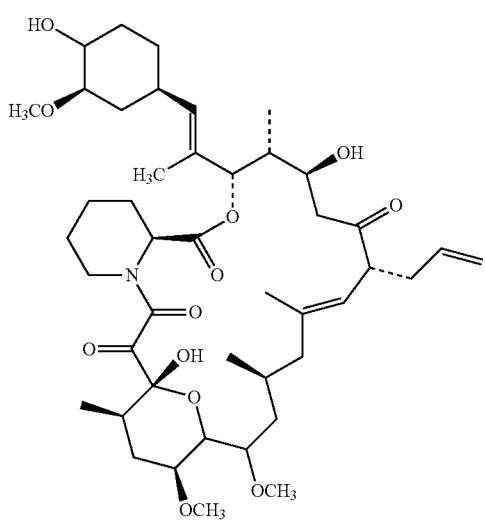
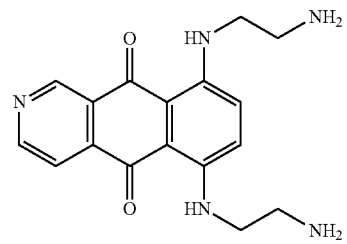
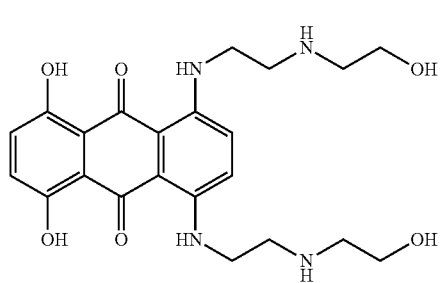
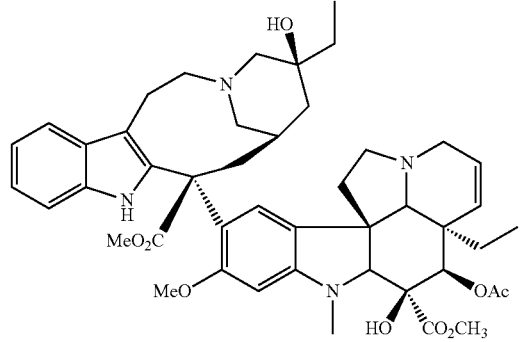
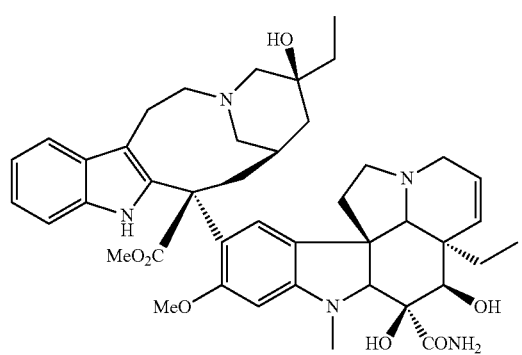
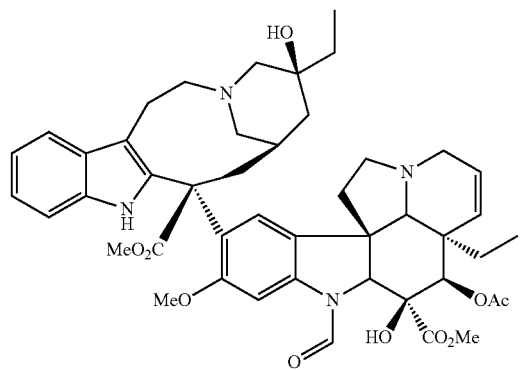

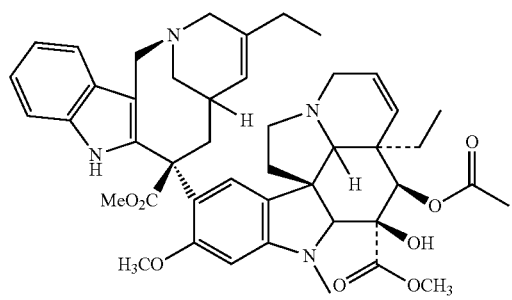
77
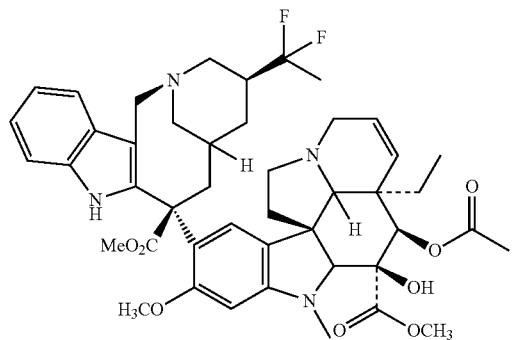
78
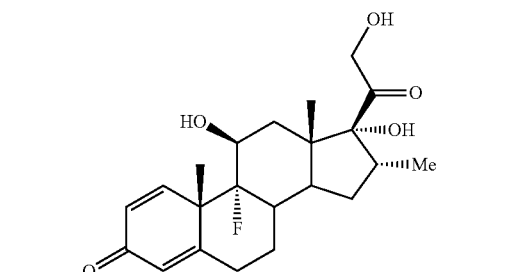
79
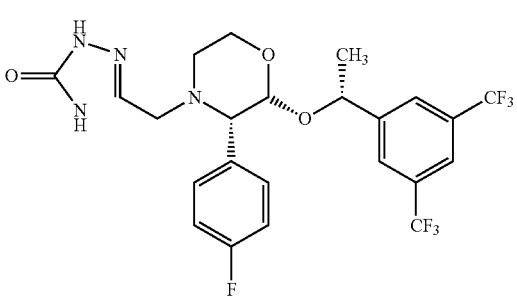
80
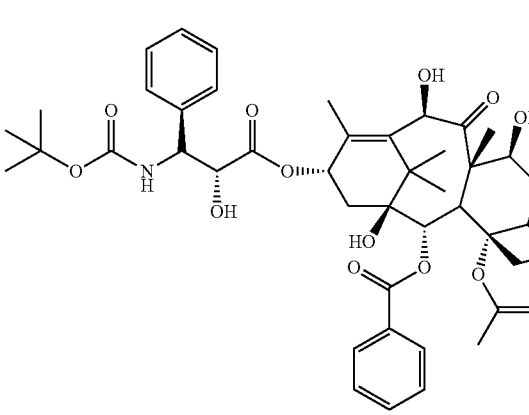
81
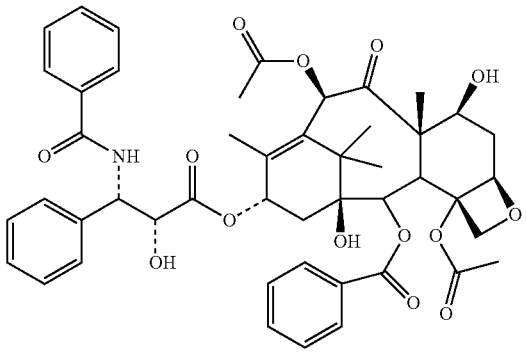
82
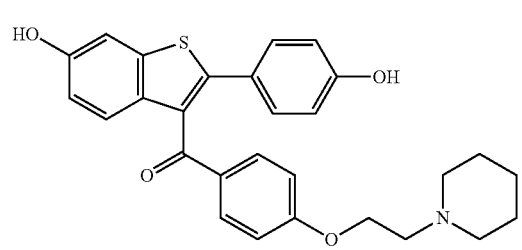
83
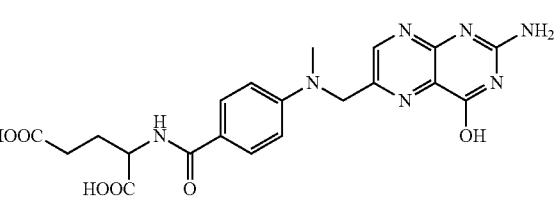
84
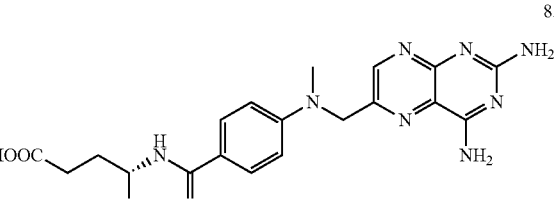
85
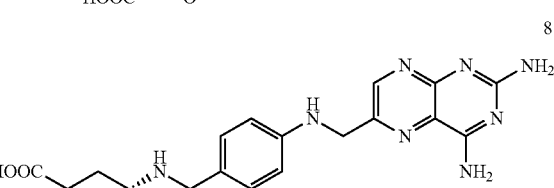
86
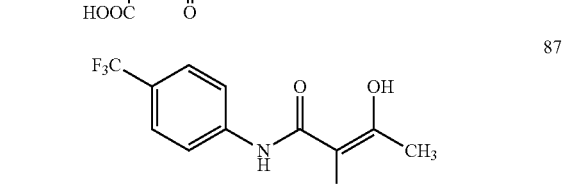
87
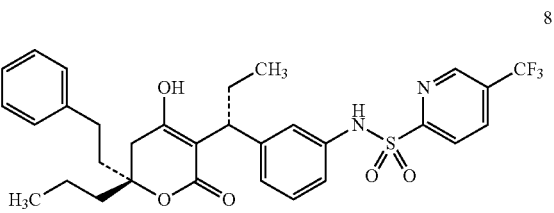
88

-continued

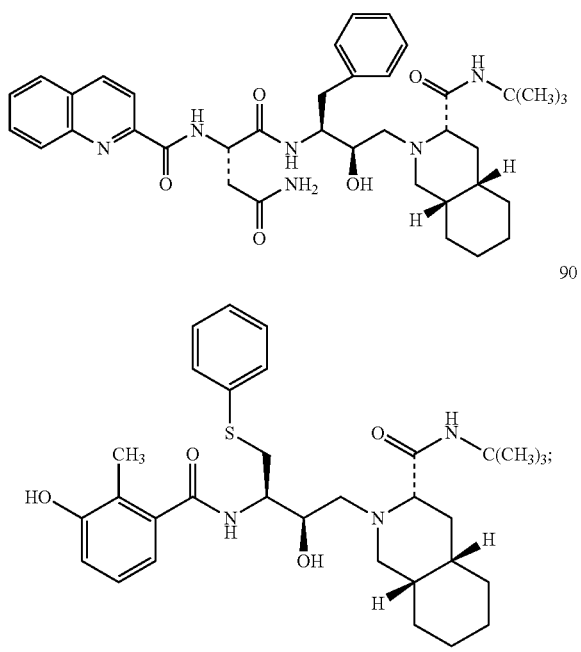

wherein W is an aryl or —(CH$_2$)$_n$SC(O)C(CH$_3$)$_m$(CH$_2$OH)$_{3-m}$;
wherein n is 2 or 3 and m is 0, 1, 2, or 3;
wherein LG is selected from the group consisting of halogen, tosylate, mesylate, triflate, acetate, trifluoromethylacetate, camphorsulfonate, 2-thioxobenzo[d]thiazol-3(2H)-yl, aryloxide, and aryloxide substituted with at least one electron withdrawing group;
wherein R is a substituted or unsubstituted C$_{1-30}$ alkyl, a substituted or unsubstituted C$_{3-10}$ cycloalkyl, a substituted or unsubstituted C$_{1-30}$ alkylaryl, a substituted or unsubstituted C$_{2-10}$ alkenyl, a substituted or unsubstituted —OC$_{1-30}$ alkyl, a substituted or unsubstituted C$_{6-12}$ aryl; and
wherein R' is a substituted or unsubstituted C$_{1-30}$ alkyl, a substituted or unsubstituted cycloalkyl, a substituted or unsubstituted C$_{1-30}$ alkylaryl, or a substituted or unsubstituted C$_{6-12}$ aryl; and
(b) optionally deprotecting the compound obtained in step (a) to obtain the enantiomerically- or diastereomerically-enriched phosphorous-containing active, salt, or pharmaceutically acceptable salt thereof of formula I-1,
wherein the enantiomerically- or diastereomerically-enriched compound of formula II-1 is obtained by crystallization from a composition comprising:
i. a first composition;
ii. a leaving group precursor;
iii. a non-nucleophilic base; and
iv. a liquid composition;
wherein the first composition comprises Rp-II-1 and Sp-II-1; and
wherein the leaving group precursor is 2,4-dinitrophenol, 4-nitrophenol, 2-nitrophenol, 2-chloro-4-nitrophenol, 2,4-dichlorophenol, or pentafluorophenol.

2. The process of claim 1, wherein the Active is a nucleoside.

3. The process of claim 1, wherein R' is a C$_{1-6}$alkyl or C$_{3-7}$cycloalkyl.

4. The process of claim 1, wherein R is methyl or isopropyl and R' is a C$_{1-6}$alkyl or C$_{3-7}$cycloalkyl.

5. The process of claim 1, wherein LG is an aryloxide substituted with at least one electron withdrawing group.

6. The process of claim 1, wherein LG is selected from among 2-nitrophenoxide, 4-nitrophenoxide, 2,4-dinitrophenoxide, pentafluorophenoxide, 2-chloro-4-nitrophenoxide, 2,4-dichlorophenoxide, and 2,4,6-trichlorophenoxide.

7. The process of claim 1, wherein the Active is a nucleoside analog.

8. The process of claim 1, wherein the Active is a non-nucleoside.

9. The process of claim 1, wherein the enantiomerically- or diastereomerically enriched phosphorous-containing active, salt, or pharmaceutically acceptable salt thereof of formula I-1 has at least 90 mol % of one enantiomer or diastereomer and at most about 10 mol % of the other enantiomer or diastereomer.

10. The process of claim 9, wherein no chiral purification technique is used.

11. The process of claim 1, wherein the enantiomerically- or diastereomerically enriched phosphorous-containing active, salt, or pharmaceutically acceptable salt thereof of formula I-1 has at least 95 mol % of one enantiomer or diastereomer and at most about 5 mol % of the other enantiomer or diastereomer.

12. The process of claim 1, wherein LG is 2,4-dinitrophenoxide, 4-nitrophenoxide, 2-nitrophenoxide, 2-chloro-4-nitrophenoxide, 2,4-dichlorophenoxide, or pentafluorophenoxide.

13. The process of claim 12, wherein LG is 4-nitrophenoxide or pentafluorophenoxide.

14. The process of claim 12, wherein the non-nucleophilic base is triethylamine.

15. The process of claim 1, wherein the crystallization occurs at a temperature between about −10° C. and about 40° C.

16. The process of claim 1, wherein the non-nucleophilic base is potassium carbonate, cesium carbonate, di-isopropylamine, di-isopropylethylamine, triethylamine, quinuclidine, napthalene-1,8-diamine, 2,2,6,6-tetramethylpiperidine, 1,8-diazabicycloundec-7-ene, 4-dimethylamino-pyridine, pyridine, a 2,6-di-C$_{1-6}$-alkyl-pyridine, a 2,4,6-tri-C$_{1-6}$-alkyl-pyridine, or a mixture thereof.

* * * * *